US010916716B2

(12) United States Patent
Molt et al.

(10) Patent No.: US 10,916,716 B2
(45) Date of Patent: Feb. 9, 2021

(54) METAL COMPLEXES COMPRISING DIAZABENZMIDAZOLOCARBENE LIGANDS AND THE USE THEREOF IN OLEDS

(71) Applicant: UDC IRELAND LIMITED, Dublin (IE)

(72) Inventors: Oliver Molt, Weinheim (DE); Nicolle Langer, Heppenheim (DE); Evelyn Fuchs, Mannheim (DE); Korinna Dormann, Bad Duerkheim (DE); Christian Schildknecht, Mannheim (DE); Soichi Watanabe, Mannheim (DE); Gerhard Wagenblast, Wachenheim (DE); Christian Lennartz, Schifferstadt (DE); Thomas Schaefer, Liestal (CH); Heinz Wolleb, Fehren (CH); Teresa Marina Figueira Duarte, Mainz (DE); Stefan Metz, Mannheim (DE); Peter Murer, Oberwil (CH)

(73) Assignee: UDC IRELAND LIMITED, Dublin (IE)

( * ) Notice: Subject to any disclaimer, the term of this patent is extended or adjusted under 35 U.S.C. 154(b) by 187 days.

(21) Appl. No.: 16/054,011

(22) Filed: Aug. 3, 2018

(65) Prior Publication Data
US 2018/0351115 A1 Dec. 6, 2018

Related U.S. Application Data

(63) Continuation of application No. 15/288,057, filed on Oct. 7, 2016, now Pat. No. 10,090,476, which is a continuation of application No. 13/516,117, filed as application No. PCT/EP2010/069541 on Dec. 13, 2010, now Pat. No. 9,487,548.

(60) Provisional application No. 61/286,046, filed on Dec. 14, 2009, provisional application No. 61/323,885, filed on Apr. 14, 2010, provisional application No. 61/391,712, filed on Oct. 11, 2010.

(30) Foreign Application Priority Data

Oct. 11, 2010 (EP) .................................... 10187176

(51) Int. Cl.
H01L 51/00 (2006.01)
C07D 405/14 (2006.01)
C07F 7/08 (2006.01)
C07F 15/00 (2006.01)
C09K 11/02 (2006.01)
C09K 11/06 (2006.01)
C07D 307/91 (2006.01)
H01L 51/50 (2006.01)

(52) U.S. Cl.
CPC ........ *H01L 51/0085* (2013.01); *C07D 307/91* (2013.01); *C07D 405/14* (2013.01); *C07F 7/0816* (2013.01); *C07F 15/0033* (2013.01); *C07F 15/0086* (2013.01); *C09K 11/025* (2013.01); *C09K 11/06* (2013.01); *H01L 51/0067* (2013.01); *H01L 51/0072* (2013.01); *H01L 51/0073* (2013.01); *H01L 51/0077* (2013.01); *H01L 51/0087* (2013.01); *H01L 51/0094* (2013.01); *C09K 2211/1007* (2013.01); *C09K 2211/1044* (2013.01); *C09K 2211/1059* (2013.01); *C09K 2211/1088* (2013.01); *C09K 2211/185* (2013.01); *H01L 51/0065* (2013.01); *H01L 51/5012* (2013.01); *H01L 51/5016* (2013.01); *H01L 51/5036* (2013.01); *H01L 51/5048* (2013.01); *H01L 51/5052* (2013.01); *H01L 51/5072* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 2005/0260447 | A1 | 11/2005 | Brooks |
| 2006/0258043 | A1 | 11/2006 | Bold |
| 2007/0224446 | A1 | 9/2007 | Nakano |
| 2008/0018221 | A1 | 1/2008 | Egen |
| 2009/0009637 | A1 | 1/2009 | Wada |

(Continued)

FOREIGN PATENT DOCUMENTS

| | | | |
|---|---|---|---|
| EP | 1097981 | A2 | 5/2001 |
| EP | 1658343 | A2 | 5/2006 |

(Continued)

OTHER PUBLICATIONS

Herrmann et al., "Metal Complexes of Stable Carbenes," Advances in Organometallic Chemistry, vol. 48 (2001), p. 27. (Year: 2001).*

*Primary Examiner* — Catherine S Branch
(74) *Attorney, Agent, or Firm* — Riverside Law LLP

(57) ABSTRACT

The present invention relates to metal-carbene complexes comprising a central atom selected from iridium and platinum, and diazabenzimidazolocarbene ligands, to organic light diodes which comprise such complexes, to light-emitting layers comprising at least one such metal-carbene complex, to a device selected from the group comprising illuminating elements, stationary visual display units and mobile visual display units comprising such an OLED and to the use of such a metal-carbene complex in OLEDs, for example as emitter, matrix material, charge transport material and/or charge or exciton blocker.

23 Claims, No Drawings

(56) References Cited

U.S. PATENT DOCUMENTS

| | | |
|---|---|---|
| 2009/0018330 A1 | 1/2009 | Molt |
| 2009/0054657 A1 | 2/2009 | Molt |
| 2009/0115322 A1 | 5/2009 | Walters |
| 2009/0134784 A1 | 5/2009 | Lin |
| 2009/0153034 A1 | 6/2009 | Lin |
| 2009/0284138 A1 | 11/2009 | Yasukawa |
| 2010/0219403 A1* | 9/2010 | Langer ............... H01L 51/0072 257/40 |
| 2011/0086454 A1 | 4/2011 | Chebotareva |
| 2011/0087026 A1 | 4/2011 | Molt |
| 2011/0089407 A1 | 4/2011 | Schmidhalter |
| 2011/0098473 A1 | 4/2011 | Molt |
| 2011/0114933 A1 | 5/2011 | Molt |
| 2011/0152491 A1 | 6/2011 | Kawano |
| 2011/0172423 A1 | 7/2011 | Fuchs |
| 2011/0198478 A1 | 8/2011 | Heuser |
| 2011/0198578 A1 | 8/2011 | Heuser |
| 2012/0012821 A1 | 1/2012 | Langer |
| 2012/0071617 A1 | 3/2012 | Dueggeli |
| 2012/0168731 A1 | 7/2012 | Schildknecht |
| 2012/0199823 A1 | 8/2012 | Molt |
| 2012/0205645 A1 | 8/2012 | Fuchs |
| 2012/0319050 A1 | 12/2012 | Metz |

FOREIGN PATENT DOCUMENTS

| | | |
|---|---|---|
| EP | 1786050 A1 | 5/2007 |
| EP | 1837926 A1 | 9/2007 |
| EP | 1970371 A1 | 9/2008 |
| EP | 1988587 A1 | 11/2008 |
| EP | 2180029 A1 | 4/2010 |
| JP | 2008021687 A | 1/2008 |
| JP | 2008066569 A | 3/2008 |
| JP | 2008074939 A | 4/2008 |
| JP | 2008084913 A | 4/2008 |
| JP | 2008127326 A | 6/2008 |
| JP | 2008207520 A | 9/2008 |
| JP | 2009021336 A | 1/2009 |
| JP | 2009059767 A | 3/2009 |
| JP | 2009114369 A | 5/2009 |
| JP | 2009114370 A | 5/2009 |
| JP | 2009135183 A | 6/2009 |
| JP | 2009170764 A | 7/2009 |
| JP | 2009182298 A | 8/2009 |
| JP | 2009267255 A | 11/2009 |
| JP | 2010021336 A | 1/2010 |
| JP | 2010040830 A | 2/2010 |
| JP | 2010114180 A | 5/2010 |
| JP | 2010135467 A | 6/2010 |
| KR | 20070090953 | 9/2007 |
| WO | 0032717 A1 | 6/2000 |
| WO | 0070655 A2 | 11/2000 |
| WO | 0215645 A1 | 2/2002 |
| WO | 02060910 A1 | 8/2002 |
| WO | 2005019373 A2 | 3/2005 |
| WO | 2005113704 A2 | 12/2005 |
| WO | 2007077810 A1 | 7/2007 |
| WO | 2007088093 A1 | 8/2007 |
| WO | 2007108362 A1 | 9/2007 |
| WO | 2007108459 A1 | 9/2007 |
| WO | 2007114244 A1 | 10/2007 |
| WO | 2007115970 A1 | 10/2007 |
| WO | 2007115981 A1 | 10/2007 |
| WO | 2007119816 A1 | 10/2007 |
| WO | 2008000727 A1 | 1/2008 |
| WO | 2008029652 A1 | 3/2008 |
| WO | 2008029729 A1 | 3/2008 |
| WO | 2008034758 A2 | 3/2008 |
| WO | 2008035571 A1 | 3/2008 |
| WO | 2008072596 A1 | 6/2008 |
| WO | 2008090912 A1 | 7/2008 |
| WO | 2008140114 A1 | 11/2008 |
| WO | 2008146838 A1 | 12/2008 |
| WO | 2008156105 A1 | 12/2008 |
| WO | 2009003898 A1 | 1/2009 |
| WO | 2009003919 A1 | 1/2009 |
| WO | 2009008099 A1 | 1/2009 |
| WO | 2009008100 A1 | 1/2009 |
| WO | 2009046266 A1 | 4/2009 |
| WO | 2009060742 A1 | 5/2009 |
| WO | 2009060757 A1 | 5/2009 |
| WO | 2009060779 A1 | 5/2009 |
| WO | 2009060780 A1 | 5/2009 |
| WO | 2009063757 A1 | 5/2009 |
| WO | 2009069442 A1 | 6/2009 |
| WO | 2009084413 A1 | 7/2009 |
| WO | 2009086028 A2 | 7/2009 |
| WO | 2009092671 A2 | 7/2009 |
| WO | 2009100991 A1 | 8/2009 |
| WO | 2009104488 A1 | 8/2009 |
| WO | 2009147011 A1 | 12/2009 |
| WO | 2009150140 | 12/2009 |
| WO | 2009150150 A1 | 12/2009 |
| WO | 2009150151 A1 | 12/2009 |
| WO | 2009153276 A1 | 12/2009 |
| WO | 2010001830 A1 | 1/2010 |
| WO | 2010004877 A1 | 1/2010 |
| WO | 2010006852 A1 | 1/2010 |
| WO | 2010040777 A1 | 4/2010 |
| WO | 2010044342 A1 | 4/2010 |
| WO | 2010046259 | 4/2010 |
| WO | 2010067746 | 6/2010 |
| WO | 2010079051 A1 | 7/2010 |
| WO | 2010079678 A1 | 7/2010 |
| WO | 2010087222 A1 | 8/2010 |
| WO | 2010090077 A1 | 8/2010 |
| WO | 2010095564 A1 | 8/2010 |
| WO | 2010097433 | 9/2010 |
| WO | 2010136343 | 12/2010 |
| WO | 2010145991 | 12/2010 |
| WO | 2011045337 | 4/2011 |
| WO | 2011051404 A1 | 5/2011 |
| WO | 2012172482 A1 | 12/2012 |

* cited by examiner

METAL COMPLEXES COMPRISING DIAZABENZMIDAZOLOCARBENE LIGANDS AND THE USE THEREOF IN OLEDS

CROSS-REFERENCE TO RELATED APPLICATIONS

The present application is a continuation of U.S. patent application Ser. No. 15/288,057, filed Oct. 7, 2016, now allowed, which is a continuation of U.S. patent application Ser. No. 13/516,117, filed Aug. 27, 2012, now U.S. Pat. No. 9,487,548, which is a 35 U.S.C. § 371 national stage patent application of International Patent Application No. PCT/EP2010/069541, filed Dec. 13, 2010, and which claims priority to U.S. Provisional Application Nos. 61/286,046, filed Dec. 14, 2009, 61/323,885, filed Apr. 14, 2010, and 61/391,712, filed Oct. 11, 2010, and European Patent Application No. 10187176.2, filed on Oct. 11, 2010, all of which applications are incorporated by reference herein in their entireties.

The present invention relates to metal-carbene complexes comprising a central atom selected from iridium and platinum, and diazabenzimidazolocarbene ligands, to OLEDs (Organic Light-Emitting Diodes) which comprise such complexes, to light-emitting layers comprising at least one such metal-carbene complex, to a device selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker.

Organic light-emitting diodes (OLEDs) exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are suitable especially for mobile applications, for example for applications in cellphones, laptops, etc. In addition, white OLEDs give great advantages over the illumination technologies known to date, especially a particularly high efficiency.

The prior art proposes numerous materials which emit light on excitation by electrical current.

WO 2005/019373 discloses transition metal complexes with carbene ligands as emitters for organic light-emitting diodes (OLEDs). The ligands of these transition metal complexes are preferably attached via a metal-carbene bond and via a bond between the metal atom and an aromatic radical. Numerous heterocycles attached to the metal atom via a carbene bond are disclosed, but no complexes which have diazabenzimidazolocarbene ligands are disclosed.

WO 2006/056418 A2 discloses the use of transition metal-carbene complexes in organic light-emitting diodes. In the corresponding transition metal complexes, a metal atom is bonded to the ligands via at least one metal-carbene bond and via a bond between the metal atom and an aromatic radical. The metal-carbene bond is preferably via an imidazole ring, to which, according to the document cited, aromatic cycles may also be fused. However, no complexes which have diazabenzimidazolocarbene ligands are disclosed.

WO 2007/088093 A1 and WO 2007/185981 A1 disclose transition metal complexes comprising ligands attached via metal-carbene bonds. Preferred carbene ligands mentioned are imidazole ligands. These may also have fused aromatic six-membered rings, where 1 to 4 of the carbon atoms present in the aromatic six-membered ring may be replaced by nitrogen. The documents cited do not disclose the positions of the nitrogens in the aromatic six-membered ring.

WO 2007/115970 A1 likewise discloses transition metal-carbene complexes, preference being given to imidazole units as the carbene ligand. An aromatic six-membered ring may likewise be fused to this imidazole unit, wherein 1 to 4 carbon atoms may be replaced by nitrogen atoms. Nor does this document comprise any disclosure as to the position of the nitrogen atoms.

Even though compounds which exhibit electroluminescence in the visible region, more particularly in the blue region, of the electromagnetic spectrum, are already known, the provision of compounds which exhibit long diode lifetimes is desirable. In the context of the present invention, electroluminescence is understood to mean both electrofluorescence and electrophosphorescence.

It is therefore an object of the present invention to provide alternative iridium and platinum complexes which are suitable for electroluminescence in the visible region, more particularly in the blue region, of the electromagnetic spectrum, which enables the production of full-color displays and white OLEDs. It is a further object of the present invention to provide corresponding complexes which can be used as a mixture with a host compound (matrix material) as a light-emitting layer in OLEDs. It is a further object of the present invention to provide corresponding complexes which have a high quantum yield and a high stability in diodes. The complexes should be usable as emitter, matrix material, charge transport material, especially hole transport material or charge blocker in OLEDs.

These objects are achieved in accordance with the invention by metal-carbene complexes of the general formula (I)

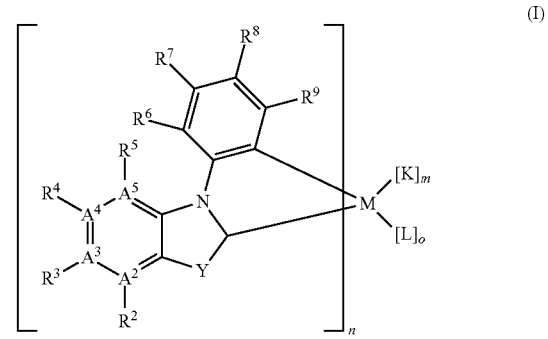

where M, n, Y, $A^2$, $A^3$, $A^4$, $A^5$, $R^1$, $R^2$, $R^3$, $R^4$, $R^5$, $R^6$, $R^7$, $R^8$, $R^9$, $R^{10}$, K, L, m and o are each defined as follows:

M is a linear or Pt,
n is an integer selected from 1, 2 and 3,
Y is $NR^1$, r, S or $C(R^{10})_2$,
$A^2$, $A^3$,
$A^4$, $A^5$ are each independently N or C, where 2 A=nitrogen atoms and at least one carbon atom is present between two nitrogen atoms in the ring,
$R^1$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^2, R^3,$ $R^4, R^5$ are each, if $A^2, A^3, A^4$ and/or $A^5$ is N, a free electron pair, or, if $A^2, A^3, A^4$ and/or $A^5$ is C, each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^3$ and $R^4$ together with $A^3$ and $A^4$ form an optionally substituted, unsaturated ring optionally interrupted by at least one further heteroatom and having a total of 5 to 18 carbon atoms and/or heteroatoms, $R^6, R^7,$ $R^8, R^9$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^6$ and $R^7$, $R^7$ and $R^8$ or $R^8$ and $R^9$, together with the carbon atoms to which they are bonded, form an unsaturated or aromatic, optionally substituted ring optionally interrupted by at least one heteroatom and having a total of 5 to 18 carbon atoms and/or heteroatoms, and/or if $A^5$ is C, $R^5$ and $R^6$ together form a saturated or unsaturated, linear or branched bridge optionally comprising heteroatoms, an aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{10}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, K is an uncharged mono- or bidentate ligand, L is a mono- or dianionic ligand, preferably monoanionic ligand, which may be mono- or bidentate, m is 0, 1 or 2, where, when m is 2, the K ligands may be the same or different, o is 0, 1 or 2, where, when o is 2, the L ligands may be the same or different.

When m and o are each 0, in accordance with the invention, homoleptic metal-carbene complexes of the general formula (I) are present. When at least one of m and o is 1 or 2, in accordance with the invention, heteroleptic metal-carbene complexes of the general formula (I) are present.

In the context of the present invention, the terms aryl radical, unit or group, heteroaryl radical, unit or group, alkyl radical, unit or group and cycloalkyl radical, unit or group are each defined as follows—unless stated otherwise:

An aryl radical, unit or group is understood to mean a radical with a base skeleton of 6 to 30 carbon atoms, preferably 6 to 18 carbon atoms, which is formed from an aromatic ring or a plurality of fused aromatic rings. Suitable base skeletons are, for example, phenyl, naphthyl, anthracenyl or phenanthrenyl. This base skeleton may be unsubstituted, which means that all carbon atoms which are substitutable bear hydrogen atoms, or may be substituted at one or more, or all, substitutable positions of the base skeleton.

Suitable substituents are, for example, alkyl radicals, preferably alkyl radicals having 1 to 8 carbon atoms, more preferably methyl, ethyl, i-propyl, t-butyl, neopentyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals, alkenyl radicals, preferably alkenyl radicals which bear one double bond, more preferably alkenyl radicals with one double bond and 1 to 8 carbon atoms, or groups with donor or acceptor action. Groups with donor action are understood to mean groups which have a +I and/or +M effect, and groups with acceptor action are understood to mean groups which have a −I and/or −M effect. Suitable groups with donor or acceptor action are halogen radicals, preferably F, Cl, Br, more preferably F, alkyl radicals, silyl radicals, siloxy radicals, alkoxy radicals, aryloxy radicals, carbonyl radicals, ester radicals, amine radicals, amide radicals, $CH_2F$ groups, $CHF_2$ groups, $CF_3$ groups, CN groups, thio groups or SCN groups. The aryl radicals most preferably bear substituents selected from the group consisting of methyl, ethyl, iso-propyl, n-propyl, n-butyl, iso-butyl, tert-butyl, neopentyl, $CF_3$, aryloxy, amine, thio groups and alkoxy, or the aryl radicals are unsubstituted. The aryl radical or the aryl group is preferably a $C_6$-aryl radical optionally substituted by at least one of the aforementioned substituents. The $C_6$-aryl radical more preferably has none, one, two or three of the aforementioned substituents.

A heteroaryl radical or a heteroaryl unit or group is understood to mean radicals having 5 to 30 carbon atoms and/or heteroatoms, which differ from the aforementioned aryl radicals in that at least one carbon atom in the base skeleton of the aryl radicals is replaced by a heteroatom. Preferred heteroatoms are N, O and S. Most preferably, one or two carbon atoms of the base skeleton of the aryl radicals are replaced by heteroatoms. The base skeleton is especially preferably selected from electron-poor systems such as pyridyl, pyrimidyl, pyrazyl and triazolyl, and five-membered heteroaromatics such as pyrrole, furan, thiophene, imidazole, pyrazole, triazole, oxazole and thiazole. The base skeleton may be substituted at one, more than one or all substitutable positions of the base skeleton. Suitable substituents are the same as have already been specified above for the aryl groups.

An alkyl radical or an alkyl group is understood to mean a radical having 1 to 20 carbon atoms, preferably 1 to 10 carbon atoms, more preferably 1 to 8 carbon atoms. This alkyl radical may be branched or unbranched and may optionally be interrupted by one or more heteroatoms, preferably N, O or S. In addition, this alkyl radical may be substituted by one or more of the substituents already specified for the aryl groups. It is likewise possible that the alkyl radical bears one or more aryl groups. All of the aryl groups listed above are suitable. Particular preference is given to the alkyl radicals selected from the group consisting of methyl, ethyl, i-propyl, n-propyl, i-butyl, n-butyl, t-butyl, sec-butyl, i-pentyl, n-pentyl, sec-pentyl, neopentyl, n-hexyl, i-hexyl and sec-hexyl. Very particular preference is given to methyl, i-propyl, tert-butyl and neopentyl.

A cycloalkyl radical or a cycloalkyl group is understood to mean a cyclic radical having 3 to 20 carbon atoms, preferably 3 to 10 carbon atoms, more preferably 3 to 8 carbon atoms. This cycloalkyl radical may optionally be interrupted by one or more heteroatoms, preferably N, O or S. In addition, this cycloalkyl radical may be unsubstituted or substituted, i.e. may be substituted by one or more of the substituents already specified for the aryl groups. It is likewise possible that the cycloalkyl radical bears one or more aryl groups. All aryl groups listed above are suitable.

The statements made for the aryl, heteroaryl, alkyl and cycloalkyl radicals apply, in accordance with the invention, independently to the radicals mentioned in the present application, where $R^2$, $R^3$, $R^4$ and $R^5$, in the case that $A^2$, $A^3$, $A^4$ and/or $A^5$ is N, are a free electron pair, which means that no substituent selected from the abovementioned group is present on these ring nitrogen atoms. In the case that $A^2$, $A^3$, $A^4$ and/or $A^5$ is C, $R^2$, $R^3$, $R^4$ and $R^5$ are each independently hydrogen and/or the substituents specified.

K in the general formula (I) is an uncharged mono- or bidentate ligand, and L in the general formula (I) is a mono- or dianionic ligand, preferably a monoanionic ligand which may be mono- or bidentate.

A bidentate ligand is understood to mean a ligand coordinated at two sites to the transition metal atom M. A monodentate ligand is understood to mean a ligand coordinated at one site on the ligand to the transition metal atom M.

Suitable mono- or dianionic ligands L, preferably monoanionic ligands L which may be mono- or bidentate, are the ligands typically used as mono- or bidentate mono- or dianionic ligands.

Suitable monoanionic monodentate ligands are, for example, halides, especially Cl⁻ and Br⁻, pseudohalides, especially CN⁻, cyclopentadienyl (Cp⁻), hydride, alkyl radicals joined to the transition metal M via a sigma bond, for example $CH_3$, alkylaryl radicals joined to the transition metal M via a sigma bond, for example benzyl.

Suitable monoanionic bidentate ligands are, for example, acetylacetonate and derivatives thereof, picolinate, Schiff bases, amino acids, arylpyridines, e.g. phenylpyridine, and the further bidentate monoanionic ligands specified in WO 02/15645, carbene ligands as specified in WO2006056418 and in EP1658343, arylazoles, e.g. 2-arylimidazoles, preference being given to 2-arylimidazoles and carbene ligands.

Suitable dianionic bidentate ligands are, for example, dialkoxides, dicarbonates, dicarboxylates, diamides, diimides, dithiolates, biscyclopentadienyls, bisphosphonates, bissulfonates and 3-phenylpyrazole.

Suitable uncharged mono- or bidentate ligands K are preferably selected from the group consisting of phosphines, both mono- and bisphosphines; phosphonates, both mono- and bisphosphonates, and derivatives thereof, arsenates, both mono- and bisarsenates, and derivatives thereof; phosphites, both mono- and bisphosphites; CO; pyridines, both mono- and bispyridines; nitriles, dinitriles, allyl, diimines, nonconjugated dienes and conjugated dienes which form a π complex with $M^1$. Particularly preferred uncharged mono- or bidentate ligands K are selected from the group consisting of phosphines, both mono- and bisphosphines, preferably trialkyl-, triaryl- or alkylarylphosphines, more preferably $PAr_3$ where Ar is a substituted or unsubstituted aryl radical and the three aryl radicals in $PAr_3$ may be the same or different, more preferably $PPh_3$, $PEt_3$, $PnBu_3$, $PEt_2Ph$, $PMe_2Ph$, $PnBu_2Ph$; phosphonates and derivatives thereof, arsenates and derivatives thereof, phosphites, CO; pyridines, both mono- and bispyridines, where the pyridines may be substituted by alkyl or aryl groups; nitriles and dienes which form a π complex with $M^1$, preferably $\eta^4$-diphenyl-1,3-butadiene, $\eta^4$-1,3-pentadiene, $\eta^4$-1-phenyl-1,3-pentadiene, $\eta^4$-1,4-dibenzyl-1,3-butadiene, $\eta^4$-2,4-hexadiene, $\eta^4$-3-methyl-1,3-pentadiene, $\eta^4$-1,4-ditolyl-1,3-butadiene, $\eta^4$-1,4-bis(trimethylsilyl)-1,3-butadiene and $\eta^2$- or $\eta^4$-cyclooctadiene (each 1,3 and each 1,5), more preferably 1,4-diphenyl-1,3-butadiene, 1-phenyl-1,3-pentadiene, 2,4-hexadiene, butadiene, $\eta^2$-cyclooctene, $\eta^4$-1,3-cyclooctadiene and $\eta^4$-1,5-cyclooctadiene. Very particularly preferred uncharged monodentate ligands are selected from the group consisting of $PPh_3$, $P(OPh)_3$, $AsPh_3$, CO, pyridine, nitriles and derivatives thereof. Suitable uncharged mono- or bidentate ligands are preferably 1,4-diphenyl-1,3-butadiene, 1-phenyl-1,3-pentadiene, 2,4-hexadiene, $\eta^4$-cyclooctadiene and $\eta^2$-cyclooctadiene (each 1,3 and each 1,5).

The number o of monoanionic ligands L in the aforementioned case is 0, 1, 2. When o>1, the L ligands may be the same or different, and are preferably the same.

The number m of uncharged ligands K depends on whether the coordination number 6 of the Ir(III) or 4 of the Pt(II) has already been attained with the aid of the carbene ligands and of the ligands L. When—in the case that Ir(III) is used—n is three and three monoanionic bidentate carbene ligands are used, m in the aforementioned case is 0. When—in the case that Pt(II) is used—n is two and two monoanionic bidentate carbene ligands are used, m in this case is likewise 0.

In a further preferred embodiment, the present invention relates to an inventive metal-carbene complex where L in the general formula (I) is a carbene ligand of the general formula (II)

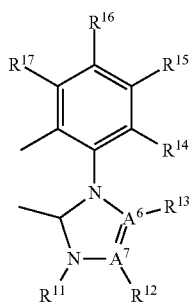

(II)

where $A^6$, $A^7$ are each independently C or N $R^{11}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^{12}$, $R^{13}$ are each independently, when A is N, a free electron pair, or, when A is C, hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, $R^{14}$, $R^{15}$, $R^{16}$, $R^{17}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{12}$ and $R^{13}$, $R^{14}$ and $R^{15}$, $R^{15}$ and $R^{16}$ or $R^{16}$ and $R^{17}$ form, together with A or the carbon atoms to which they are bonded, an unsaturated or aromatic, optionally substituted ring optionally interrupted by at least one heteroatom and having a total of 5 to 18 carbon atoms and/or heteroatoms, and/or if $A^6$ is C, $R^{13}$ and $R^{14}$ together form a saturated or unsaturated, linear or branched bridge optionally comprising heteroatoms, aromatic units, heteroaromatic units and/or functional groups and having a total of 1 to 30 carbon atoms and/or heteroatoms, to which is optionally fused a substituted or unsubstituted, five- to eight-membered ring comprising carbon atoms and/or heteroatoms.

In a further preferred embodiment, the present invention relates to an inventive metal-carbene complex where L in the general formula (I) is a heterocyclic noncarbene ligand of the general formula (III)

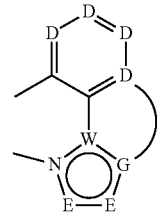

(III)

in which the symbols in the ligand of the general formula IV are each defined as follows:

D are each independently $CR^{18}$ or N, preferably $CR^{18}$;

W is C, N, preferably C;

E are each independently $CR^{19}$, N, $NR^{20}$, preferably $CR^{19}$ or N;

G is $CR^{21}$, N, $NR^{22}$, S, O, preferably $NR^{21}$ $R^{18}$, $R^{19}$ $R^{21}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or in each case 2 $R^{18}$, $R^{19}$ and $R^{21}$ radicals, together with the carbon atoms to which they are bonded, form a saturated, unsaturated or aromatic, optionally substituted ring optionally interrupted by at least one heteroatom and having a total of 5 to 18 carbon atoms and/or heteroatoms, $R^{20}$, $R^{22}$ are each independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action; preferably o,o'-dialkylated aryl radical, where the solid curved line is an optional bridge between one of the D groups and the G group; where the bridge may be defined as follows:

alkylene, arylene, heteroarylene, alkynylene, alkenylene, $NR^{23}$, O, S, $SiR^{24}R^{25}$ and $(CR^{26}R^{27})_d$, where one or more nonadjacent $(CR^{26}R^{27})$ groups may be replaced by $NR^{23}$, O, S, $SiR^{24}R^{25}$, where d is 2 to 10;
and
23,
$R^{24}$, $R^{25}$, $R^{26}$, $R^{27}$
are each H, alkyl, aryl, heteroaryl, alkenyl, alkynyl.

For the inventive embodiment wherein in each case 2 $R^{18}$, $R^{19}$ and $R^{21}$ radicals, together with the carbon atoms to which they are bonded, form a saturated, unsaturated or aromatic, optionally substituted ring optionally interrupted by at least one heteroatom and having a total of 5 to 18 carbon atoms and/or heteroatoms, for example, two $R^{18}$ radicals, two $R^{19}$ radicals or one $R^{19}$ radical and one $R^{21}$ radical form a corresponding ring.

Ligands L which are very particularly preferred in accordance with the invention are depicted below:

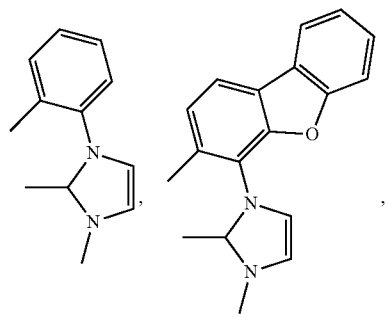

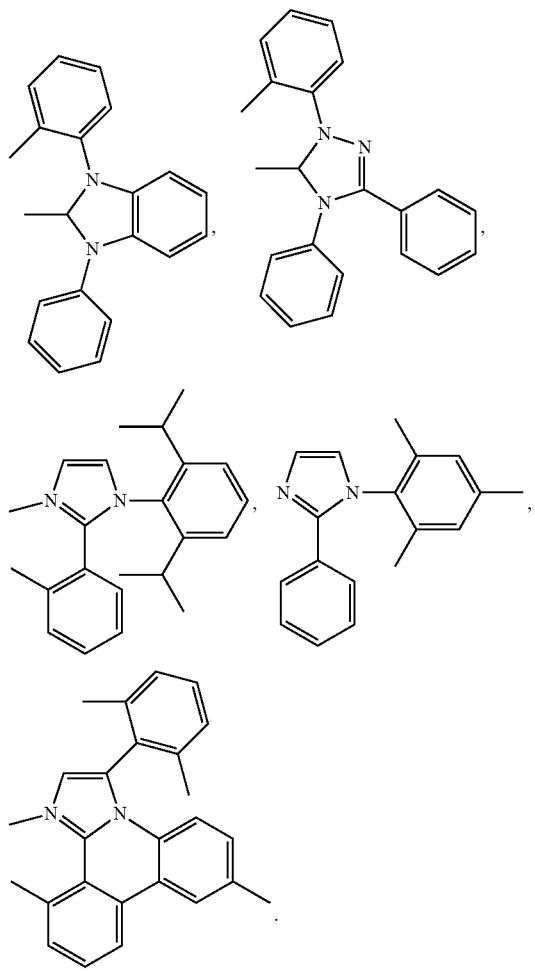

Further preferred ligands L:

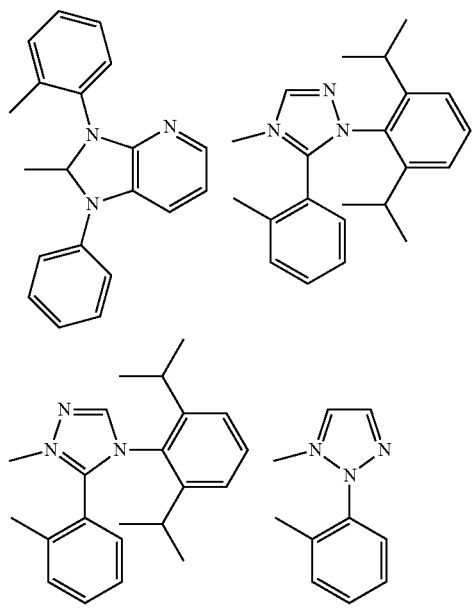

In a preferred embodiment, M, n, Y, $A^2$, $A^3$, $A^4$, $A^5$, $R^1$, $R^2$, $R^3$, $R^4$, $R^5$, $R^6$, $R^7$, $R^8$, $R^9$, $R^{10}$, K, L, n and o in the general formula (I) are each defined as follows:

According to the invention, M is Ir or Pt, preferably Ir. Ir is present in the inventive complexes in the +3 oxidation state. Pt is present in the inventive complexes in the +2 oxidation state.

n is generally 1, 2 or 3. If M is Ir, n is preferably 3. If M is Pt, n is preferably 1.

According to the invention, Y is $NR^1$, O, S or $C(R^{25})_2$, preferably $NR^1$.

According to the invention, $A^2$, $A^3$, $A^4$ and $A^5$ are each independently C or N, where 2 A=nitrogen atoms and at least one carbon atom is present between two nitrogen atoms in the ring. In general, one or two carbon atoms are present between two nitrogen atoms.

Preference is given in accordance with the invention to the following embodiments:

1. $A^2$ and $A^5$ are each N, and $A^3$ and $A^4$ are each C, i.e. the inventive metal-carbene complexes comprise, in this preferred embodiment, at least one pyrazinoimidazole unit which is attached via a metal-carbene bond and is of the general formula (Ia)

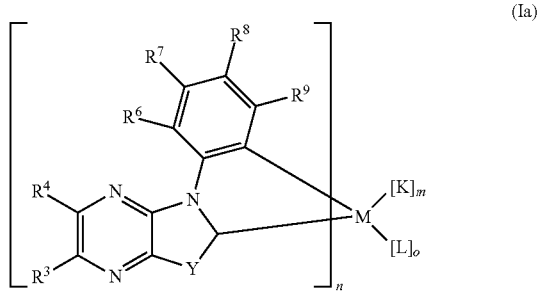

(Ia)

2. $A^2$ and $A^4$ are each N, $A^3$ and $A^5$ are each C, i.e. the inventive metal-carbene complexes comprise, in this preferred embodiment, at least one pyrimidinoimidazole unit which is attached via a metal-carbene bond and is of the general formula (Ib)

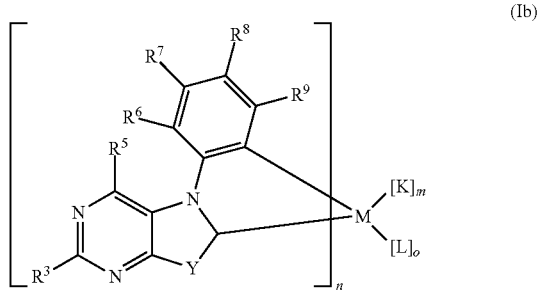

(Ib)

3. $A^3$ and $A^5$ are each N, $A^2$ and $A^4$ are each C, i.e. the inventive metal-carbene complexes comprise, in this preferred embodiment, at least one pyrimidinoimidazole unit which is attached via a metal-carbene bond and is of the general formula (Ic)

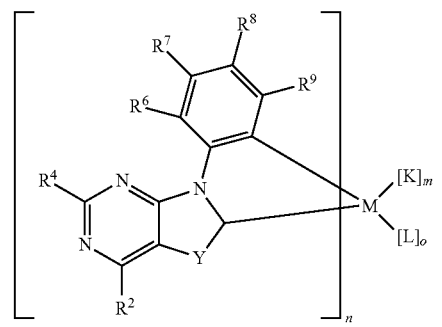

(Ic)

In the general formulae (Ia), (Ib) and (Ic), the same definitions apply as in the general formula (I).

In the preferred case that Y is $NR^1$, $R^1$ in a preferred embodiment is a linear or branched alkyl radical having 1 to 6 carbon atoms, substituted or unsubstituted aryl radical having 6 to 30 carbon atoms, substituted or unsubstituted heteroaryl radical having a total of 5 to 18 carbon atoms and/or heteroatoms.

$R^1$ is more preferably linear or branched alkyl radical having 1 to 6 carbon atoms, substituted or unsubstituted phenyl radical, substituted or unsubstituted heteroaryl radical having a total of 5 or 6 carbon atoms and/or heteroatoms.

$R^1$ is most preferably selected from phenyl, tolyl, mesityl, thiophenyl, furanyl, pyridyl, methyl, isopropyl and neopentyl.

The present invention therefore relates especially to an inventive metal-carbene complex in which Y is $NR^1$ where $R^1$ is selected from the group consisting of phenyl, tolyl, mesityl, thiophenyl, furanyl, pyridyl, methyl, isopropyl and neopentyl.

In a preferred embodiment, $R^2$, $R^3$, $R^4$, $R^5$ are each independently hydrogen, a linear or branched alkyl radical having 1 to 20 carbon atoms, a substituted or unsubstituted aryl radical having 6 to 30 carbon atoms, a substituted or unsubstituted heteroaryl radical having 5 to 18 carbon atoms and/or heteroatoms or silyl radical.

In a preferred embodiment, $R^2$, $R^3$, $R^4$, $R^5$ are each, if $A^2$, $A^3$, $A^4$ and/or $A^5$ is N, a free electron pair, or, if $A^2$, $A^3$, $A^4$ and/or $A^5$ is C, each independently hydrogen, linear or branched alkyl radical having 1 to 6 carbon atoms, substituted or unsubstituted aryl radical having 6 to 30 carbon atoms, substituted or unsubstituted heteroaryl radical having a total of 5 to 18 carbon atoms and/or heteroatoms or silyl radical or $R^3$ and $R^4$ together with $A^3$ and $A^4$ form an optionally substituted, unsaturated ring optionally interrupted by at least one further heteroatom and having a total of 5 to 18 carbon atoms and/or heteroatoms.

According to the invention, an unsaturated ring is a mono-, di- or polyunsaturated, preferably monounsaturated, ring. According to the invention, an aromatic ring is not covered by this definition. More particularly, $R^3$ and $R^4$ together with $A^3$ and $A^4$ do not form a phenyl ring.

$R^2$ is more preferably a free electron pair if $A^2$ is N, or hydrogen if $A^2$ is C.

$R^3$ is more preferably a free electron pair if $A^3$ is N, or hydrogen or linear or branched alkyl radical having 1 to 20 carbon atoms or optionally substituted, saturated, unsaturated or aromatic ring having a total of 5 to 18 carbon atoms and/or heteroatoms, more preferably branched alkyl radical or o,o'-dialkylated phenyl ring, if $A^3$ is C.

$R^4$ is more preferably a free electron pair if $A^4$ is N, or hydrogen or linear or branched alkyl radical having 1 to 20 carbon atoms or optionally substituted, saturated, unsaturated or aromatic ring having a total of 5 to 18 carbon atoms and/or heteroatoms, more preferably branched alkyl radical or o,o'-dialkylated phenyl ring, if $A^4$ is C.

$R^3$ and $R^4$ most preferably form, together with $A^3$ and $A^4$ if $A^3$ and $A^4$ are each C, an optionally substituted, unsaturated ring having a total of 5 to 18 carbon atoms, though the case that $A^2$ and $A^5$ are each N and $R^3$ and $R^4$ together with $A^3$ and $A^4$ form a phenyl ring is ruled out in accordance with the invention.

$R^5$ is more preferably a free electron pair if $A^5$ is N, or hydrogen if $A^5$ is C.

In a further preferred embodiment, $R^6$, $R^7$, $R^8$, $R^9$ are each independently hydrogen or linear or branched alkyl radical having 1 to 20 carbon atoms or o,o'-dialkylated phenyl radicals, more preferably hydrogen.

In a further preferred embodiment, $R^6$ and $R^7$ or $R^7$ and $R^8$ or $R^8$ and $R^9$ form, together with the phenyl ring, i.e. with the carbon atoms to which the radicals are attached, an unsaturated or aromatic, optionally substituted ring optionally interrupted by at least one heteroatom and having a total of 5, 6 or 7 carbon atoms and/or heteroatoms. The two particular radicals more preferably form, together with the phenyl ring, the following heterocycles: dibenzofuran, dibenzothiophene, fluorene, acridane, xanthene, thioxanthene, phenazine or phenoxazine.

Alternatively or additionally, $R^5$ and $R^6$ together may form a saturated or unsaturated, linear or branched bridge optionally comprising heteroatoms, aromatic units, heteroaromatic units and/or functional groups and having a total of 1 to 30 carbon atoms and/or heteroatoms, to which is optionally fused a substituted or unsubstituted, five- to eight-membered, preferably six-membered, ring comprising carbon atoms and/or heteroatoms.

$R^{25}$ is, if present, preferably independently in accordance with the invention, a linear or branched alkyl radical having 1 to 20 carbon atoms, a substituted or unsubstituted aryl radical having 6 to 30 carbon atoms, a substituted or unsubstituted heteroaryl radical having 5 to 18 carbon atoms and/or heteroatoms, more preferably a linear alkyl radical or a substituted or unsubstituted phenyl radical.

In a particularly preferred embodiment, the present invention relates to an inventive metal-carbene complex where M, n, Y, $A^2$, $A^3$, $A^4$, $A^5$, $R^1$, $R^2$, $R^3$, $R^4$, $R^5$, $R^6$, $R^7$, $R^8$, $R^9$, L, m and o are each defined as follows:

M is Ir,
n is 1, 2 or 3,
Y is $NR^1$,
$A^2$, $A^3$, $A^4$, $A^5$ are each independently N or C, where 2 A=nitrogen atoms and at least one carbon atom is present between two nitrogen atoms in the ring,
$R^1$ is a linear or branched alkyl radical having 1 to 6 carbon atoms, substituted or unsubstituted aryl radical having 6 to 30 carbon atoms, substituted or unsubstituted heteroaryl radical having a total of 5 to 18 carbon atoms and/or heteroatoms,
$R^2$, $R^3$, $R^4$, $R^5$ are each, if $A^2$, $A^3$, $A^4$ and/or $A^5$ is N, a free electron pair, or, if $A^2$, $A^3$, $A^4$ and/or $A^5$ is C, each independently hydrogen, linear or branched alkyl radical having 1 to 6 carbon atoms, substituted or unsubstituted aryl radical having 6 to 30 carbon atoms, substituted or unsubstituted heteroaryl radical having a total of 5 to 18 carbon atoms and/or heteroatoms, or $R^3$ and $R^4$ together with $A^3$ and $A^4$ form an optionally substituted, unsaturated ring optionally interrupted by at least one further heteroatom and having a total of 5 to 18 carbon atoms and/or heteroatoms, $R^6$, $R^7$, $R^8$, $R^9$ are each independently hydrogen, linear or branched alkyl radical optionally interrupted by at least one heteroatom, optionally bearing at least one functional group and having 1 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, L is a monoanionic bidentate ligand,
m is 0,
o is 0, 1 or 2.

The present invention more preferably relates to an inventive metal-carbene complex where M, n, Y, $A^2$, $A^3$, $A^4$, $A^5$, $R^1$, $R^2$, $R^3$, $R^4$, $R^5$, $R^6$, $R^7$, $R^8$, $R^9$, L, m and o are each defined as follows:

M is Ir,
n is 1, 2 or 3,
Y is $NR^1$,
$A^2$, $A^3$,
$A^4$, $A^5$ $A^2$ and $A^5$ are each N and $A^3$ and $A^4$ are each C or $A^2$ and $A^4$ are each N and $A^3$ and $A^5$ are each C or $A^3$ and $A^5$ are each N and $A^2$ and $A^4$ are each C, $R^1$ is a linear or branched alkyl radical having 1 to 6 carbon atoms, substituted or unsubstituted phenyl radical, substituted or unsubstituted heteroaryl radical having a total of 6 to 18 carbon atoms and/or heteroatoms, $R^2$, $R^3$, $R^4$, $R^5$ are each, if $A^2$, $A^3$, $A^4$ and/or $A^5$ is N, a free electron pair or, if $A^2$, $A^3$, $A^4$ and/or $A^5$ is C, each independently hydrogen, linear or branched alkyl radical having 1 to 6 carbon atoms, substituted, especially o,o'-dialkylated, or unsubstituted phenyl radical, or $R^3$ and $R^4$ together with $A^3$ and $A^4$ form an optionally substituted, monounsaturated ring having a total of 5 to 7 carbon atoms, $R^6$, $R^7$, $R^8$, $R^9$ are each independently hydrogen, linear or branched alkyl radical having 1 to 20 carbon atoms, o,o'-dialkylated aryl radical having 6 to 30 carbon atoms, L is a monoanionic bidentate ligand,
m is 0,
o is 0, 1 or 2.

The further abovementioned preferred and particularly preferred embodiments apply correspondingly.

Very particularly preferred inventive metal-carbene complexes of the general formula (I) are shown below.
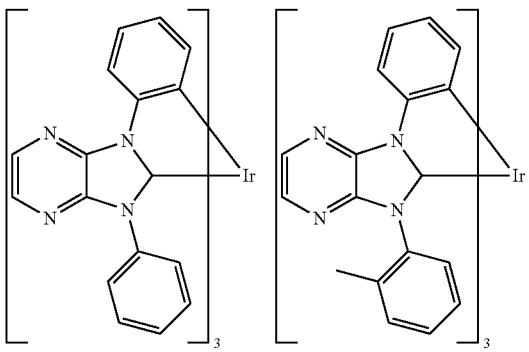
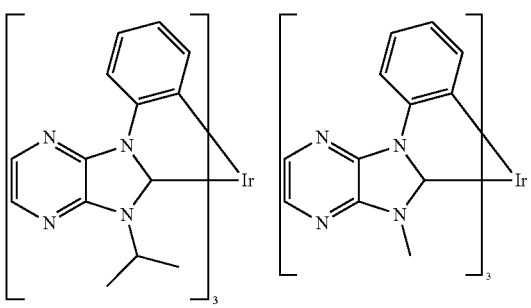
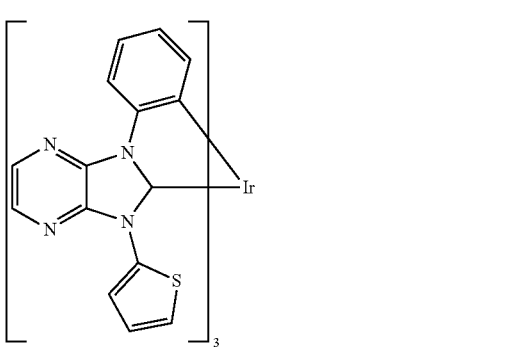
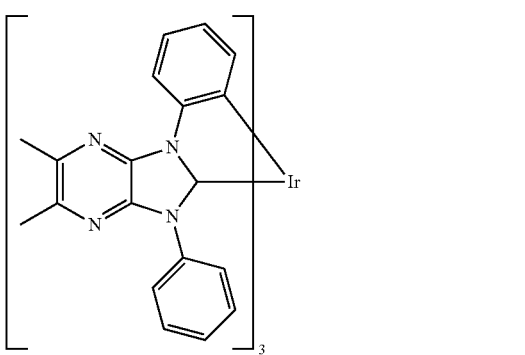
-continued
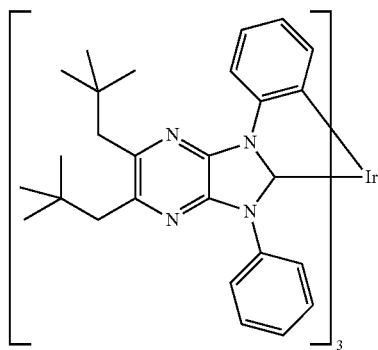
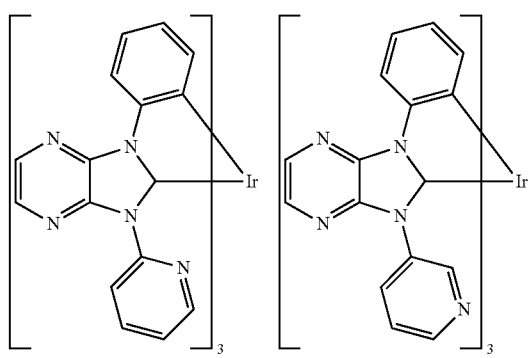
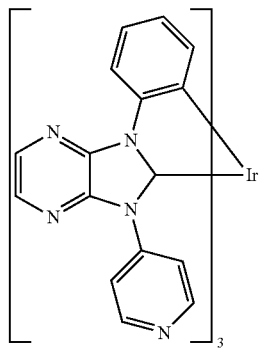
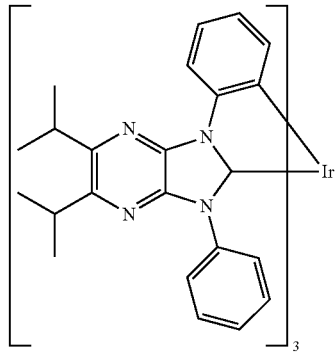

-continued
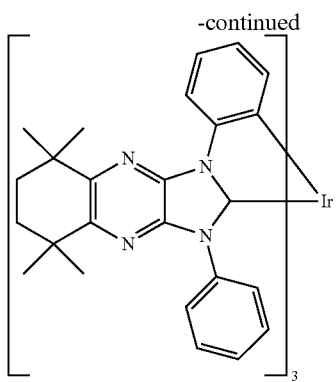
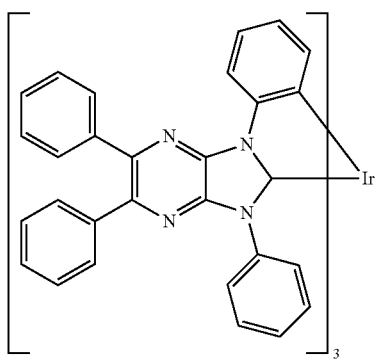
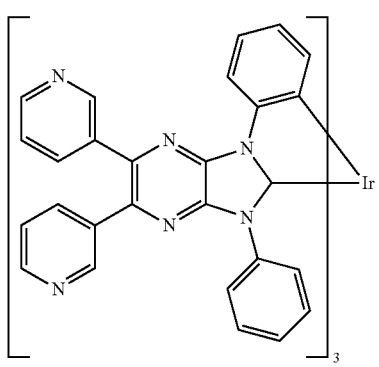
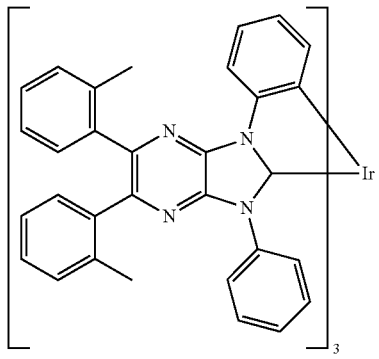
-continued
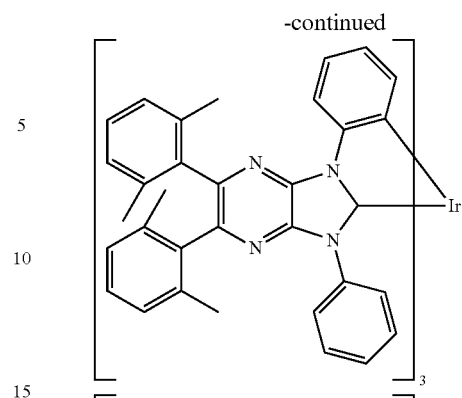
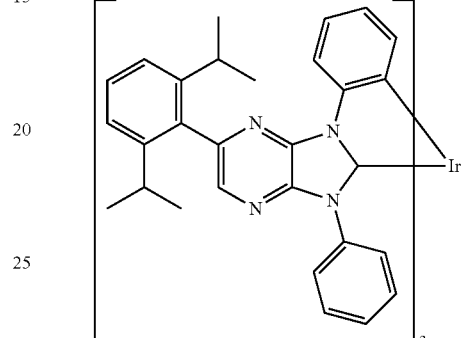
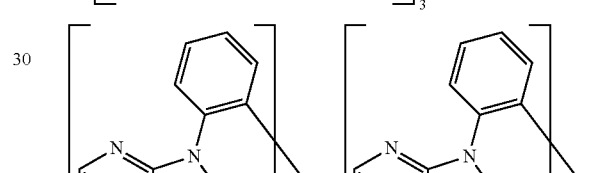
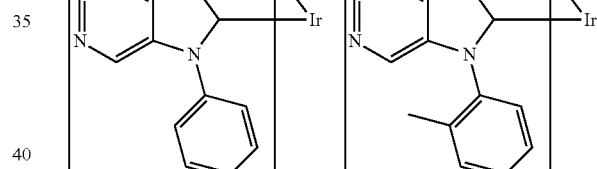
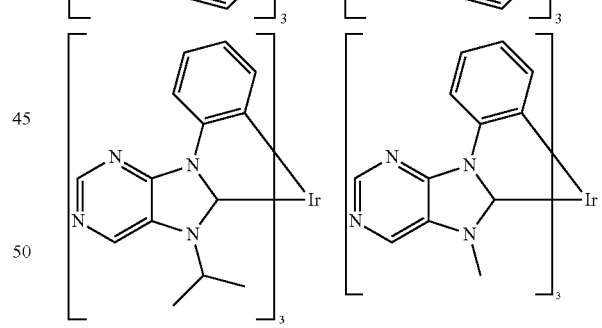
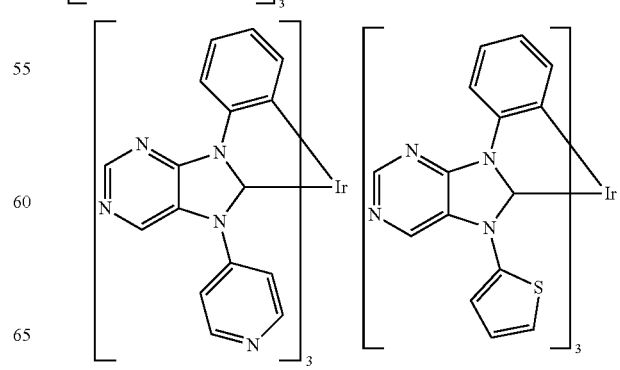

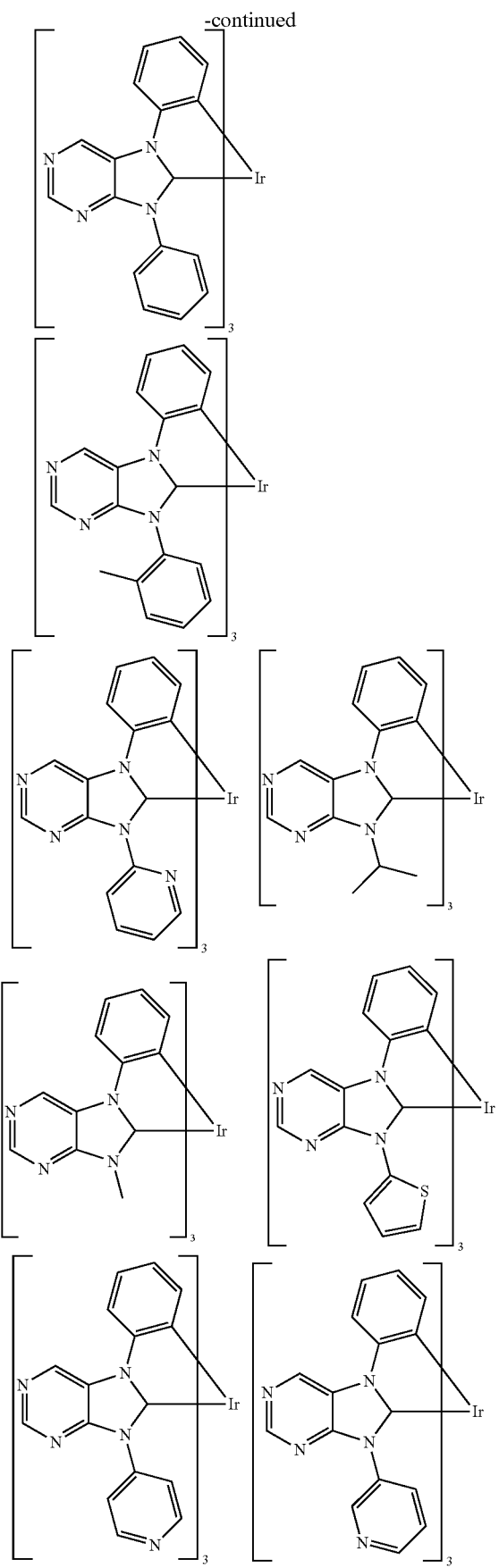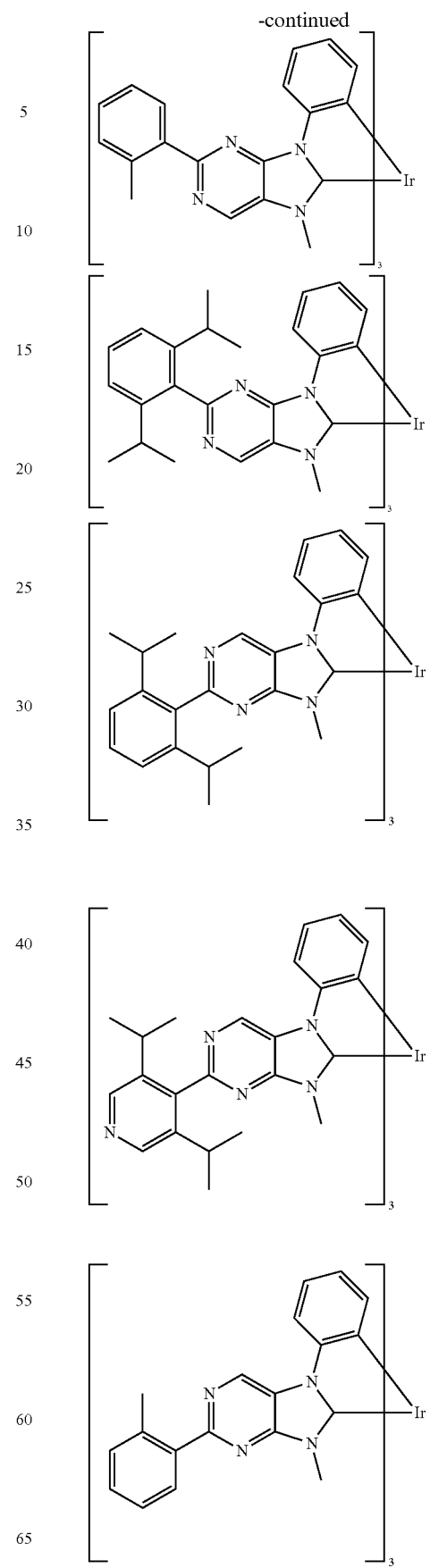

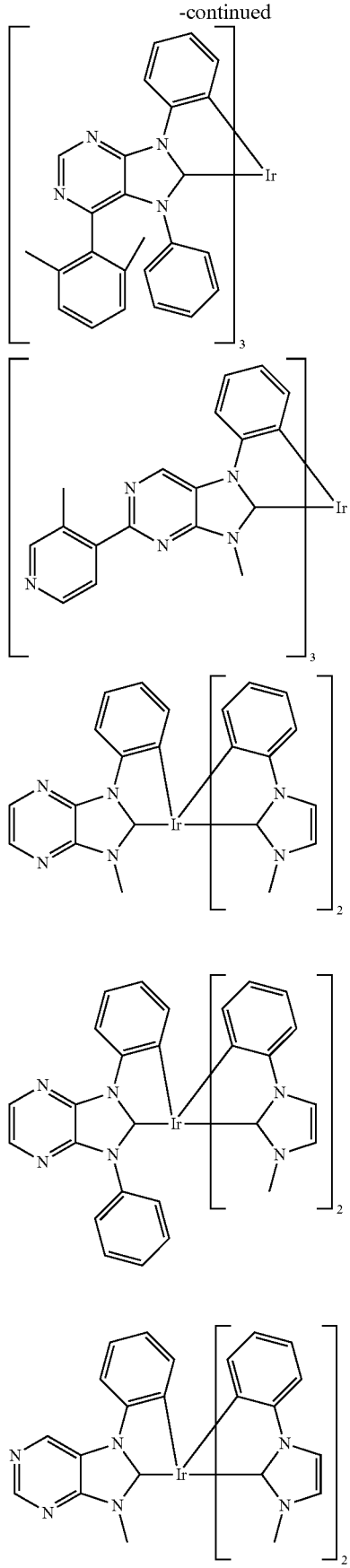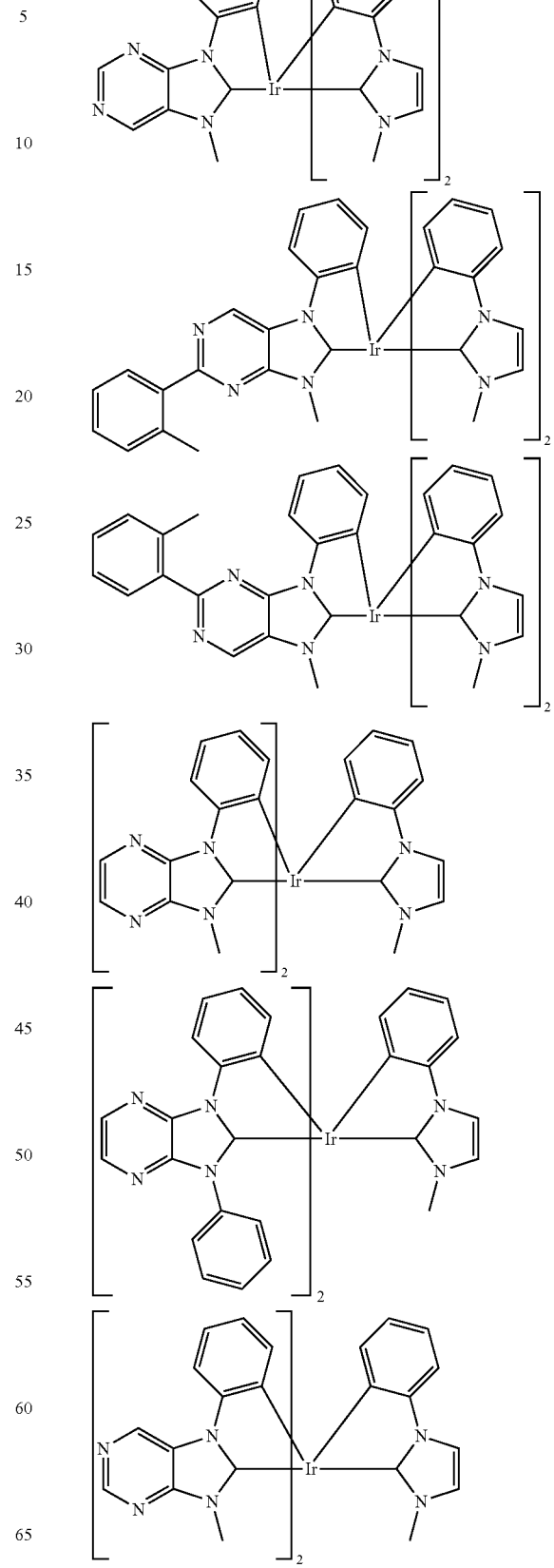

-continued
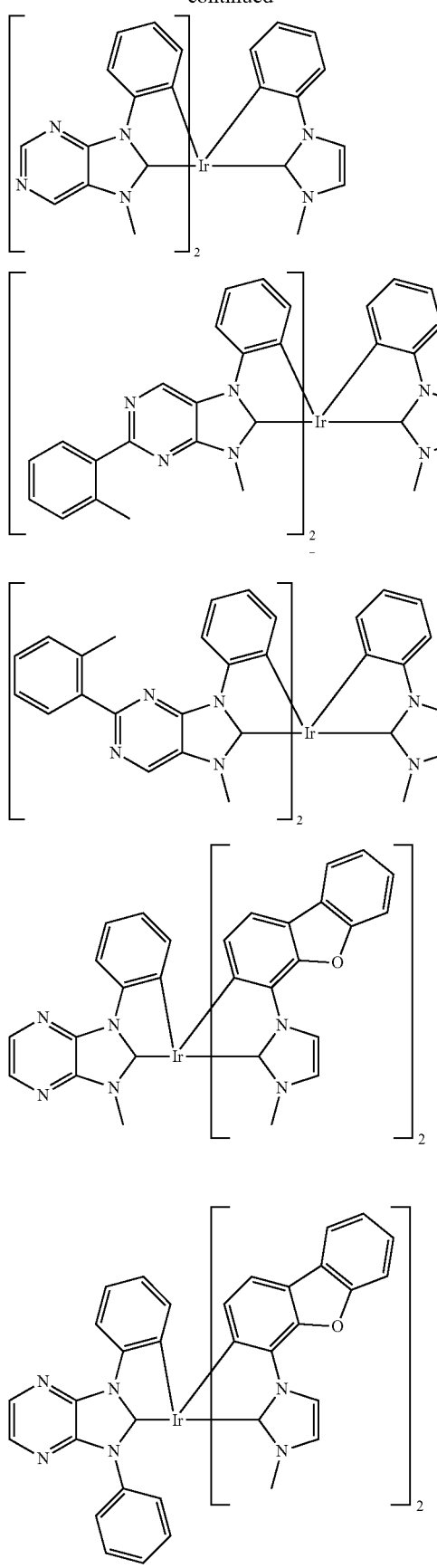
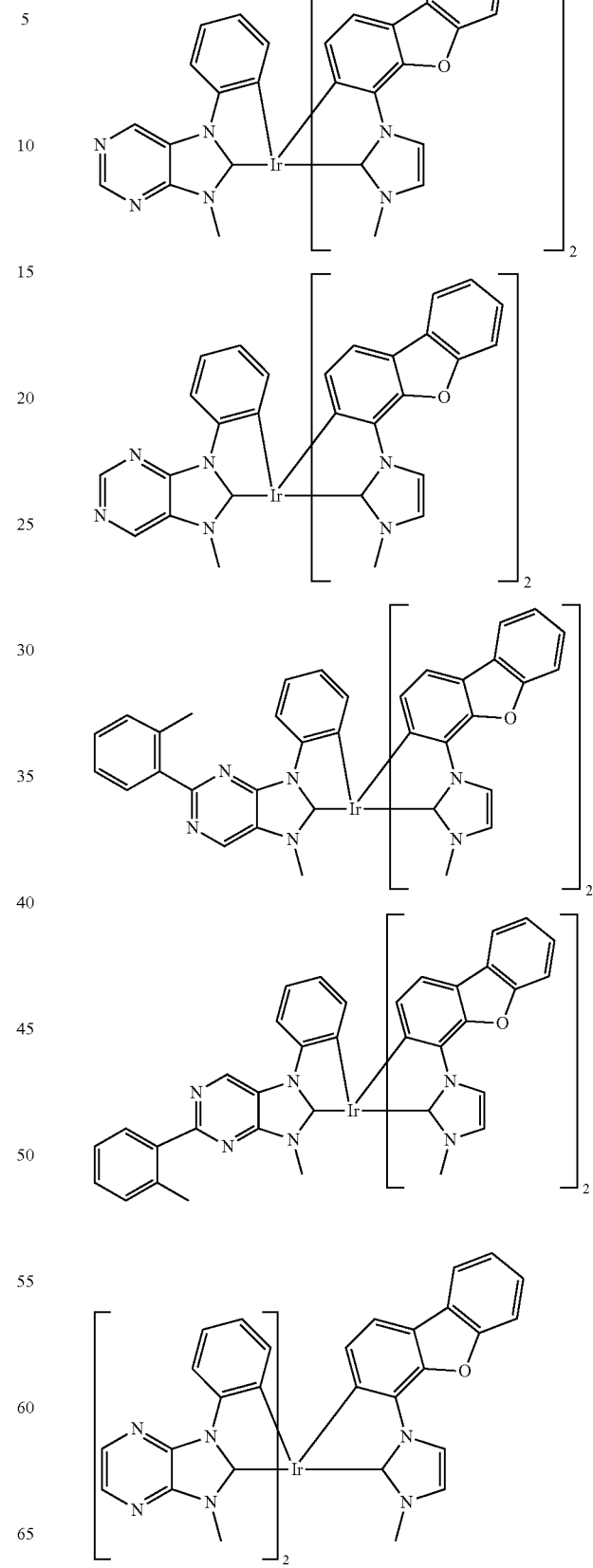

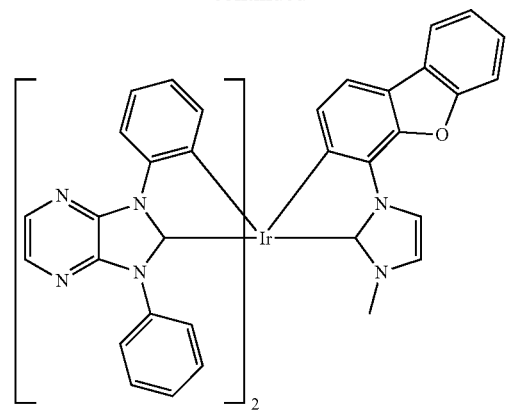
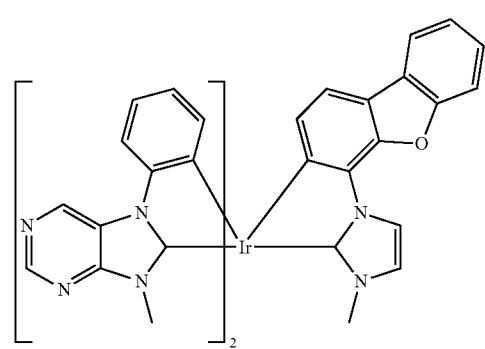
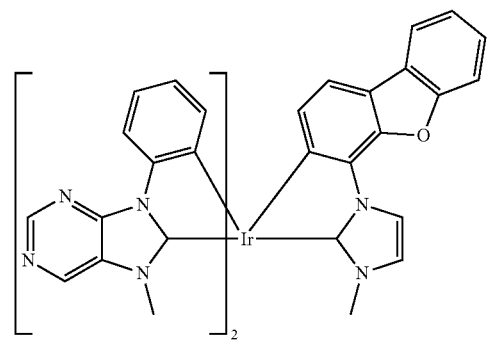
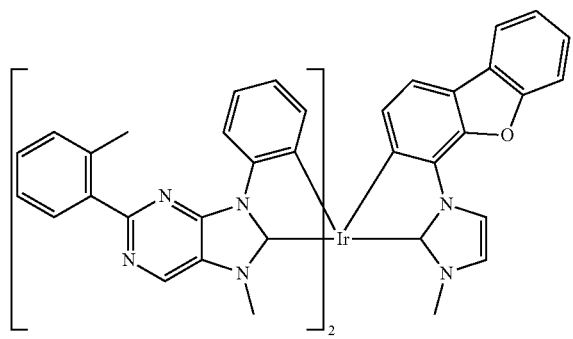
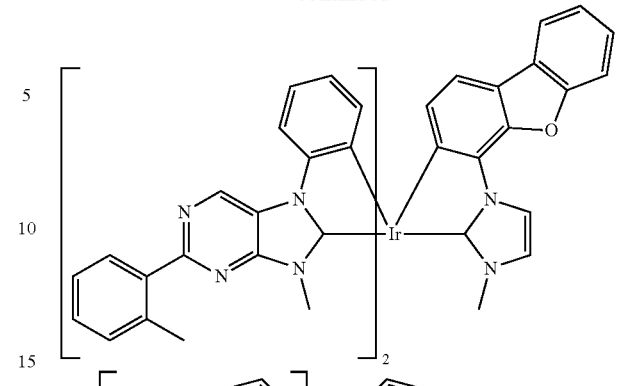
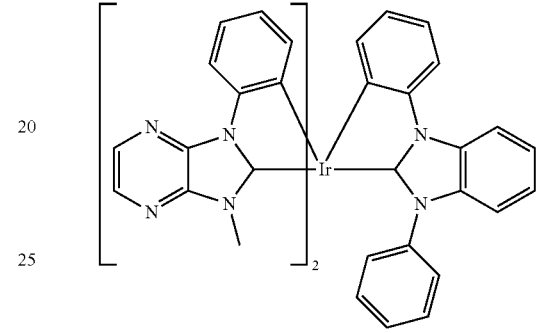
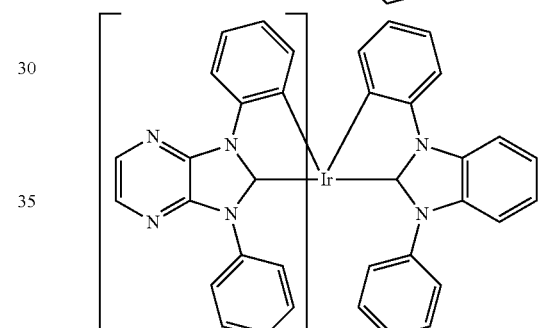
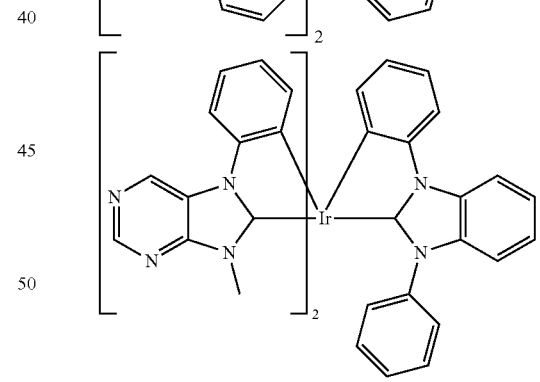
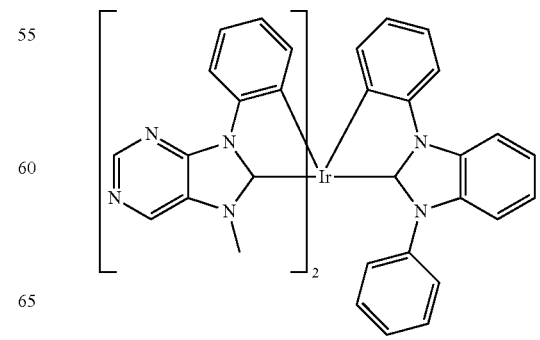

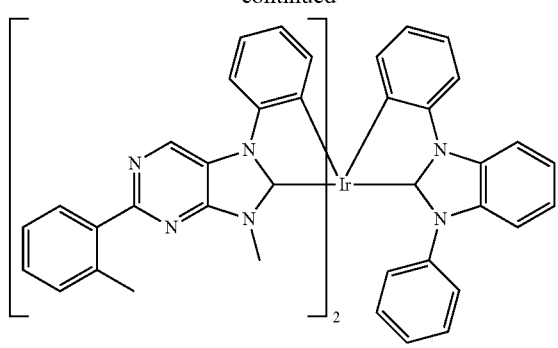
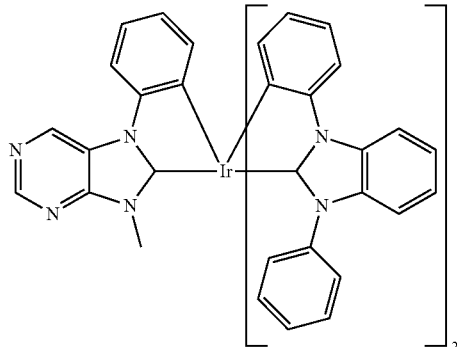
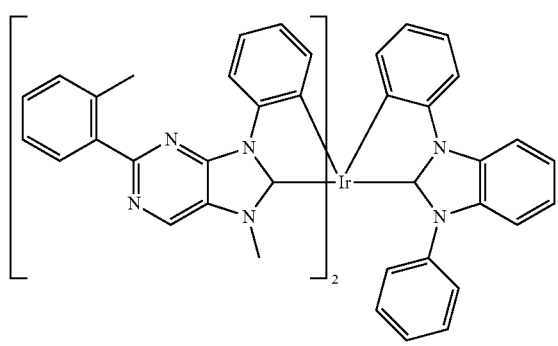
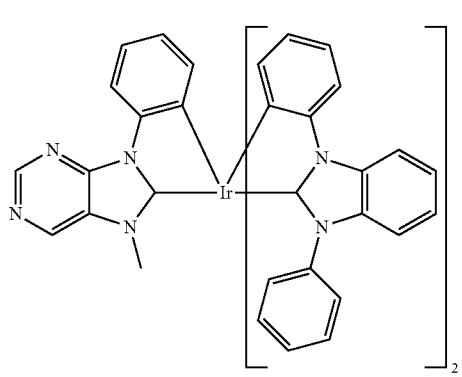
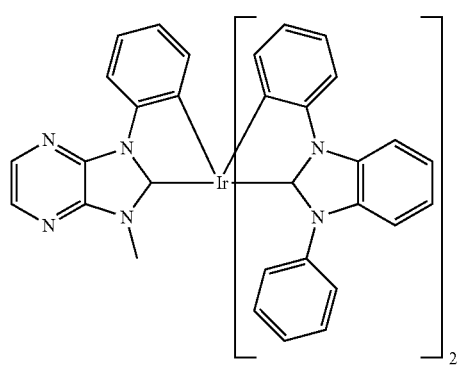
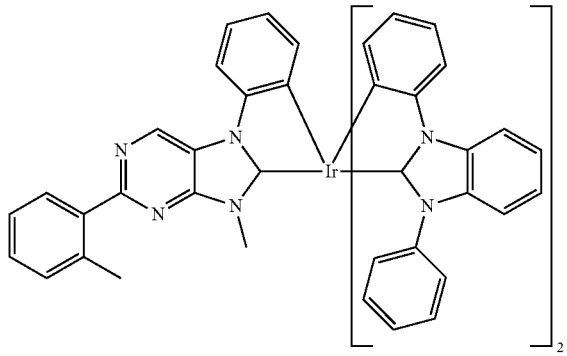
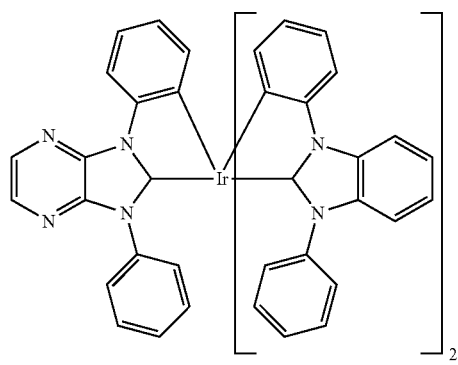
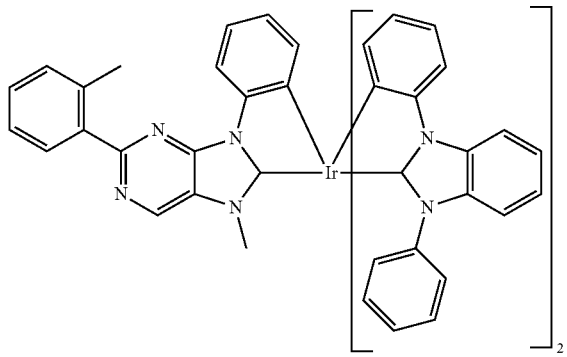

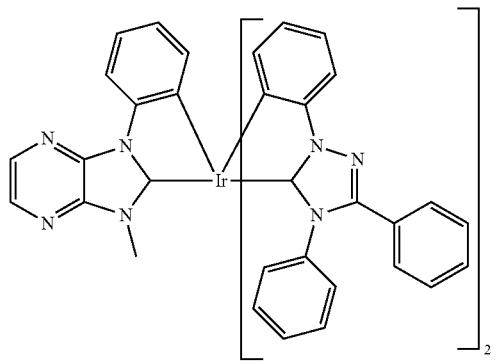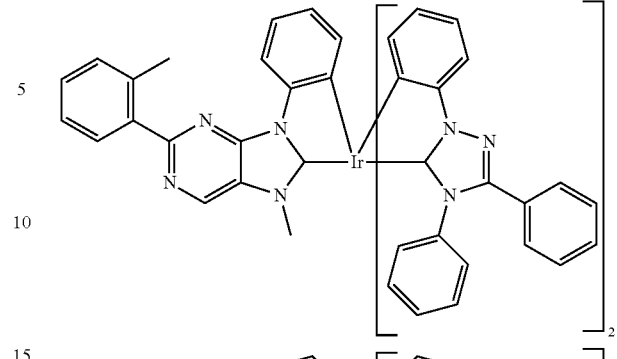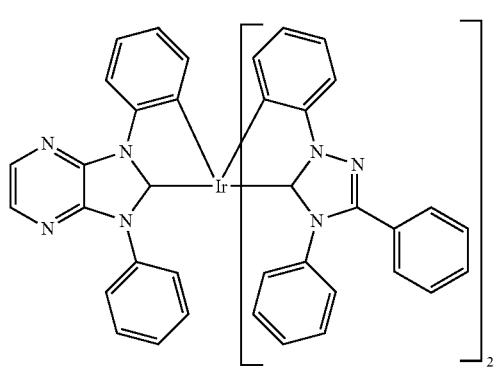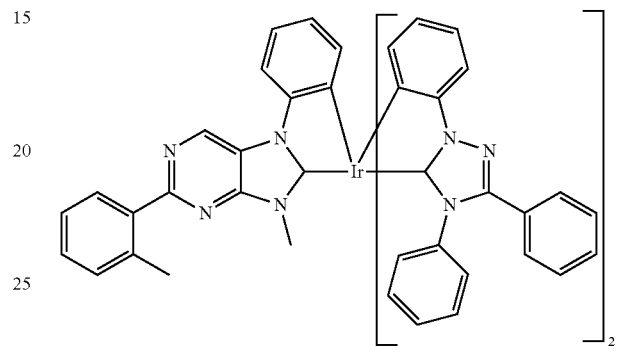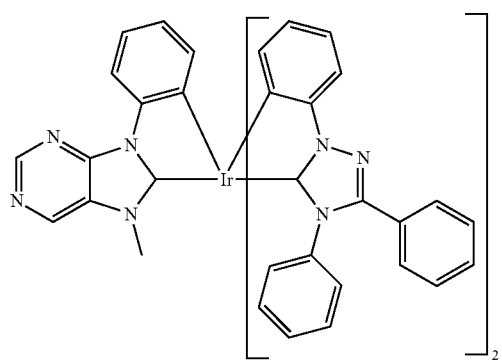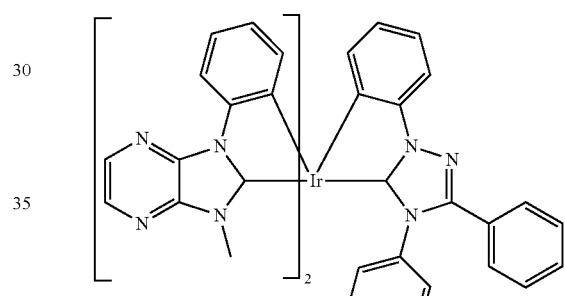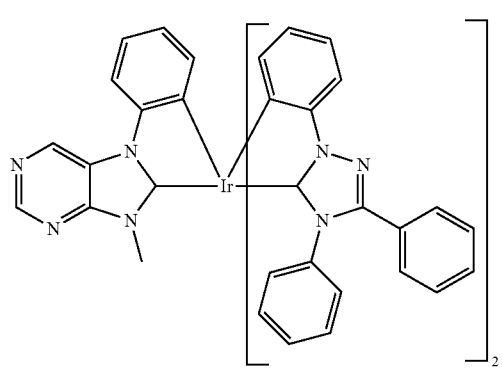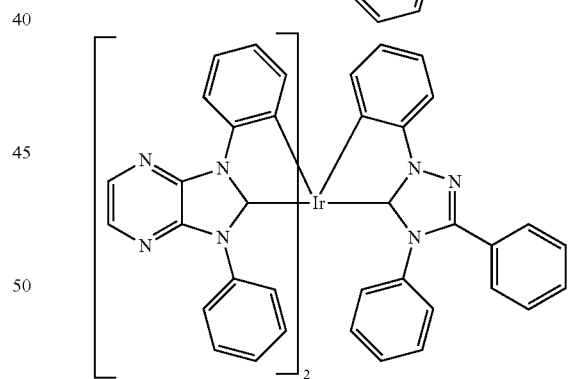

-continued
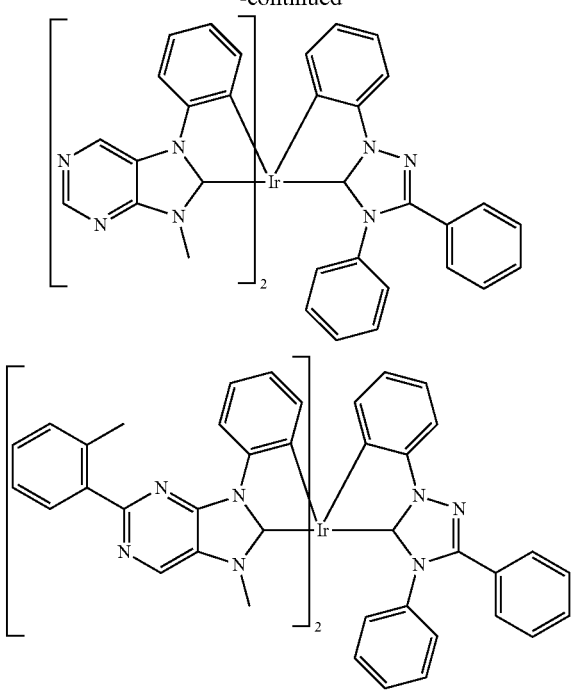
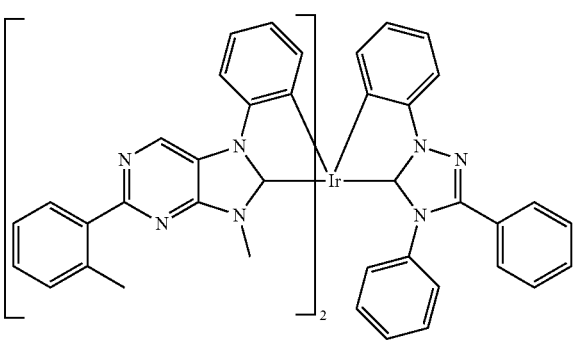
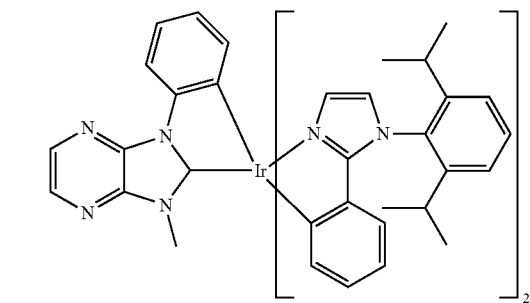
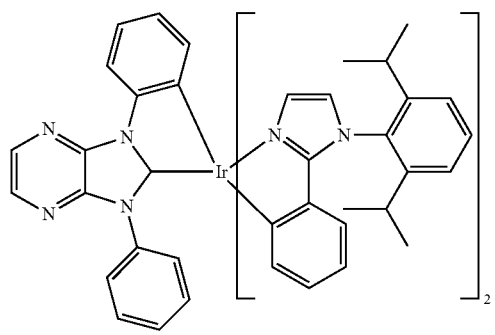
-continued
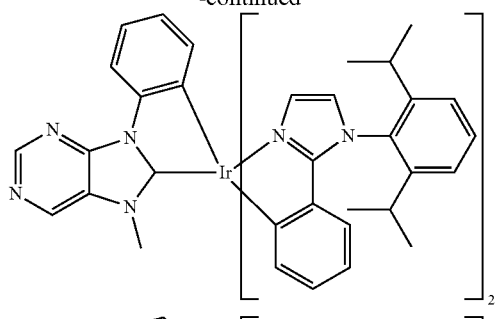
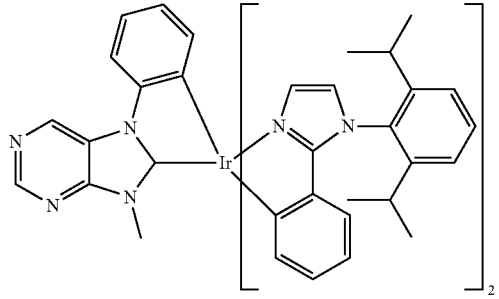
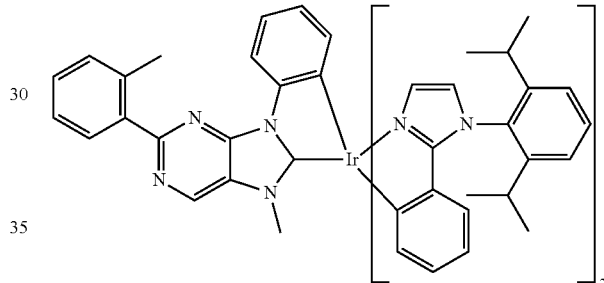
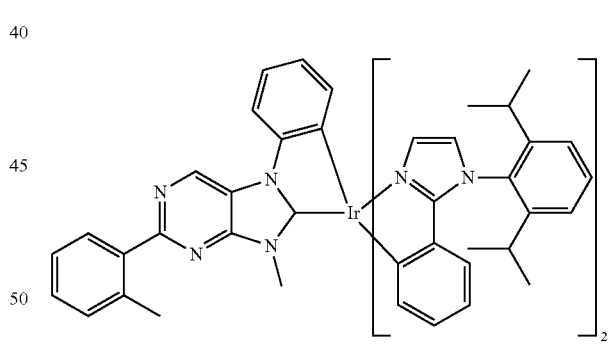
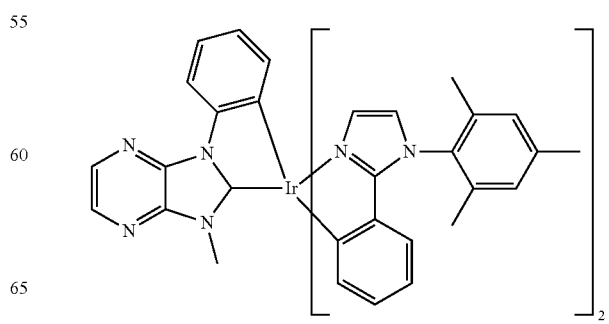

-continued
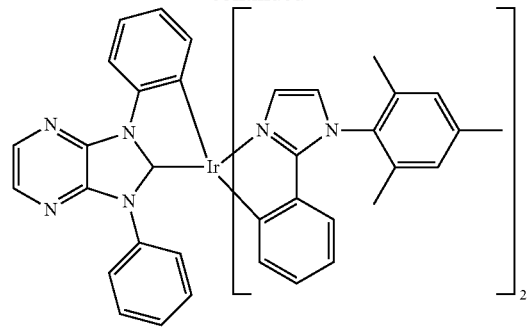
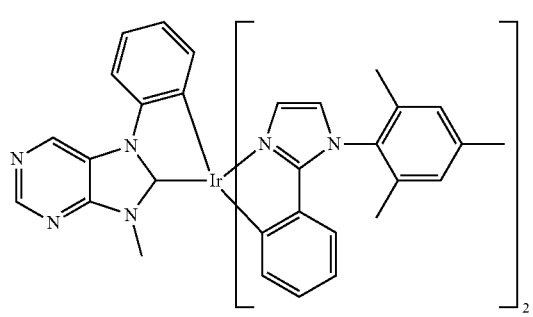
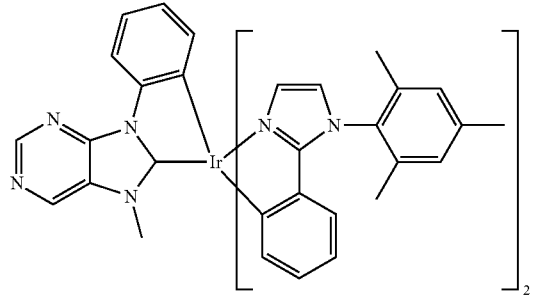
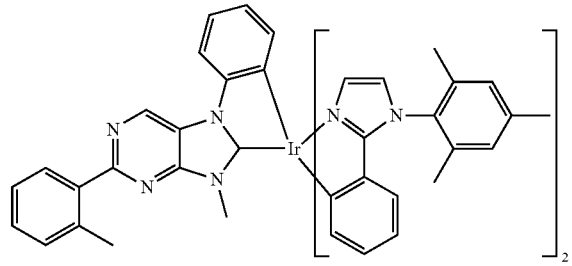
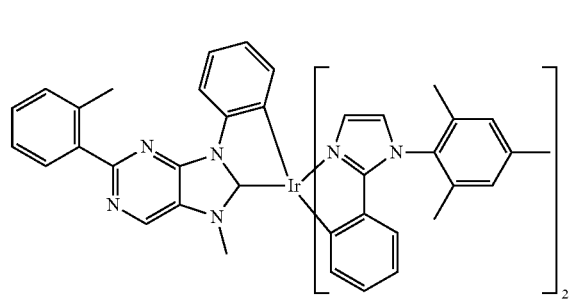
-continued
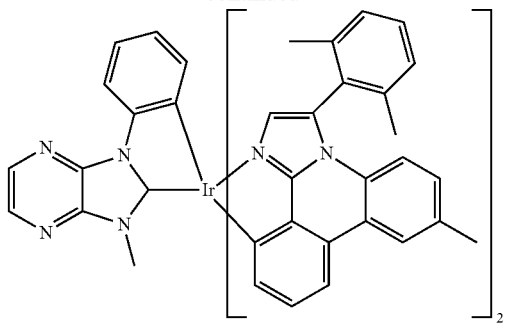
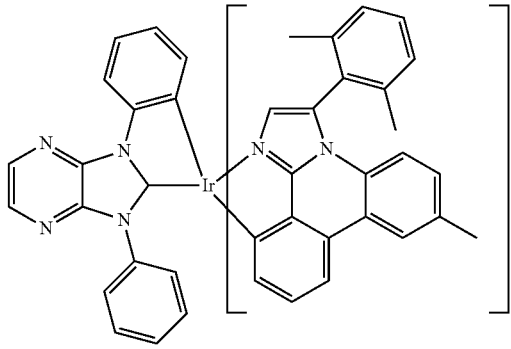
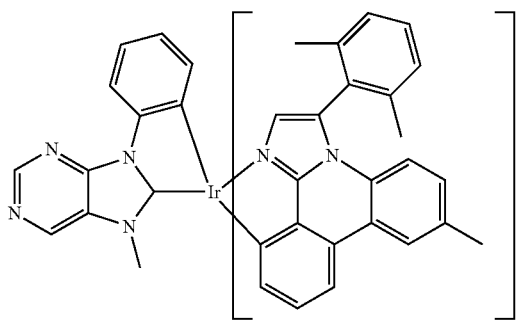
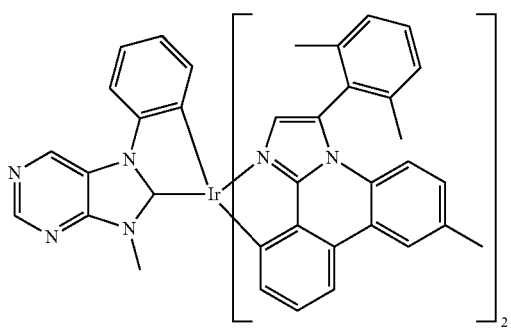
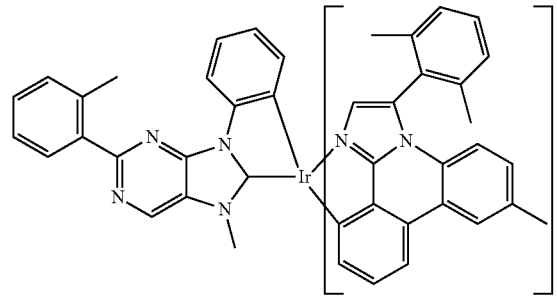

-continued

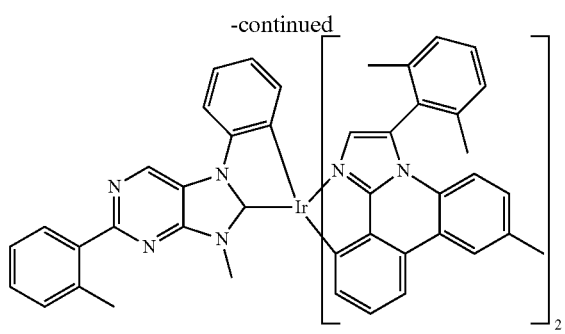

The inventive homoleptic metal-carbene complexes may be present in the form of facial or meridional isomers, preference being given to the facial isomers.

In the case of the heteroleptic metal-carbene complexes, four different isomers may be present, preference being given to the pseudo-facial isomers.

The present invention additionally also relates to a process for preparing the inventive metal-carbene complexes by contacting suitable compounds comprising M with the appropriate ligands or ligand precursors.

In a preferred embodiment of the process according to the invention, a suitable compound comprising the appropriate metal M, i.e. iridium or platinum, preferably iridium, and appropriate carbene ligands, preferably in deprotonated form as the free carbene or in the form of a protected carbene, for example as the silver-carbene complex, are contacted. Suitable precursor compounds comprise the appropriate substituents $R^1$ to $R^9$ and $R^{25}$ which should be present in the complexes of the general formula (I).

The present invention therefore relates more particularly to the process according to the invention wherein the ligand precursor used is a corresponding Ag-carbene complex.

In a further preferred embodiment of the process according to the invention, the ligand precursors used are organic compounds which are reacted with suitable M-comprising compounds. The carbene can be released from precursors of the carbene ligands by removing volatile substances, for example lower alcohols such as methanol, ethanol, for example at elevated temperature and/or under reduced pressure and/or using molecular sieves which bind the alcohol molecules eliminated. This process is performed especially in the case of use of the compounds of the general formula (XII). Corresponding processes are known to those skilled in the art.

The present invention also relates to the process according to the invention wherein the ligand precursor used is a compound of the general formula (IV)

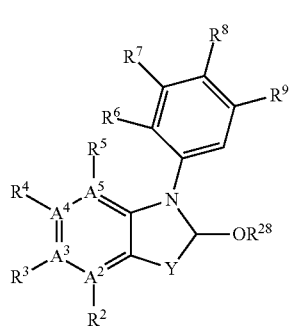

(IV)

wherein Y, $A^2$, $A^3$, $A^4$, $A^5$, $R^2$, $R^3$, $R^4$, $R^5$, $R^6$, $R^7$, $R^8$ and $R^9$ are each as already defined above for the compounds of the general formula (I), and $R^{28}$ is defined as follows:
$R^{28}$ is independently $SiR^{29}R^{30}R^{31}$, aryl, heteroaryl, alkyl, cycloalkyl or heterocycloalkyl,
$R^{29}$, $R^{30}$
$R^{31}$ are each independently aryl, heteroaryl, alkyl, cycloalkyl or heterocycloalkyl.

The definitions of aryl, heteroaryl, alkyl, cycloalkyl and heterocycloalkyl have been specified above.

In a particularly preferred embodiment, $R^{28}$ is alkyl, especially $C_1$-$C_{20}$-alkyl, preferably $C_1$-$C_{10}$-alkyl, more preferably $C_1$-$C_8$-alkyl, for example methyl, ethyl, propyl such as n-propyl, isopropyl, butyl such as n-butyl, isobutyl, tert-butyl, pentyl, hexyl, heptyl or octyl.

$R^{28}$ in the compound of the general formula (IV) is most preferably methyl or ethyl.

Compounds of the general formula (IV) are generally obtainable by processes known to those skilled in the art. In the case, which is particularly preferred in accordance with the invention, that Y is $NR^1$, corresponding compounds of the general formula (IV) can be obtained by reacting compounds of the general formula (V)

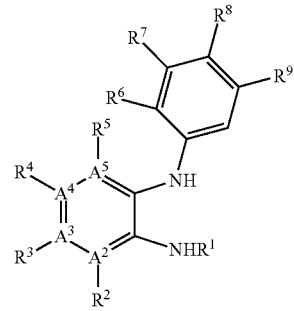

(V)

with compounds of the general formula (VI)

$$HC(OR^{28})_3 \quad (VI),$$

where $A^2$, $A^3$, $A^4$, $A^5$, $R^1$, $R^2$, $R^3$, $R^4$, $R^5$, $R^6$, $R^7$, $R^8$, $R^9$ and $R^{28}$ are each as already defined above for the compounds of the general formula (I) or (IV).

This preparation of the compounds of the general formula (IV) can be effected in the presence or in the absence of a solvent. Suitable solvents are specified below. In a preferred embodiment, the compounds of the general formula (IV) are prepared in substance, or the compound of the general formula (VI) is added in an excess, such that it functions as a solvent.

Compounds of the general formulae (V) and (VI) are commercially available and/or obtainable by processes known to those skilled in the art; for example, compounds of the general formula (V) are obtainable by reacting the appropriate chlorides with the appropriate amines.

The compounds of the general formula (IV) are prepared generally at a temperature of 10 to 150° C., preferably 40 to 120° C., more preferably 60 to 110° C.

The reaction time is generally 2 to 48 hours, preferably 6 to 24 hours, more preferably 8 to 16 hours.

After the reaction has ended, the desired product can be isolated and purified by customary processes known to those skilled in the art, for example filtration, recrystallization, column chromatography, etc.

Appropriate compounds, especially complexes, comprising the appropriate metal M, preferably iridium, are known to those skilled in the art. Particularly suitable compounds comprising platinum or iridium comprise, for example, ligands such as halides, preferably chloride, 1,5-cyclooctadiene (COD), cyclooctene (COE), phosphines, cyanides, alkoxides, pseudohalides and/or alkyl.

Particularly preferred complexes comprising the appropriate metal, especially iridium, are selected from the group consisting of $[Ir(COD)Cl]_2$, $[Ir(COE)_2Cl]_2$ $IrCl_3 \times H_2O$, $Ir(acac)_3$, $Ir(COD)_2BF_4$, $Ir(COD)_2BARF$ (BARF=tetrakis[3,5-bis(trifluoromethyl)phenyl]borate)), $Pt(COD)Cl_2$, $Pt(acac)_2$, $[Pt(C_6H_{10})Cl_2]_2$, $K_2PtCl_6$ and mixtures thereof.

The carbene ligand precursors are deprotonated, preferably before the reaction, for example, by basic compounds known to those skilled in the art, for example basic metalates, basic metal acetates, acetylacetonates or alkoxides, or bases such as $KO^tBu$, $NaO^tBu$, $LiO^tBu$, NaH, silylamides, $Ag_2O$ and phosphazene bases. Particular preference is given to deprotonating with $Ag_2O$ to obtain the corresponding Ag-carbene, which is reacted with the compound comprising M to give the inventive complexes.

The process according to the invention for preparing the complexes of the general formula (I) using the compounds of the general formula (IV) has the advantage that the compounds of the general formula (IV) are stable intermediates which can be handled readily and can be isolated under standard laboratory conditions. In addition, the compounds of the general formula (IV) are soluble in customary organic solvents, such that the preparation of the inventive complexes of the general formula (I) in homogeneous solution is possible, such that a workup of the desired product, i.e. of the complexes of the general formula (I) is more readily possible, for example for isolation and/or purification.

The contacting is preferably effected in a solvent. Suitable solvents are known per se to those skilled in the art and are preferably selected from the group consisting of aromatic or aliphatic solvents, for example benzene, toluene, xylene or mesitylene, cyclic or acyclic ethers, for example dioxane or THF, alcohols, esters, amides, ketones, nitriles, halogenated compounds and mixtures thereof. Particularly preferred solvents are toluene, xylenes, mesitylene and dioxane.

The molar ratio of metal-noncarbene complex used to carbene ligand precursor used is generally 1:10 to 10:1, preferably 1:1 to 1:6, more preferably 1:2 to 1:5.

The contacting is generally effected at a temperature of 20 to 200° C., preferably 50 to 150° C., more preferably 60 to 130° C.

The reaction time depends on the desired carbene complex and is generally 0.02 to 50 hours, preferably 0.1 to 24 hours, more preferably 1 to 12 hours.

The complexes of the general formula (I) obtained after the reaction can optionally be purified by processes known to those skilled in the art, for example washing, crystallization or chromatography, and optionally isomerized under conditions likewise known to those skilled in the art, for example with acid mediation, thermally or photochemically.

The aforementioned metal-carbene complexes and mixtures thereof are outstandingly suitable as emitter molecules in organic light-emitting diodes (OLEDs). Variations in the ligands make it possible to provide corresponding complexes which exhibit electroluminescence in the red, green and especially in the blue region of the electromagnetic spectrum. The inventive metal-carbene complexes of the general formula (I) are therefore outstandingly suitable as emitter substances, since they have emission (electroluminescence) in the visible region of the electromagnetic spectrum, for example at 400 to 800 nm, preferably 400 to 600 nm. The inventive complexes make it possible to provide compounds which have electroluminescence in the red, green and in the blue region of the electromagnetic spectrum. It is thus possible, with the aid of the inventive complexes as emitter substances, to provide industrially usable OLEDs.

In addition, the inventive metal-carbene complexes of the general formula (I) can be used as matrix material, charge transport material, especially hole transport material, and/or charge blocker.

The inventive metal-carbene complexes of the general formula (I) are preferably used as an emitter and/or hole transport material, more preferably as an emitter.

Particular properties of the inventive metal-carbene complexes of the general formula (I) are particularly good efficiencies and long lifetimes when used in OLEDs.

The present application therefore further provides an OLED comprising at least one inventive metal-carbene complex of the general formula (I). The inventive metal-carbene complex of the general formula (I) is used in the OLED preferably as an emitter, matrix material, charge transport material, especially hole transport material, and/or charge blocker, more preferably as an emitter and/or hole transport material, most preferably as an emitter.

The present application also provides for the use of the metal-carbene complexes of the general formula (I) in OLEDs, preferably as an emitter, matrix material, charge transport material, especially hole transport material, and/or charge blocker, more preferably as an emitter and/or hole transport material, most preferably as an emitter.

Organic light diodes are in principle formed from a plurality of layers, e.g.:
anode (1)
hole-transporting layer (2)
light-emitting layer (3)
electron-transporting layer (4)
cathode (5)

It is, however, also possible that the OLED does not have all of the layers mentioned; for example, an OLED comprising layers (1) (anode), (3) (light-emitting layer) and (5) (cathode) is likewise suitable, in which case the functions of layers (2) (hole-transporting layer) and (4) (electron-transporting layer) are assumed by the adjoining layers. OLEDs having layers (1), (2), (3) and (5) or layers (1), (3), (4) and (5) are likewise suitable.

The metal-carbene complexes of the general formula (I) are preferably used as emitter molecules and/or matrix materials in the light-emitting layer (3). The inventive metal-carbene complexes of the general formula (I) may also—in addition to use as emitter molecules and/or matrix materials in the light-emitting layer (3) or instead of use in the light-emitting layer—also be used as a charge transport material in the hole-transporting layer (2) or in the electron-transporting layer (4) and/or as a charge blocker, preference being given to use as a charge transport material in the hole-transporting layer (2) (hole transport material).

The present application therefore further provides a light-emitting layer comprising at least one of the inventive metal-carbene complexes of the general formula (I), preferably as emitter molecule. Preferred metal-carbene complexes of the general formula (I) have already been specified above.

The metal-carbene complexes of the general formula (I) used in accordance with the invention may be present in the light-emitting layer in substance, i.e. without further additions. However, it is also possible that, in addition to the metal-carbene complexes of the general formula (I) used in accordance with the invention, further compounds are present in the light-emitting layer. For example, a fluorescent dye may be present in order to alter the emission color of the metal-carbene complex used as the emitter molecule. In addition, a diluent material (matrix material) may be used. This diluent material may be a polymer, for example poly (N-vinylcarbazole) or polysilane. The diluent material may, however, likewise be a small molecule, for example 4,4'-N, N'-dicarbazolebiphenyl (CDP) or tertiary aromatic amines. When a diluent material is used, the proportion of the inventive metal-carbene complexes of the general formula (I) in the light-emitting layer is generally less than 40% by weight, preferably 3 to 30% by weight. The inventive metal-carbene complexes of the general formula (I) are preferably used in a matrix. The light-emitting layer thus preferably comprises at least one inventive metal-carbene complex of the general formula (I) and at least one matrix material.

Suitable matrix materials are—in addition to the aforementioned dilution materials—in principle the materials specified hereinafter as hole and electron transport materials, and also carbon complexes, for example the carbene complexes of the formula (I) or the carbene complexes mentioned in WO 2005/019373. Particularly suitable are carbazole derivatives, for example 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), and the matrix materials specified in the following applications: WO2008/034758, WO2009/003919.

Dibenzofurans are additionally suitable as matrix materials, for example the dibenzofurans disclosed in US 2007/0224446 A1, for example those dibenzofurans in which at least one of the R1 to R8 radicals is a heterocyclic group, for example compound A-15, and the dibenzofurans disclosed in WO 2009/069442 A1, WO 2010/090077 A1 and JP 2006/321750 A.

Further suitable matrix materials, which may be small molecules or (co)polymers of the small molecules mentioned, are specified in the following publications:

WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913H-1 to H-70, WO2007077810 compounds 1 to 44, preferably 1, 2, 4-6, 8, 19-22, 26, 28-30, 32, 36, 39-44, WO0201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co) polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO02007108362, WO02009003898, WO2009003919, WO2010040777, US2007224446 and WO06128800.

In a particularly preferred embodiment, one or more compounds of the general formula (X) specified hereinafter are used as matrix material. Preferred embodiments of the compounds of the general formula (X) are likewise specified hereinafter.

The individual layers among the aforementioned layers of the OLED may in turn be formed from two or more layers. For example, the hole-transporting layer may be formed from one layer, into which holes are injected from the electrode, and a layer which transports the holes away from the hole-injecting layer into the light-emitting layer. The electron-transporting layer may likewise consist of a plurality of layers, for example of a layer in which electrons are injected through the electrode and a layer which receives electrons from the electron-injecting layer and transports them into the light-emitting layer. These layers mentioned are each selected according to factors such as energy level, thermal resistance and charge carrier mobility, and also energy difference of the layers mentioned with the organic layers or the metal electrodes. The person skilled in the art is capable of selecting the construction of the OLEDs such that it is matched optimally to the heteroleptic complexes according to the present invention used as emitter substances in accordance with the invention.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer should be aligned to the work function of the cathode.

The present application further provides an OLED comprising at least one inventive light-emitting layer. The further layers in the OLED may be formed from any material which is typically used in such layers and is known to those skilled in the art.

Suitable materials for the aforementioned layers (anode, cathode, hole and electron injection materials, hole and electron transport materials and hole and electron blocker materials, matrix materials, fluorescence and phosphorescence emitters) are known to those skilled in the art and are specified, for example, in H. Meng, N. Herron, *Organic Small Molecule Materials for Organic Light-Emitting Devices in Organic Light-Emitting Materials and Devices*, eds: Z. Li, H. Meng, Taylor & Francis, 2007, Chapter 3, pages 295 to 411.

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole transport materials for layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole transport material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis [(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino-9,9-spirobifluorene (spiro-TTB), N,N'-bis(naphthalen-1-yl)-N, N'-bis(phenyl)-9,9-spirobifluorene (spiro-NPB) and 9,9-bis (4-(N,N-bis-biphenyl-4-yl-amino)phenyl-9H-fluorene, benzidine compounds such as N,N'-bis(naphthalen-1-yl)-N, N'-bis(phenyl)benzidine and porphyrin compounds such as copper phthalocyanines. Customarily used hole-transporting polymers are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—it is possible to use carbene complexes as hole conductor materials, in which case the band gap of the at least one hole conductor material is generally greater than the band gap of the emitter material used. In the context of the present application, band gap is understood to mean the triplet energy.

Suitable carbene complexes are, for example, the inventive carbine complexes of the general formula (I), carbene complexes as described in WO 2005/019373 A2, WO 2006/056418 A2, WO 2005/113704, WO 2007/115970, WO 2007/115981 and WO 2008/000727. One example of a suitable carbene complex is Ir(DPBIC)$_3$ with the formula:

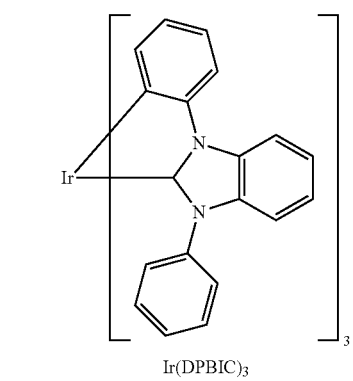

Ir(DPBIC)$_3$

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example $MoO_2$, $MoO_3$, $WO_x$, $ReO_3$ and/or $V_2O_5$, preferably $MoO_3$ and/or $ReO_3$, more preferably $ReO_3$ or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8, 8-tetracyanoquinodimethane, 2,5-difluoro-7,7,8,8-tetracyanoquinodimethane, dicyanomethylene-1,3,4,5,7,8-hexafluoro-6H-naphthalen-2-ylidene)malononitrile ($F_6$-TNAP), Mo(tfd)$_3$ (from Kahn et al., J. Am. Chem. Soc. 2009, 131 (35), 12530-12531), compounds as described in EP1988587 and in EP2180029 and quinone compounds as mentioned in EP 09153776.1.

Suitable electron-transporting materials for layer (4) of the inventive OLEDs comprise metals chelated with oxinoid compounds, such as tris(8-hydroxyquinolato)aluminum (Alq$_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1, 3,4-oxadiazole (PBD) and 3-(4-biphenylyl)-4-phenyl-5-(4-t-butylphenyl)-1,2,4-triazole (TAZ). In addition, dibenzofurans are suitable as electron-transporting materials, for example the dibenzofurans disclosed in US 2007/0224446

A1, for example those dibenzofurans in which at least one of the R1 to R8 radicals is a heterocyclic group, e.g. compound A-15, and the dibenzofurans disclosed in WO 2009/069442 A1, WO 2010/090077 A1 and JP 2006/321750 A. Layer (4) may serve both to ease the electron transport and as a buffer layer or as a barrier layer in order to prevent quenching of the exciton at the interfaces of the layers of the OLED. Layer (4) preferably improves the mobility of the electrons and reduces quenching of the exciton.

It is likewise possible to use mixtures of at least two materials in the electron-transporting layer, in which case at least one material is electron-conducting. Preferably, in such mixed electron-transporting layers, at least one phenanthroline compound is used, preferably BCP, or at least one pyridine compound according to the formula (VIII) below, preferably a compound of the formula (VIIIaa) below. More preferably, in mixed electron-transporting layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII).

The electron-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transporting layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassium phthalate, $W(hpp)_4$ from EP 1786050, or with compounds as described in EP1837926 B1.

The present invention therefore also relates to an inventive OLED which comprises an electron-transporting layer comprising at least two different materials, of which at least one material is electron-conducting.

In a preferred embodiment, the electron-transporting layer comprises at least one compound of the general formula (VII)

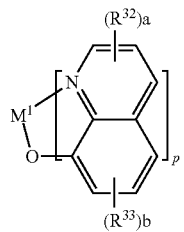

in which
$R^{32}$ and $R^{33}$ are each independently F, $C_1$-$C_8$-alkyl, or $C_6$-$C_{14}$-aryl, which is optionally substituted by one or more $C_1$-$C_8$-alkyl groups, or two $R^{32}$ and/or $R^{33}$ substituents together form a fused benzene ring which is optionally substituted by one or more $C_1$-$C_8$-alkyl groups;
a and b are each independently 0, or 1, 2 or 3,
$M^1$ is an alkaline metal atom or alkaline earth metal atom,
p is 1 when $M^1$ is an alkali metal atom, p is 2 when $M^1$ is an alkalin earth metal atom.

A very particularly preferred compound of the formula (VII) is

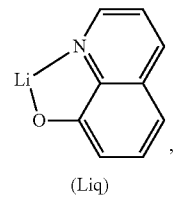

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transporting layer comprises at least one compound of the formula (VIII),

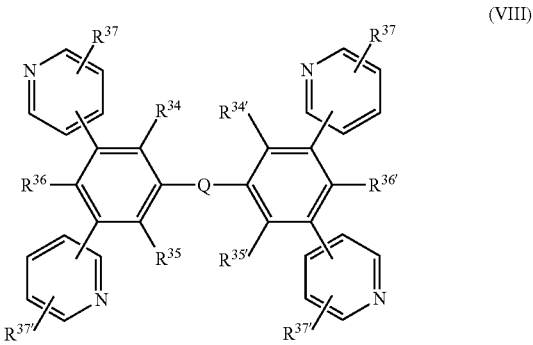

in which
$R^{34}$, $R^{35}$, $R^{36}$, $R^{37}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E and/or interrupted by D, $C_6$-$C_{24}$-aryl, $C_6$-$C_{24}$-aryl which is substituted by G, $C_2$-$C_{20}$-heteroaryl or $C_2$-$C_{20}$-heteroaryl which is substituted by G,
Q is an arylene or heteroarylene group, each of which is optionally substituted by G;
D is —CO—; —COO—; —S—; —SO—; —SO$_2$—; —O—; —NR$^{40}$—; —SiR$^{45}$R$^{46}$—; —POR$^{47}$—; —CR$^{38}$=CR$^{39}$—; or —C≡C—; and
E is —OR$^{44}$; —SR$^{44}$; —NR$^{40}$R$^{41}$; —COR$^{43}$; —COOR$^{42}$; —CONR$^{40}$R$^{41}$; —CN; or F;
G is E, $C_1$-$C_{18}$-alkyl, $C_1$-$C_{18}$-alkyl which is interrupted by D, $C_1$-$C_{18}$-perfluoroalkyl, $C_1$-$C_{18}$-alkoxy, or $C_1$-$C_{18}$-alkoxy which is substituted by E and/or interrupted by D, wherein
$R^{38}$ and $R^{39}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;
$R^{40}$ and $R^{41}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or $R^{40}$ and $R^{41}$ together form a 6-membered ring;

$R^{42}$ and $R^{43}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{44}$ is $C_6$-$C_{18}$-aryl; $C_6$-$C_{18}$-aryl which is substituted by $C_1$-$C_{18}$-alkyl or $C_1$-$C_5$-alkoxy; $C_1$-$C_{18}$-alkyl; or $C_1$-$C_{18}$-alkyl which is interrupted by —O—, $R^{45}$ and $R^{46}$ are each independently $C_1$-$C_{18}$-alkyl, $C_6$-$C_{18}$-aryl or $C_6$-$C_{18}$-aryl which is substituted by $C_1$-$C_1$S-alkyl, $R^{47}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (VIII) are compounds of the formula (VIIIa)

(VIIIa)

in which Q is:

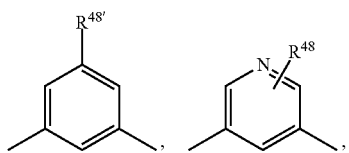

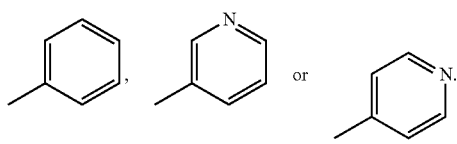

$R^{48}$ is H or $C_1$-$C_{18}$-alkyl and
$R^{48'}$ is H, $C_1$-$C_{18}$-alkyl or Particular preference is given to a compound of the formula (VIIIaa)

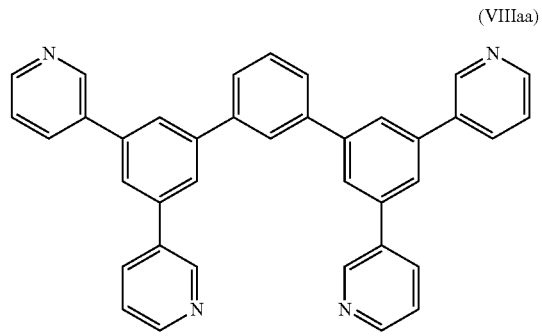 [SMILES: c1cncc(-c2cc(-c3cccnc3)cc(-c3cccc(-c4cc(-c5cccnc5)cc(-c5cccnc5)c4)c3)c2)c1]

(VIIIaa)

In a further, very particularly preferred embodiment, the electron-transporting layer comprises a compound of the formula

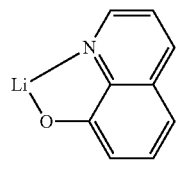

(Liq)

(Liq) and a compound of the formula

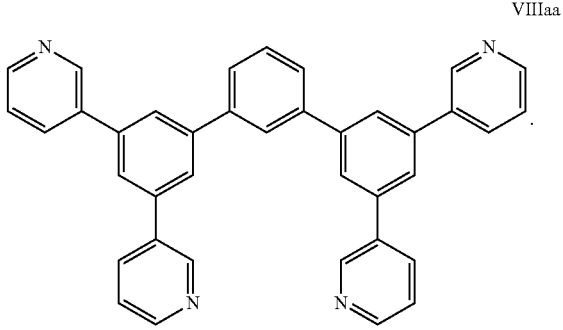 [SMILES: c1cncc(-c2cc(-c3cccnc3)cc(-c3cccc(-c4cc(-c5cccnc5)cc(-c5cccnc5)c4)c3)c2)c1]

VIIIaa

In a preferred embodiment, the electron-transporting layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008-127326, or the compounds can be prepared analogously to the processes disclosed in the aforementioned documents.

The preparation of the compounds of the formula (VII) is described, for example, in Christoph Schmitz et al. Chem. Mater. 12 (2000) 3012-3019 and WO00/32717, or the compounds can be prepared analogously to the processes disclosed in the aforementioned documents.

In a preferred embodiment, the invention relates to an inventive OLED wherein the electron-transporting layer comprises at least one phenanthroline derivative and/or pyridine derivative.

In a further preferred embodiment, the invention relates to an inventive OLED wherein the electron-transporting layer comprises at least one phenanthroline derivative and/or pyridine derivative and at least one alkali metal hydroxyquinolate complex.

In a further preferred embodiment, the invention relates to an inventive OLED wherein the electron-transporting layer comprises at least one phenanthroline derivative and/or pyridine derivative and 8-hydroxyquinolatolithium.

Some of the materials mentioned above as hole transport materials and electron-transporting materials can fulfill several functions. For example, some of the electron-transporting materials are simultaneously hole-blocking materials if they have a low-lying HOMO.

The cathode (5) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. In addition, lithium-comprising organometallic compounds such as 8-hydroxyquinolatolithium (Liq), CsF, NaF, KF, $Cs_2CO_3$ or LiF may be applied between the organic layer and the cathode as an electron injection layer in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:
  a hole injection layer between the anode (1) and the hole-transporting layer (2); a blocking layer for electrons between the hole-transporting layer (2) and the light-emitting layer (3);
  a blocking layer for holes between the light-emitting layer (3) and the electron-transporting layer (4);
  an electron injection layer between the electron-transporting layer (4) and the cathode (5).

As already mentioned above, however, it is also possible that the OLED does not have all of the layers (1) to (5) mentioned; for example, an OLED comprising layers (1) (anode), (3) (light-emitting layer) and (5) (cathode) is likewise suitable, in which case the functions of layers (2) (hole-transporting layer) and (4) (electron-transporting layer) are assumed by the adjoining layers. OLEDs having layers (1), (2), (3) and (5) or layers (1), (3), (4) and (5) are likewise suitable.

Those skilled in the art know how suitable materials have to be selected (for example on the basis of electrochemical investigations). Suitable materials for the individual layers are known to those skilled in the art and disclosed, for example, in WO 00/70655.

In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform.

In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

In general, the different layers have the following thicknesses: anode (2) 500 to 5000 Å, preferably 1000 to 2000 Å (angstrom); hole-transporting layer (3) 50 to 1000 Å, preferably 200 to 800 Å; light-emitting layer (4) 10 to 1000 Å, preferably 100 to 800 Å; electron-transporting layer (5) 50 to 1000 Å, preferably 200 to 800 Å; cathode (6) 200 to 10 000 Å, preferably 300 to 5000 Å. In addition, it is likewise possible to combine several layers by mixing. For example, the hole-transporting material can be mixed with the materials of the light-emitting layer and then applied together. The position of the recombination zone of holes and electrons in the inventive OLED and thus the emission spectrum of the OLED may be influenced by the relative thickness and concentration ratios of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

In a preferred embodiment, the present invention relates to an OLED comprising at least one inventive metal-carbene complex, and at least one compound of the general formula (X)

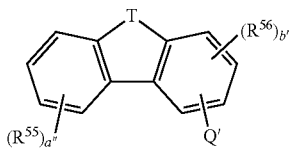

in which

T is NR$^{57}$, S, O or PR$^{57}$, preferably S or O, more preferably O;

R$^{57}$ is aryl, heteroaryl, alkyl, cycloalkyl or heterocycloalkyl;

Q' is —NR$^{58}$R$^{59}$, —P(O)R$^{60}$R$^{61}$, —PR$^{62}$R$^{63}$, —S(O)$_2$R$^{64}$, —S(O)R$^{65}$, —SR$^{66}$ or —OR$^{67}$, preferably —NR$^{58}$R$^{59}$; more preferably

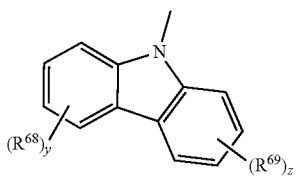

in which

R$^{68}$, R$^{69}$ are each independently alkyl, cycloalkyl, heterocycloalkyl, aryl or heteroaryl; preferably methyl, carbazolyl, dibenzofuryl or dibenzothienyl;

y, z are each independently 0, 1, 2, 3 or 4, preferably 0 or 1;

R$^{55}$, R$^{56}$ are each independently alkyl, cycloalkyl, heterocycloalkyl, aryl, heteroaryl, SiR$^{70}$R$^{71}$R$^{72}$, a Q' group or a group with donor or acceptor action;

a" is 0, 1, 2, 3 or 4;

b' is 0, 1, 2 or 3;

R$^{58}$, R$^{59}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action;

R$^{70}$, R$^{71}$, R$^{72}$, R$^{60}$, R$^{61}$, R$^{62}$, R$^{63}$, R$^{64}$, R$^{65}$, R$^{66}$, R$^{67}$ are each independently aryl, heteroaryl, alkyl, cycloalkyl or heterocycloalkyl, or two units of the general formula (X) are bridged to one another via a linear or branched, saturated or unsaturated bridge optionally interrupted by at least one heteroatom, via a bond or via O.

Preference is given to compounds of the formula (X) in which:

T is S or O, preferably O, and

Q' is

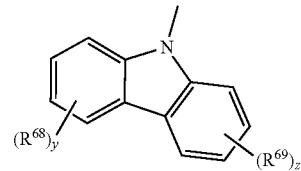

in which

R$^{68}$, R$^{69}$ are each independently alkyl, cycloalkyl, heterocycloalkyl, aryl or heteroaryl; preferably methyl, carbazolyl, dibenzofuryl or dibenzothienyl;

y, z are each independently 0, 1, 2, 3 or 4, preferably 0 or 1.

Particularly preferred compounds of the formula (X) have the following formula (Xa):

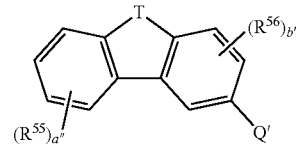

in which the symbols and indices Q', T, R$^{55}$, R$^{56}$, a" and b' are each as defined above.

Very particularly preferred compounds of the formula (X) have the formula (Xaa):

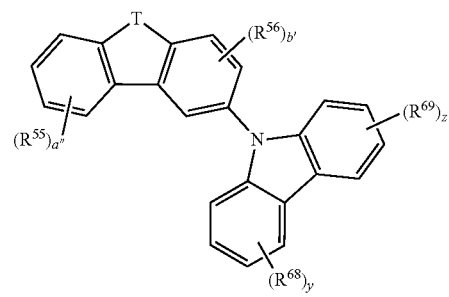

in which the symbols and indices R$^{68}$, R$^{69}$ y, z, T, R$^{55}$, R$^{56}$, a" and b' are each as defined above.

In a very particularly preferred embodiment, in formula (Xaa):

T is O or S, preferably O;

a" is 1;

b' is 0;

y, z are each independently 0 or 1; and

R$^{68}$, R$^{69}$ are each independently methyl, carbazolyl, dibenzofuryl or dibenzothienyl R$^{55}$ is substituted phenyl, carbazolyl, dibenzofuryl or dibenzothienyl.

In a further preferred embodiment, the compounds of the formula (X) have the formula (XI) or (XI*):

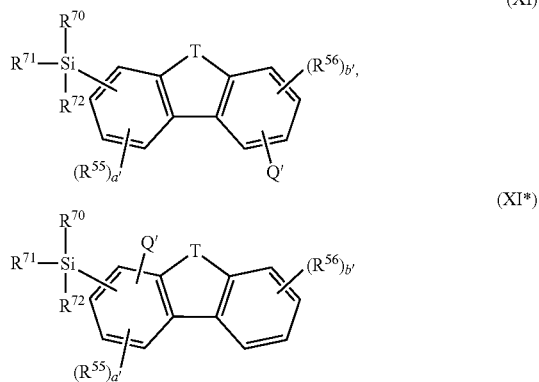

in which

T is NR$^{57}$, S, O or PR$^{57}$;

R$^{57}$ is aryl, heteroaryl, alkyl, cycloalkyl or heterocycloalkyl;

Q' is —NR$^{58}$R$^{59}$, —P(O)R$^{60}$R$^{61}$, —PR$^{62}$R$^{63}$, —S(O)$_2$R$^{64}$, —S(O)R$^{65}$, —SR$^{66}$ or —OR$^{67}$;

R$^{70}$, R$^{71}$, R$^{72}$ are each independently aryl, heteroaryl, alkyl, cycloalkyl, heterocycloalkyl, where at least one of the R$^{70}$, R$^{71}$, R$^{72}$ radicals comprises at least two carbon atoms, or OR$^{73}$, R$^{55}$, R$^{56}$ are each independently alkyl, cycloalkyl, heterocycloalkyl, aryl, heteroaryl, a Q group or a group with donor or acceptor action;

a', b' for the compound of the formula (XI): are each independently 0, 1, 2, 3; for the compound of the formula (XI*), a' is 0, 1, 2 and b' is 0, 1, 2, 3, 4;

R$^{58}$, R$^{59}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action;

R$^{73}$ are each independently SiR$^{74}$R$^{75}$R$^{76}$, aryl, heteroaryl, alkyl, cycloalkyl or heterocycloalkyl, optionally substituted by an OR$^{77}$ group, R$^{77}$ are each independently SiR$^{74}$R$^{75}$R$^{76}$, aryl, heteroaryl, alkyl, cycloalkyl or heterocycloalkyl, R$^{60}$, R$^{61}$, R$^{62}$, R$^{63}$, R$^{64}$, R$^{65}$, R$^{66}$, R$^{67}$, R$^{74}$, R$^{75}$, R$^{76}$ are each independently aryl, heteroaryl, alkyl, cycloalkyl or heterocycloalkyl, or two units of the general formulae (XI) and/or (XI*) are bridged to one another via a linear or branched, saturated or unsaturated bridge optionally interrupted by at least one heteroatom or via O, where this bridge in the general formulae (XI) and/or (XI*) is in each case attached to the silicon atoms in place of R$^{71}$.

The compounds of the general formula (X) can be used as a matrix (diluent material), hole/exciton blocker, electron/exciton blocker, electron transport material or hole transport material in combination with the complexes claimed, which then serve as emitters. Inventive OLEDs which include both at least one compound of the formula (X) and a compound of the formula (I) exhibit particularly good efficiencies and lifetimes. Depending on the function in which the compound of the formula (X) is used, it is present in pure form or in different mixing ratios. In a particularly preferred embodiment, one or more compounds of the formula (X) are used as matrix material in the light-emitting layer.

For the compounds of the general formula (X), especially for the R$^{55}$ to R$^{77}$ radicals: The terms aryl radical or group, heteroaryl radical or group, alkyl radical or group, cycloalkyl radical or group, heterocycloalkyl radical or group, alkenyl radical or group, alkynyl radical or group, and groups with donor and/or acceptor action are each defined as follows:

An aryl radical (or group) is understood to mean a radical having a base skeleton of 6 to 30 carbon atoms, preferably 6 to 18 carbon atoms, which is formed from an aromatic ring or a plurality of fused aromatic rings. Suitable base skeletons are, for example, phenyl, naphthyl, anthracenyl or phenanthrenyl, indenyl or fluorenyl. This base skeleton may be unsubstituted (which means that all carbon atoms which are substitutable bear hydrogen atoms), or may be substituted at one, more than one or all substitutable positions of the base skeleton.

Suitable substituents are, for example, deuterium, alkoxy radicals, aryloxy radicals, alkylamino groups, arylamino groups, carbazolyl groups, silyl groups, SiR$^{78}$R$^{79}$R$^{80}$ suitable silyl groups SiR$^{78}$R$^{79}$R$^{80}$ being specified below, alkyl radicals, preferably alkyl radicals having 1 to 8 carbon atoms, more preferably methyl, ethyl or i-propyl, aryl radicals, preferably C$_6$-aryl radicals, which may in turn be substituted or unsubstituted, heteroaryl radicals, preferably heteroaryl radicals which comprise at least one nitrogen atom, more preferably pyridyl radicals and carbazolyl radicals, alkenyl radicals, preferably alkenyl radicals which bear one double bond, more preferably alkenyl radicals having one double bond and 1 to 8 carbon atoms, alkynyl radicals, preferably alkynyl radicals having one triple bond, more preferably alkynyl radicals having one triple bond and 1 to 8 carbon atoms or groups with donor or acceptor action. Suitable groups with donor or acceptor action are specified below. The substituted aryl radicals most preferably bear substituents selected from the group consisting of methyl, ethyl, isopropyl, alkoxy, heteroaryl, halogen, pseudohalogen and amino, preferably arylamino. The aryl radical or the aryl group is preferably a C$_6$-C$_{18}$-aryl radical, more preferably a C$_6$-aryl radical, which is optionally substituted by at least one or more than one of the aforementioned substituents. The C$_6$-C$_{18}$-aryl radical, preferably C$_6$-aryl radical, more preferably has none, one, two, three or four, most preferably none, one or two, of the aforementioned substituents.

A heteroaryl radical or a heteroaryl group is understood to mean radicals which differ from the aforementioned aryl radicals in that at least one carbon atom in the base skeleton of the aryl radicals is replaced by a heteroatom, and in that the base skeleton of the heteroaryl radicals preferably has 5 to 18 ring atoms. Preferred heteroatoms are N, O and S. Heteroaryl radicals suitable with particular preference are nitrogen-containing heteroaryl radicals. Most preferably, one or two carbon atoms of the base skeleton are replaced by heteroatoms, preferably nitrogen. The base skeleton is especially preferably selected from systems such as pyridine, pyrimidine and five-membered heteroaromatics such as pyrrole, furan, pyrazole, imidazole, thiophene, oxazole, thiazole, triazole. In addition, the heteroaryl radicals may be fused ring systems, for example benzofuryl, benzothienyl, benzopyrrolyl, dibenzofuryl, dibenzothienyl, phenanthrolinyl, carbazolyl radicals, azacarbazolyl radicals or diazacarbazolyl radicals. The base skeleton may be substituted at one, more than one or all substitutable positions of the base skeleton. Suitable substituents are the same as have already been specified for the aryl groups.

An alkyl radical or an alkyl group is understood to mean a radical having 1 to 20 carbon atoms, preferably 1 to 10 carbon atoms, more preferably 1 to 8, most preferably 1 to 4 carbon atoms. This alkyl radical may be branched or unbranched and optionally be interrupted by one or more heteroatoms, preferably Si, N, O or S, more preferably N, O or S. In addition, this alkyl radical may be substituted by one or more of the substituents specified for the aryl groups. In addition, the alkyl radicals present in accordance with the invention may have at least one halogen atom, for example F, Cl, Br or I, especially F. In a further embodiment, the alkyl radicals present in accordance with the invention may be fully fluorinated. It is likewise possible that the alkyl radical bears one or more (hetero)aryl groups. In the context of the present application, for example, benzyl radicals are thus substituted alkyl radicals. In this context, all of the (hetero) aryl groups listed above are suitable. The alkyl radicals are more preferably selected from the group consisting of methyl, ethyl, isopropyl, n-propyl, n-butyl, iso-butyl and tert-butyl, very particular preference being given to methyl and ethyl.

A cycloalkyl radical or a cycloalkyl group is understood to mean a radical having 3 to 20 carbon atoms, preferably 3 to 10 carbon atoms, more preferably 3 to 8 carbon atoms. This base skeleton may be unsubstituted (which means that all carbon atoms which are substitutable bear hydrogen atoms) or substituted at one, more than one or all substitutable positions of the base skeleton. Suitable substituents are the groups already mentioned above for the aryl radicals. It is likewise possible that the cycloalkyl radical bears one or more (hetero)aryl groups. Examples of suitable cycloalkyl radicals are cyclopropyl, cyclopentyl and cyclohexyl.

A heterocycloalkyl radical or a heterocycloalkyl group is understood to mean radicals which differ from the aforementioned cycloalkyl radicals in that at least one carbon atom in the base skeleton of the cycloalkyl radicals is replaced by a heteroatom. Preferred heteroatoms are N, O and S. Most preferably, one or two carbon atoms of the base skeleton of the cycloalkyl radicals are replaced by heteroatoms. Examples of suitable heterocycloalkyl radicals are radicals derived from pyrrolidine, piperidine, piperazine, tetrahydrofuran, dioxane.

An alkenyl radical or an alkenyl group is understood to mean a radical which corresponds to the aforementioned alkyl radicals having at least two carbon atoms, with the difference that at least one C—C single bond of the alkyl radical is replaced by a C—C double bond. The alkenyl radical preferably has one or two double bonds.

An alkynyl radical or an alkynyl group is understood to mean a radical which corresponds to the aforementioned alkyl radicals having at least two carbon atoms, with the difference that at least one C—C single bond of the alkyl radical is replaced by a C—C triple bond. The alkynyl radical preferably has one or two triple bonds.

An $SiR^{78}R^{79}R^{80}$ group is understood to mean a silyl radical in which $R^{78}$, $R^{79}$ and $R^{80}$ are each independently alkyl, cycloalkyl, heterocycloalkyl, aryl, heteroaryl or $OR^{73}$.

An $SiR^{74}R^{75}R^{76}$ group is understood to mean a silyl radical in which $R^{74}$, $R^{75}$ and $R^{76}$ are each independently alkyl, cycloalkyl, heterocycloalkyl, aryl, heteroaryl or $OR^{73}$.

In the context of the present application, a group or a substituent with donor or acceptor action is understood to mean the following groups:

Groups with donor action are understood to mean groups which have a +I and/or +M effect, and groups with acceptor action are understood to mean groups which have a −I and/or −M effect. Preferred suitable groups are selected from $C_1$-$C_{20}$-alkoxy, $C_6$-$C_{30}$-aryloxy, $C_1$-$C_{20}$-alkylthio, $C_6$-$C_3$-arylthio, $SiR^{81}R^{82}R^{83}$, $OR^{73}$, halogen radicals, halogenated $C_1$-$C_{20}$-alkyl radicals, carbonyl (—CO($R^{81}$)), carbonylthio (—C=O ($SR^{81}$)), carbonyloxy (—C=O($OR^{81}$)), oxycarbonyl (—OC=O($R^{81}$)), thiocarbonyl (—SC=O($R^{81}$)), amino (—$NR^{81}R^{82}$), pseudohalogen radicals, amido (—C=O ($NR^{81}$)), —$NR^{81}$C=O ($R^{83}$), phosphonate (—P(O) ($OR^{81}$)$_2$, phosphate (—OP(O) ($OR^{81}$)$_2$), phosphine (—$PR^{81}R^{82}$), phosphine oxide (—P(O)$R^{81}_2$), sulfate (—OS (O)$_2OR^{81}$), sulfoxide (—S(O)$R^{81}$), sulfonate (—S(O)$_2OR^{81}$), sulfonyl (—S(O)$_2R^{81}$, sulfonamide (—S (O)$_2NR^{81}R^{82}$), $NO_2$, boronic esters (—OB($OR^{81}$)$_2$), imino (—C=$NR^{81}R^{82}$)), borane radicals, stannane radicals, hydrazine radicals, hydrazone radicals, oxime radicals, nitroso groups, diazo groups, vinyl groups, sulfoximines, alanes, germanes, boroximes and borazines.

The $R^{81}$, $R^{82}$ and $R^{83}$ radicals mentioned in the aforementioned groups with donor or acceptor action are each independently:

substituted or unsubstituted $C_1$-$C_{20}$-alkyl or substituted or unsubstituted $C_6$-$C_{30}$-aryl, or $OR^{76}$, suitable and preferred alkyl and aryl radicals having been specified above. The $R^{81}$, $R^{82}$ and $R^{83}$ radicals are more preferably $C_1$-$C_6$-alkyl, e.g. methyl, ethyl or i-propyl, or phenyl. In a preferred embodiment—in the case of $SiR^{81}R^{82}R^{83}$—$R^{81}$, $R^{82}$ and $R^{83}$ are preferably each independently substituted or unsubstituted $C_1$-$C_{20}$-alkyl or substituted or unsubstituted aryl, preferably phenyl.

Preferred substituents with donor or acceptor action are selected from the group consisting of:

$C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{81}R^{82}R^{83}$ where $R^{81}$, $R^{82}$ and $R^{83}$ are preferably each independently substituted or unsubstituted alkyl or substituted or unsubstituted aryl, preferably phenyl; more preferably, at least one of the $R^{81}$, $R^{82}$ and $R^{83}$ radicals is substituted or unsubstituted phenyl, suitable substituents having been specified above; halogen radicals, preferably F, Cl, more preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diarylamino, more preferably diarylamino; pseudohalogen radicals, preferably CN, —C(O)O$C_1$-$C_4$-alkyl, preferably —C(O)OMe, P(O)$R_2$, preferably P(O)Ph$_2$.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^{81}R^{82}R^{83}$, suitable $R^{81}$, $R^{82}$ and $R^{83}$ radicals already having been specified, diarylamino ($NR^{84}R^{85}$ where $R^{84}$, $R^{85}$ are each $C_6$-$C_{30}$-aryl), —C(O)O$C_1$-$C_4$-alkyl, preferably —C(O)OMe, P(O)Ph$_2$.

Halogen groups are preferably understood to mean F, Cl and Br, more preferably F and Cl, most preferably F.

Pseudohalogen groups are preferably understood to mean CN, SCN and OCN, more preferably CN.

The aforementioned groups with donor or acceptor action do not rule out the possibility that further radicals and substituents mentioned in the present application, but not included in the above list of groups with donor or acceptor action, have donor or acceptor action.

The aryl radicals or groups, heteroaryl radicals or groups, alkyl radicals or groups, cycloalkyl radicals or groups, heterocycloalkyl radicals or groups, alkenyl radicals or groups and groups with donor and/or acceptor action may—as mentioned above—be substituted or unsubstituted. In the context of the present application, an unsubstituted group is understood to mean a group in which the substitutable atoms of the group bear hydrogen atoms. In the context of the present application, a substituted group is understood to mean a group in which one or more substitutable atom(s) bear(s) a substituent in place of a hydrogen atom at least at one position. Suitable substituents are the substituents specified above for the aryl radicals or groups.

When radicals having the same numbering occur more than once in the compounds according to the present application, these radicals may each independently have the definitions specified.

The T radical in the compounds of the formula (X) is $NR^{57}$, S, O or $PR^{57}$, preferably $NR^{57}$, S or O, more preferably O or S, most preferably O.

The $R^{57}$ radical is aryl, heteroaryl, alkyl, cycloalkyl or heterocycloalkyl, preferably aryl, heteroaryl or alkyl, more preferably aryl, where the aforementioned radicals may be unsubstituted or substituted. Suitable substituents have been specified above. $R^{65}$ is more preferably phenyl which may be substituted by the aforementioned substituents or unsubstituted. $R^{57}$ is most preferably unsubstituted phenyl.

The Q' group in the compounds of the formula (X) is $-NR^{58}R^{59}$, $-P(O)R^{60}R^{61}$, $-PR^{62}R^{63}$, $-S(O)_2R^{64}$, $-S(O)R^{65}$, $-SR^{66}$ or $-OR^{67}$; preferably $NR^{58}R^{59}$, $-P(O)R^{60}R^{61}$ or $-OR^{67}$, more preferably $-NR^{58}R^{59}$.

The $R^{58}$ to $R^{67}$ and $R^{74}$ to $R^{76}$ radicals are each defined as follows:

$R^{58}$, $R^{59}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action;

$R^{60}$, $R^{61}$, $R^{62}$, $R^{63}$, $R^{64}$, $R^{65}$, $R^{66}$, $R^{67}$, $R^{74}$, $R^{75}$, $R^{76}$ are each independently aryl, heteroaryl, alkyl, cycloalkyl or heterocycloalkyl, preferably aryl or heteroaryl, where the radicals may be unsubstituted or substituted by one or more of the radicals selected from alkyl, cycloalkyl, heterocycloalkyl, aryl, heteroaryl and a group with donor or acceptor action, more preferably unsubstituted or substituted phenyl, suitable substituents having been specified above, for example tolyl or a group of the formula

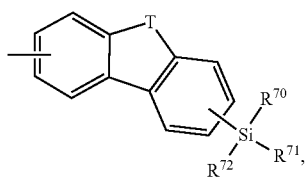

in which the T group and the $R^{70}$, $R^{71}$ and $R^{72}$ radicals are each independently as defined for the compounds of the formula (XI) or (XI*).

$R^{60}$, $R^{61}$, $R^{62}$, $R^{63}$, $R^{64}$, $R^{65}$, $R^{66}$ and $R^{67}$ are most preferably each independently phenyl, tolyl or a group of the formula

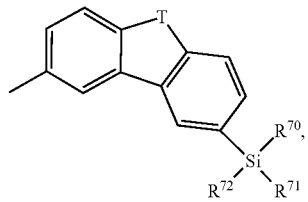

in which T is NPh, S or O.

Examples of $-NR^{58}R^{59}$ groups suitable with preference are selected from the group consisting of pyrrolyl, 2,5-dihydro-1-pyrrolyl, pyrrolidinyl, indolyl, indolinyl, isoindolinyl, carbazolyl, azacarbazolyl, diazacarbazolyl, imidazolyl, imidazolinyl, benzimidazolyl, pyrazolyl, indazolyl, 1,2,3-triazolyl, benzotriazolyl, 1,2,4-triazolyl, tetrazolyl, 1,3-oxazolyl, 1,3-thiazolyl, piperidyl, morpholinyl, 9,10-dihydroacridinyl and 1,4-oxazinyl, where the aforementioned groups may be unsubstituted or substituted by one or more substituents selected from alkyl, cycloalkyl, heterocycloalkyl, aryl, heteroaryl and a group with donor or acceptor action; the $-NR^{58}R^{59}$ group is preferably selected from carbazolyl, pyrrolyl, indolyl, imidazolyl, benzimidazolyl, azacarbazolyl and diazacarbazolyl, where the aforementioned groups may be unsubstituted or substituted by one or more substituents selected from alkyl, cycloalkyl, heterocycloalkyl, aryl, heteroaryl and a group with donor or acceptor action; the $-NR^{58}R^{59}$ group is more preferably carbazolyl which may be unsubstituted or substituted by one or more substituents selected from alkyl, cycloalkyl, heterocycloalkyl, aryl, heteroaryl and a group with donor or acceptor action.

Particularly preferred $-NR^{58}R^{59}$ groups are:

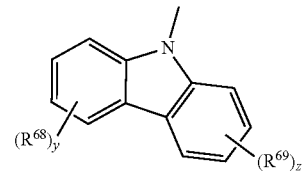

in which $R^{68}$, $R^{69}$ are each independently alkyl, cycloalkyl, heterocycloalkyl, aryl or heteroaryl; preferably methyl, carbazolyl, dibenzofuryl or dibenzothienyl;

y, z are each independently 0, 1, 2, 3 or 4, preferably 0 or 1; for example:

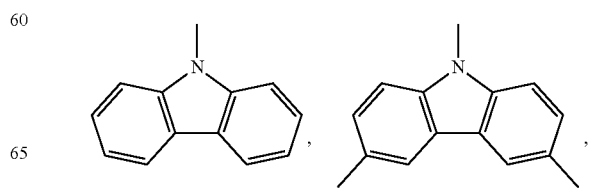

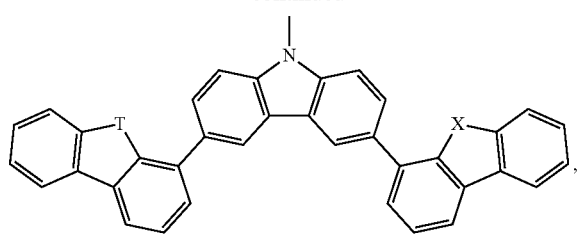
in which X is NPh, S or O;
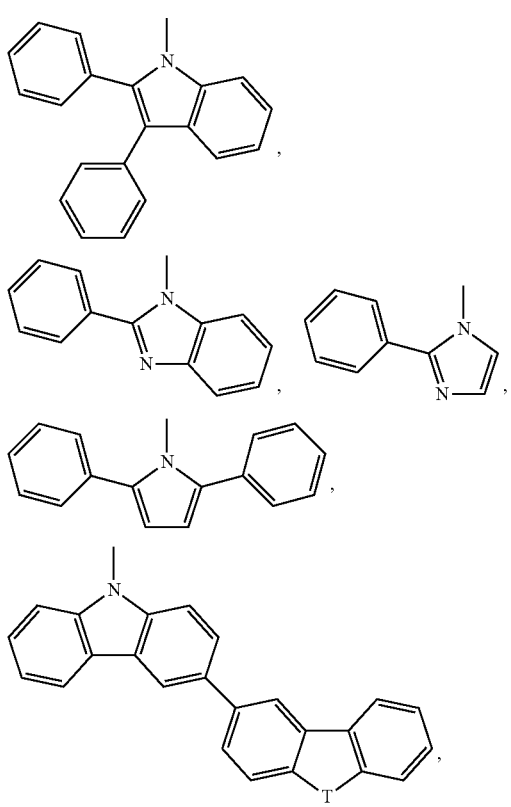
in which X is NPh, S or O,
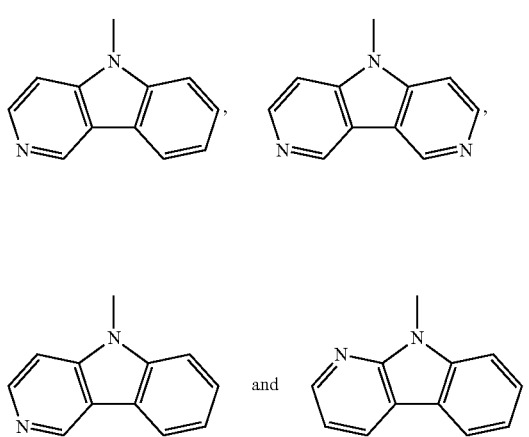
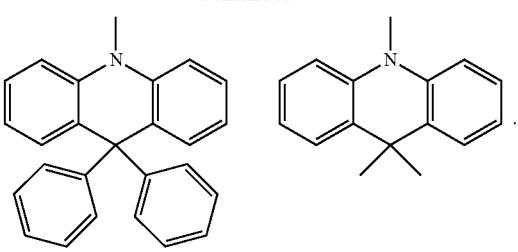
Particularly preferred —P(O)R⁶⁰R⁶¹ groups are:
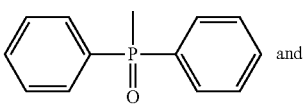
and
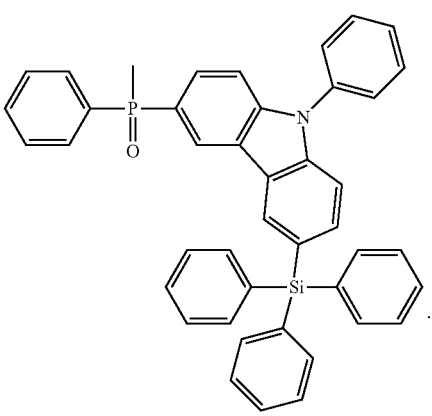
A particularly preferred PR⁶²R⁶³ group is:
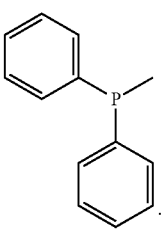
Particularly preferred groups —S(O)₂R⁶⁴ and —S(O)R⁶⁵ are:
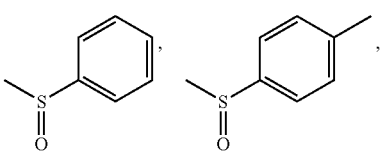
and
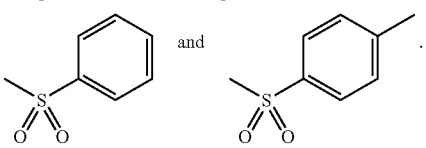

Particularly preferred groups —SR$^{66}$ and —OR$^{67}$ are:

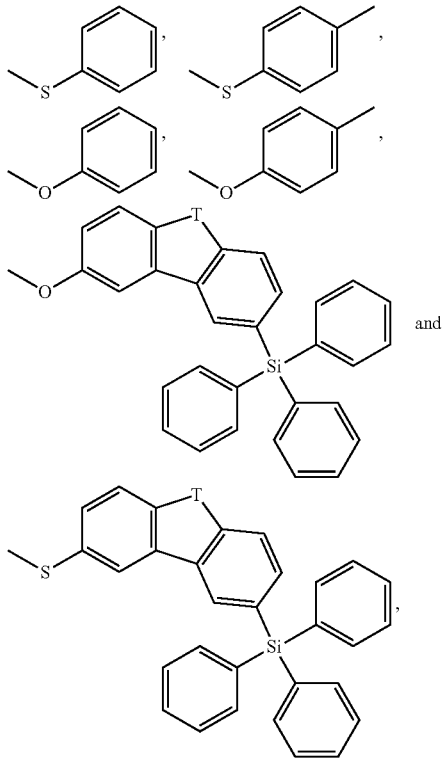

in which T is in each case NPh, S or O.

R$^{55}$, R$^{56}$ in the compounds of the formula (X) are each independently alkyl, cycloalkyl, heterocycloalkyl, aryl, heteroaryl, a further A group or a group with donor or acceptor action; preferably each independently alkyl, aryl, heteroaryl or a group with donor or acceptor action. For example, R$^{55}$ or R$^{56}$ may each independently be:

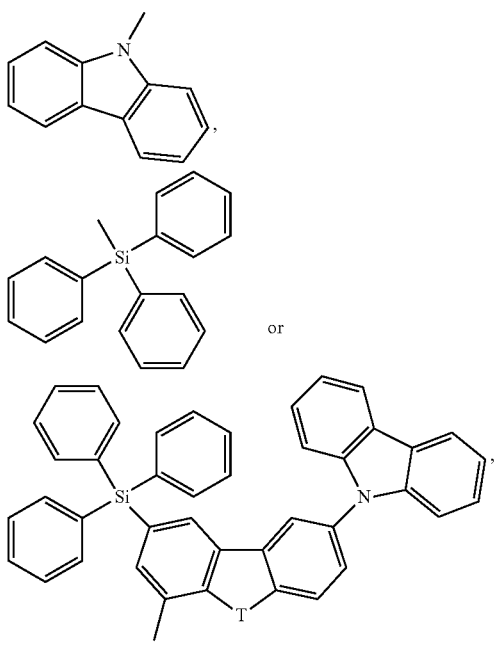

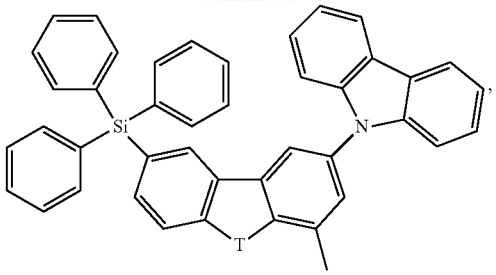

in which X is NPh, S or O.

In the compounds of the formula (X) a" R$^{55}$ groups and/or b' R$^{56}$ groups may be present, where a" and b' are:

a" is 0, 1, 2, 3 or 4; preferably independently 0, 1 or 2;
b' is 0, 1, 2 or 3; preferably independently 0, 1 or 2.

Most preferably at least a" or b' is 0, very especially preferably a" and b' are each 0 or a" is 1 and b' is 0.

R$^{73}$ in the compounds of the general formula (XI) is generally independently SiR$^{74}$R$^{75}$R$^{76}$, aryl, heteroaryl, alkyl, cycloalkyl or heterocycloalkyl, optionally substituted by an OR$^{77}$ group.

R$^{77}$ in compounds of the general formula (XI) is generally independently aryl, heteroaryl, alkyl, cycloalkyl or heterocycloalkyl.

The OR$^{77}$ substituent optionally present may generally be present in the radicals mentioned at all sites which appear suitable to the person skilled in the art.

In a further embodiment, two units of the general formula (XI) and/or (XI*) are bridged to one another via a linear or branched, saturated or unsaturated bridge optionally interrupted by at least one heteroatom or via O, where this bridge in the general formula (XI) and/or (XI*) is in each case attached to the silicon atoms in place of R$^{71}$.

This bridge is preferably selected from the group consisting of —CH$_2$—, —C$_2$H$_4$—, —C$_3$H$_6$—, —C$_4$H$_8$—, —C$_6$H$_{12}$—, —C$_8$H$_{16}$—, —C$_9$H$_{18}$—, —CH(C$_8$H$_{17}$)CH$_2$—, —C$_2$H$_4$(CF$_2$)$_8$ C$_2$H$_4$—, —C≡C—, -1,4-(CH$_2$)$_2$-phenyl-(CH$_2$)$_2$—, 1,3-(CH$_2$)$_2$-phenyl-(CH$_2$)$_2$—, -1,4-phenyl-, -1,3-phenyl-, —O—, —O—Si(CH$_3$)$_2$—O—, —O—Si(CH$_3$)$_2$—O— Si(CH$_3$)$_2$—O—, —O—

In a preferred embodiment of the present application, the compounds of the general formula (X) have the general formula (XIa), (XIb), (XIc), (XId) or (XIe), i.e. they are preferred embodiments of the compounds of the general formula (XI) or (XI*):

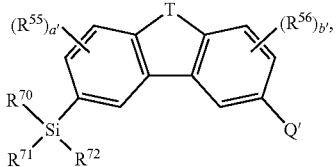
(XIa)

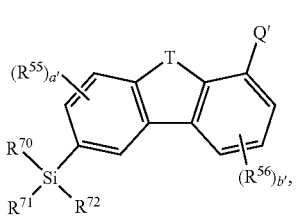
(XIb)

-continued

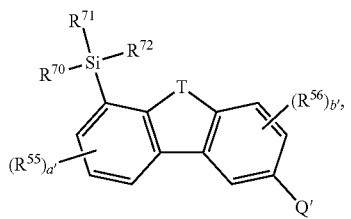
(XIc)

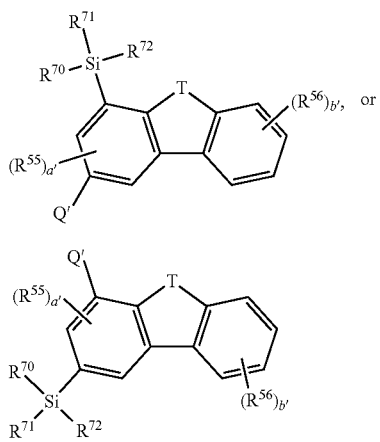
(XId)

(XIe)

in which the Q', T, $R^{70}$, $R^{71}$, $R^{72}$, $R^{55}$, $R^{56}$ radicals and groups, and a' and b', are each as defined above.

In another embodiment preferred in accordance with the invention, $R^{70}$, $R^{71}$ or $R^{72}$ in the compounds of the general formula (XI) or (XI*) are aromatic units of the general formulae (XIi) and/or (XIi*)

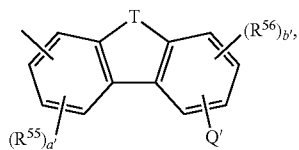
(XIi)

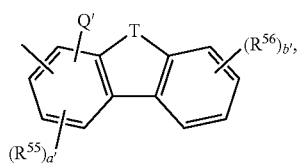
(XIi*)

where $R^{55}$, $R^{56}$, Q', T, a' and b' are each as defined above.

The present invention therefore relates, in one embodiment, to an inventive OLED where $R^{70}$, $R^{71}$ or $R^{72}$ in the compounds of the general formula (XI) or (XI*) are aromatic units of the general formulae (XIi) and/or (XIi*)

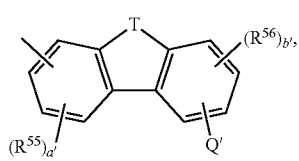
(XIi)

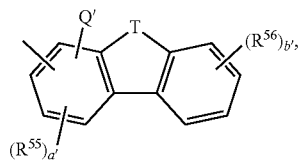
(XIi*)

where $R^{56}$, $R^{56}$, Q', T, a' and b' are each as defined above.

In a preferred embodiment, the present invention relates to an OLED wherein the compound of the general formula (XI) or (XI*) is selected from the following group:

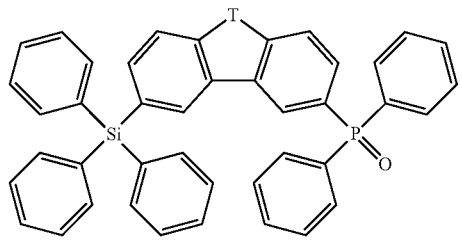

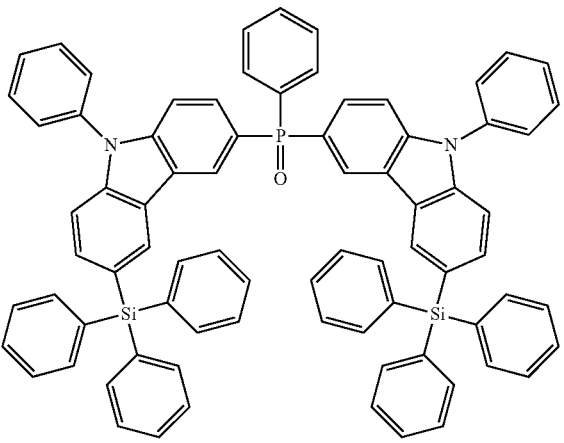

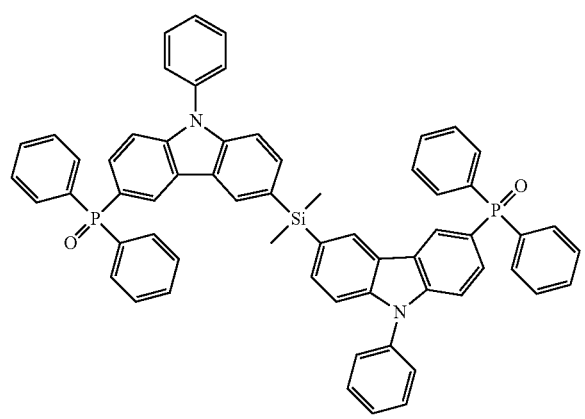

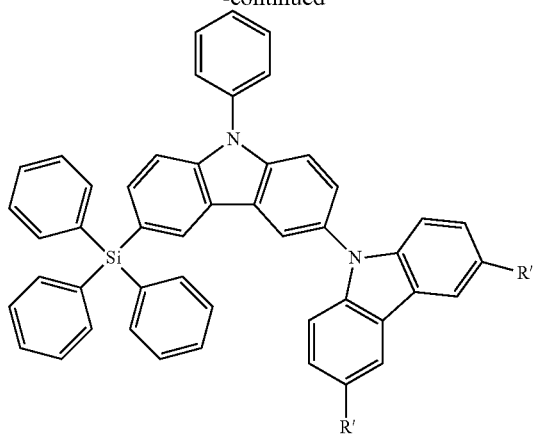
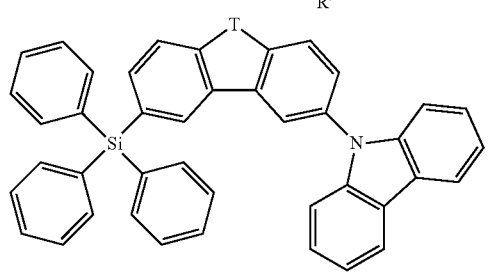
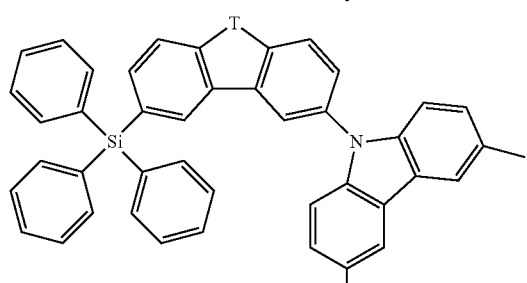
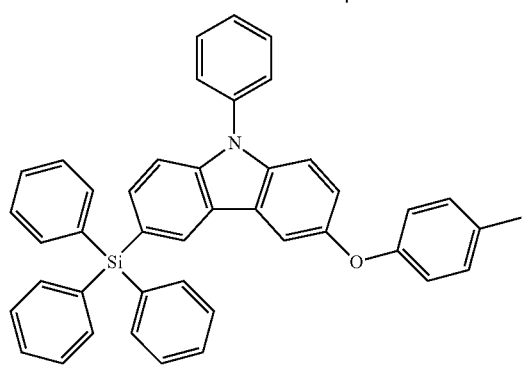
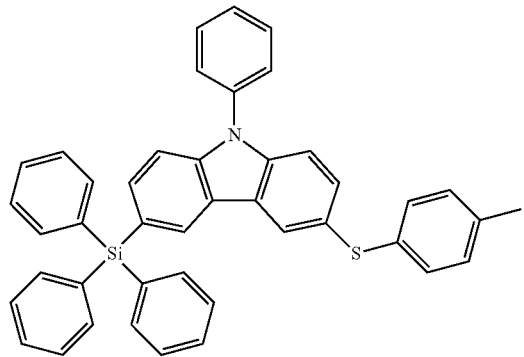
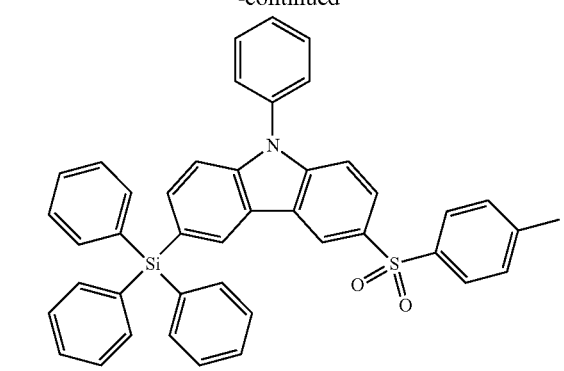
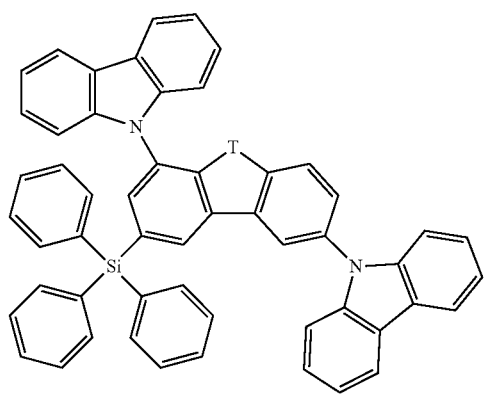
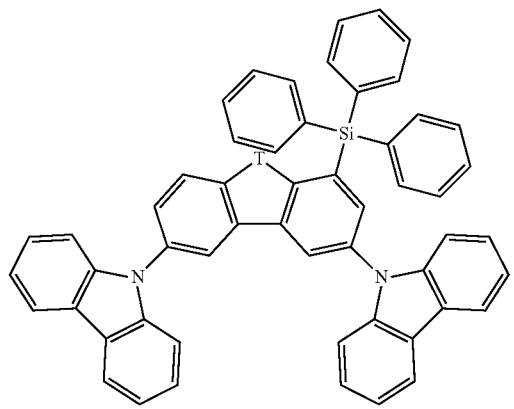
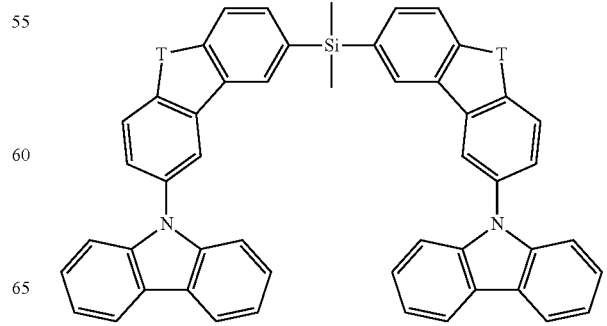

-continued
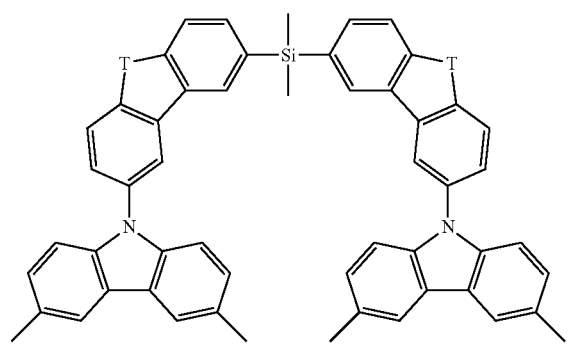
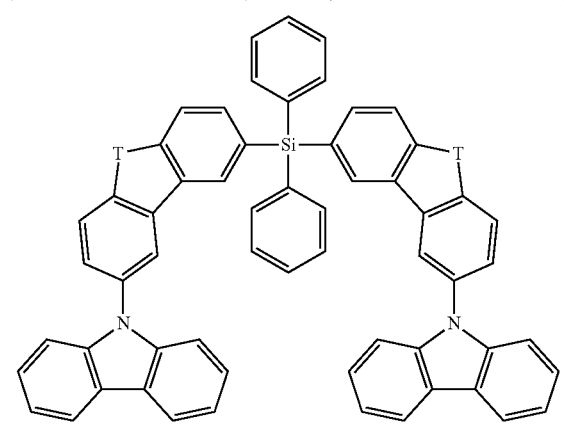
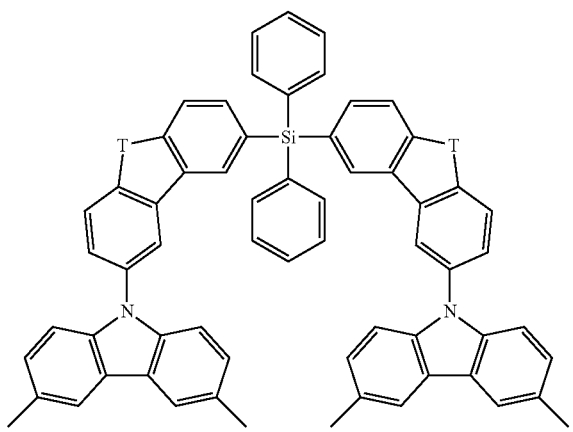
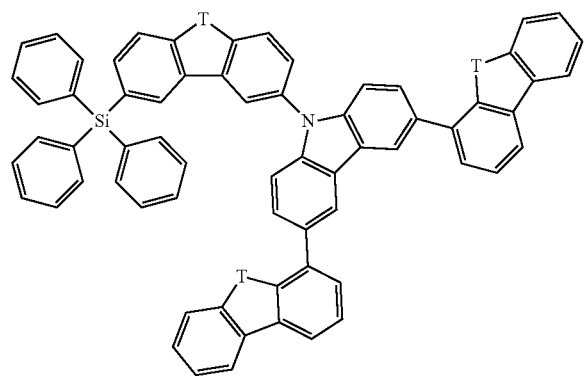
-continued
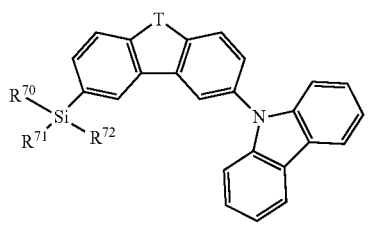
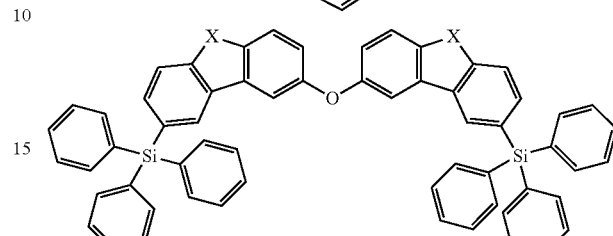
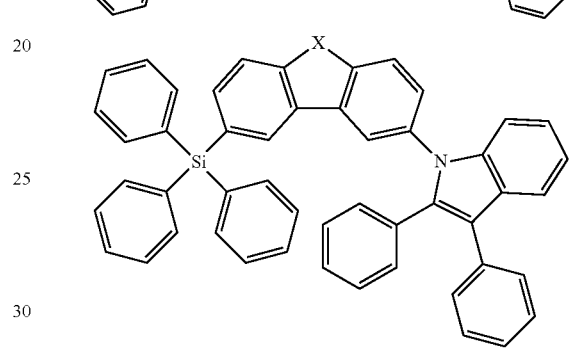
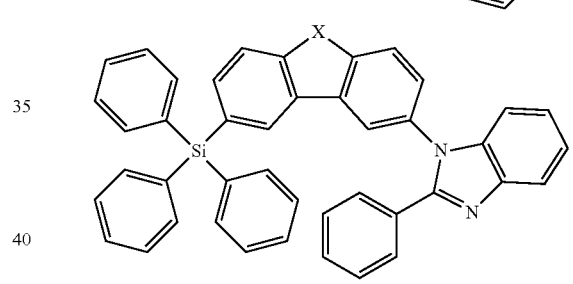
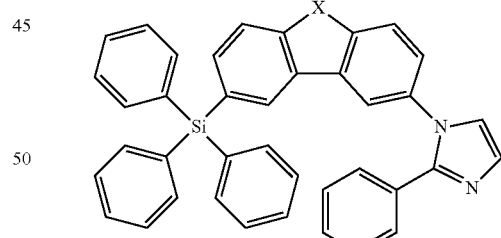
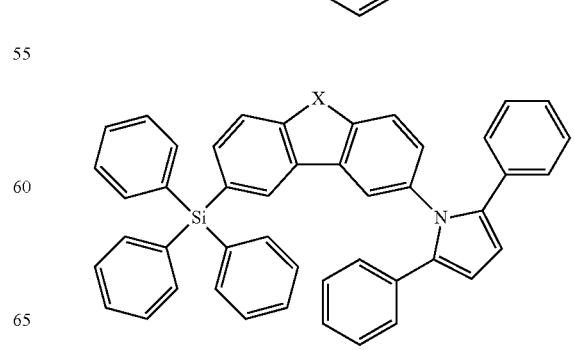

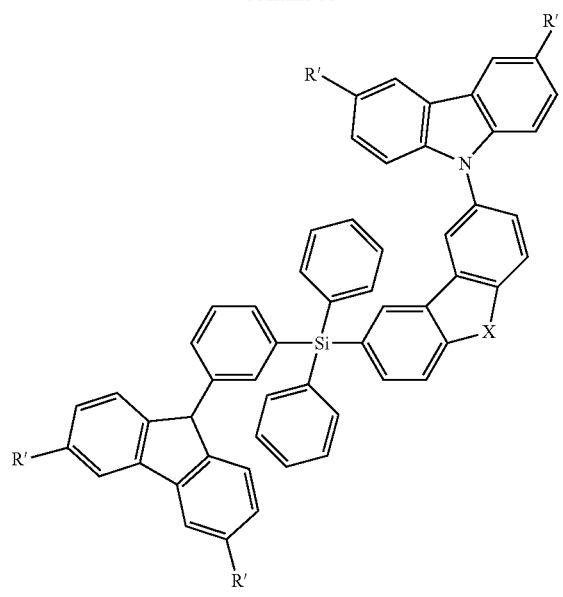
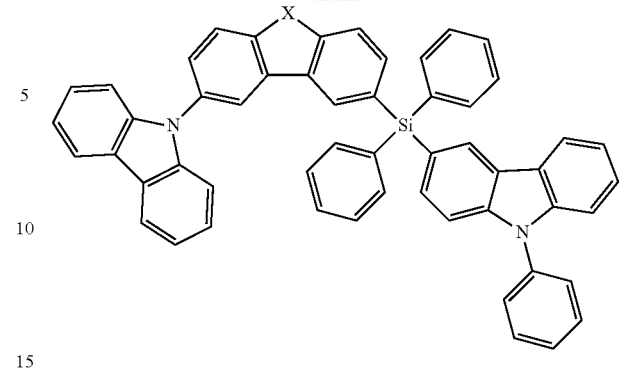
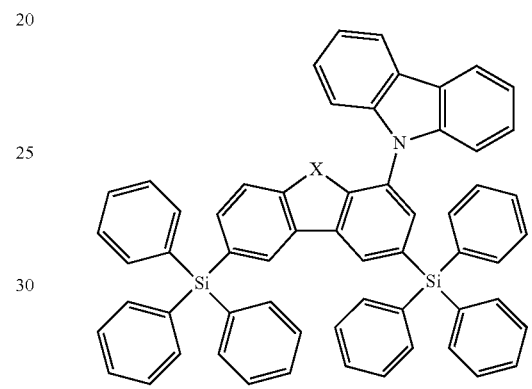
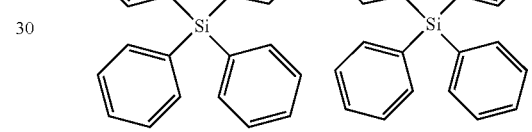
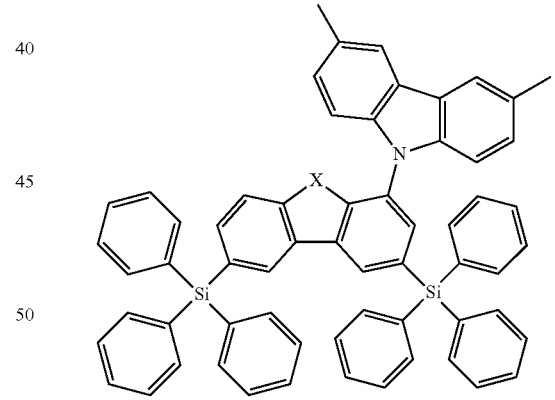
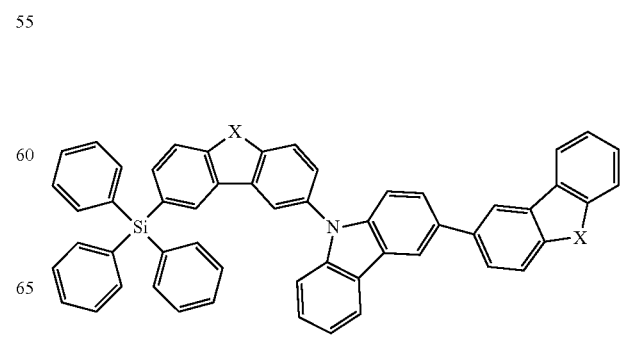

-continued
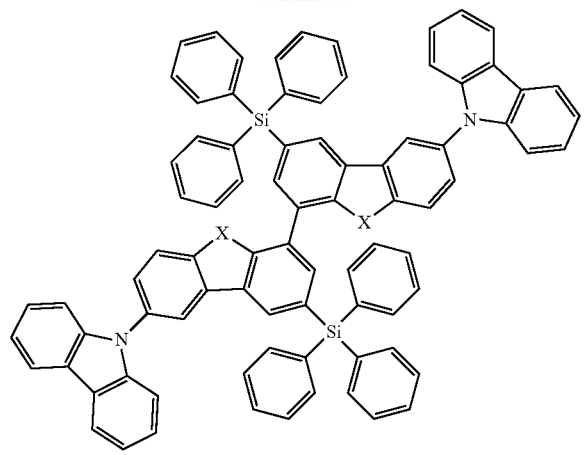
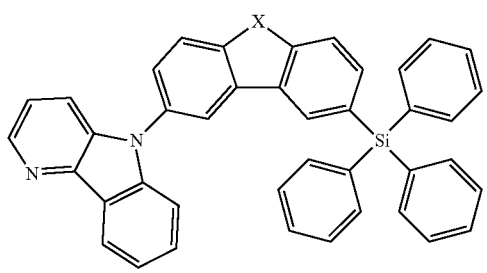
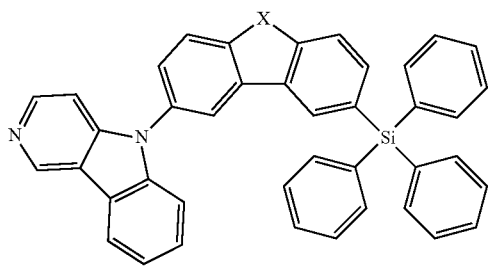
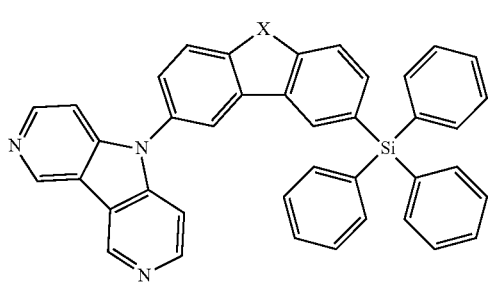
-continued
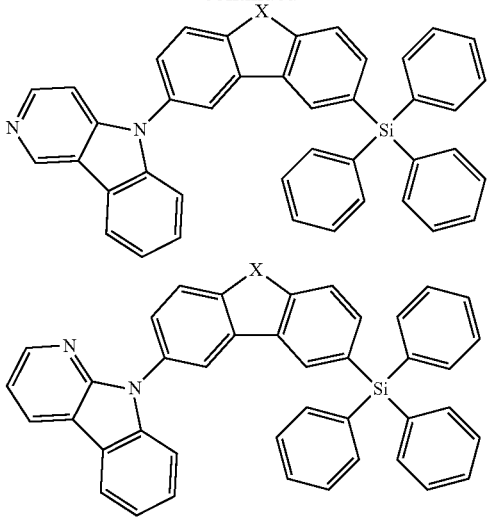
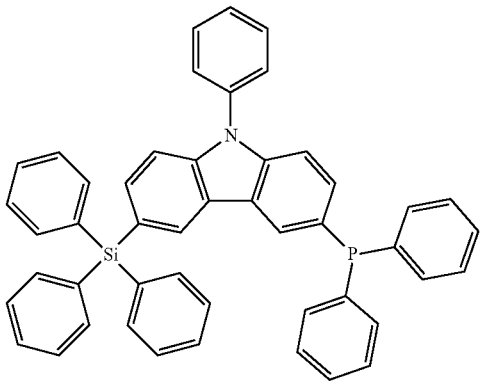
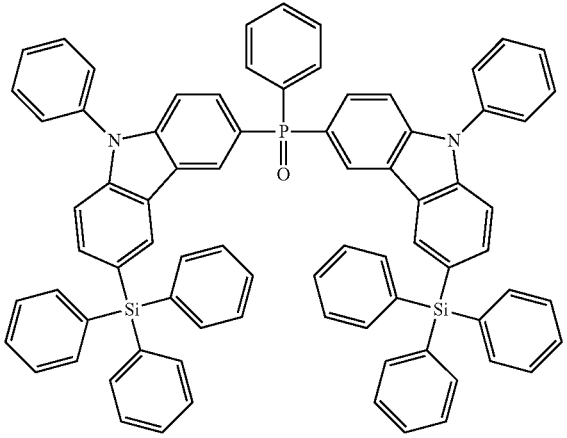 [SMILES: O=P(c1ccccc1)(c1ccc2c(c1)c1cc([Si](c3ccccc3)(c3ccccc3)c3ccccc3)ccc1n2-c1ccccc1)c1ccc2c(c1)c1cc([Si](c3ccccc3)(c3ccccc3)c3ccccc3)ccc1n2-c1ccccc1]
In these particularly preferred compounds of the general formula (XI) or (XI*):
T is S or O, and
R' is H or CH$_3$; and
$R^{70}$, $R^{71}$, $R^{72}$ are each phenyl, carbazolyl, dibenzofuran or dibenzothiophene.

Further particularly suitable compounds of the general formula (XI) or (XI*) are:
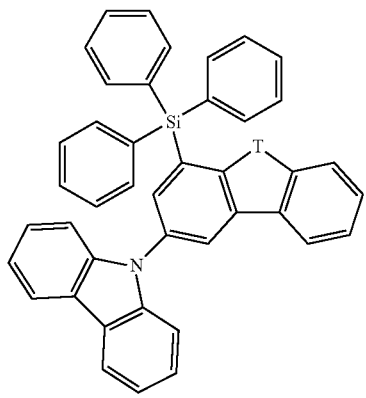
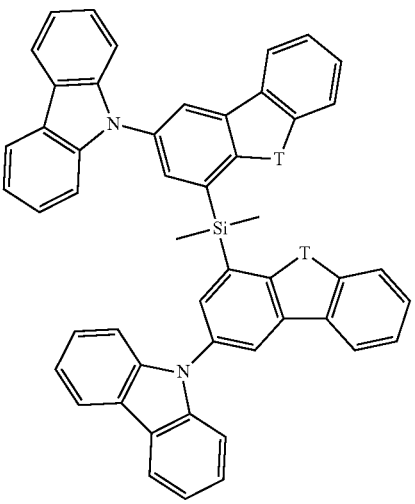
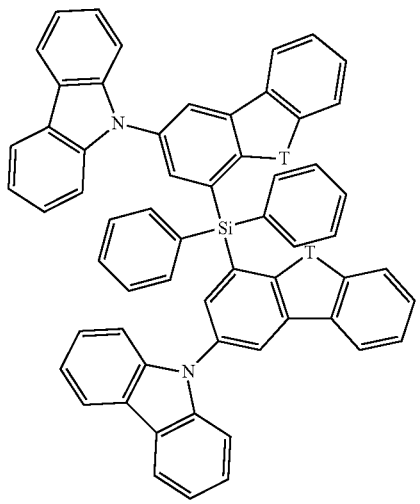
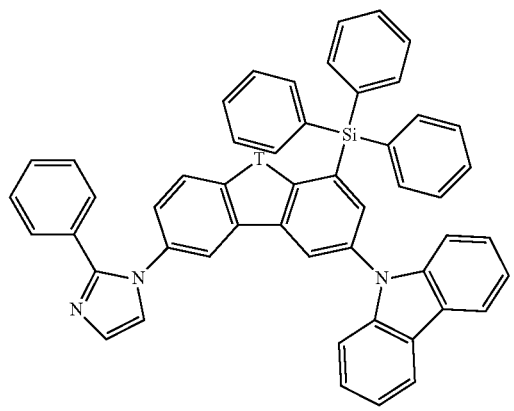
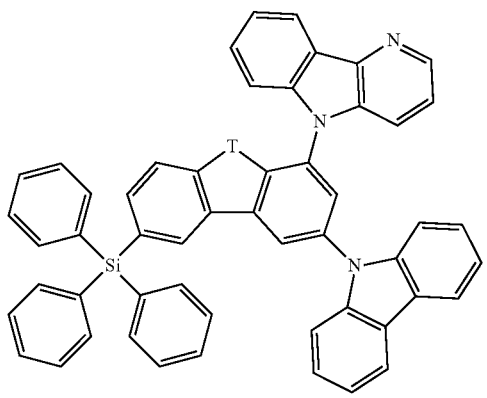
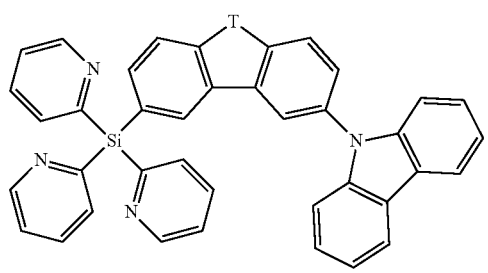
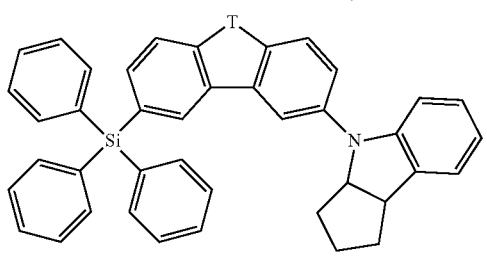

-continued
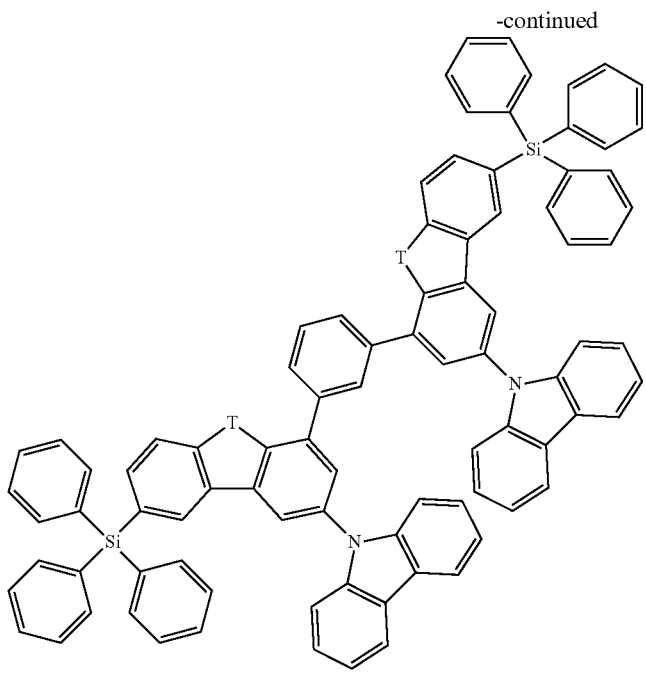
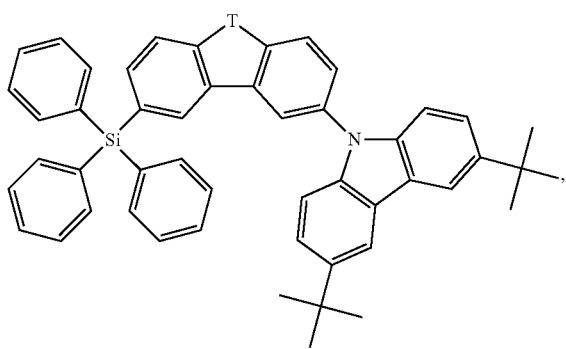
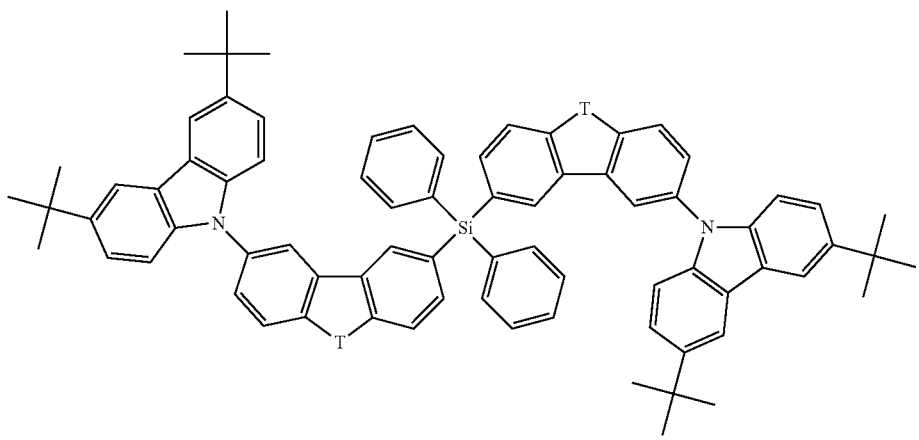

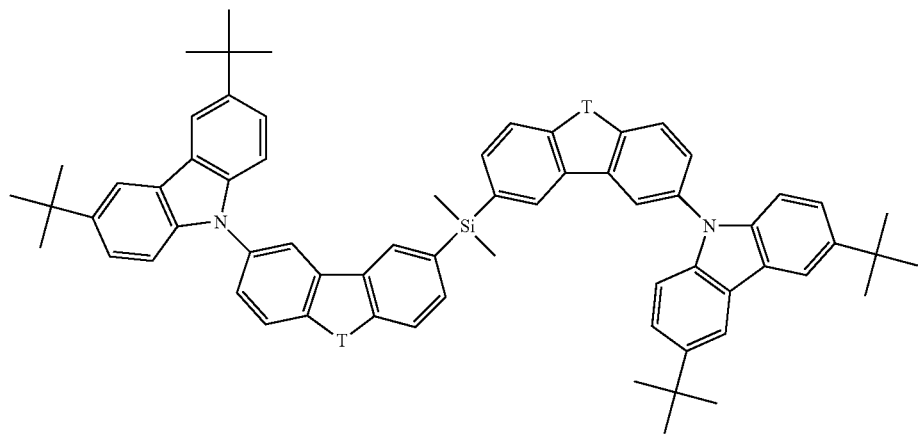
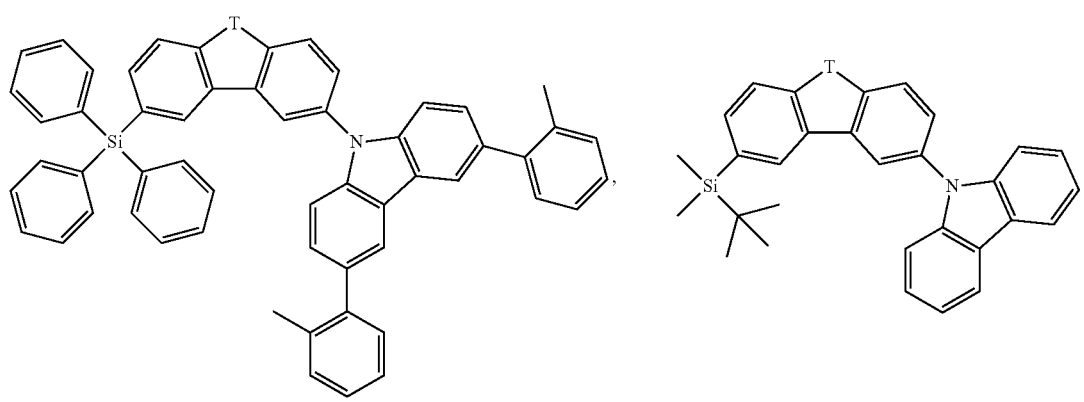
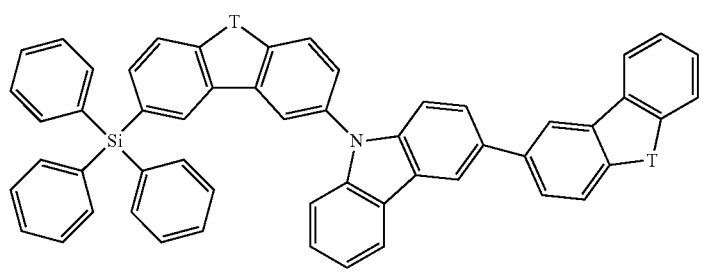
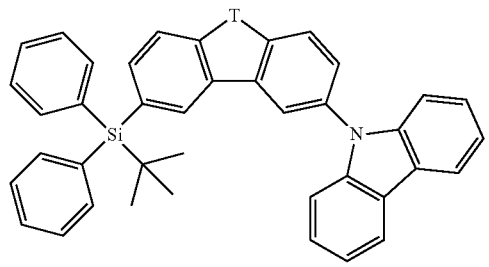
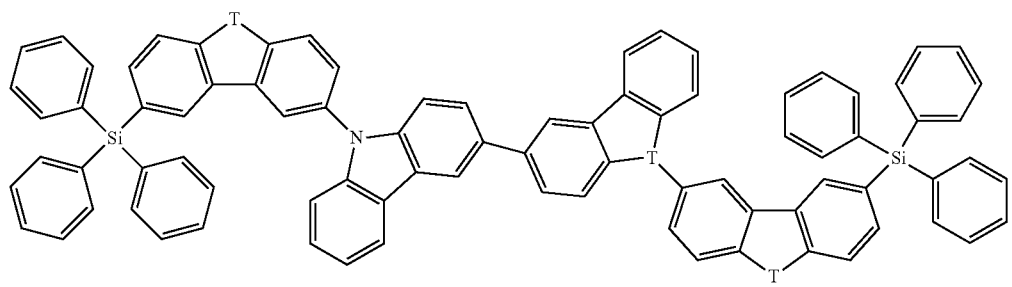

-continued
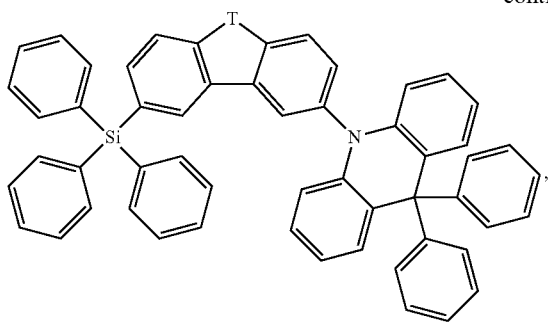
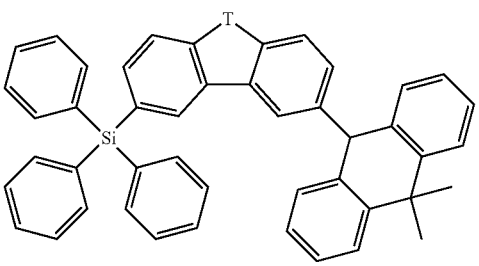
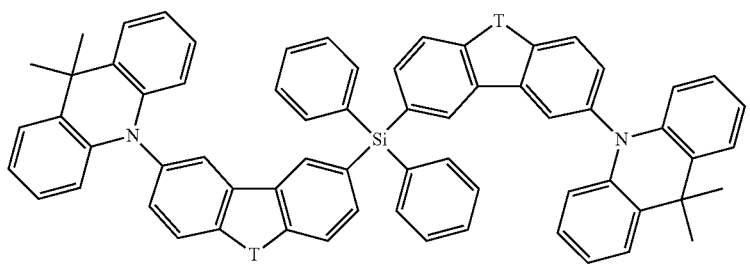
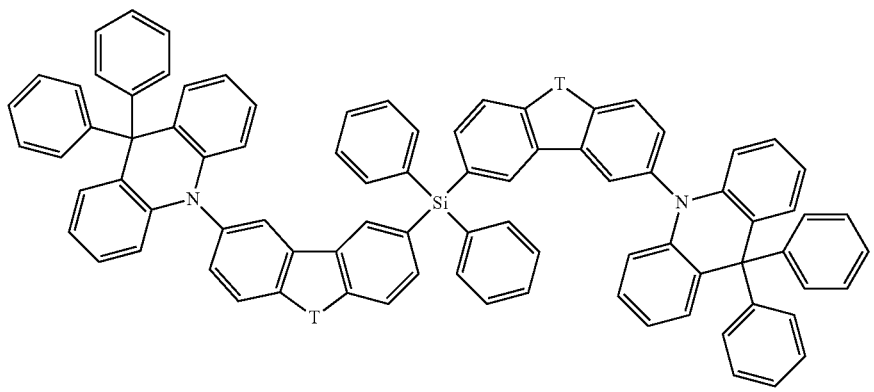
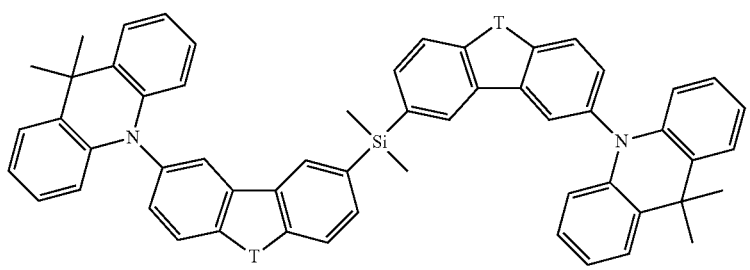
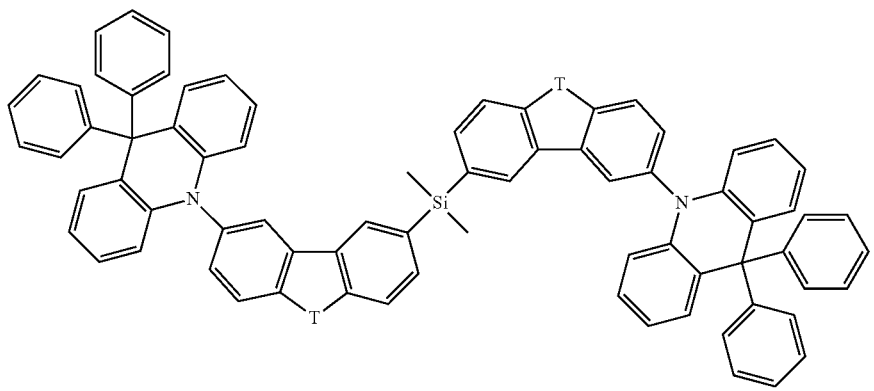

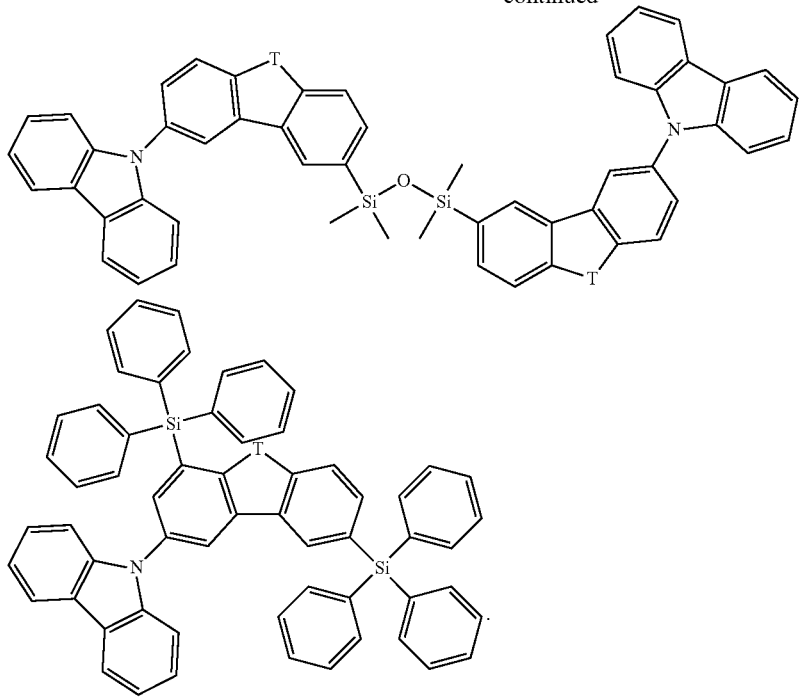

In these particularly preferred compounds of the general formula (XI) or (XI*) too, T is O or S, preferably O.

Further inventive compounds of the general formula (XI) or (XI*) correspond to the following formula (XII)

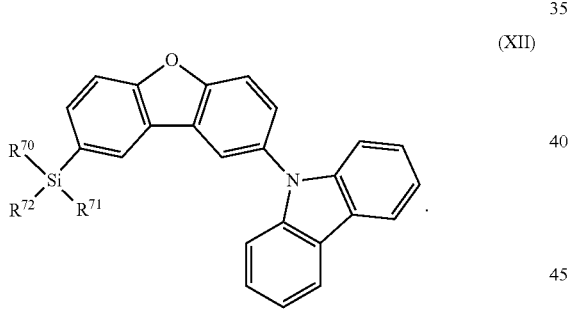

(XII)

In the general formula (XII), $R^{70}$, $R^{71}$, $R^{72}$ are each defined as follows:

| No. | $R^{70}$ | $R^{71}$ | $R^{72}$ |
|---|---|---|---|
| 1 | methyl | methyl | ethyl |
| 2 | methyl | methyl | i-propyl |
| 3 | methyl | methyl | n-propyl |
| 4 | methyl | methyl | n-butyl |
| 5 | methyl | methyl | i-butyl |
| 6 | methyl | methyl | t-butyl |
| 7 | methyl | methyl | n-pentyl |
| 8 | methyl | methyl | n-hexyl |
| 9 | methyl | methyl | —$CH_2CH_2C(CH_3)_3$ |
| 10 | methyl | methyl | n-$C_8H_{17}$ |
| 11 | methyl | methyl | i-$C_8H_{17}$ |
| 12 | methyl | methyl | n-$C_{10}H_{21}$ |
| 13 | methyl | methyl | n-$C_{12}H_{25}$ |
| 16 | methyl | methyl | n-$C_{18}H_{37}$ |
| 17 | methyl | methyl | n-$C_{30}H_{61}$ |
| 19 | methyl | methyl | cyclohexyl |

-continued

| No. | R⁷⁰ | R⁷¹ | R⁷² |
|---|---|---|---|
| 20 | methyl | methyl | C(CH₃)₂Ph |
| 21 | methyl | methyl | —C(CH₃)₂CH(CH₃)₂ |
| 22 | methyl | methyl | —CCH₂CH(CH₃)(C₂H₅) |
| 23 | methyl | methyl | —CH₂CH(C₁₀H₂₁)₂ |
| 24 | methyl | methyl | —CH₂CH(C₁₂H₂₅)₂ |
| 25 | methyl | methyl | —CH₂CH₂(C₃F₆)CF₃ |
| 26 | methyl | methyl | —CH₂CH₂(C₇F₁₄)CF₃ |
| 27 | methyl | methyl | —CH₂CH₂(C₅F₁₀)CF₃ |
| 29 | methyl | methyl | —CH₂CH₂CF₃ |
| 30 | methyl | methyl | phenyl |
| 31 | methyl | methyl | 2-biphenyl |
| 32 | methyl | methyl | p-tolyl |
| 33 | methyl | methyl | C₆F₅ |
| 34 | methyl | methyl | 3,5-(CF₃)₂phenyl |
| 35 | methyl | methyl | —CH₂C(CH₃)₂phenyl |
| 36 | methyl | methyl | 9-fluorenyl |
| 37 | methyl | methyl | 3,6-di(tert-butyl)-9-fluorenyl |
| 15 | methyl | methyl | R⁸⁶ |
| 38 | methyl | methyl | —OMe |
| 39 | methyl | methyl | —OEt |
| 40 | methyl | methyl | 2,4,6-t-butylphenoxy |
| 41 | methyl | methyl | —O—tBu (tert-butoxy) |
| 42 | methyl | methyl | —OSiEt₃ |
| 43 | methyl | ethyl | ethyl |
| 44 | methyl | ethyl | phenyl |
| 45 | methyl | ethyl | R⁸⁶ |
| 46 | methyl | n-propyl | n-propyl |
| 47 | methyl | n-propyl | phenyl |
| 48 | methyl | n-propyl | R⁸⁶ |
| 49 | methyl | i-propyl | i-propyl |
| 50 | methyl | i-propyl | phenyl |
| 51 | methyl | i-propyl | R⁸⁶ |
| 52 | methyl | n-butyl | n-butyl |
| 53 | methyl | n-butyl | phenyl |
| 54 | methyl | n-butyl | R⁸⁶ |
| 55 | methyl | i-butyl | i-butyl |
| 56 | methyl | i-butyl | phenyl |
| 57 | methyl | i-butyl | R⁸⁶ |
| 58 | methyl | t-butyl | t-butyl |
| 59 | methyl | t-butyl | phenyl |
| 60 | methyl | t-butyl | R⁸⁶ |
| 61 | methyl | n-pentyl | n-pentyl |
| 62 | methyl | n-pentyl | n-hexyl |
| 63 | methyl | n-pentyl | phenyl |
| 64 | methyl | n-pentyl | R⁸⁶ |
| 65 | methyl | n-hexyl | hexyl |
| 66 | methyl | n-hexyl | phenyl |
| 67 | methyl | n-hexyl | R⁸⁶ |
| 68 | methyl | n-heptyl | R⁸⁶ |
| 69 | methyl | n-octyl | R⁸⁶ |
| 70 | methyl | n-decyl | R⁸⁶ |
| 71 | methyl | n-C₁₂H₂₅ | R⁸⁶ |
| 72 | methyl | n-C₁₈H₃₇ | R⁸⁶ |
| 73 | methyl | n-C₂₂H₄₅ | R⁸⁶ |
| 74 | methyl | n-C₃₀H₆₁ | R⁸⁶ |
| 75 | methyl | cyclopentyl | cyclopentyl |
| 76 | methyl | cyclopentyl | phenyl |
| 77 | methyl | cyclopentyl | R⁸⁶ |
| 78 | methyl | cyclohexyl | cyclohexyl |
| 79 | methyl | cyclohexyl | phenyl |
| 80 | methyl | cyclohexyl | R⁸⁶ |
| 81 | methyl | —CF₂CHF₂ | R⁸⁶ |
| 82 | methyl | —CH₂CH₂CF₃ | R⁸⁶ |
| 83 | methyl | —CH₂CH₂(CF₂)₃CF₃ | R⁸⁶ |
| 84 | methyl | —CH₂CH₂(CF₂)₅CF₃ | R⁸⁶ |
| 85 | methyl | —CH₂CH₂(CF₂)₇CF₃ | R⁸⁶ |
| 86 | methyl | phenyl | phenyl |
| 87 | methyl | phenyl | p-tolyl |
| 89 | methyl | phenyl | mesityl |
| 90 | methyl | phenyl | R⁸⁶ |
| 91 | methyl | p-tolyl | p-tolyl |
| 92 | methyl | p-tolyl | R⁸⁶ |
| 93 | methyl | mesityl | mesityl |
| 94 | methyl | mesityl | R5 |
| 95 | methyl | R⁸⁶ | R⁸⁶ |
| 96 | methyl | methoxy | methoxy |
| 97 | methyl | ethoxy | ethoxy |

-continued

| No. | $R^{70}$ | $R^{71}$ | $R^{72}$ |
|---|---|---|---|
| 98 | methyl | —OSiEt$_3$ | —OSiEt$_3$ |
| 99 | methyl | —O—SiMe$_2$—CH$_2$CH$_2$(CF$_2$)$_4$CF$_3$ | —O—SiMe$_2$—CH$_2$CH$_2$(CF$_2$)$_4$CF$_3$ |
| 100 | ethyl | ethyl | ethyl |
| 101 | ethyl | ethyl | n-propyl |
| 102 | ethyl | ethyl | i-propyl |
| 103 | ethyl | ethyl | n-butyl |
| 104 | ethyl | ethyl | i-butyl |
| 105 | ethyl | ethyl | t-butyl |
| 106 | ethyl | ethyl | phenyl |
| 107 | ethyl | ethyl | R5 |
| 108 | ethyl | phenyl | phenyl |
| 109 | ethyl | phenyl | $R^{86}$ |
| 110 | ethyl | $R^{86}$ | $R^{86}$ |
| 111 | ethyl | ethoxy | ethoxy |
| 112 | n-propyl | n-propyl | n-propyl |
| 113 | n-propyl | n-propyl | phenyl |
| 114 | n-propyl | n-propyl | $R^{86}$ |
| 115 | n-propyl | phenyl | phenyl |
| 116 | n-propyl | phenyl | $R^{86}$ |
| 117 | n-propyl | $R^{86}$ | $R^{86}$ |
| 118 | i-propyl | i-propyl | i-propyl |
| 119 | i-propyl | i-propyl | phenyl |
| 120 | i-propyl | i-propyl | $R^{86}$ |
| 121 | i-propyl | i-propyl | 2-biphenyl |
| 122 | i-propyl | i-propyl | ethoxy |
| 123 | i-propyl | phenyl | phenyl |
| 124 | i-propyl | phenyl | $R^{86}$ |
| 125 | i-propyl | $R^{86}$ | $R^{86}$ |
| 126 | n-butyl | n-butyl | n-butyl |
| 127 | n-butyl | n-butyl | phenyl |
| 128 | n-butyl | n-butyl | $R^{86}$ |
| 129 | n-butyl | n-hexyl | $R^{86}$ |
| 130 | n-butyl | phenyl | phenyl |
| 131 | n-butyl | phenyl | $R^{86}$ |
| 132 | n-butyl | $R^{86}$ | $R^{86}$ |
| 133 | sec-butyl | sec-butyl | sec-butyl |
| 134 | sec-butyl | sec-butyl | phenyl |
| 135 | sec-butyl | sec-butyl | $R^{86}$ |
| 136 | sec-butyl | phenyl | phenyl |
| 137 | sec-butyl | phenyl | $R^{86}$ |
| 138 | sec-butyl | $R^{86}$ | $R^{86}$ |
| 139 | i-butyl | i-butyl | i-butyl |
| 140 | i-butyl | i-butyl | n-C$_8$H$_{17}$ |
| 141 | i-butyl | i-butyl | n-C$_{18}$H$_{37}$ |
| 142 | i-butyl | i-butyl | phenyl |
| 143 | i-butyl | i-butyl | $R^{86}$ |
| 144 | i-butyl | phenyl | phenyl |
| 145 | i-butyl | phenyl | $R^{86}$ |
| 146 | i-butyl | $R^{86}$ | $R^{86}$ |
| 147 | t-butyl | t-butyl | t-butyl |
| 148 | t-butyl | t-butyl | n-C$_8$H$_{17}$ |
| 149 | t-butyl | t-butyl | phenyl |
| 150 | t-butyl | t-butyl | $R^{86}$ |
| 151 | t-butyl | phenyl | phenyl |
| 152 | t-butyl | phenyl | R5 |
| 153 | t-butyl | $R^{86}$ | $R^{86}$ |
| 154 | n-pentyl | n-pentyl | n-pentyl |
| 155 | n-pentyl | n-pentyl | phenyl |
| 156 | n-pentyl | n-pentyl | $R^{86}$ |
| 157 | n-pentyl | phenyl | phenyl |
| 158 | n-pentyl | phenyl | $R^{86}$ |
| 159 | n-pentyl | $R^{86}$ | $R^{86}$ |
| 160 | cyclopentyl | cyclopentyl | cyclopentyl |
| 161 | cyclopentyl | cyclopentyl | phenyl |
| 162 | cyclopentyl | cyclopentyl | $R^{86}$ |
| 163 | cyclopentyl | phenyl | phenyl |
| 164 | cyclopentyl | phenyl | $R^{86}$ |
| 165 | cyclopentyl | $R^{86}$ | $R^{86}$ |
| 166 | n-hexyl | n-hexyl | n-hexyl |
| 167 | n-hexyl | n-hexyl | phenyl |
| 168 | n-hexyl | n-hexyl | $R^{86}$ |
| 169 | n-hexyl | phenyl | phenyl |
| 170 | n-hexyl | phenyl | $R^{86}$ |
| 171 | n-hexyl | $R^{86}$ | $R^{86}$ |
| 172 | —CH$_2$CH$_2$C(CH$_3$)$_3$ | —CH$_2$CH$_2$C(CH$_3$)$_3$ | —CH$_2$CH$_2$C(CH$_3$)$_3$ |
| 173 | —CH$_2$CH$_2$C(CH$_3$)$_3$ | —CH$_2$CH$_2$C(CH$_3$)$_3$ | $R^{86}$ |
| 174 | —CH$_2$CH$_2$C(CH$_3$)$_3$ | $R^{86}$ | $R^{86}$ |

-continued

| No. | $R^{70}$ | $R^{71}$ | $R^{72}$ |
| --- | --- | --- | --- |
| 175 | t-hexyl | t-hexyl | t-hexyl |
| 176 | t-hexyl | t-hexyl | $R^{86}$ |
| 177 | t-hexyl | $R^{86}$ | $R^{86}$ |
| 178 | n-heptyl | n-heptyl | n-heptyl |
| 179 | n-heptyl | n-heptyl | $R^{86}$ |
| 180 | n-heptyl | $R^{86}$ | $R^{86}$ |
| 181 | n-octyl | n-octyl | n-octyl |
| 182 | n-octyl | n-octyl | $R^{86}$ |
| 183 | n-octyl | $R^{86}$ | $R^{86}$ |
| 184 | i-octyl | i-octyl | i-octyl |
| 185 | i-octyl | i-octyl | $R^{86}$ |
| 186 | i-octyl | $R^{86}$ | $R^{86}$ |
| 187 | n-nonyl | n-nonyl | n-nonyl |
| 188 | n-nonyl | n-nonyl | $R^{86}$ |
| 189 | n-nonyl | $R^{86}$ | $R^{86}$ |
| 190 | cyclohexyl | cyclohexyl | cyclohexyl |
| 191 | cyclohexyl | cyclohexyl | $R^{86}$ |
| 192 | cyclohexyl | $R^{86}$ | $R^{86}$ |
| 193 | cyclooctyl | cyclooctyl | cyclooctyl |
| 194 | cyclooctyl | cyclooctyl | $R^{86}$ |
| 195 | cyclooctyl | $R^{86}$ | $R^{86}$ |
| 196 | n-$C_{10}H_{21}$ | n-$C_{10}H_{21}$ | n-$C_{10}H_{21}$ |
| 197 | n-$C_{10}H_{21}$ | n-$C_{10}H_{21}$ | $R^{86}$ |
| 198 | n-$C_{10}H_{21}$ | $R^{86}$ | $R^{86}$ |
| 199 | n-$C_{11}H_{23}$ | n-$C_{11}H_{23}$ | n-$C_{11}H_{23}$ |
| 200 | n-$C_{11}H_{23}$ | n-$C_{11}H_{23}$ | $R^{86}$ |
| 201 | n-$C_{11}H_{23}$ | $R^{86}$ | $R^{86}$ |
| 202 | n-$C_{12}H_{25}$ | n-$C_{12}H_{25}$ | n-$C_{12}H_{25}$ |
| 203 | n-$C_{12}H_{25}$ | n-$C_{12}H_{25}$ | $R^{86}$ |
| 204 | n-$C_{12}H_{25}$ | $R^{86}$ | $R^{86}$ |
| 205 | n-$C_{14}H_{29}$ | n-$C_{14}H_{29}$ | n-$C_{14}H_{29}$ |
| 206 | n-$C_{14}H_{29}$ | n-$C_{14}H_{29}$ | $R^{86}$ |
| 207 | n-$C_{14}H_{29}$ | $R^{86}$ | $R^{86}$ |
| 208 | n-$C_{16}H_{33}$ | n-$C_{16}H_{33}$ | n-$C_{16}H_{33}$ |
| 209 | n-$C_{16}H_{33}$ | n-$C_{16}H_{33}$ | $R^{86}$ |
| 210 | n-$C_{16}H_{33}$ | $R^{86}$ | $R^{86}$ |
| 211 | n-$C_{18}H_{37}$ | n-$C_{18}H_{37}$ | $R^{86}$ |
| 212 | n-$C_{18}H_{37}$ | $R^{86}$ | $R^{86}$ |
| 213 | n-$C_{18}H_{37}$ | OEt | OEt |
| 214 | n-$C_{18}H_{37}$ | $R^{86}$ | OMe |
| 215 | n-$C_{20}H_{41}$ | n-$C_{20}H_{41}$ | n-$C_{20}H_{41}$ |
| 216 | n-$C_{20}H_{41}$ | n-$C_{20}H_{41}$ | $R^{86}$ |
| 217 | n-$C_{20}H_{41}$ | $R^{86}$ | $R^{86}$ |
| 218 | n-$C_{22}H_{45}$ | n-$C_{22}H_{45}$ | n-$C_{22}H_{45}$ |
| 219 | n-$C_{22}H_{45}$ | n-$C_{22}H_{45}$ | $R^{86}$ |
| 220 | n-$C_{22}H_{45}$ | $R^{86}$ | $R^{86}$ |
| 221 | n-$C_{26}H_{53}$ | n-$C_{26}H_{53}$ | n-$C_{26}H_{53}$ |
| 222 | n-$C_{26}H_{53}$ | n-$C_{26}H_{53}$ | $R^{86}$ |
| 223 | n-$C_{26}H_{53}$ | $R^{86}$ | $R^{86}$ |
| 224 | n-$C_{30}H_{61}$ | n-$C_{30}H_{61}$ | n-$C_{30}H_{61}$ |
| 225 | n-$C_{30}H_{61}$ | n-$C_{30}H_{61}$ | $R^{86}$ |
| 226 | n-$C_{30}H_{61}$ | $R^{86}$ | $R^{86}$ |
| 227 | —$CH_2$-cyclohexyl | —$CH_2$-cyclohexyl | $R^{86}$ |
| 228 | —$CH_2CH_2CF_3$ | —$CH_2CH_2CF_3$ | —$CH_2CH_2CF_3$ |
| 229 | —$CH_2CH_2CF_3$ | —$CH_2CH_2CF_3$ | $R^{86}$ |
| 230 | —$CH_2CH_2CF_3$ | $R^{86}$ | $R^{86}$ |
| 231 | —$CH_2CH_2(CF_2)_3CF_3$ | —$CH_2CH_2(CF_2)_3CF_3$ | —$CH_2CH_2(CF_2)_3CF_3$ |
| 232 | —$CH_2CH_2(CF_2)_3CF_3$ | —$CH_2CH_2(CF_2)_3CF_3$ | $R^{86}$ |
| 233 | —$CH_2CH_2(CF_2)_3CF_3$ | $R^{86}$ | $R^{86}$ |
| 234 | —$CH_2CH_2(CF_2)_5CF_3$ | —$CH_2CH_2(CF_2)_5CF_3$ | —$CH_2CH_2(CF_2)_5CF_3$ |
| 235 | —$CH_2CH_2(CF_2)_5CF_3$ | —$CH_2CH_2(CF_2)_5CF_3$ | $R^{86}$ |
| 236 | —$CH_2CH_2(CF_2)_5CF_3$ | $R^{86}$ | $R^{86}$ |
| 237 | —$CH_2CH_2(CF_2)_7CF_3$ | —$CH_2CH_2(CF_2)_7CF_3$ | —$CH_2CH_2(CF_2)_7CF_3$ |
| 238 | —$CH_2CH_2(CF_2)_7CF_3$ | —$CH_2CH_2(CF_2)_7CF_3$ | $R^{86}$ |
| 239 | —$CH_2CH_2(CF_2)_7CF_3$ | $R^{86}$ | $R^{86}$ |
| 240 | —$CH_2CH_2(CF_2)_9CF_3$ | —$CH_2CH_2(CF_2)_9CF_3$ | —$CH_2CH_2(CF_2)_9CF_3$ |
| 241 | —$CH_2CH_2(CF_2)_9CF_3$ | —$CH_2CH_2(CF_2)_9CF_3$ | $R^{86}$ |
| 242 | —$CH_2CH_2(CF_2)_9CF_3$ | $R^{86}$ | $R^{86}$ |
| 243 | —$CH_2CH_2(CF_2)_{11}CF_3$ | —$CH_2CH_2(CF_2)_{11}CF_3$ | —$CH_2CH_2(CF_2)_{11}CF_3$ |
| 244 | —$CH_2CH_2(CF_2)_{11}CF_3$ | —$CH_2CH_2(CF_2)_{11}CF_3$ | $R^{86}$ |
| 245 | —$CH_2CH_2(CF_2)_{11}CF_3$ | $R^{86}$ | $R^{86}$ |
| 246 | —$CF_2CHF_2$ | —$CF_2CHF_2$ | —$CF_2CHF_2$ |
| 247 | —$CF_2CHF_2$ | —$CF_2CHF_2$ | $R^{86}$ |
| 248 | —$CF_2CHF_2$ | $R^{86}$ | $R^{86}$ |
| 249 | —$(CF_2)_3CHF_2$ | —$(CF_2)_3CHF_2$ | —$(CF_2)_3CHF_2$ |
| 250 | —$(CF_2)_3CHF_2$ | —$(CF_2)_3CHF_2$ | $R^{86}$ |
| 251 | —$(CF_2)_3CHF_2$ | $R^{86}$ | $R^{86}$ |

-continued

| No. | $R^{70}$ | $R^{71}$ | $R^{72}$ |
|---|---|---|---|
| 14 | phenyl | phenyl | phenyl |
| 252 | phenyl | phenyl | p-tolyl |
| 253 | phenyl | phenyl | m-tolyl |
| 254 | phenyl | phenyl | o-tolyl |
| 255 | phenyl | phenyl | 2-xylyl |
| 256 | phenyl | phenyl | 5-xylyl |
| 257 | phenyl | phenyl | mesityl |
| 258 | phenyl | phenyl | 9-fluorenyl |
| 18 | phenyl | phenyl | $R^{86}$ |
| 259 | phenyl | phenyl | —O—tBu (tert-butoxy) |
| 260 | phenyl | p-tolyl | p-tolyl |
| 261 | phenyl | m-tolyl | m-tolyl |
| 262 | phenyl | o-tolyl | o-tolyl |
| 263 | phenyl | 2-xylyl | 2-xylyl |
| 264 | phenyl | 5-xylyl | 5-xylyl |
| 265 | phenyl | mesityl | mesityl |
| 266 | phenyl | $R^{86}$ | $R^{86}$ |
| 267 | phenyl | ethoxy | ethoxy |
| 268 | p-tolyl | p-tolyl | p-tolyl |
| 269 | p-tolyl | p-tolyl | $R^{86}$ |
| 270 | p-tolyl | $R^{86}$ | $R^{86}$ |
| 271 | m-tolyl | m-tolyl | m-tolyl |
| 272 | m-tolyl | m-tolyl | $R^{86}$ |
| 273 | o-tolyl | o-tolyl | o-tolyl |
| 274 | o-tolyl | o-tolyl | $R^{86}$ |
| 275 | 2-xylyl | 2-xylyl | 2-xylyl |
| 276 | 2-xylyl | 2-xylyl | $R^{86}$ |
| 277 | 5-xylyl | 5-xylyl | 5-xylyl |
| 278 | 5-xylyl | 5-xylyl | $R^{86}$ |
| 279 | mesityl | mesityl | mesityl |
| 280 | mesityl | mesityl | $R^{86}$ |
| 281 | $C_6F_5$ | $C_6F_5$ | $C_6F_5$ |
| 282 | $C_6F_5$ | $C_6F_5$ | $R^{86}$ |
| 283 | $C_6F_5$ | $R^{86}$ | $R^{86}$ |
| 284 | $R^{86}$ | $R^{86}$ | $R^{86}$ |
| 285 | $R^{86}$ | ethoxy | ethoxy |
| 286 | $R^{86}$ | n-butoxy | n-butoxy |
| 287 | $R^{86}$ | $R^{86}$ | methoxy |
| 288 | $R^{86}$ | $R^{86}$ | ethoxy |
| 289 | $R^{86}$ | $R^{86}$ | OSiMe3 |
| 290 | $R^{86}$ | $R^{86}$ | —$(CH_2)_{11}$O—$(CH_2)_2OCH_3$ |
| 291 | methoxy | methoxy | methoxy |
| 292 | ethoxy | ethoxy | ethoxy |
| 293 | i-propoxy | i-propoxy | i-propoxy |
| 294 | t-butoxy | t-butoxy | t-butoxy |
| 295 | $OSiMe_3$ | $OSiMe_3$ | $OSiMe_3$ |
| 296 |  | cyclobutyl | methyl |
| 297 |  | cyclobutyl | $R^{86}$ |
| 298 |  | cyclobutyl | p-methoxyphenyl |
| 299 |  | cyclopentyl | methyl |
| 300 |  | cyclopentyl | $R^{86}$ |
| 301 |  | cyclohexyl | methyl |
| 302 |  | cyclohexyl | $R^{86}$ |

In this table, $R86 =$ 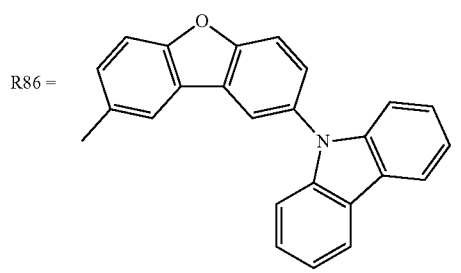 [SMILES: Cc1ccc2oc3ccc(-n4c5ccccc5c5ccccc54)cc3c2c1]

Particularly preferred compounds in which two units of the general formulae (XI) and/or (XI*) are bridged to one another via a linear or branched, saturated or unsaturated bridge optionally interrupted by at least one heteroatom or via 0, where this bridge in the general formulae (XI) and/or (XI*) is in each case attached to the silicon atoms in place of $R^{71}$, correspond to the general formula (XII)

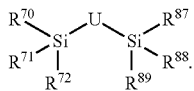

(XIII)

In formula (XIII), U, $R^{70}$, $R^{71}$, $R^{72}$, $R^{87}$, $R^{88}$ and $R^{89}$ are each defined as follows:

| No. | R70 | R71 | R72 | R87 | R88 | R89 | U |
|---|---|---|---|---|---|---|---|
| 303 | methyl | $R^{86}$ | $R^{86}$ | methyl | R5 | $R^{86}$ | —$CH_2$— |
| 304 | methyl | methyl | $R^{86}$ | methyl | methyl | $R^{86}$ | —$CH_2$— |
| 305 | $R^{86}$ | $R^{86}$ | $R^{86}$ | $R^{86}$ | $R^{86}$ | $R^{86}$ | —$CH_2$— |
| 306 | methyl | $R^{86}$ | $R^{86}$ | methyl | R5 | $R^{86}$ | —$C_2H_4$— |
| 307 | methyl | methyl | $R^{86}$ | methyl | methyl | $R^{86}$ | —$C_2H_4$— |
| 308 | $R^{86}$ | $R^{86}$ | $R^{86}$ | $R^{86}$ | $R^{86}$ | $R^{86}$ | —$C_2H_4$— |
| 309 | methyl | $R^{86}$ | $R^{86}$ | methyl | $R^{86}$ | $R^{86}$ | —$C_3H_6$— |
| 310 | methyl | methyl | $R^{86}$ | methyl | methyl | $R^{86}$ | —$C_3H_6$— |
| 311 | $R^{86}$ | $R^{86}$ | $R^{86}$ | $R^{86}$ | $R^{86}$ | $R^{86}$ | —$C_3H_6$— |
| 312 | methyl | $R^{86}$ | $R^{86}$ | methyl | $R^{86}$ | $R^{86}$ | —$C_4H_8$— |
| 313 | methyl | methyl | $R^{86}$ | methyl | methyl | $R^{86}$ | —$C_4H_8$— |
| 314 | $R^{86}$ | $R^{86}$ | $R^{86}$ | $R^{86}$ | $R^{86}$ | $R^{86}$ | —$C_4H_8$— |
| 315 | methyl | $R^{86}$ | $R^{86}$ | methyl | $R^{86}$ | $R^{86}$ | —$C_6H_{12}$— |
| 316 | methyl | methyl | $R^{86}$ | methyl | methyl | $R^{86}$ | —$C_6H_{12}$— |
| 317 | $R^{86}$ | $R^{86}$ | $R^{86}$ | $R^{86}$ | $R^{86}$ | $R^{86}$ | —$C_6H_{12}$— |
| 318 | methyl | $R^{86}$ | $R^{86}$ | methyl | $R^{86}$ | $R^{86}$ | —$C_8H_{16}$— |
| 319 | methyl | methyl | $R^{86}$ | methyl | methyl | $R^{86}$ | —$C_8H_{16}$— |
| 320 | $R^{86}$ | $R^{86}$ | $R^{86}$ | $R^{86}$ | $R^{86}$ | $R^{86}$ | —$C_8H_{16}$— |
| 321 | methyl | $R^{86}$ | $R^{86}$ | methyl | $R^{86}$ | $R^{86}$ | —$C_9H_{18}$— |
| 322 | methyl | methyl | $R^{86}$ | methyl | methyl | $R^{86}$ | —$C_9H_{18}$— |
| 323 | $R^{86}$ | $R^{86}$ | $R^{86}$ | $R^{86}$ | $R^{86}$ | $R^{86}$ | —$C_9H_{18}$— |
| 324 | $R^{86}$ | $R^{86}$ | $R^{86}$ | $R^{86}$ | $R^{86}$ | $R^{86}$ | —$CH(C_8H_{17})CH_2$— |
| 325 | methyl | $R^{86}$ | $R^{86}$ | methyl | $R^{86}$ | $R^{86}$ | —$C_2H_4(CF_2)_8C_2H_4$— |
| 326 | methyl | methyl | $R^{86}$ | methyl | methyl | $R^{86}$ | —$C_2H_4(CF_2)_8C_2H_4$— |
| 327 | $R^{86}$ | $R^{86}$ | $R^{86}$ | $R^{86}$ | $R^{86}$ | $R^{86}$ | —$C_2H_4(CF_2)_8C_2H_4$— |
| 328 | methyl | $R^{86}$ | $R^{86}$ | methyl | $R^{86}$ | $R^{86}$ | —C≡C— |
| 329 | methyl | methyl | $R^{86}$ | methyl | methyl | $R^{86}$ | —C≡C— |
| 330 | $R^{86}$ | $R^{86}$ | $R^{86}$ | $R^{86}$ | $R^{86}$ | $R^{86}$ | —C≡C— |
| 331 | methyl | $R^{86}$ | $R^{86}$ | methyl | $R^{86}$ | $R^{86}$ | -1,4-$(CH_2)_2$-phenyl-$(CH_2)_2$— |
| 332 | methyl | methyl | $R^{86}$ | methyl | methyl | $R^{86}$ | -1,4-$(CH_2)_2$-phenyl-$(CH_2)_2$— |
| 333 | $R^{86}$ | $R^{86}$ | $R^{86}$ | $R^{86}$ | $R^{86}$ | $R^{86}$ | -1,4-$(CH_2)_2$-phenyl-$(CH_2)_2$— |
| 334 | methyl | $R^{86}$ | $R^{86}$ | methyl | $R^{86}$ | $R^{86}$ | -1,3-$(CH_2)_2$-phenyl-$(CH_2)_2$— |
| 335 | methyl | methyl | $R^{86}$ | methyl | methyl | $R^{86}$ | -1,3-$(CH_2)_2$-phenyl-$(CH_2)_2$— |
| 336 | $R^{86}$ | $R^{86}$ | $R^{86}$ | $R^{86}$ | $R^{86}$ | $R^{86}$ | -1,3-$(CH_2)_2$-phenyl-$(CH_2)_2$— |
| 337 | methyl | $R^{86}$ | $R^{86}$ | methyl | $R^{86}$ | $R^{86}$ | -1,4-$(CH_2)_3$-phenyl-$(CH_2)_3$— |
| 338 | methyl | methyl | $R^{86}$ | methyl | methyl | $R^{86}$ | -1,4-$(CH_2)_3$-phenyl-$(CH_2)_3$— |
| 339 | $R^{86}$ | $R^{86}$ | $R^{86}$ | $R^{86}$ | $R^{86}$ | $R^{86}$ | -1,4-$(CH_2)_3$-phenyl-$(CH_2)_3$— |
| 340 | methyl | $R^{86}$ | $R^{86}$ | methyl | $R^{86}$ | $R^{86}$ | -1,3-$(CH_2)_3$-phenyl-$(CH_2)_3$— |
| 341 | methyl | methyl | $R^{86}$ | methyl | methyl | $R^{86}$ | -1,3-$(CH_2)_3$-phenyl-$(CH_2)_3$— |
| 342 | $R^{86}$ | $R^{86}$ | $R^{86}$ | $R^{86}$ | $R^{86}$ | $R^{86}$ | -1,3-$(CH_2)_3$-phenyl-$(CH_2)_3$— |
| 343 | methyl | $R^{86}$ | $R^{86}$ | methyl | $R^{86}$ | $R^{86}$ | -1,4-phenyl- |
| 344 | methyl | methyl | $R^{86}$ | methyl | methyl | $R^{86}$ | -1,4-phenyl- |
| 345 | $R^{86}$ | $R^{86}$ | $R^{86}$ | $R^{86}$ | $R^{86}$ | $R^{86}$ | -1,4-phenyl- |
| 346 | methyl | $R^{86}$ | $R^{86}$ | methyl | $R^{86}$ | $R^{86}$ | -1,3-phenyl- |
| 347 | methyl | methyl | $R^{86}$ | methyl | methyl | $R^{86}$ | -1,3-phenyl- |
| 348 | $R^{86}$ | $R^{86}$ | $R^{86}$ | $R^{86}$ | $R^{86}$ | $R^{86}$ | -1,3-phenyl- |
| 28 | methyl | methyl | $R^{86}$ | methyl | methyl | $R^{86}$ | —O— |
| 349 | methyl | $R^{86}$ | $R^{86}$ | methyl | $R^{86}$ | $R^{86}$ | —O— |
| 350 | methyl | methyl | $R^{86}$ | methyl | methyl | $R^{86}$ | —O—Si$(CH_3)_2$—O— |
| 351 | methyl | methyl | $R^{86}$ | methyl | methyl | $R^{86}$ | —O—Si$(CH_3)$(Ph)—O— |
| 352 | methyl | methyl | $R^{86}$ | methyl | methyl | $R^{86}$ | —O—Si$(CH_3)_2$—O—Si$(CH_3)_2$—O— |
| 353 | methyl | methyl | $R^{86}$ | methyl | methyl | $R^{86}$ | —O—Si$(CH_3)_2$—O—Si$(CH_3)_2$—O—Si$(CH_3)_2$—O— |
| 354 | methyl | —OSiMe$_3$ | $R^{86}$ | methyl | —OSiMe$_3$ | $R^{86}$ | —O— |
| 355 | methyl | phenyl | $R^{86}$ | methyl | phenyl | $R^{86}$ | —O— |
| 356 | i-propyl | i-propyl | $R^{86}$ | i-propyl | i-propyl | $R^{86}$ | —O— |

| No. | R70 | R71 | R72 | R87 | R88 | R89 | U |
|---|---|---|---|---|---|---|---|
| 357 | cyclopentyl | cyclopentyl | $R^{86}$ | cyclopentyl | cyclopentyl | $R^{86}$ | —O— |
| 358 | phenyl | phenyl | $R^{86}$ | phenyl | phenyl | $R^{86}$ | —O— |
| 359 | phenyl | $R^{86}$ | $R^{86}$ | phenyl | $R^{86}$ | $R^{86}$ | —O— |
| 360 | $R^{86}$ | $R^{86}$ | $R^{86}$ | $R^{86}$ | $R^{86}$ | $R^{86}$ | —O— |

In this table, $R^{86}$ =

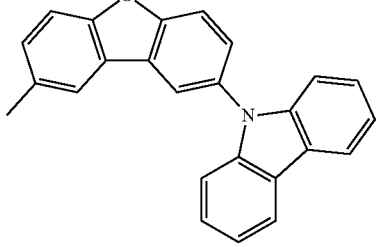

Further suitable compounds of the formula (XI) and/or (XI*) are specified hereinafter. R therein is independently Me, phenyl or $R^{86}$ where at least one R radical is $R^{86}$:

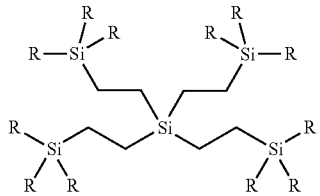

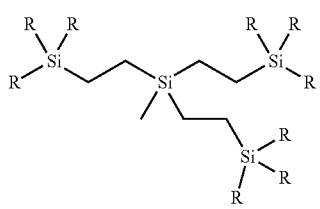

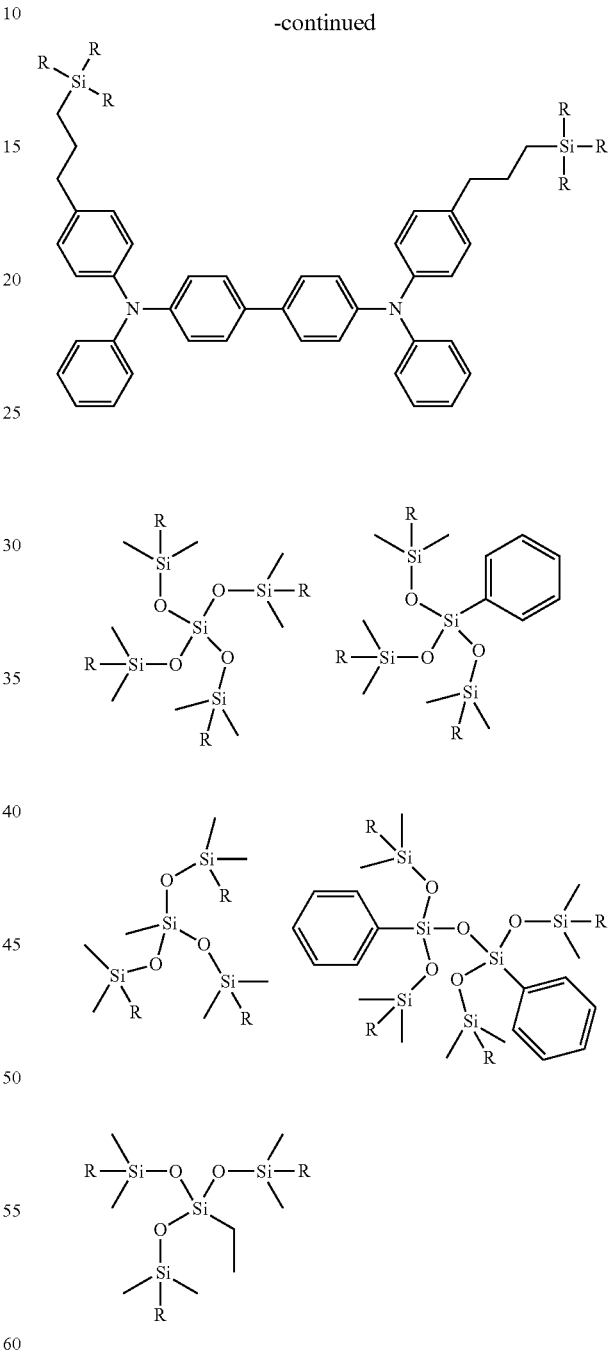

In a very particularly preferred embodiment, the present invention relates to an OLED which, as well as at least one metal-carbene complex of the general formula (I), comprises at least one compound of the general formula (X), in which case the compound of the formula (X) is most preferably at least one of the compounds specified below:

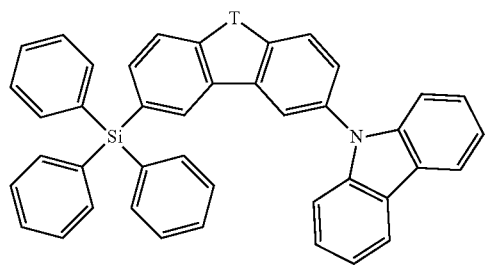
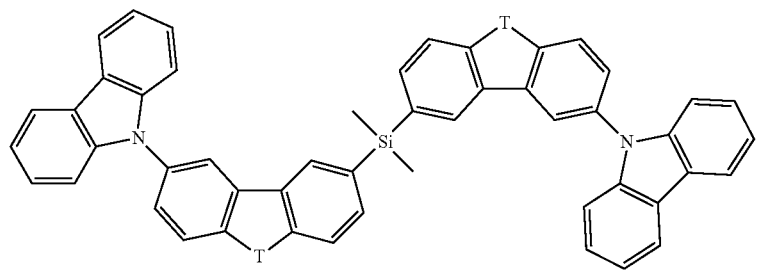
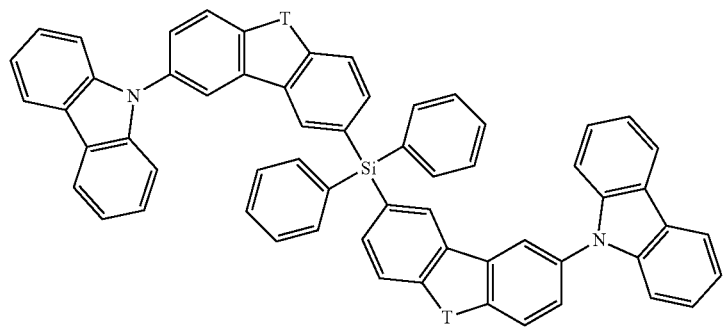
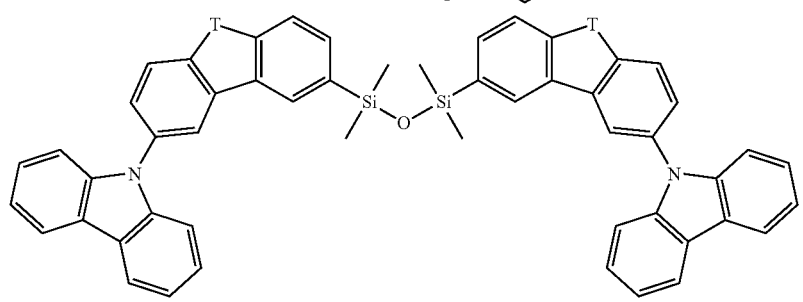
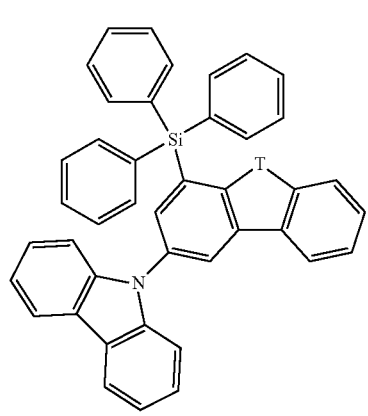
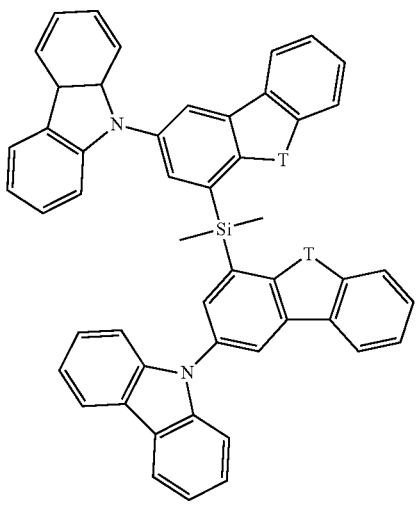

-continued
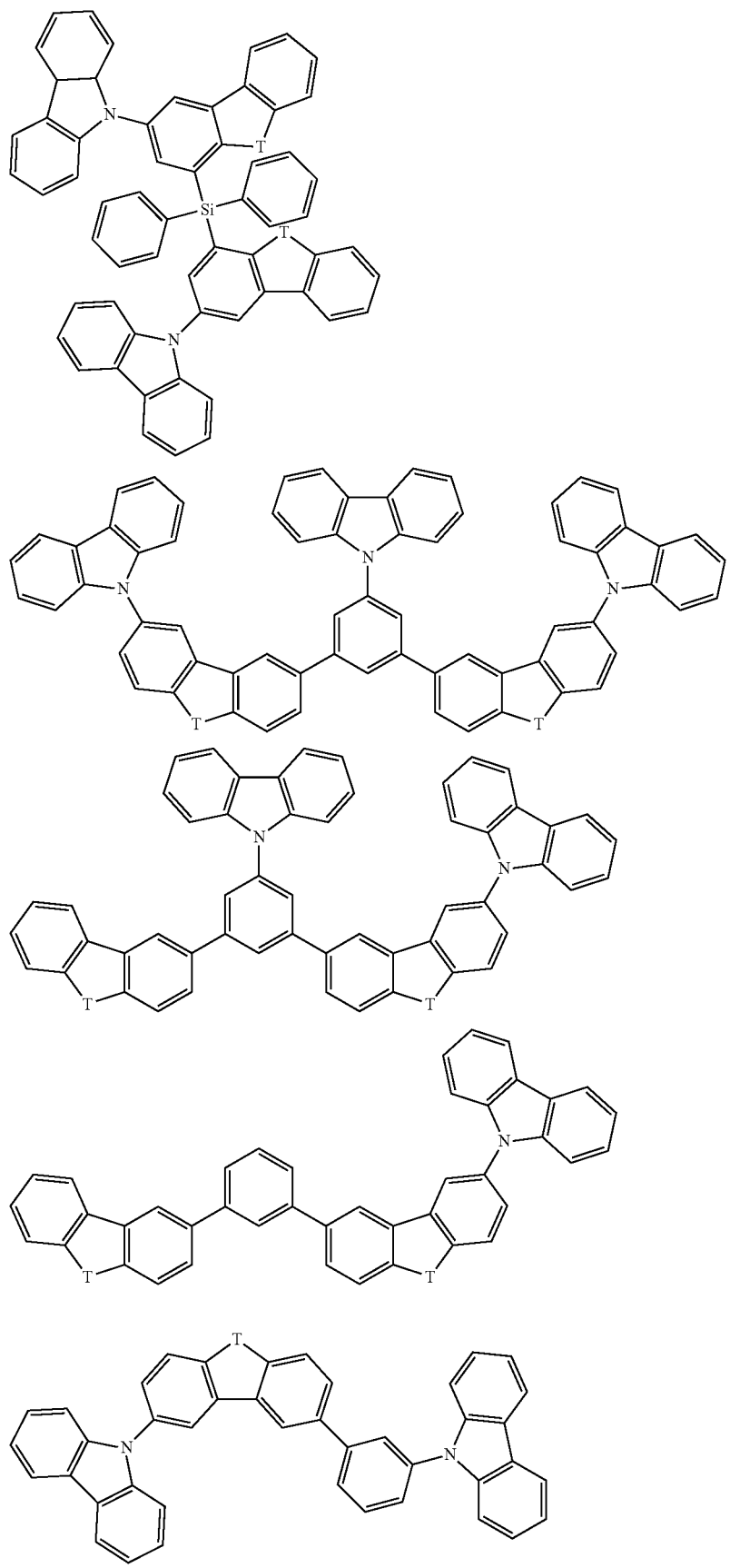

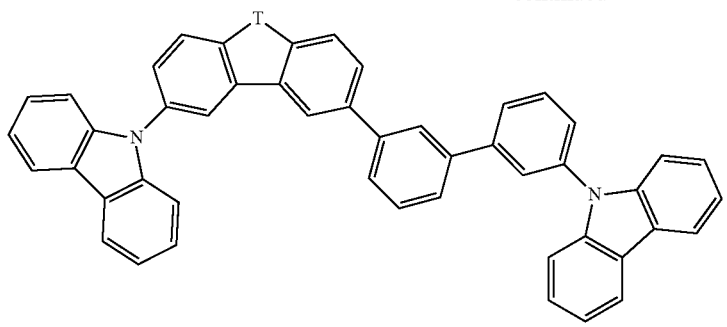
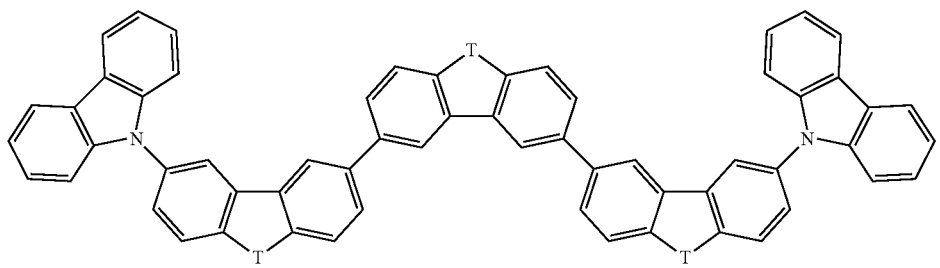
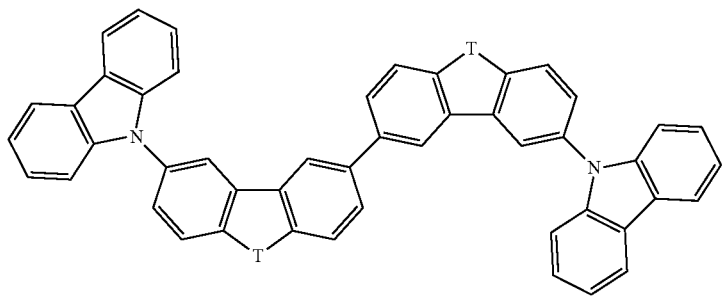
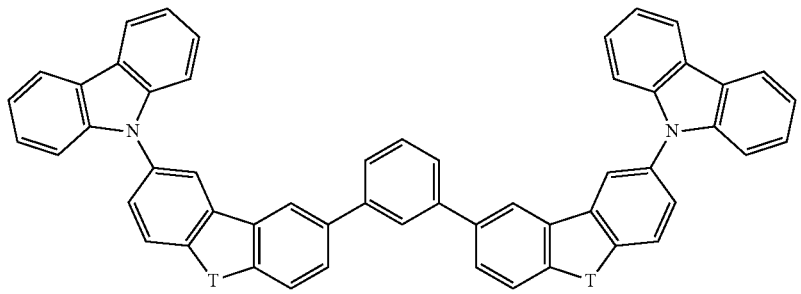
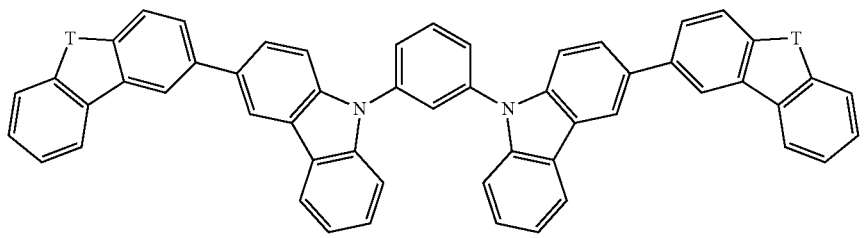

-continued
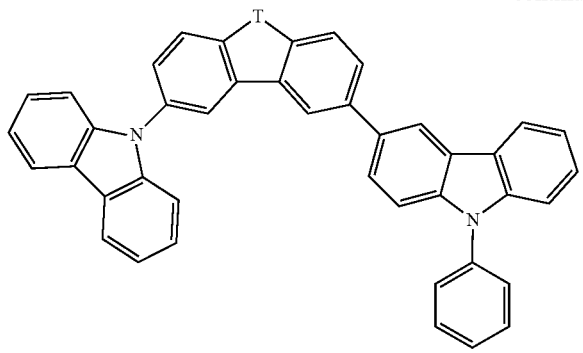
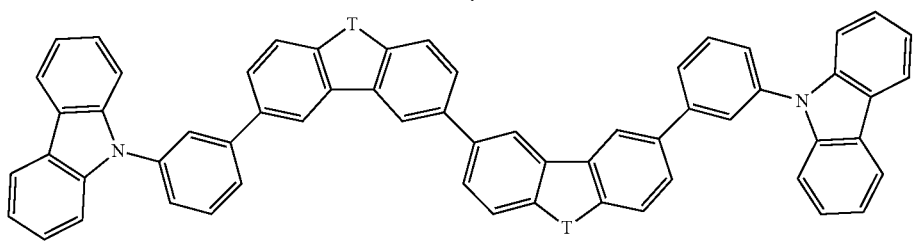
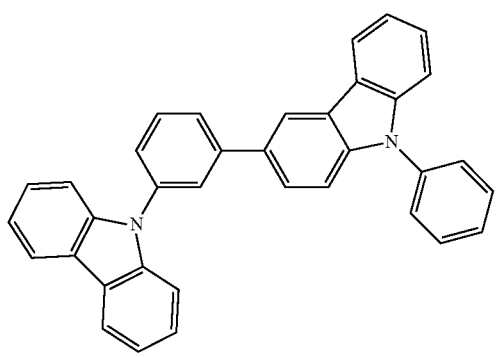
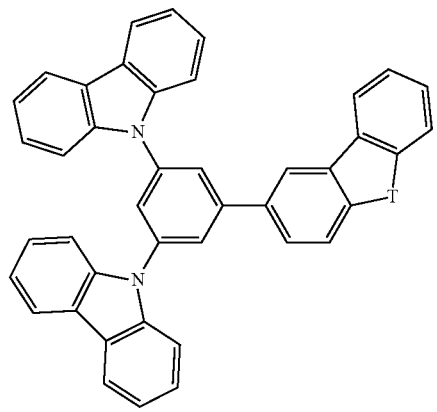
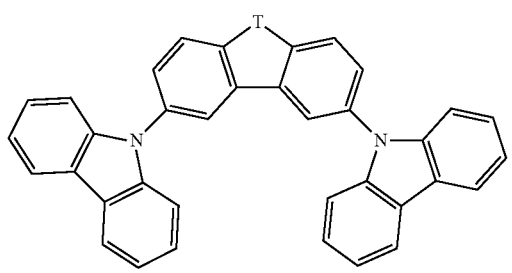
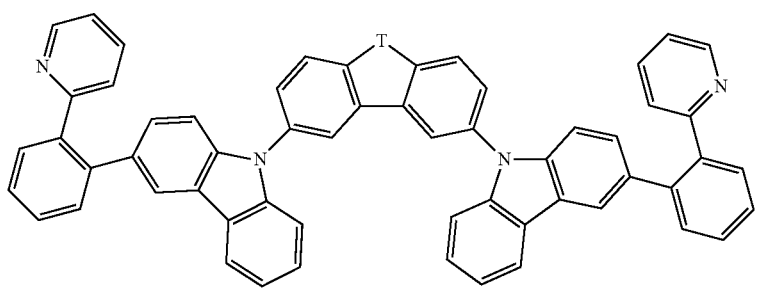

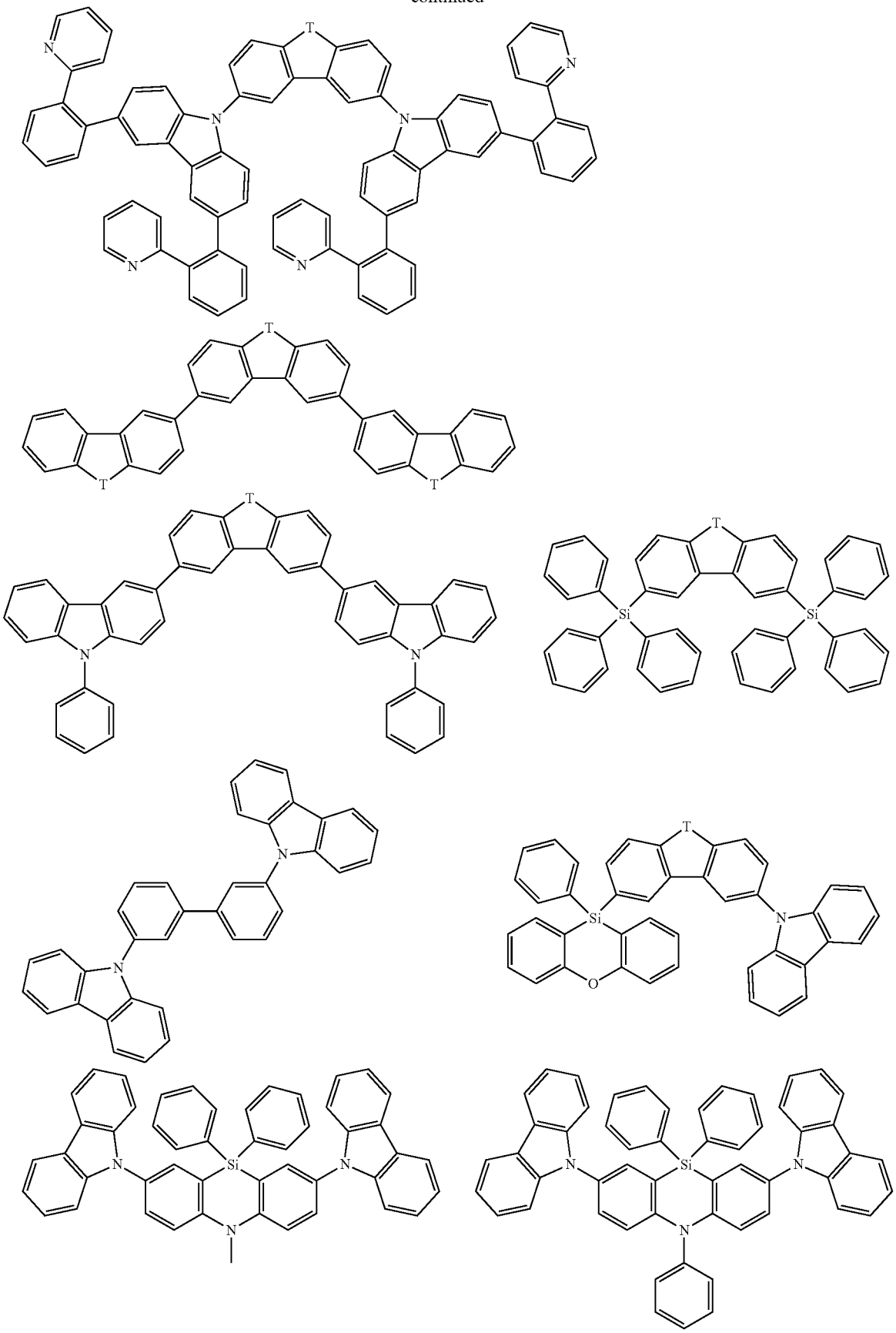

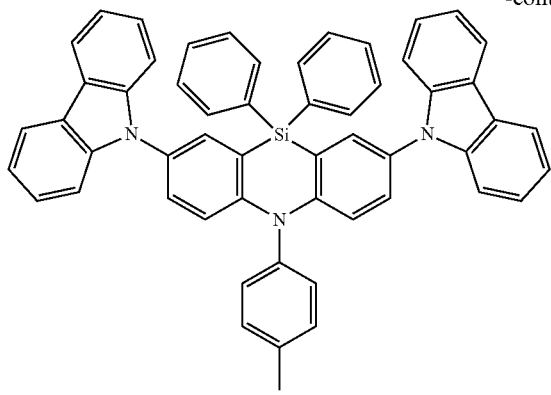

In the aforementioned compounds, T is O or S, preferably O. When more than one T occurs in the molecule, all T groups have the same definition.

In addition to the compounds of the formula (X), according to the present invention, it is also possible to use crosslinked or polymeric materials comprising repeat units based on the general formula (X) in crosslinked or polymerized form together with at least one metal-carbene complex of the general formula (I). Like the compounds of the general formula (X), the latter are preferably used as matrix materials.

The crosslinked or polymeric materials have outstanding solubility in organic solvents, excellent film-forming properties and relatively high glass transition temperatures. In addition, high charge carrier mobilities, high stabilities of color emission and long operating times of the corresponding components can be observed when crosslinked or polymeric materials according to the present invention are used in organic light-emitting diodes (OLEDs).

The crosslinked or polymerized materials are particularly suitable as coatings or in thin films since they are thermally and mechanically stable and relatively defect-free.

The crosslinked or polymerized materials comprising repeat units based on the general formula (X) can be prepared by a process comprising steps (a) and (b):
(a) preparation of a crosslinkable or polymerizable compound of the general formula (X) where at least one of the a" $R^{55}$ radicals or at least one of the b' $R^{56}$ radicals is a crosslinkable or polymerizable group attached via a spacer, and
(b) crosslinking or polymerization of the compound of the general formula (X) obtained from step (a).

The crosslinked or polymerized materials may be homopolymers, which means that exclusively units of the general formula (X) are present in crosslinked or polymerized form. They may also be copolymers, which means that further monomers are present in addition to the units of the general formula (X), for example monomers with hole-conducting and/or electron-conducting properties, in crosslinked or polymerized form.

In a further preferred embodiment of the inventive OLED, it comprises an emission layer comprising at least one inventive metal-carbene complex of the general formula (I), at least one matrix material of the formula (X), and optionally at least one further hole-transporting matrix material.

The inventive OLEDs can be used in all devices in which electroluminescence is useful. Suitable devices are preferably selected from stationary and mobile visual display units and illumination means. The present invention therefore also relates to a device selected from the group consisting of stationary visual display units and mobile visual display units and illumination means, comprising an inventive OLED.

Stationary visual display units are, for example, visual display units of computers, televisions, visual display units in printers, kitchen appliances and advertising panels, illuminations and information panels. Mobile visual display units are, for example, visual display units in cellphones, laptops, digital cameras, mp-3 players, smartphones, vehicles, and destination displays on buses and trains.

The inventive metal-carbene complexes of the general formula (I) can additionally be used in OLEDs with inverse structure. In these inverse OLEDs, the inventive complexes are in turn preferably used in the light-emitting layer. The structure of inverse OLEDs and the materials typically used therein are known to those skilled in the art.

The present invention further provides a white OLED comprising at least one inventive metal-carbene complex of the general formula (I). In a preferred embodiment, the metal-carbene complex of the general formula (I) is used as emitter material in the white OLED. Preferred embodiments of the metal-carbene complex of the general formula (I) have been specified above. In addition to the at least one metal-carbene complex of the general formula (I), the white OLED may comprise
(i) at least one compound of the formula (X). The compound of the formula (X) is preferably used as matrix material. Preferred compounds of the formula (X) have been specified above; and/or
(ii) at least one compound of the formula (VII) and/or (IX). The compounds of the formula (VII) and/or (IX) are preferably used as electron transport material. Preferred compounds of the formulae (VII) and (IX) have been specified above.

In order to obtain white light, the OLED must generate light which colors the entire visible range of the spectrum. However, organic emitters normally emit only in a limited portion of the visible spectrum—i.e. are colored. White light can be generated by the combination of different emitters. Typically, red, green and blue emitters are combined. However, the prior art also discloses other methods for formation of white OLEDs, for example the triplet harvesting approach. Suitable structures for white OLEDs or methods for formation of white OLEDs are known to those skilled in the art.

In one embodiment of a white OLED, several dyes are layered one on top of another in the light-emitting layer of an OLED and hence combined (layered device). This can be achieved by mixing all dyes or by direct series connection of different-colored layers.

The expression "layered OLED" and suitable embodiments are known to those skilled in the art.

In general, the different layers then have the following thicknesses: anode (2) 500 to 5000 Å (angstrom), preferably 1000 to 2000 Å; hole-transporting layer (3) 50 to 1000 Å, preferably 200 to 800 Å, either a light-emitting layer comprising a mixture of different emitters (4): 10 to 1000 Å, preferably 100 to 800 Å, or several light-emitting layers in succession, each individual layer comprising a different emitter (4a, b, c, . . . ): each 10 to 1000 Å, preferably each 50 to 600 Å, electron-transporting layer (5) 50 to 1000 Å, preferably 200 to 800 Å, cathode (6) 200 to 10 000 Å, preferably 300 to 5000 Å.

In a further embodiment of a white OLED, several different-colored OLEDs are stacked one on top of another (stacked device). For the stacking of two OLEDs, what is called a charge generation layer (CG layer) is used. This CG layer may be formed, for example, from one electrically n-doped and one electrically p-doped transport layer. The expression "stacked OLED" and suitable embodiments are known to those skilled in the art.

In general, the different layers then have the following thicknesses: anode (2) 500 to 5000 Å (angstrom), preferably 1000 to 2000 Å; first hole-transporting layer (3) 50 to 1000 Å, preferably 200 to 800 Å, first light-emitting layer (4) 10 to 1000 Å, preferably 50 to 600 Å, first electron-transporting layer (5) 50 to 1000 Å, preferably 200 to 800 Å, electrically n-doped layer 50 to 1000 Å, preferably 100 to 800 Å, electrically p-doped layer 50 to 1000 Å, preferably 100 to 800 Å, second hole-transporting layer (3) to 50 to 1000 Å, preferably 200 to 800 Å, second light-emitting layer (4) 10 to 1000 Å, preferably 50 to 600 Å, second electron-transporting layer (5) 50 to 1000 Å, preferably 200 to 800 Å, electrically n-doped layer 50 to 1000 Å, preferably 100 to 800 Å, electrically p-doped layer 50 to 1000 Å, preferably 100 to 800 Å, third hole-transporting layer (3) to to 1000 Å, preferably 200 to 800 Å, third light-emitting layer (4) 10 to 1000 Å, preferably 50 to 600 Å, third electron-transporting layer (5) to 50 to 1000 Å, preferably 200 to 800 Å, cathode (6) 200 to 10 000 Å, preferably 300 to 5000 Å.

In further embodiments of this "stacked device concept", it is also possible to stack only two OLEDs or to stack more than three OLEDs.

In a further embodiment of white OLEDs, the two concepts mentioned for white light generation can also be combined. For example, a single-color OLED (for example blue) can be stacked with a multicolor layered OLED (for example red-green). Further combinations of the two concepts are conceivable and known to those skilled in the art.

The inventive metal-carbene complex of the formula (I) can be used in any of the layers mentioned above in white OLEDs. In a preferred embodiment, it is used in one or more or all light-emitting layer(s) of the OLED(s), in which case the structure of the invention metal-carbene complex is varied as a function of the use of the complex. Suitable and preferred components for the further layers of the light OLED(s) or materials suitable as matrix material in the light-emitting layer(s) and preferred matrix materials are likewise specified above.

The present invention also relates to an organic electronic component, preferably an organic light-emitting diode (OLED), organic photovoltaic cell (OPV), organic field-effect transistor (OFET) or light-emitting electrochemical cell (LEEC), comprising at least one inventive metal-carbene complex of the general formula (I).

EXAMPLES

The examples which follow, more particularly the methods, materials, conditions, process parameters, apparatus and the like detailed in the examples, are intended to support the present invention, but not to restrict the scope of the present invention.

All experiments are carried out in protective gas atmosphere.

The percentages and ratios mentioned in the examples below—unless stated otherwise—are % by weight and weight ratios.

Example 1

2,3-Bis(N-phenylamino)pyrazine

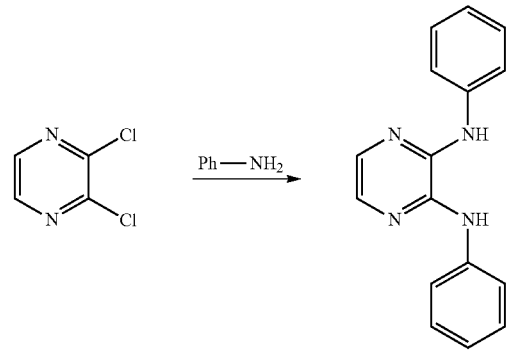 [SMILES: Clc1nccnc1Cl ; Nc1ccccc1 ; c1ccc(Nc2nccnc2Nc2ccccc2)cc1]

A mixture of 2,3-dichloropyrazine (10.0 g, 67 mmol) in aniline (35.3 ml, 376 mmol) is stirred at 105° C. overnight. After cooling to 80° C., water (100 ml) is added. The mixture is adjusted to pH 11 with 50% sodium hydroxide solution and extracted with dichloromethane and ethyl acetate. The combined organic phases are concentrated to dryness and the crude product is purified by column chromatography (silica gel, n-hexane/ethyl acetate 4:1). Yield: 16.2 g (92%).

$^1$H NMR (CD$_2$Cl$_2$, 500 MHz): δ=6.27 (br s, 2H), 7.00 (m$_c$, 2H), 7.26-7.30 (m, 8H), 7.72 (s, 2H).

1,3-Diphenylpyrazinoimidazolium iodide

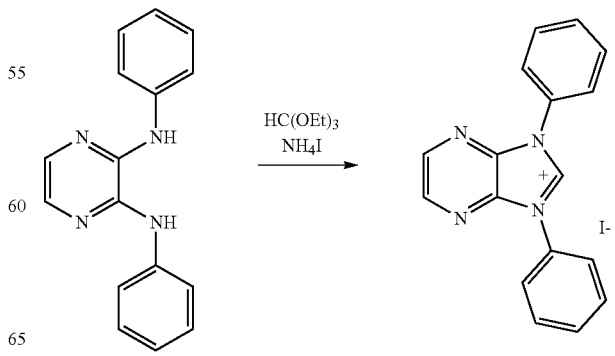

A mixture of 2,3-bis(N-phenylamino)pyrazine (15.5 g, 59 mmol) in triethyl orthoformate (100 ml) is admixed with ammonium iodide (17.1 g, 118 mmol) and stirred overnight at 80° C. After cooling to room temperature, the solid is filtered off with suction, washed with petroleum ether and dried in a vacuum drying cabinet at 70° C. Yield: 19.5 g (82%).

$^1$H NMR ($d_6$-DMSO, 500 MHz): δ=7.77 ($m_c$, 2H), 7.84 ($m_c$, 4H), 8.03-8.08 (m, 4H), 9.08 (s, 2H), 11.20 (s, 1H).

Complex fac-Em1:

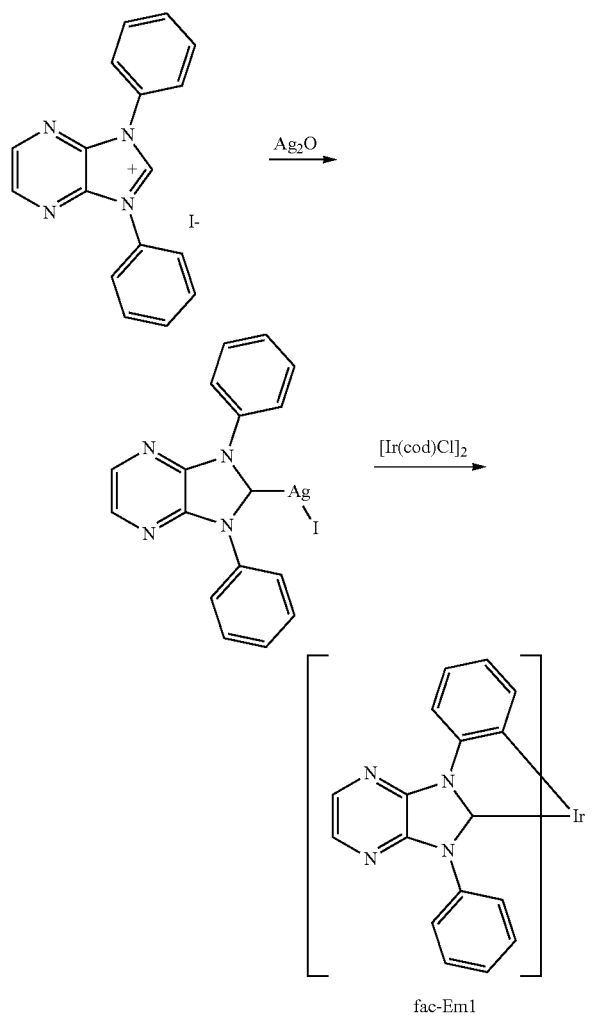

fac-Em1

A suspension of 1,3-diphenylpyrazinoimidazolium iodide (1.6 g, 4.0 mmol) in dioxane (95 ml) is admixed with molecular sieve (14 g) and silver(I) oxide (742 mg, 3.2 mmol) and stirred overnight at room temperature. Subsequently, a solution of chloro(1,5-cyclooctadiene)iridium(I) dimer (269 mg, 0.4 mmol) in o-xylene (130 ml) is added. The mixture is stirred at reflux overnight. After cooling to 80° C., the residue is filtered off with suction and washed with o-xylene. The combined filtrates are concentrated to dryness and the residue is dissolved at 75° C. in toluene (40 ml). The solution is concentrated and left to stand overnight at room temperature. The precipitate is filtered off, washed with cyclohexane and dried in a vacuum drying cabinet at 65° C. Yield: 0.8 g (95%).

$^1$H NMR ($d_6$-DMSO, 500 MHz, 100° C.): δ=6.51-6.59 (m, 9H), 6.70 ($m_e$, 3H), 6.81 ($m_e$, 3H), 6.90 (br m, 6H), 7.09 ($m_c$, 3H), 8.16 (d, 3H), 8.42 (d, 3H), 8.66 (dd, 3H).

Photoluminescence (2% in a PMMA film):
$\lambda_{max}$=474 nm, CIE: (0.16; 0.24), QY=93%

Example 2

2-N-Isopropylamino-3-chloropyrazine

A solution of 2-amino-3-chloropyrazine (2.7 g, 20.8 mmol) in dichloromethane (54 ml) and glacial acetic acid (27 ml) is admixed at 1° C. with acetone (4.1 ml, 56.3 mmol) and borane-dimethyl sulfide complex (2.2 ml, 22.9 mmol) and stirred overnight at room temperature. A second portion of borane-dimethyl sulfide complex (0.8 ml) is added at 1° C. and the mixture is again stirred overnight at room temperature. Finally, a third portion of borane-dimethyl sulfide complex (0.6 ml) and acetone (1.0 ml) is added at 1° C. and the mixture is again stirred overnight at room temperature. The solution is adjusted to pH 9 at <10° C. with aqueous ammonia (38 ml). The organic phase is removed and washed with water. After drying over sodium sulfate, the solution is concentrated and left to stand overnight. The precipitate which forms is filtered off and washed with a little dichloromethane. The combined filtrates are concentrated to dryness and dried in a vacuum drying cabinet at 40° C. Yield: 2.3 g (64%).

$^1$H NMR (CD$_2$Cl$_2$, 500 MHz): δ=1.22 (d, 6H), 4.16 (sept, 1H), 5.00 (br s, 1H), 7.46 (d, 1H), 7.88 (d, 1H).

2-N-Phenylamino-3-N-isopropylaminopyrazine

A mixture of 2-isopropylamino-3-chloropyrazine (5.1 g, 30 mmol) in aniline (9 ml, 99 mmol) is stirred overnight at 125° C. After cooling to 90° C., water is added. At room temperature, dichloromethane is added and the solution is adjusted to pH 9 with aqueous ammonia. The organic phase is removed, washed with water, dried over sodium sulfate and concentrated to dryness. The crude product is purified by column chromatography (silica gel, toluene/ethyl acetate 8:1). Yield: 4.6 g (68%).

$^1$H NMR (CD$_2$Cl$_2$, 500 MHz): δ=1.23 (d, 6H), 4.15 (br s, 1H), 4.18 (sept, 1H), 5.95 (br s, 1H), 6.96-7.02 (m, 1H), 7.23-7.32 (m, 4H), 7.45 (d, 1H), 7.64 (d, 1H).

1-Phenyl-3-isopropylpyrazinoimidazolium iodide

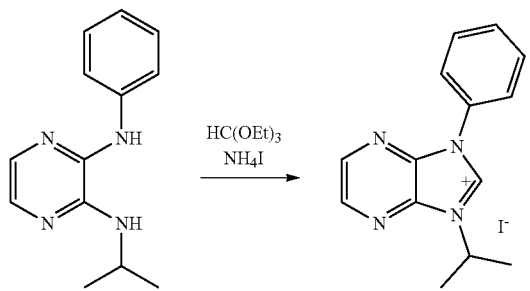

A mixture of 2-N-phenylamino-3-N-isopropylaminopyrazine (1.2 g, 5.2 mmol) in triethyl orthoformate (6 ml) is admixed with ammonium iodide (0.8 g, 5.7 mmol) and stirred overnight at 80° C. After cooling to room temperature, the solid is filtered off with suction, washed with a little ethanol and petroleum ether, and dried in a vacuum drying cabinet at 50° C. Yield: 1.1 g (60%).

$^1$H NMR (d6-DMSO, 500 MHz): δ=1.76 (d, 6H), 5.23 (sept, 1H), 7.67-7.84 (m, 3H), 7.91-8.02 (m, 2H), 8.98 (d, 1H), 9.02 (d, 1H), 10.72 (s, 1H).

Complex Mer-Em2:

A suspension of 1-phenyl-3-isopropylpyrazinoimidazolium iodide (166 mg, 0.48 mmol) in dioxane (8 ml) is admixed with molecular sieve (1 g) and silver(I) oxide (89 mg, 0.38 mmol) and stirred overnight at room temperature. Chloro(1,5-cyclooctadiene)-iridium(I) dimer (30 mg, 0.05 mmol) is added and the mixture is stirred overnight at reflux. After cooling to room temperature, the residue is filtered off with suction and washed with dichloromethane. The combined filtrates are concentrated to dryness and the residue is purified by column chromatography (silica gel, toluene/ethyl acetate 4:1).

Yield: 65 mg (80%).

$^1$H NMR (CD$_2$Cl$_2$, 500 MHz): δ=0.72 (d, 3H), 0.77 (d, 3H), 0.87 (d, 3H), 1.36 (d, 3H), 1.45 (d, 3H), 1.77 (d, 3H), 4.37-4.53 (m, 2H), 4.65 (sept, 1H), 6.57 (dd, 1H), 6.65-6.74 (m, 3H), 6.94-7.24 (m, 5H), 8.17 (d, 1H), 8.22 (d, 1H), 8.23 (d, 1H), 8.28 (d, 1H), 8.30 (d, 1H), 8.33 (d, 1H), 8.60 (dd, 1H), 8.63 (dd, 1H), 8.67 (dd, 1H).

Photoluminescence (2% in a PMMA film):

λ$_{max}$=516 nm, CIE: (0.29; 0.51), QY=66%

Complex Fac-Em2:

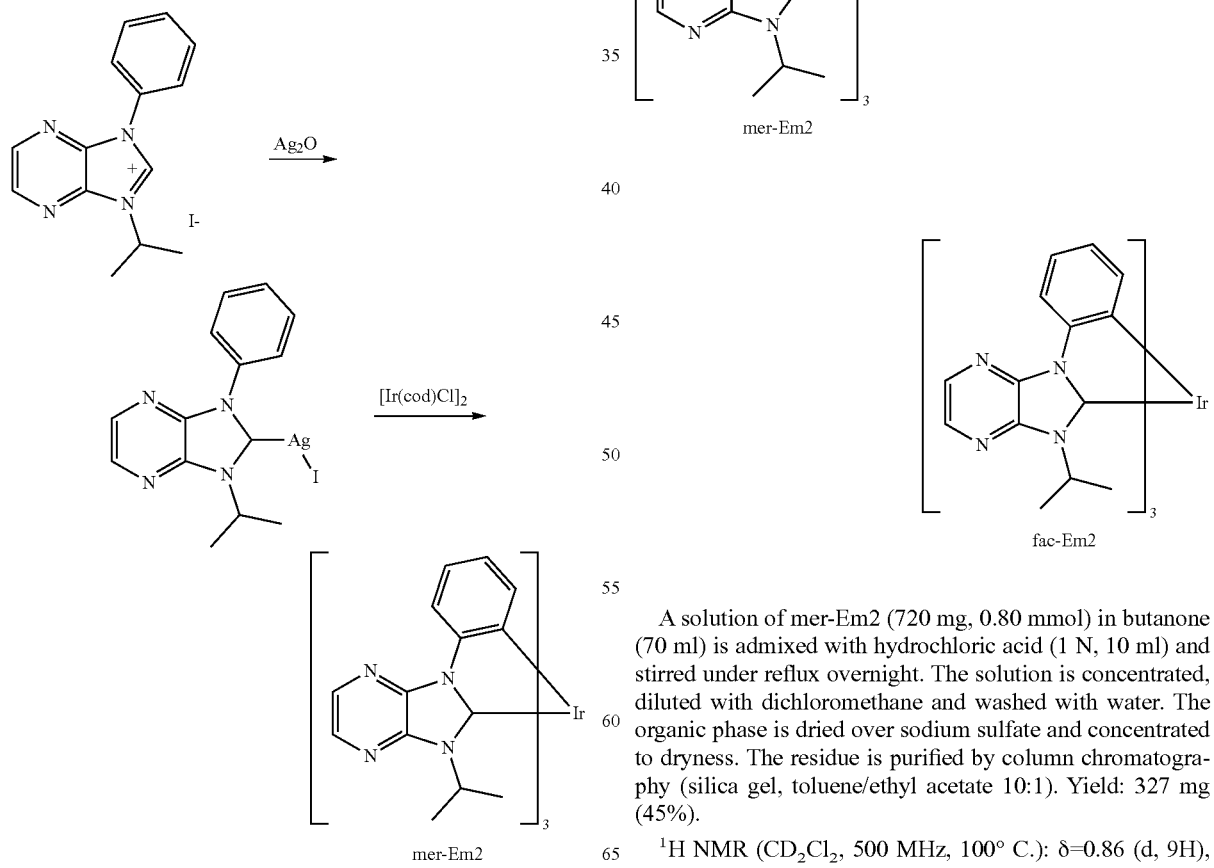

A solution of mer-Em2 (720 mg, 0.80 mmol) in butanone (70 ml) is admixed with hydrochloric acid (1 N, 10 ml) and stirred under reflux overnight. The solution is concentrated, diluted with dichloromethane and washed with water. The organic phase is dried over sodium sulfate and concentrated to dryness. The residue is purified by column chromatography (silica gel, toluene/ethyl acetate 10:1). Yield: 327 mg (45%).

$^1$H NMR (CD$_2$Cl$_2$, 500 MHz, 100° C.): δ=0.86 (d, 9H), 1.70 (d, 9H), 4.54 (sept, 3H), 6.36 (d, 3H), 6.64 (dd, 3H), 7.02 (dd, 3H), 8.17 (d, 3H), 8.28 (d, 3H), 8.60 (d, 3H).

Photoluminescence (2% in a PMMA film):
$\lambda_{max}$=474 nm, CIE: (0.16; 0.27), QY=90%

Example 3

2-N-Phenylamino-3-aminopyrazine

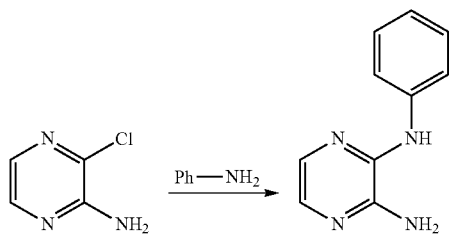

A mixture of 2-amino-3-chloropyrazine (5.0 g, 39 mmol) in aniline (12 ml, 131 mmol) is twice stirred overnight at 100° C. After cooling to room temperature, the mixture is diluted with dichloromethane (80 ml), stirred overnight and filtered. The solid is dissolved in dichloromethane (200 ml) and washed with saturated aqueous sodium hydrogencarbonate solution. The organic phase is concentrated to dryness and the residue is dried in a vacuum drying cabinet at 70° C. Yield: 5.3 g (74%).

$^1$H NMR (CD$_2$Cl$_2$, 500 MHz): δ=4.43 (br s, 2H), 6.23 (br s, 1H), 7.03 (dd, 1H), 7.32 (dd, 2H), 7.40 (d, 2H), 7.59 (d, 1H), 7.62 (d, 1H).

1-Phenylpyrazinoimidazole

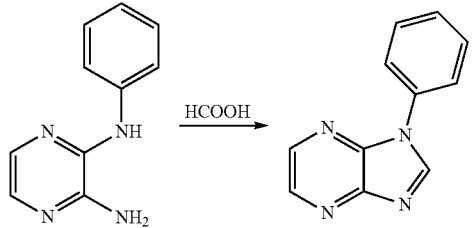 [SMILES: Nc1nccnc1Nc1ccccc1 ; "HCOOH" ; c1ccc(-n2cnc3nccnc32)cc1]

A solution of 2-N-phenylamino-3-aminopyrazine (5.3 g, 29 mmol) in formic acid (160 ml) is stirred overnight under reflux and then concentrated to dryness. The residue is taken up in dichloromethane (100 ml) and washed with saturated aqueous sodium hydrogencarbonate solution. The aqueous phase is extracted with dichloromethane (2×50 ml) and the combined organic phases are concentrated to dryness. Yield: 5.6 g (98%)

$^1$H NMR (CD$_2$Cl$_2$, 500 MHz): δ=7.49 (dd, 1H), 7.60 (dd, 2H), 7.76 (d, 2H), 8.39 (d, 1H), 8.56 (d, 1H), 8.63 (s, 1H).

1-Phenyl-3-methylpyrazinoimidazolium tetrafluoroborate

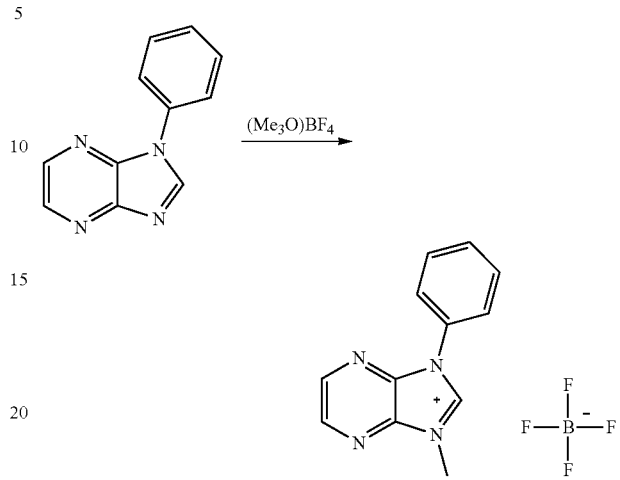

A solution of 1-phenylpyrazinoimidazole (5.5 g, 28 mmol) in dichloromethane (400 ml) is admixed with trimethyloxonium tetrafluoroborate (4.2 g, 28 mmol) and stirred overnight at reflux. The precipitate is filtered off and dried. The product is obtained in a purity of approx. 75%. Yield: 7.3 g (87%).

$^1$H NMR (d$_6$-DMSO, 500 MHz): δ=4.19 (s, 3H), 7.71 (dd, 1H), 7.78 (dd, 2H), 7.91 (d, 2H), 8.99 (d, 1H), 9.04 (d, 1H), 10.70 (s, 1H).

1-Phenyl-3-methylpyrazinoimidazolium iodide

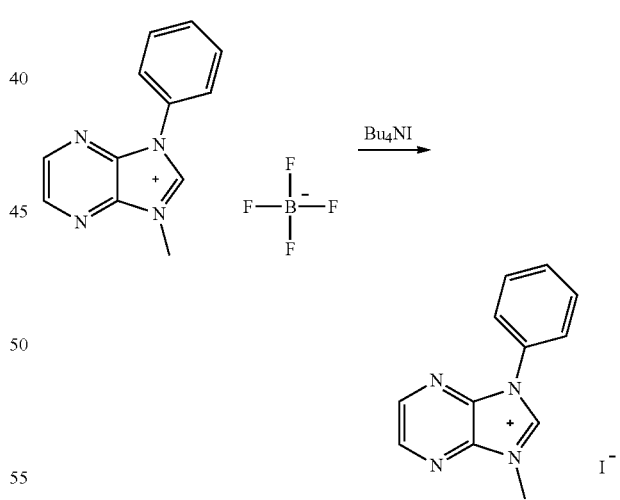

A solution of 1-phenyl-3-methylpyrazinoimidazolium tetrafluoroborate (7.3 g, 25 mmol, purity: 75%) in acetonitrile (70 ml) is admixed with a solution of tetrabutylammonium iodide (27.2 g, 74 mmol) in acetonitrile (67 ml) and stirred overnight at room temperature. The precipitate is filtered off with suction and washed with petroleum ether. The product is obtained in a purity of approx. 75%. Yield: 6.0 g (72%).

$^1$H NMR (d$_6$-DMSO, 500 MHz): δ=4.19 (s, 3H), 7.71 (dd, 1H), 7.78 (dd, 2H), 7.92 (d, 2H), 8.99 (d, 1H), 9.04 (d, 1H), 10.72 (s, 1H).

Complex Mer-Em3:

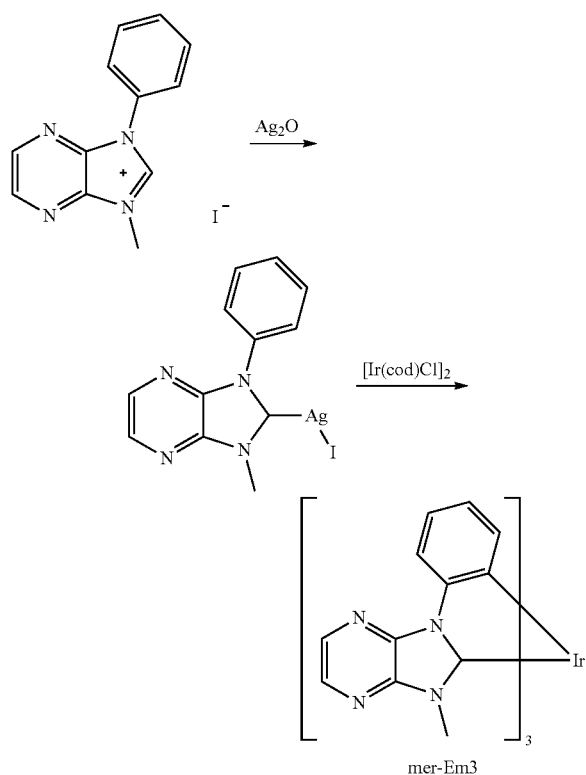

A suspension of 1-phenyl-3-methylpyrazinoimidazolium iodide (1.0 g, 2.3 mmol) in dioxane (60 ml) is admixed with molecular sieve (8.4 g) and silver(I) oxide (0.4 g, 1.8 mmol) and stirred overnight at room temperature. A solution of chloro(1,5-cyclooctadiene)iridium(I) dimer (153 mg, 0.2 mmol) in o-xylene (83 ml) is added and the mixture is stirred overnight at reflux. After cooling to room temperature, the residue is filtered off with suction and washed with acetone. The combined filtrates are concentrated to dryness and the residue is purified by column chromatography (silica gel, dichloromethane). Yield: 44 mg (13%).

$^1$H NMR (CD$_2$Cl$_2$, 500 MHz): δ=3.22 (s, 3H), 3.36 (s, 3H), 3.37 (s, 3H), 6.60 (dd, 1H), 6.70-6.78 (m, 3H), 6.87 (dd, 1H), 6.92 (dd, 1H), 7.01-7.10 (m, 3H), 8.22 (d, 1H), 8.27 (d, 1H), 8.28 (d, 1H), 8.32 (d, 1H), 8.35 (d, 1H), 8.36 (d, 1H), 8.60 (dd, 1H), 8.67 (dd, 1H), 8.68 (dd, 1H).

Photoluminescence (2% in a PMMA film):
λ$_{max}$=515 nm, CIE: (0.29; 0.50), QY=74%

Complex Fac-Em3:

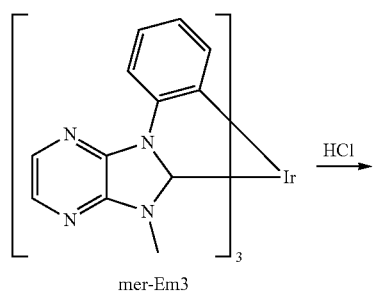

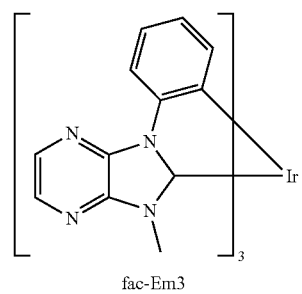

A solution of mer-Em3 in butanone is admixed with hydrochloric acid and stirred overnight under reflux. The solution is concentrated, diluted with dichloromethane and washed with water. The organic phase is dried over sodium sulfate and concentrated to dryness. The residue is purified by column chromatography.

Example 4

μ-Dichloro Dimer D1:

N-(2,6-Diisopropylphenyl)-2-phenylimidazole is synthesized analogously to example 14 in WO2006/121811.

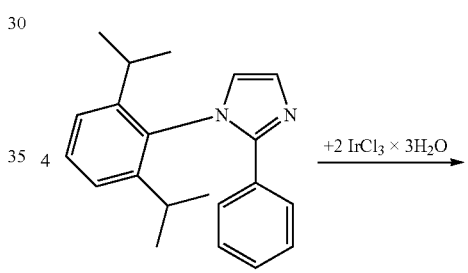

3.50 g (11.5 mmol) of 1-(2,6-diisopropylphenyl)-2-phenyl-1H-imidazole are initially charged in 200 ml of 2-ethoxyethanol/water (ratio 3/1) and admixed with 1.84 g (5.2 mmol) of iridium(III) chloride trihydrate. The reaction mixture is heated at reflux for 18 h. After cooling, 50 ml of distilled water are added. The precipitate is filtered off, washed with distilled water and dried. This gives 3.50 g (80%) of □-dichloro dimer D1 as a yellow powder.

$^1$H NMR (CD$_2$Cl$_2$, 400 MHz):

δ=0.95 (d, 12H), 1.18 (d, 12H), 1.27 (d, 12H), 1.34 (d, 12H), 2.80-2.91 (m, 8H), 6.08 (d, 4H), 6.24 (d, 4H), 6.39 (pt, 4H), 6.53 (pt, 4H), 6.97 (d, 4H), 7.39-7.45 (m, 8H), 7.59 (t, 4H), 7.67 (d, 4H).

Complex Mer-Em7:

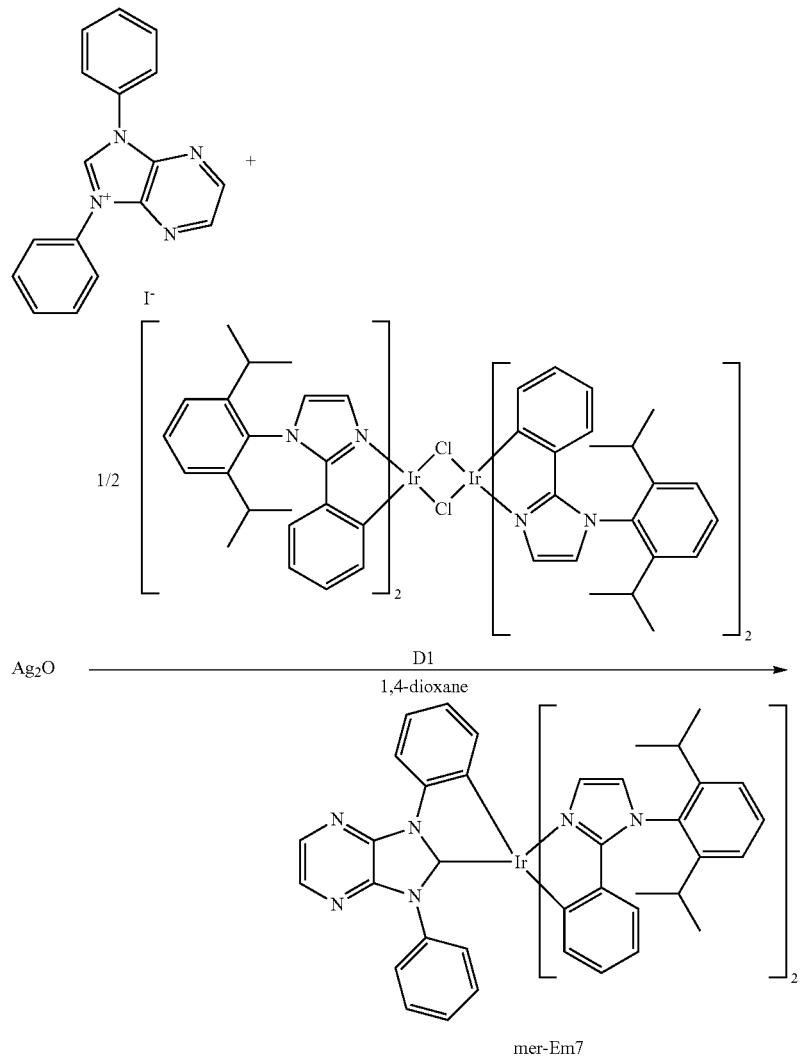

A suspension of 1,3-diphenylpyrazinoimidazolium iodide (0.5 g, 1.25 mmol) in anhydrous dioxane (100 ml) is admixed with molecular sieve (10 g) and silver(I) oxide (0.19 g, 0.81 mmol) and stirred overnight at room temperature. Subsequently, a solution of chloro dimer D1 (0.52 g, 0.31 mmol) in dioxane (74 ml) is added dropwise. Thereafter, the mixture is stirred under reflux for one hour. The reaction mixture is cooled and filtered. The filtrate is freed of the solvent under reduced pressure, washed with methanol and then purified by column chromatography (silica gel, eluent cyclohexane/acetone=1/0.25). This gives 0.40 g of mer-Em7 as an orange powder (63%).

$^1$H NMR (CD$_2$Cl$_2$, 500 MHz):

δ=0.89 (d, 3H), 0.90 (d, 6H), 0.92 (d, 3H), 1.09 (d, 3H), 1.16 (d, 3H), 1.21 (d, 3H), 1.24 (d, 3H), 2.13 (sept, 1H), 2.66 (m, 2H), 2.73 (sept, 1H), 6.08-6.23 (m, 5H), 6.45-6.48 (m, 3H), 6.66 (d, 1H), 6.70-6.76 (m, 3H), 6.85-6.92 (m, 2H), 6.98 (m, 4H), 7.08-7.13 (m, 2H), 7.31 (t, 2H), 7.35 (d, 1H), 7.39 (d, 1H), 7.50 (t, 1H), 7.55 (t, 1H), 8.21 (d, 1H), 8.41 (d, 1H), 8.80 (d, 1H).

Photoluminescence (2% in a PMMA film):
$\lambda_{max}$=565 nm, CIE: (0.44; 0.49)

Complex Fac-Em7:

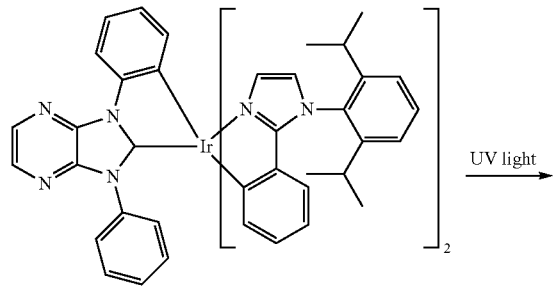

mer-Em7

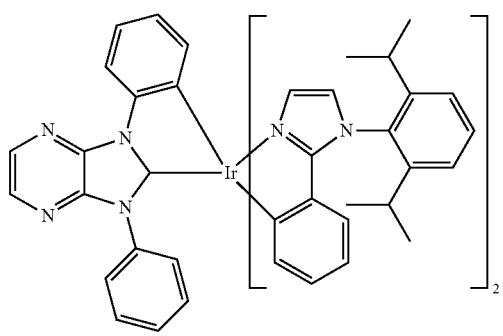

fac-Em7

The complex fac-Em7 (isomer to mer-Em7) is obtained by irradiation of a solution of mer-Em7 in 3-methoxypropionitrile with a blacklight blue lamp (Osram, L18W/73, $\lambda_{max}$=370-380 nm) and subsequent purification by column chromatography.

Example 5

Complex K1:

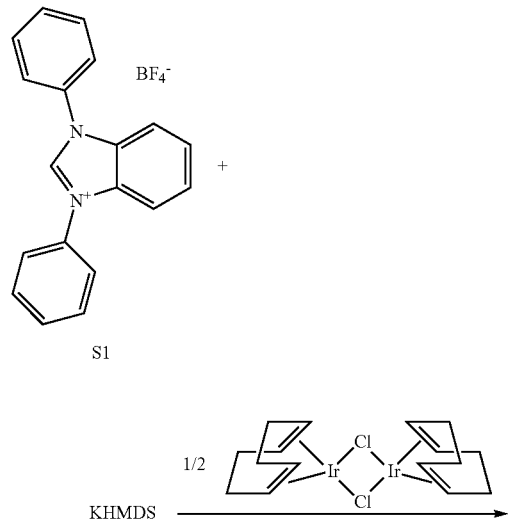

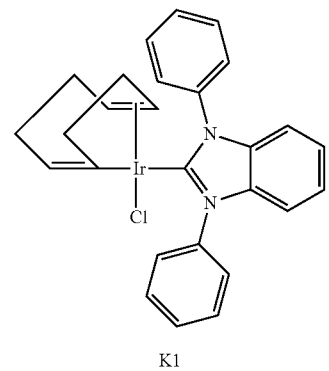

K1

5.00 g (14.0 mmol) of benzimidazolium salt S1 are suspended in 80 ml of anhydrous toluene and cooled to −8° C. Then 28 ml of potassium bis(trimethylsilyl)amide (KHMDS, 0.5M in toluene, 14.0 mmol) are added within 10 min. The mixture is stirred at room temperature for one hour and then added dropwise at −78° C. within 15 min to a solution of 4.70 g (7.0 mmol) of [(μ-Cl)Ir(η$^4$-1,5-COD)]$_2$ in 120 ml toluene. The reaction mixture is stirred at room temperature for 1.5 h and then heated at reflux for 19 h. After cooling, the precipitate is filtered off and washed with toluene. The combined toluene phases are concentrated to dryness and purified by column chromatography (silica gel, eluent methylene chloride). This gives 5.8 g (68%) of K1 as a yellow powder.

$^1$H NMR (CD$_2$Cl$_2$, 500 MHz):
δ=1.17 (m, 2H), 1.34 (m, 4H), 1.61 (m, 2H), 2.43 (m, 2H), 4.31 (m, 2H), 7.18 (m, 2H), 7.25 (m, 2H), 7.51 (m, 6H), 7.96 (m, 4H).

Complex Em8:

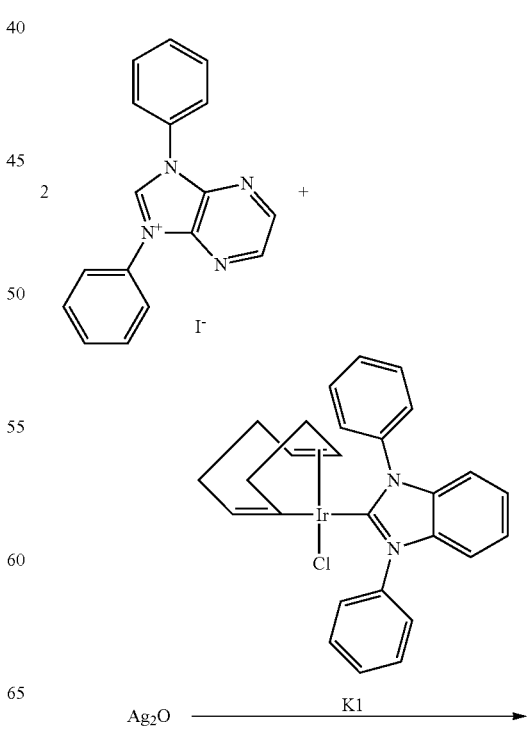

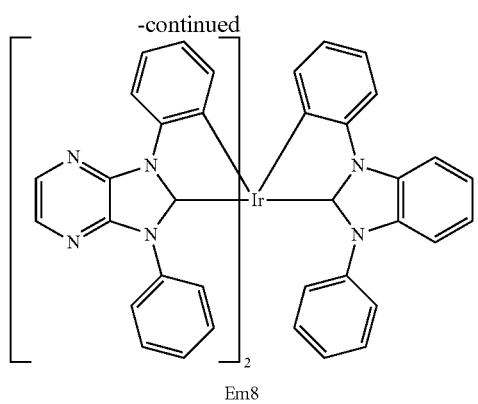

Em8

A suspension of 1,3-diphenylpyrazinoimidazolium iodide (3.17 g, 7.92 mmol) in anhydrous 1,4-dioxane (140 ml) is admixed with molecular sieve (15 g) and silver(I) oxide (1.48 g, 6.34 mmol) and stirred overnight at room temperature. Subsequently, a solution of complex K1 (1.60 g, 2.64 mmol) in anhydrous o-xylene (200 ml) is added dropwise. Thereafter, the mixture is stirred under reflux for 24 hours. The reaction mixture is cooled and filtered. The filtrate is freed of the solvent under reduced pressure and purified by column chromatography (silica gel, eluent ethyl acetate/cyclohexane=1/2). This gives 0.80 g of Em8 (30%).

$^1$H NMR (CD$_2$Cl$_2$, 500 MHz):

δ=6.20-7.40 (very flat broad signal, 8H), 6.26 (d, 1H), 6.36-6.42 (m, 3H), 6.59 (d, 1H), 6.66 (t, 2H), 6.76-6.85 (m, 6H), 7.06-7.17 (m, 4H), 7.29 (t, 1H), 7.33 (t, 1H), 8.01 (m, 2H), 8.04 (d, 1H), 8.18 (d, 1H), 8.27 (d, 1H), 8.31 (d, 1H), 8.70 (d, 1H), 8.77 (d, 1H).

Photoluminescence (2% in a PMMA film):

$\lambda_{max}$=480 nm, CIE: (0.17; 0.31)

Example 6

Complex D2:

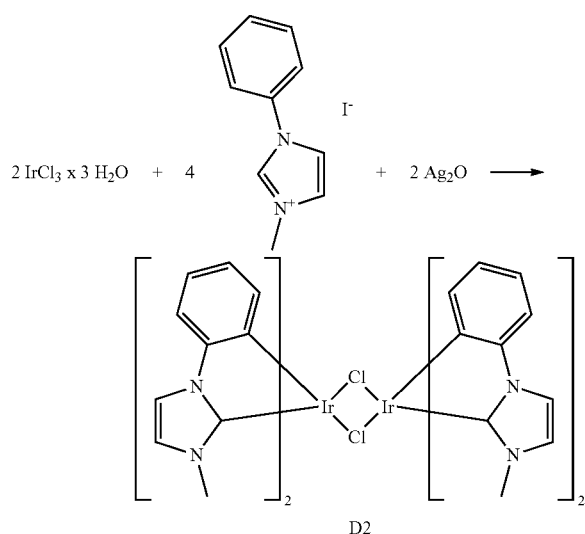

D2

4.29 g (18.5 mmol) of silver oxide, 9.47 g (33.1 mmol) of imidazolium iodide and 3.56 g (10.1 mmol) of iridium trichloride trihydrate are suspended in 350 ml of 2-ethoxyethanol and stirred in the dark at 120° C. for 15 h. Thereafter, the solvent is removed under reduced pressure and the residue is extracted with methylene chloride. The extract is concentrated to about a quarter of its volume and admixed with methanol. The solid which precipitates out is filtered off and dried. This gives 1.7 g of complex D2 (31%).

$^1$H NMR (CD$_2$Cl$_2$, 500 MHz):

δ=7.59 (d, 4H), 7.17 (d, 4H), 6.99 (d, 4H), 6.73 (pt, 4H), 6.45 (pt, 4H), 6.09 (d, 4H), 3.91 (s, 12H).

Complex Em9:

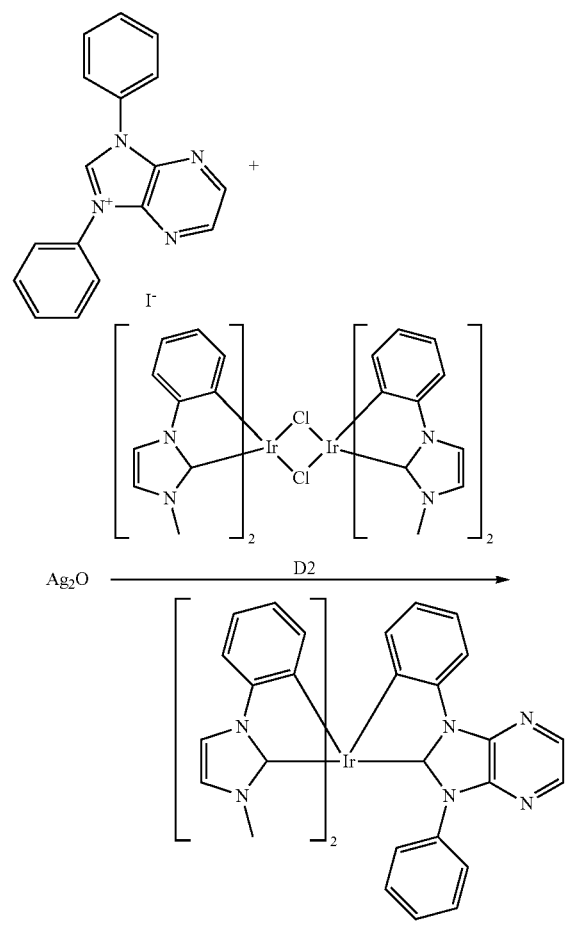

Em9

A suspension of 1,3-diphenylpyrazinoimidazolium iodide (0.59 g, 1.48 mmol) in anhydrous 1,4-dioxane (35 ml) is admixed with molecular sieve (5 g) and silver(I) oxide (0.28 g, 1.18 mmol) and stirred overnight at room temperature. Subsequently, a suspension of complex D2 (0.40 g, 0.37 mmol) in anhydrous o-xylene (50 ml) is added. Thereafter, the mixture is stirred under reflux for 3.5 hours. The reaction mixture is cooled and filtered. The filtrate is freed of the solvent under reduced pressure and purified by column chromatography (silica gel, eluent dichloromethane).

This gives a fraction 1 of 0.11 g (20%, orange powder, R$_F$=0.39, 20/80 isomer mixture) and a fraction 2 of 0.23 g (40%, yellow powder, R$_F$=0.31, 40/60 isomer mixture) as mixtures of two different isomers each of Em9.

Fraction 1:

MS (Maldi):

m/e=779 (M+H$^+$)

Photoluminescence (2% in a PMMA film):
λ$_{max}$=547 nm, CIE: (0.40; 0.54)
Fraction 2:
MS (Maldi):
m/e=779 (M+H$^+$)
Photoluminescence (2% in a PMMA film):
λ$_{max}$=526 nm, CIE: (0.33; 0.55)

Example 7

Complex K2:

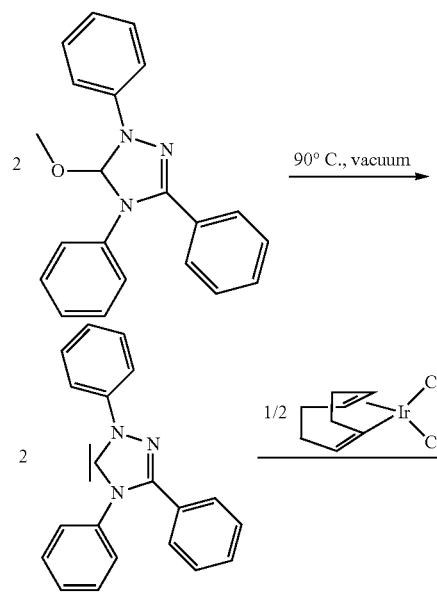

Complex Em10:

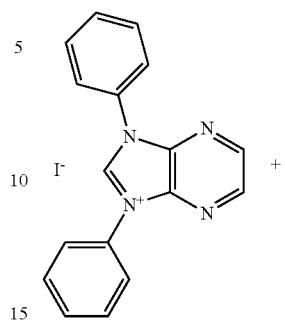

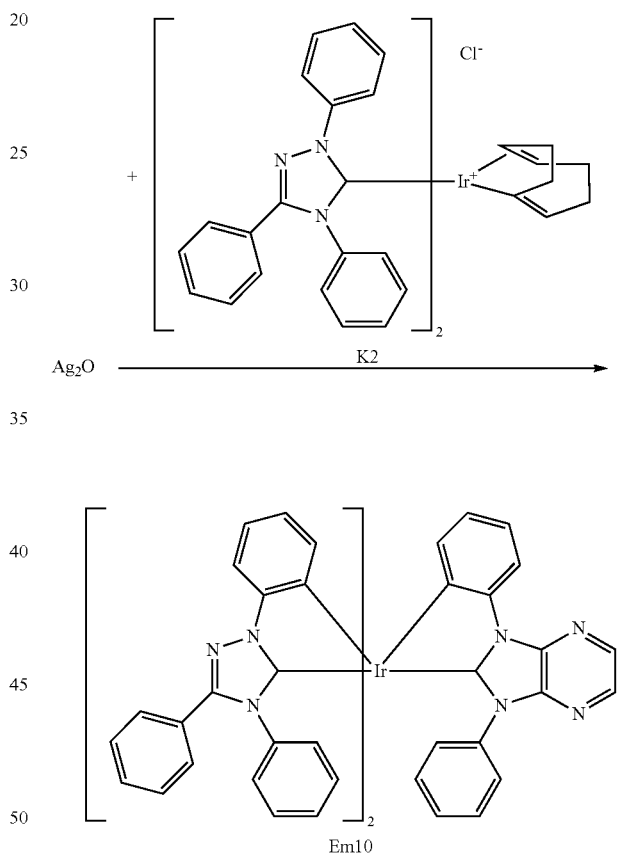

3.10 g (9.41 mmol) of 5-methoxy-1,3,4-triphenyl-4,5-dihydro-1H-[1,2,4]-triazole are heated to 90° C. under reduced pressure (10$^{-3}$ mbar) for 16 h. After cooling, the residue is taken up in 120 ml of anhydrous toluene and admixed with a solution of 1.38 g (2.03 mmol) of μ-chloro (1,5-cyclooctadiene)iridium(I) dimer in 120 ml of anhydrous toluene. The reaction mixture is heated gradually to 50° C. and stirred at this temperature for 1 h. After cooling, the orange-red precipitate is filtered off, washed with toluene and dried. This gives 2.68 g of K2 (70%).

$^1$H NMR (CD$_2$Cl$_2$, 500 MHz):

δ=1.19 (m, 2H), 1.29 (m, 2H), 2.14 (m, 2H), 2.26 (m, 2H), 2.77 (m, 2H), 4.95 (m, 2H), 7.25-7.44 (m, 26H), 7.82 (d, 4H).

A suspension of 0.5 g (1.25 mmol) of 1,3-diphenylpyrazinoimidazolium iodide in dry dioxane (40 ml) is admixed with 10 g of molecular sieve and 0.22 g (0.95 mmol) of silver(I) oxide and stirred overnight at room temperature. Subsequently, 0.94 g (1.01 mmol) of complex K2 is added in portions. The reaction mixture is heated under reflux overnight. After cooling, the precipitate is filtered off. The filtrate is concentrated to dryness, purified by column chromatography (silica gel, eluent: cyclohexane/acetone) and washed with a little methanol. This gives 0.21 g of emitter Em10 (20%).

Example 8

Complex K3:

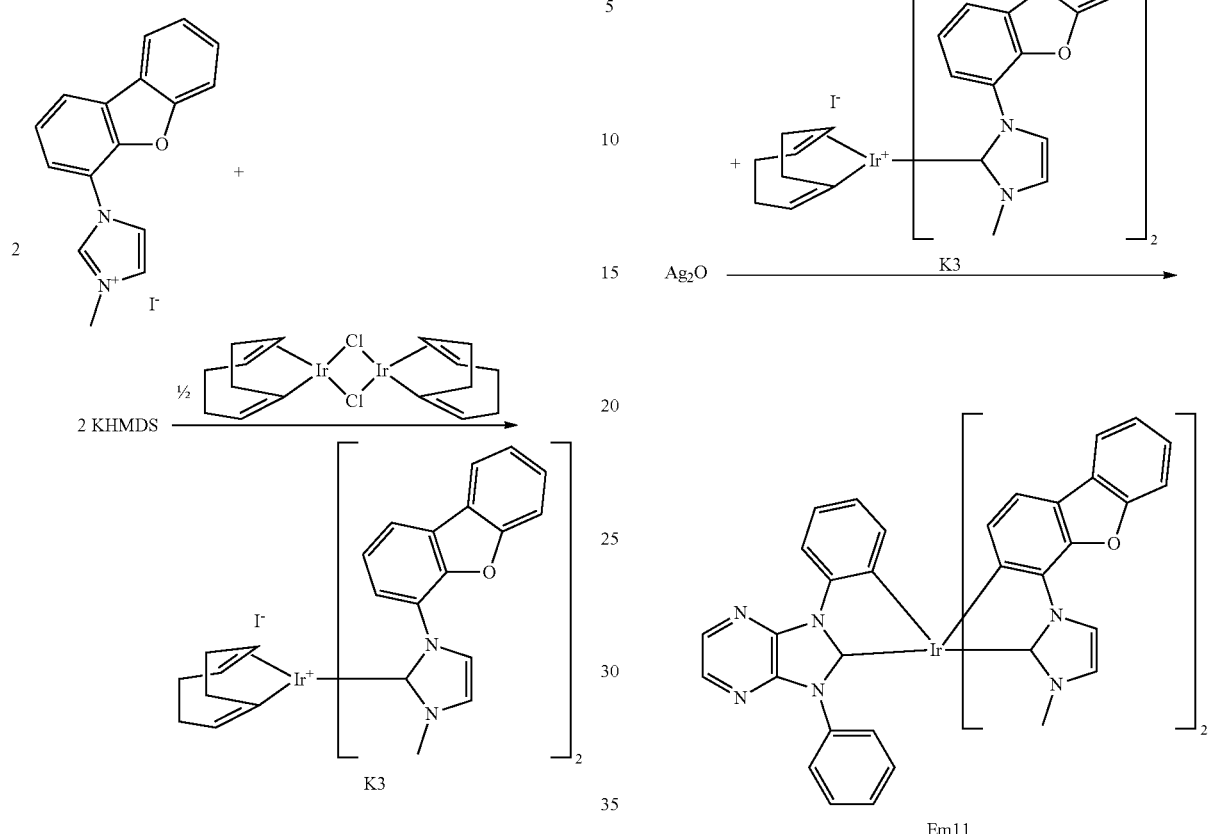

10.4 g (27.6 mmol) of 3-dibenzofuran-4-yl-1-methyl-3H-imidazol-1-ium iodide in 230 ml of anhydrous toluene are admixed at room temperature gradually with 55.3 ml of potassium bis(trimethylsilyl)amide solution (KHMDS, 0.5M in toluene, 27.6 mmol) and stirred for one hour. Subsequently, a solution of 4.68 g (6.9 mmol) of μ-chloro (1,5-cyclooctadiene)iridium(I) dimer in 230 ml of anhydrous toluene is added dropwise. The reaction mixture is heated at reflux overnight. After cooling, the precipitate is filtered off, washed with a little water and extracted with ethanol. Drying the extract gives 6.8 g of K3 (53%) as an orange-red powder.

$^1$H NMR (CD$_2$Cl$_2$, 500 MHz):

δ=1.49 (m, 2H), 1.84 (m, 2H), 2.02 (m, 2H), 2.16 (m, 2H), 3.29 (m, 2H), 4.85 (m, 2H), 6.53 (s, 2H), 6.93 (s, 2H), 7.37 (d, 2H), 7.47-7.62 (m, 8H), 8.14 (d, 2H), 8.25 (d, 2H).

Complex Em11:

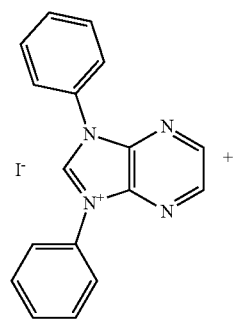

Em11 is synthesized analogously to Em10.

Example 9

Production of an OLED—Comparison of Different Emitters

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer AJ20-1000 from Plexcore is spun on from solution.

Thereafter, the organic materials specified below are applied by vapor deposition to the cleaned substrate at about $10^{-7}$-$10^{-9}$ mbar at a rate of approx. 0.5-5 nm/min. The hole conductor and exciton blocker applied to the substrate is Ir(DPBIC)$_3$ with a thickness of 45 nm, of which the first 35 nm are doped with MoO$_x$ (10% for diodes with CEm and fac-Em2, 50% for diodes with fac-Em1) to improve the conductivity.

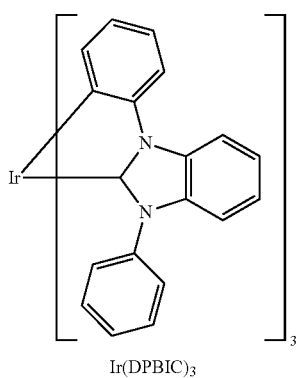

Ir(DPBIC)₃

(for preparation of Ir(DPBIC)₃ see Ir complex (7) in the application PCT/EP/04/09269).

Subsequently, a mixture of emitter (10% for CEm, 20% for fac-Em1 and fac-Em2) and of the compound Ma1 (90% and 80%, resp.) is applied by vapor deposition with a thickness of 40 nm, the latter compound functioning as a matrix material. Subsequently, the material Ma1 (for fac-Em1) is applied by vapor deposition with a thickness of 5 nm or Ma5 (5 nm for Em1, 10 nm for fac-Em2) as an exciton and hole blocker.

The synthesis of Ma1 is described in WO2010079051, that of Ma5 in WO2009003898.

Ma1

Ma5

The prior art comparative emitter used is CEm:

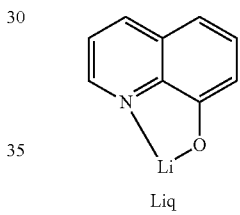

CEm

Next, as an electron transporter, a mixture of Liq and BCP (2,9-dimethyl-4,7-diphenyl-1,10-phenanthroline) (50:50 for fac-Em1, 0:100 for CEm and fac-Em2) is applied by vapor deposition in a thickness of 40 nm for fac-Em1, 30 nm for CEm and fac-Em2, as are a 1.0 nm-thick liq layer for fac-Em1, a 0.7 nm LiF layer for CEm and fac-Em2 and finally a 100 nm-thick Al electrode. All components are adhesive-bonded to a glass lid in an inert nitrogen atmosphere.

Liq

To characterize the OLED, electroluminescence spectra are recorded at different currents and voltages. In addition, the current-voltage characteristic is measured in combination with the light output emitted. The light output can be converted to photometric parameters by calibration with a photometer. The lifetime $t_{1/2}$ of the diode is defined by the time taken for the luminance to fall to 50% of its initial value. The lifetime measurement is carried out at a constant current.

For the different emitters in the above-described OLED structure, the following electrooptical data are obtained:

| Emitter | CIE | lm/W @ 300 nits | $t_{1/2}$ @ 300 nits (normalized to the value of CEm) |
|---|---|---|---|
| CEm | 0.15, 0.15 | 6.5 | 100% |
| fac-Em2 | 0.17, 0.30 | 6.4 | 714% |
| fac-Em1 | 0.17, 0.28 | 4.5 | 5300% |

Example 10

Influence of the Matrix Material (Part 1)

The emission layer of the structure described in example 9 is varied. The doping level of MoO$_x$ is 50%. A mixture of emitter fac-Em1 (20%) and different matrix materials (80%) is applied by vapor deposition with a thickness of 20 nm. The hole/exciton blocker (5 nm) used in each case is the matrix material. The electron conductor used is a mixture of BCP and liq (50:50) in a thickness of 40 nm. The electron injector used is liq (1 nm). In addition to Ma1, the following materials are used:

Ma2

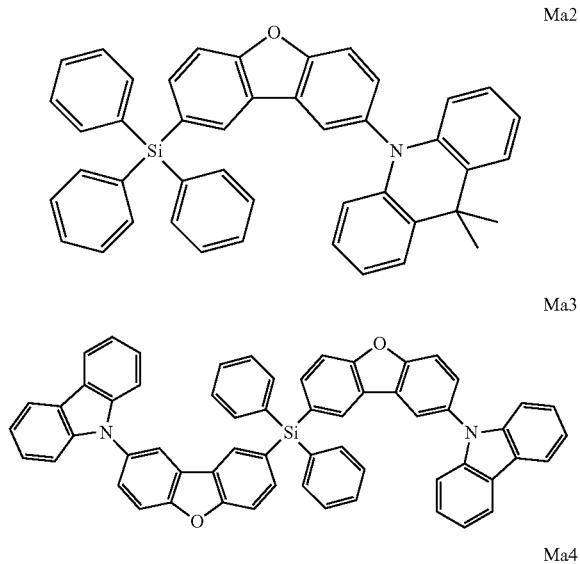

Ma3

Ma4

The syntheses of Ma2, Ma3 and Ma4 are described in WO2010079051.

Ma5

Ma6

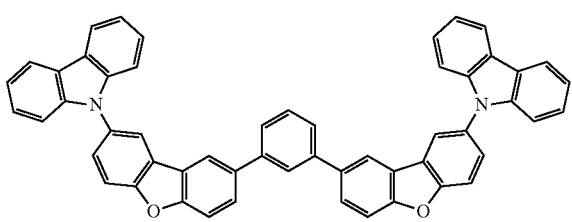

Ma6 can be prepared by a process known to a person skilled in the art. 9-(8-Bromodibenzofuran-2-yl)-9H-carbazole (see WO2010079051) is reacted with n-BuLi in THF and 2-isopropoxy-4,4,5,5-tetramethyl-1,3,2-dioxaborolane to give 9-[8-(4,4,5,5-tetramethyl-[1,3,2]dioxaborolan-2-yl)dibenzofuran-2-yl]-9H-carbazole (analogously to stage 1 of Example 18), which is then reacted in a Suzuki coupling known to those skilled in the art with 1,3-diiodbenzene to give Ma6.

Ma7

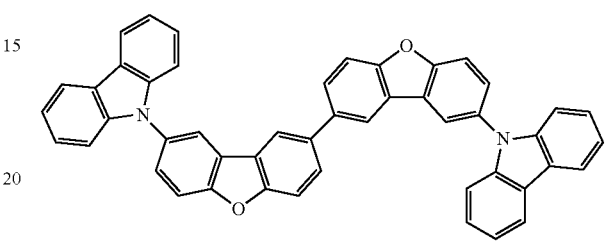

The synthesis of Ma7 is described in Example 19.

For the different matrix materials in the above-described OLED structure, the following electrooptical data are obtained (normalized to the value of Ma5):

| Matrix | CIE | EQE @ 300 nits | lm/W @ 300 nits | Voltage @ 300 nits |
| --- | --- | --- | --- | --- |
| Ma2[a,b,c,d,e] | 0.17, 0.28 | 98% | 120% | 95% |
| Ma3[f] | 0.17, 0.28 | 106% | 160% | 77% |
| Ma1 | 0.17, 0.26 | 119% | 164% | 80% |
| Ma4[f,g] | 0.17, 0.28 | 109% | 176% | 72% |
| Ma5 | 0.16, 0.23 | 100% | 100% | 100% |
| Ma6[a] | 0.17, 0.29 | 120% | 171% | 83% |
| Ma7[a,f,h] | 0.17, 0.31 | 133% | 275% | 60% |

[a] 10% MoO$_x$ doping
[b] Emission layer 40 nm
[c] Ma1 as hole/exciton blocker 10 nm
[d] Electron conductor: 20 nm BCP: Ma1 80:20
[e] Electron injector: LiF (0.7 nm)
[f] Doping level 30% emitter in 70% matrix
[g] Electron conductor layer 35 nm
[h] Hole/exciton blocker 10 nm, electron conductor 20 nm, electron injector CsF Example 10a The emission layer of the structure described in Example 10 is varied. The emission layer used is a mixture of fac-Em1 (30%) and matrix (see table below, 70%). The hole conductor layer used is a layer of 40 nm of Ir(DPBIC)$_3$, of which the first 35 nm have been doped with ReO$_3$ (5%). The hole/exciton blocker used is a layer of 5 nm of Ma7. The electron conductor used is a mixture of liq and ETM1 (50:50, 40 nm). The electron injector used is KF in a thickness of 4 nm.

ETM1

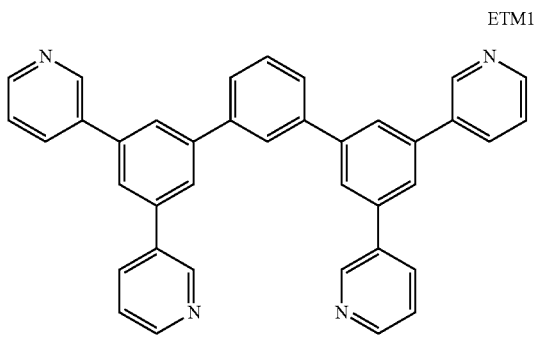 [SMILES: c1cncc(-c2cc(-c3cccnc3)cc(-c3cccc(-c4cc(-c5cccnc5)cc(-c5cccnc5)c4)c3)c2)c1]

ETM1 is commercially available.

Ma8

Ma9

Ma10

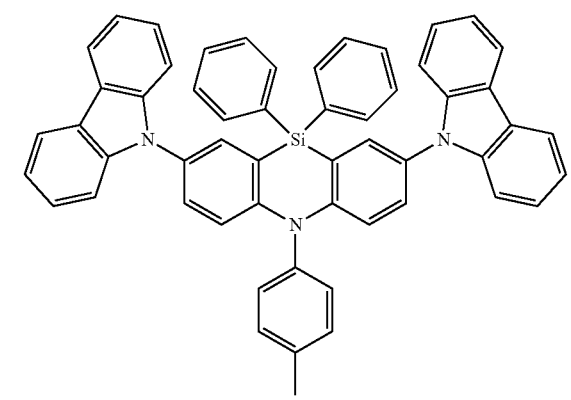

The syntheses of Ma8, Ma9 and Ma10 are described in JP2006083167.

For the different matrix materials in the above-described OLED structure, the following electrooptical data are obtained normalized to the value of Ma8):

| Matrix | CIE | EQE @ 300 nits |
|---|---|---|
| Ma8 | 0.18, 0.31 | 100% |
| Ma9 | 0.17, 0.30 | 145% |
| Ma10 | 0.17, 0.31 | 128% |
| Ma7* | 0.16, 0.26 | 154% |

*Doping level emitter 10%

Example 10b

A diode with the emitter Em8 is constructed analogously to Example 10. The hole conductor layer is 40 nm thick. Em8 is doped at a level of 30% into Ma4. The electron conductor layer used is ETM1 in a thickness of 40 nm. The electron injector used is KF (2 nm).

The diode exhibits the color coordinates CIE 0.19, 0.37. At 300 cd/m$^2$, the voltage is 3.5 V and the luminous efficiency is 11 lm/W.

Example 10c

A diode is constructed analogously to Example 10a for Ma7. The emitter used is Em8 instead of fac-Em1.

The diode exhibits the color coordinates CIE 0.17, 0.31.

Example 10d

A diode is constructed analogously to Example 10a for Ma7. The emitter used is Em8 instead of fac-Em1. The matrix is varied. For the different matrix materials in the above-described OLED structure, the following electrooptical data are obtained (normalized to the value of Ma10):

| Matrix | CIE | EQE @ 300 nits | lm/W @ 300 nits | Voltage @ 300 nits |
|---|---|---|---|---|
| Ma10 | 0.17, 0.32 | 100% | 100% | 100% |
| Ma8 | 0.17, 0.30 | 128% | 133% | 94% |
| Ma9 | 0.17, 0.30 | 149% | 156% | 92% |

Example 10e

A diode is constructed analogously to Example 10a. The emitter used is fac-Em12 instead of fac-Em1 in a dopant concentration of 20% in the matrix Ma4 (80%). The hole/exciton blocker is used in a thickness of 10 nm.

The diode exhibits the color coordinates CIE 0.19, 0.36. At 300 cd/m$^2$ the voltage is 4.0 V and the external quantum efficiency 13%.

Example 10f

A diode is constructed analogously to Example 10a. The emitter used is fac-Em14 instead of fac-Em1 in a dopant concentration of 20% in the matrix Ma4 (80%). The hole/exciton blocker is used in a thickness of 10 nm.

The diode exhibits the color coordinates CIE 0.20, 0.27.

Example 10g

A diode is constructed analogously to Example 10a. The hole conductor and exciton blocker applied to the substrate is Ir(DPBIC)$_3$ with a thickness of 45 nm, of which the first 35 nm have been doped with MoO$_x$ (10%) to improve the conductivity. The hole/exciton blocker is applied in a thickness of 10 nm. The emitter used is fac-Em13 instead of fac-Em1 in a dopant concentration of 20% in the matrix Ma4 (80%).

The diode exhibits the color coordinates CIE 0.14, 0.22. At 300 cd/m², the voltage is 3.7 V.

Example 10h

A diode is constructed analogously to Example 10g. The emitter used is fac-Em13 in a dopant concentration of 20% in the matrix Ma7 (80%).

The diode exhibits the color coordinates CIE 0.14, 0.22. At 300 cd/m² the voltage is 3.6 V and the external quantum efficiency 16%.

Example 11

Influence of the Matrix Material (Part 2)

The emission layer of the structure described in example 10 is varied. A mixture of emitter fac-Em1 (20%) and one or two matrix materials is applied by vapor deposition with a thickness of 20 nm. When two matrix materials are used, the two matrix materials are used in equal ratios. The hole/exciton blocker used in each case is Ma1.

The following electrooptical data are obtained:

| Matrix | CIE | Voltage @ 300 nits (normalized to the value of Ma1) |
|---|---|---|
| Ma1 | 0.17, 0.26 | 100% |
| Ir(DPBIC)₃ | 0.16, 0.24 | 83% |
| Ma1 + Ir(DPBIC)₃ | 0.16, 0.23 | 77% |
| Ma11 | 0.17, 0.29 | 93% |
| Ma11 + Ir(DPBIC)₃ | 0.16, 0.25 | 73% |

Ma11

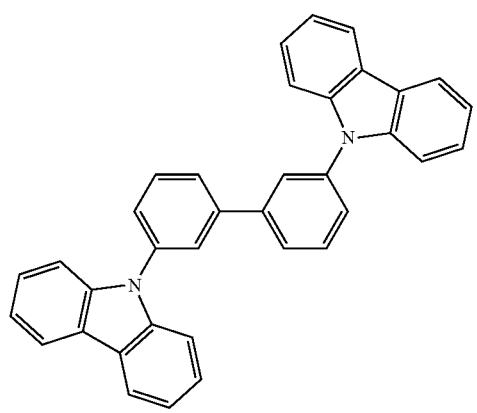

Ma11 is commercially available.

Example 11a

Construction as in Example 10a. The emission layer used is a mixture of Ir(DPBIC)₃ (35%), fac-Em1 (30%) and matrix (35%, see table below). The hole/exciton blocker used in each case is the matrix material.

Ma12

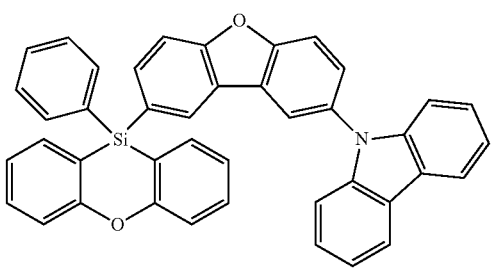

Ma13

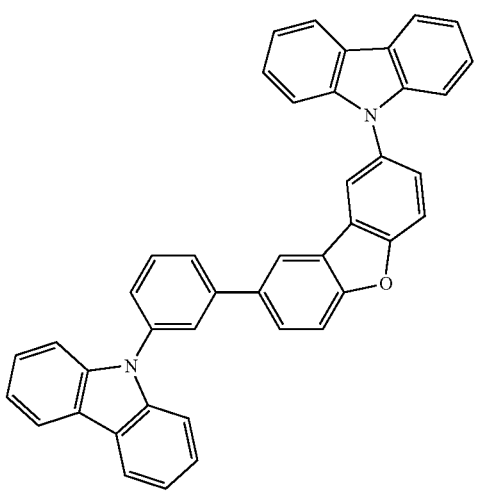

Ma14

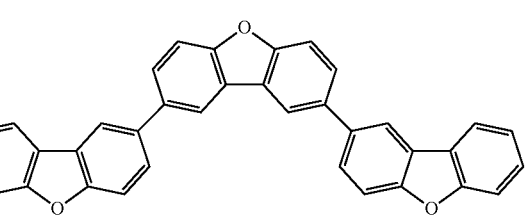

The synthesis of Ma13 is described in WO2009008100.
The synthesis of Ma12 is described in Example 20 and the synthesis of Ma14 is described in Example 18.

For the different matrix materials in the above-described OLED structure, the following electrooptical data are obtained (normalized to the value of Ma9):

| Matrix | CIE | EQE @ 300 nits | lm/W @ 300 nits | Voltage @ 300 nits |
|---|---|---|---|---|
| Ma9* | 0.18, 0.32 | 100% | 100% | 100% |
| Ma7 | 0.18, 0.33 | 105% | 112% | 97% |
| Ma4 | 0.17, 0.32 | 102% | 107% | 94% |
| Ma12ᵃ | 0.17, 0.30 | 117% | 124% | 91% |
| Ma13 | 0.17, 0.31 | 116% | 107% | 106% |
| Ma14 | 0.17, 0.31 | 104% | 121% | 86% |

*The hole/exciton blocker used is Ma7
ᵃElectron injection layer 2 nm

Example 11 b

Construction as in Example 10a. The emission layer used is a mixture of Ir(DPBIC)₃ (45%), Em8 (10%) and matrix (45%, see table below).

For the different matrix materials in the OLED structure described above, the following electrooptical data are obtained (normalized to the value of Ma9):

| Matrix | CIE | EQE @ 300 nits | lm/W @ 300 nits | Voltage @ 300 nits |
|---|---|---|---|---|
| Ma9* | 0.17, 0.31 | 100% | 100% | 100% |
| Ma4 | 0.17, 0.34 | 107% | 131% | 87% |
| Ma7 | 0.17, 0.35 | 106% | 129% | 87% |
| Ma13[a] | 0.17, 0.32 | 93% | 118% | 79% |

*The hole/exciton blocker used is Ma7
[a] The electron injector used is CsF (4 nm)

Example 11c

Construction as in Example 11a. The hole conductor and exciton blocker applied to the substrate is Ir(DPBIC)$_3$ with a thickness of 40 nm, of which the first 35 nm have been doped with MoO$_x$ (50%) to improve the conductivity. The emission layer used is a mixture of Ir(DPBIC)$_3$ (40%), fac-Em12 (20%) and Ma4 (40%). The electron conductor layer used is a mixture of ETM1:Liq (75:25) in a thickness of 40 nm. The electron injector used is KF (2 nm).

The diode exhibits the color coordinates CIE 0.20, 0.40. At 300 cd/m$^2$, the voltage is 3.0 V and the external quantum efficiency 13%.

Example 11d

Structure as in Example 1 b. The emission layer used is a mixture of Ir(DPBIC)$_3$ (45%), fac-Em14 (10%) and Ma4 (45%).

The diode exhibits the color coordinates CIE 0.26, 0.39. At 300 cd/m$^2$, the voltage is 3.0 V.

Example 11e

A diode is constructed analogously to Example 11a. The hole conductor and exciton blocker applied to the substrate is Ir(DPBIC)$_3$ with a thickness of 45 nm, of which the first 35 nm have been doped with MoO$_x$ (10%) to improve the conductivity. The hole/exciton blocker used is Ma7 (5 nm). The emission layer used is a mixture of Ir(DPBIC)$_3$ (40%), fac-Em13 (30%) and Ma4 (30%).

The diode exhibits the color coordinates CIE 0.15, 0.26. At 300 cd/m$^2$, the voltage is 3.4 V.

Example 11f

A diode is constructed analogously to Example 11a. The hole conductor and exciton blocker applied to the substrate is Ir(DPBIC)$_3$ with a thickness of 45 nm, of which the first 35 nm have been doped with MoO$_x$ (10%) to improve the conductivity. The hole/exciton blocker is applied in a thickness of 10 nm. The emission layer used is a mixture of Ir(DPBIC)$_3$ (40%), fac-Em13 (30%) and Ma7 (30%).

The diode exhibits the color coordinates CIE 0.14, 0.25. At 300 cd/m$^2$, the external quantum efficiency is 15%.

Example 11g

A diode is constructed analogously to Example 11a. The emission layer used is a mixture of Ir(DPBIC)$_3$ (40%), fac-Em13 (30%) and Ma15 (30%).

The diode exhibits the color coordinates CIE 0.14, 0.23. At 300 cd/m$^2$, the external quantum efficiency is 17%.

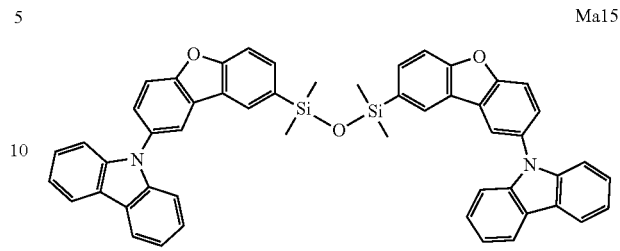

Ma15

Synthesis of Ma15 is described in WO2010079051.

Example 11h

A diode is constructed analogously to Example 11a for Ma12. Instead of Ma12, Ma16 (see synthesis in JP2009267255) is used.

The diode exhibits the color coordinates CIE 0.18, 0.34 and a voltage of 3.3 V at 300 cd/m$^2$.

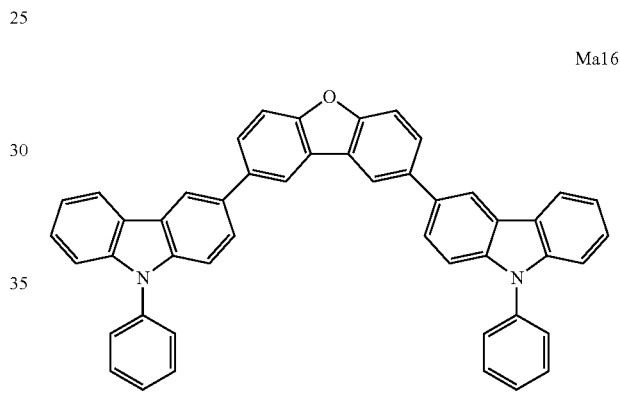

Ma16

Example 11i

White Diodes

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer AJ20-1000 from Plexcore is spun on from solution.

Layered White (Example 11Ia)

After the hole injection layer, the organic materials specified hereinafter are applied to the cleaned substrate by vapor deposition at a rate of approx. 0.5-5 nm/min at about $10^{-7}$-$10^{-9}$ mbar. The hole conductor and exciton blocker applied to the substrate is Ir(DPBIC)$_3$ with a thickness of 20 nm, of which the first 10 nm have been doped with 10% MoO$_x$ to improve the conductivity.

Subsequently, a mixture of 10% emitter Red1 and 90% of the compound Ma7 is applied by vapor deposition with a thickness of 6 nm, the latter compound functioning as matrix material. In a further configuration 11ib, the aforementioned mixture is replaced by a mixture of 10% emitter Red1, 60% of the matrix Ma7 and 30% of the matrix Ir(DPBIC)$_3$.

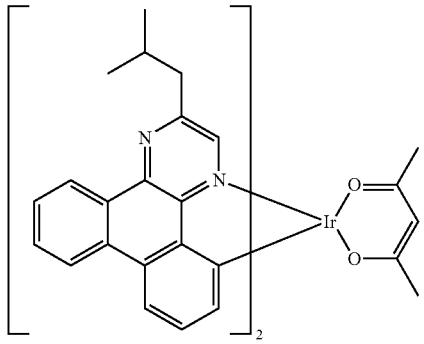

Red1 (for Synthesis See Example 21)

Subsequently, a mixture of the materials fac-Em1, Ma7 and Ir(DPBIC)$_3$ is applied by vapor deposition with a layer thickness of 30 nm. The mixing ratio is 40% emitter fac-Em1, 30% of the matrix Ma7 and 30% of the second matrix Ir(DPBIC)$_3$. Subsequently, the material Ma7 is applied with a layer thickness of 10 nm as a hole and exciton blocker. The subsequent electron conductor layer used is a Cs$_2$CO$_3$-doped BCP layer with a layer thickness of 30 nm. An aluminum cathode of thickness 100 nm concludes the diode.

All components are adhesive bonded to a glass lid in an inert nitrogen atmosphere.

Stacked White (Example 11ic)

After the hole injection layer, the organic materials specified hereinafter are applied by vapor deposition to the clean substrate at a rate of approx. 0.5-5 nm/min at about $10^{-7}$-$10^{-9}$ mbar. The hole conductor and exciton blocker applied to the substrate is Ir(DPBIC)$_3$ with a thickness of 20 nm, of which the first 10 nm have been doped with 10% MoO$_x$ to improve the conductivity.

Subsequently, a mixture of the materials fac-Em1, Ma1 and Ir(DPBIC)$_3$ is applied by vapor deposition with a thickness of 20 nm. The mixing ratio is 30% emitter fac-Em1, 40% of the matrix Ma1 and 30% of the matrix Ir(DPBIC)$_3$. Subsequently, a pure layer of 10 nm of Ma1 is applied as an exciton and hole blocker.

The subsequent combination of 20 nm of BCP doped with Cs$_2$CO$_3$ and 60 nm of Ir(DPBIC)$_3$ (in a further configuration 11id with 90 nm of Ir(DPBIC)$_3$) doped with 10% MoO$_x$ serves as the charge-generating layer.

Subsequently, Ir(DPBIC)$_3$ as a hole conductor and exciton blocker is applied to the substrate with a thickness of 10 nm. Subsequently, a mixture of the materials Red1, NPD and Ma17 is applied with a thickness of 20 nm. The mixing ratio is 10% emitter Red1, 40% of the matrix NPD and 50% of the second matrix Ma17.

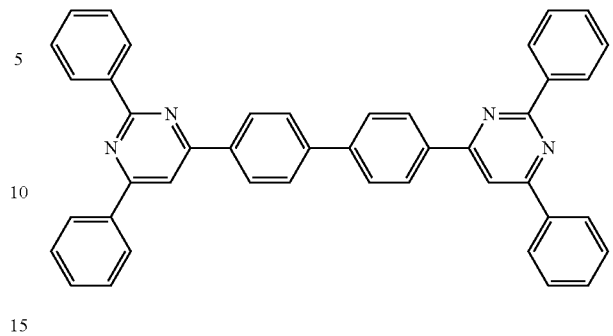

Compound E2 from WO04039786

Subsequently, a pure layer of 10 nm of BAlq is applied as an exciton and hole blocker.

The subsequent electron conductor layer used is a Cs$_2$CO$_3$-doped BCP layer with a layer thickness of 50 nm. An aluminum cathode of thickness 100 nm concludes the diode.

All components are adhesive bonded to a glass lid in an inert nitrogen atmosphere.

To characterize the OLED, electroluminescence spectra are recorded at different currents and voltages. In addition, the current-voltage characteristic is measured in combination with the light output emitted. The light output can be converted to photometric parameters by calibration with a photometer.

For the two working examples of a white OLED, the following electrooptical data are obtained:

| Ex. | CIE | lm/W @ 1000 nits | EQE* @ 1000 nits |
|---|---|---|---|
| 11ia | 0.33, 0.36 | 14.8 lm/W | 13.8% |
| 11ib | 0.29, 0.36 | 16.4 lm/W | 12.9% |
| 11ic | 0.3, 0.3 | 18.5 lm/W | 30.0% |
| 11id | 0.35, 0.37 | 21.5 lm/W | 29.3% |

*EQE—external quantum efficiency. Measured in the forward direction assuming a Lambertian light intensity distribution.

Example 11j: Liquid-Processed Emission Layer

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer AJ20-1000 from Plexcore is spun on from solution.

Thereafter, the hole conductor and exciton blocker Ir(DPBIC)$_3$ is applied from the liquid phase. For this purpose, a solution of Ir(DPBIC)$_3$ in THF is spun on with a concentration of 10 mg/ml at a speed of 5000 revolutions per minute (rpm) (spin-coating).

Subsequently, the emission layer consisting of the emitter fac-Em1 and the host Ma7 is likewise applied from the liquid phase. For this purpose, a solution of fac-Em1 and Ma7 in methylene chloride with a concentration of 10 mg/ml is spun on at a speed of 5000 rpm. The weight ratio of the solids between emitter and host is 30:70.

Thereafter, the organic materials mentioned hereinafter are applied by vapor deposition under reduced pressure at a rate of approx. 0.5-5 nm/min at about $10^7$-$10^{-9}$ mbar to the layers already present.

First, 10 nm of pure Ma7 is applied by vapor deposition as an exciton blocker. Subsequently, the electron conductor ETM1:Liq (50:50) is applied by vapor deposition with a layer thickness of 20 nm.

The electron injector which then follows is 1 nm of CsF, and 100 nm of aluminum are applied as a cathode. The component is adhesive bonded to a glass lid in an inert nitrogen atmosphere and exhibits the color coordinates CIE x=0.20, y=0.35.

Example 12

Influence of a Mixed Electron Conductor Layer

The electron-transporting layer of the structure described in example 9 for fac-Em1 is varied. The following electrooptical data are obtained:

| Electron conductor (20 nm) | CIE | lm/W @ 300 nits | $t_{1/2}$ @ 300 nits (normalized to the value of BCP) |
|---|---|---|---|
| BCP | 0.16, 0.22 | 3.2 | 100% |
| BCP:Liq 50% | 0.17, 0.26 | 9.0 | 2780% |

Example 13

Emitter Em12:

2,3-Bis-(N-4'-methylphenylamino)pyrazine

A mixture of 2,3-dichloropyrazine (13.4 g, 90 mmol) in p-toluidine (21.2 g, 198 mmol) is stirred at 110° C. overnight. After cooling to room temperature, the mixture is taken up in dichloromethane (200 ml) and extracted by shaking with 25% sodium hydroxide solution. The combined organic phases are dried over sodium sulfate and concentrated to dryness. The residue is stirred with petroleum ether, filtered off with suction and washed with cyclohexane. Yield: 15.7 g (60%).

$^1$H NMR (CD$_2$Cl$_2$, 500 MHz): δ=2.30 (s, 6H), 6.24 (br s, 2H), 7.10 (d, 4H), 7.18 (d, 4H), 7.67 (s, 2H).

2-Ethoxy-1,3-bis(4'-methylphenyl)pyrazinoimidazoline

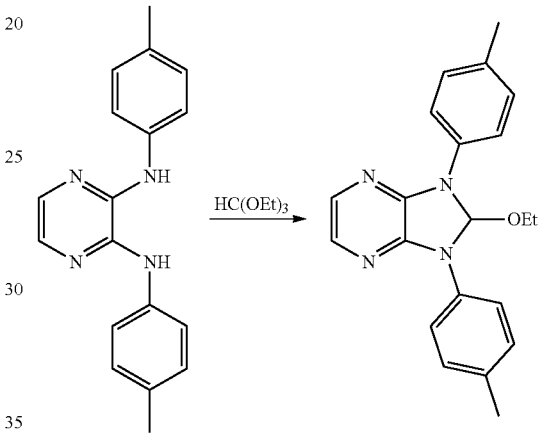

A mixture of 2,3-bis(N-4'-methylphenylamino)pyrazine (4.0 g, 14 mmol) in triethyl orthoformate (65 ml) is stirred at 75° C. overnight. After cooling to room temperature, the mixture is filtered and the filtrate is concentrated to dryness. The residue is recrystallized from methyl tert-butyl ether. Yield: 3.3 g (70%).

$^1$H NMR (CD$_2$Cl$_2$, 500 MHz): δ=0.99 (t, 3H), 2.32 (s, 6H), 3.24 (q, 2H), 7.16 (s, 1H), 7.21 (d, 4H), 7.42 (s, 2H), 7.85 (d, 4H).

Complex Fac-Em12:

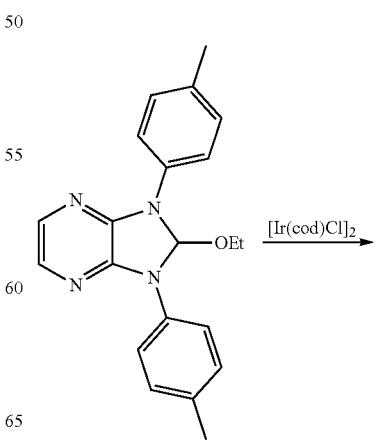

-continued

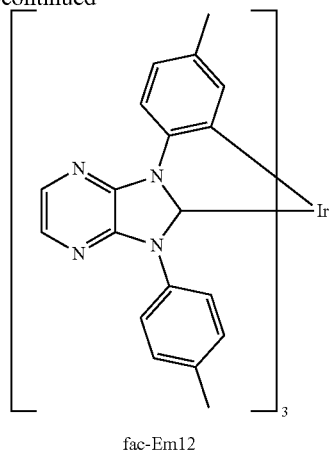

fac-Em12

A solution of 2-ethoxy-1,3-bis(4'-methylphenyl)pyrazino-imidazoline (3.5 g, 10 mmol) in o-xylene (60 ml) is admixed with 3 Å molecular sieve (6 g) and chloro(1,5-cyclooctadiene)iridium(I) dimer (672 mg, 1.0 mmol). The mixture is stirred at 115° C. overnight. After cooling to 80° C., the residue is filtered off with suction and washed with dichloromethane. The combined filtrates are concentrated to dryness and the residue is washed with warm isopropanol. The crude product is purified by column chromatography (silica gel, toluene→dichloromethane). Yield: 0.8 g (37%).

$^1$H NMR (CD$_2$Cl$_2$, 500 MHz): δ=1.85 (s, 9H), 2.06 (s, 9H), 6.44 (s, 3H), 6.91 (d, 3H), 7.97 (d, 3H), 8.27 (d, 3H), 8.56 (d, 3H). The 12 protons of the non-cyclometalated tolyl ring are discernible only as a very broad elevation in the aromatic region at room temperature owing to the rotation of the aromatic system.

Photoluminescence (2% in a PMMA film):
λ$_{max}$=485 nm, CIE: (0.18; 0.36), QY=85%

Example 14

Emitter Em113:
Pyrazine Compound (a)

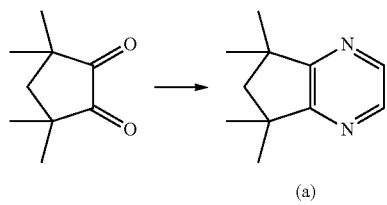

(a)

(a) A mixture of 3,3,5,5-tetramethylcyclopentane-1,2-dione (for synthesis see: T. Laitalainen, *Finn. Chem. Lett.* 1982, 10) (30.5 g, 188 mmol) and ethylenediamine (15.9 ml, 235 mmol) in ethanol (1.45 l) is stirred under reflux overnight. After cooling to 45° C., manganese(IV) oxide (36.0 g, 414 mmol) and potassium hydroxide (11.6 g, 207 mmol) are added, and the mixture is stirred under reflux for 5 h. After cooling to 70° C., the mixture is filtered and the filtrate is neutralized with 10% hydrochloric acid at room temperature. The suspension is filtered and the filtrate is concentrated to dryness. The residue is column-filtered through silica gel with dichloromethane. Yield: 22.7 g (69%).

$^1$H NMR (CD$_2$Cl$_2$, 500 MHz): δ=1.33 (s, 12H), 1.98 (s, 2H), 8.30 (s, 2H).

Pyrazine Compound (b)

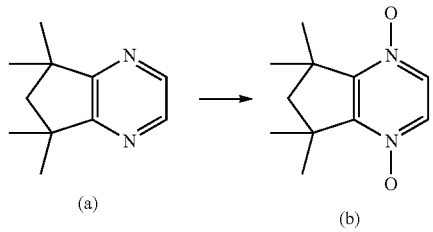

A mixture of pyrazine compound (a) (18.1 g, 98 mmol) and water (750 ml) is admixed with potassium peroxomonosulfate (Oxone, 144 g, 234 mmol), and stirred at 50° C. overnight. The aqueous phase is extracted with dichloromethane, washed twice with water, dried over sodium sulfate and concentrated to dryness. Yield: 17.0 g (84%).

$^1$H NMR (CD$_2$Cl$_2$, 500 MHz): δ=1.51 (s, 12H), 1.97 (s, 2H), 7.78 (s, 2H).

Pyrazine Compound (c)

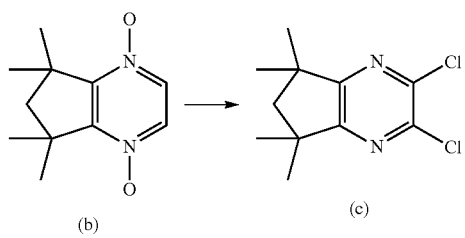

A mixture of pyrazine compound (b) (18.3 g, 83 mmol) in phosphoryl chloride (325 ml) is stirred under reflux overnight. After cooling to room temperature, the solution is cautiously added dropwise to a mixture of ice-water (5 l) and dichloromethane (1.5 l). After neutralization with concentrated sodium hydroxide solution, the organic phase is removed, washed three times with water, dried over sodium sulfate and concentrated to dryness. This affords a mixture of product (approx. 80%) and monochlorinated by-product (approx. 20%), which is used without further workup. Pure product can be obtained by stirring in petroleum ether. Overall yield: 19.2 g (94%).

$^1$H NMR (CD$_2$Cl$_2$, 500 MHz): δ=1.29 (s, 12H), 1.99 (s, 2H).

Pyrazine Compound (d)

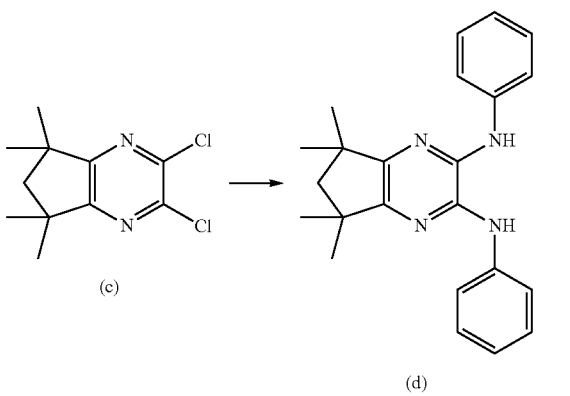 [SMILES: CC1(C)CC(C)(C)c2nc(Cl)c(Cl)nc21 ; CC1(C)CC(C)(C)c2nc(Nc3ccccc3)c(Nc3ccccc3)nc21]

(c) → (d)

A mixture of pyrazine compound (c) (5.5 g, 22 mmol) and aniline (24.6 ml, 270 mmol) in o-xylene (65 ml) is stirred at 150° C. overnight. After cooling to room temperature, the precipitate is filtered off with suction and washed with toluene. The combined filtrates are concentrated to dryness in the presence of silica gel. The residue is filtered through silica gel with a mixture of cyclohexane and ethyl acetate, and the filtrate is concentrated to dryness. Yield: 6.6 g (81%).

$^1$H NMR (CD$_2$Cl$_2$, 500 MHz): δ=1.28 (s, 12H), 1.95 (s, 2H), 6.25 (br s, 2H), 6.90-6.95 (m, 2H), 7.21-7.27 (m, 8H).

Pyrazine Compound (e)

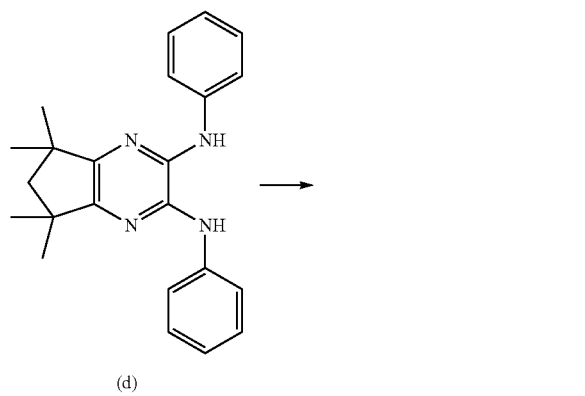

(d) → (e)

A mixture of pyrazine compound (d) (0.50 g, 0.7 mmol) in triethyl orthoformate (3.5 ml) is admixed with ammonium iodide (0.31 g, 2.1 mmol), and stirred at 85° C. for 2 h. After cooling to room temperature, the solids are filtered off with suction, washed with triethyl orthoformate, cold ethanol and n-heptane, and dried in a vacuum drying cabinet at 65° C. Yield: 0.16 g (46%).

$^1$H NMR (d$_6$-DMSO, 500 MHz): δ=1.41 (s, 12H), 2.19 (s, 2H), 7.74 (dd, 2H), 7.82 (dd, 4H), 8.01 (d, 4H), 10.98 (s, 1H).

Complex Fac-Em13:

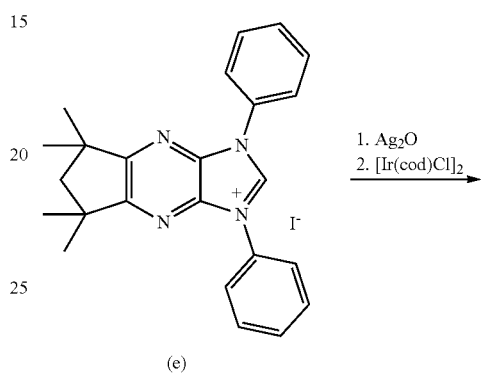

(e) 
1. Ag$_2$O
2. [Ir(cod)Cl]$_2$

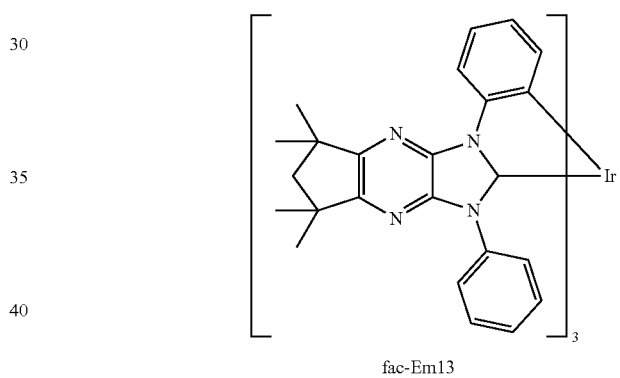

fac-Em13

A suspension of pyrazine compound (e) (1.1 g, 2.1 mmol) in dioxane (60 ml) is admixed with 4 Å molecular sieve (11 g) and silver(I) oxide (0.5 g, 2.1 mmol), and stirred at room temperature overnight. Subsequently, a solution of chloro (1,5-cyclooctadiene)iridium(I) dimer (142 mg, 0.2 mmol) in o-xylene (75 ml) is added. The mixture is stirred at reflux overnight. After cooling to 80° C., the residue is filtered off with suction. The filtrate is concentrated on a rotary evaporator down to a volume of approx. 60 ml and left to stand overnight. The precipitate is filtered off, washed with toluene and n-hexane and dried in a vacuum drying cabinet at 85° C. Yield: 0.3 g (57%).

$^1$H NMR (CD$_2$Cl$_2$, 500 MHz): δ=1.15 (s, 9H), 1.35 (s, 9H), 1.46 (s, 9H), 1.59 (s, 9H), 2.11 (me, 6H), 6.67 (d, 3H), 6.73 (dd, 3H), 6.79 (dd, 3H), 7.14 (dd, 3H), 8.86 (d, 3H). 12 of the 15 protons of the non-cyclometalated phenyl ring are discernible only as a very broad elevation in the aromatic region at room temperature owing to the rotation of the aromatic system.

Photoluminescence (2% in a PMMA film):

$\lambda_{max}$=474 nm, CIE: (0.14; 0.24), QY=91%

Example 15

Emitter Em14:

2,3-Bis(N-4'-fluorophenylamino)pyrazine

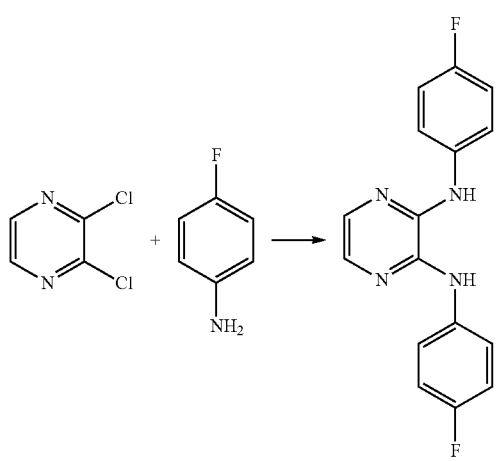 [SMILES: Clc1nccnc1Cl ; Nc1ccc(F)cc1 ; Fc1ccc(Nc2nccnc2Nc2ccc(F)cc2)cc1]

A mixture of 2,3-dichloropyrazine (8.6 g, 58 mmol) and 4-fluoroaniline (66.3 g, 148 mmol) in o-xylene (100 ml) is stirred at 130° C. overnight and at 140° C. for 4 h. After cooling to room temperature, the mixture is concentrated to dryness and the residue is taken up in dichloromethane (300 ml), water (100 ml) and ammonia (25% in water, 100 ml). The organic phase is removed, washed twice with water, dried over sodium sulfate and concentrated to dryness. The residue is stirred with petroleum ether, filtered off with suction and washed with methyl tert-butyl ether. Yield: 12.7 g (73%).

$^1$H NMR (CD$_2$Cl$_2$, 500 MHz): δ=6.30 (br s, 2H), 7.03 (dd, 4H), 7.31 (dd, 4H), 7.72 (s, 2H).

2-Ethoxy-1,3-bis(4'-fluorophenyl)pyrazinoimidazoline

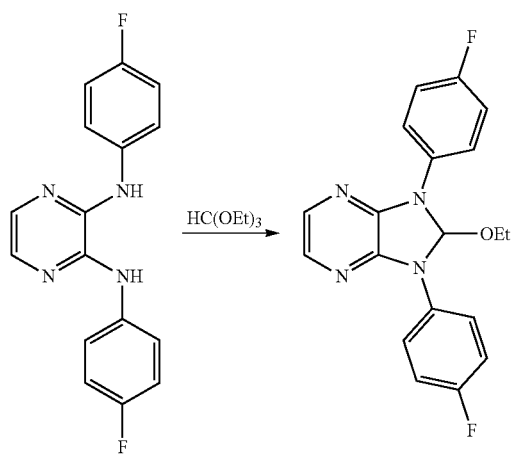 [SMILES: Fc1ccc(Nc2nccnc2Nc2ccc(F)cc2)cc1 ; CCOC1N(c2ccc(F)cc2)c2nccnc2N1c1ccc(F)cc1 ; "HC(OEt)3"]

A mixture of 2,3-bis(N-4'-fluorophenylamino)pyrazine (1.2 g, 4 mmol) in triethyl orthoformate (36 ml) is admixed with sodium sulfate (4.7 g) and 5 Å molecular sieve (4.7 g), and stirred at 100° C. for 24 h. After cooling to room temperature, the mixture is filtered through sodium sulfate and cotton wool, and washed with methyl tert-butyl ether. The combined filtrates are concentrated to dryness. The residue is stirred with n-pentane and filtered off with suction. Yield: 0.6 g (42%).

$^1$H NMR (CD$_2$Cl$_2$, 500 MHz): δ=1.01 (t, 3H), 3.26 (q, 2H), 7.08-7.16 (m, 5H), 7.46 (s, 2H), 7.98 (dd, 4H).

Complex Fac-Em14:

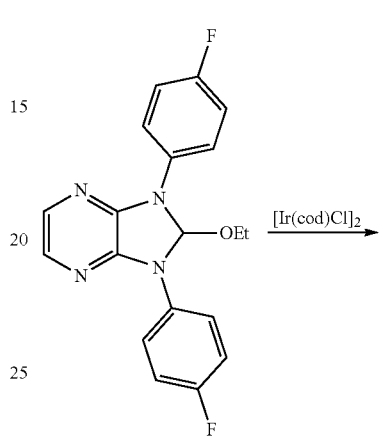

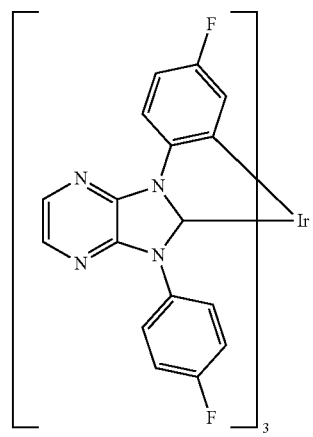

fac-Em14

A solution of 2-ethoxy-1,3-bis(4'-fluorophenyl)pyrazinoimidazoline (560 mg, 1.60 mmol) in o-xylene (60 ml) is admixed with sodium sulfate (4.7 g), 5 Å molecular sieve (4.7 g) and chloro(1,5-cyclooctadiene)iridium(I) dimer (107 mg, 0.16 mmol). The mixture is stirred at 110° C. overnight. After again adding chloro(1,5-cyclooctadiene)iridium(I) dimer (107 mg, 0.16 mmol), the mixture is stirred at 110° C. for 5 h. After cooling to 80° C., the residue is filtered off with suction and washed with dichloromethane. The combined filtrates are concentrated to dryness and the residue is purified by column chromatography (silica gel, chloroform→toluene). Yield: 133 mg (19%).

$^1$H NMR (CD$_2$Cl$_2$, 500 MHz): δ=6.30 (dd, 3H), 6.84 (ddd, 3H), 8.09 (d, 3H), 8.36 (d, 3H), 8.71 (dd, 3H). The 12 protons of the non-cyclometalated 4-fluorophenyl ring are discernible only as a very broad elevation in the aromatic region at room temperature owing to the rotation of the aromatic ring.

Photoluminescence (2% in a PMMA film):

$\lambda_{max}$=458 nm, CIE: (0.17; 0.17), QY=58%

Example 16

Emitter Em15

2-Ethoxy-1,3-diphenyl-2,3-dihydro-1H-imidao[4,5-b]pyrazine

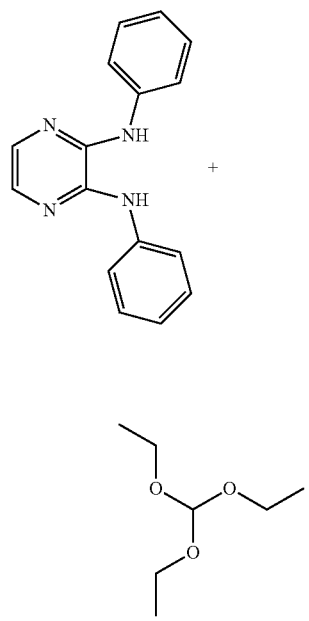

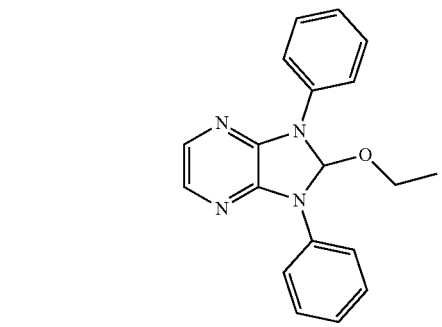

15.30 g (58.3 mmol) of 2,3-Bis(N-phenylamino)pyrazine, 68.00 g of sodium sulfate and 68.00 g of molecular sieve (4A) are heated to 90° C. in 270 ml of triethyl orthoformate for 45 h. After cooling, the solids are filtered off and washed with methyl tert-butyl ether. The filtrate is freed of the solvent under reduced pressure. The red-brown oil obtained is repeatedly stirred with a little n-heptane and dried again under reduced pressure. The residue is purified by column chromatography (silica gel, eluent: 4/1 cyclohexane/acetone). This gives 11.39 g (61%) of 2-ethoxy-1,3-diphenyl-2,3-dihydro-1H-imidao[4,5-b]pyrazine.

$^1$H NMR (DMSO-D$_6$, 500 MHz): δ=0.88 (t, 3H), 3.17 (q, 2H), 7.16-7.20 (m, 2H), 7.45-7.48 (m, 4H), 7.52 (s, 2H), 7.76 (s, 1H), 8.04-8.06 (m, 4H).

Complex Em15

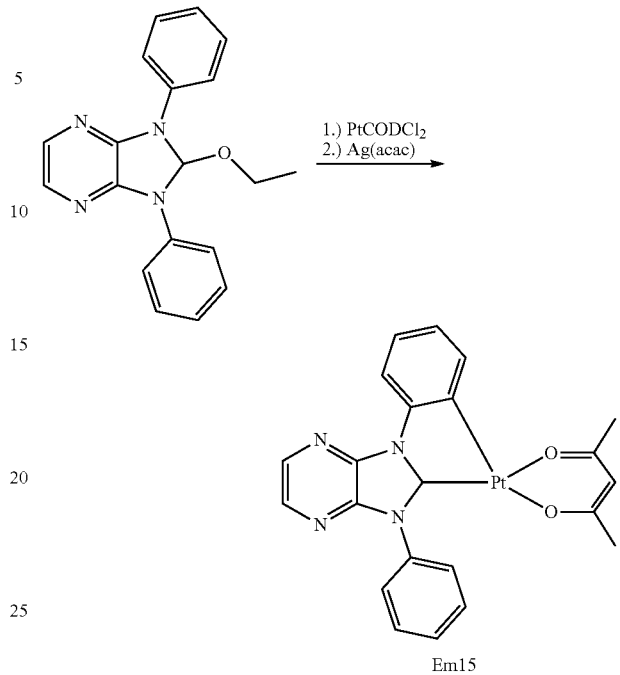

1.85 g (4.90 mmol) of dichloro(1,5-cyclooctadiene)platinum(II) are added at room temperature to a solution of 1.85 g (5.82 mmol) of 2-ethoxy-1,3-diphenyl-2,3-dihydro-1H-imidazo[4,5-b]pyrazine in 60 ml of butanone. The suspension is heated under reflux for 4 hours. Then 1.64 g (7.84 mmol) of silver(I) acetylacetonate are added at room temperature. Thereafter, the mixture is heated under reflux overnight. After cooling, the suspension is filtered. The filtrate is freed of the solvent under reduced pressure and purified by column chromatography (silica gel, eluent: methylene chloride). This gives 0.24 g of Em115 (9%).

$^1$H NMR (CD$_2$Cl$_2$, 500 MHz): δ=1.36 (s, 3H), 2.02 (s, 3H), 5.36 (s, 1H), 7.07 (dt, 1H), 7.17 (dt, 1H), 7.57-7.65 (m, 5H), 7.81 (dd, 1H), 8.20 (dd, 1H), 8.30 (d, 1H), 8.43 (d, 1H).

Photoluminescence (2% in PMMA film):
λ$_{max}$=484 nm, CIE: (0.22; 0.34)

Example 17

Emitter Em16
Complex K4

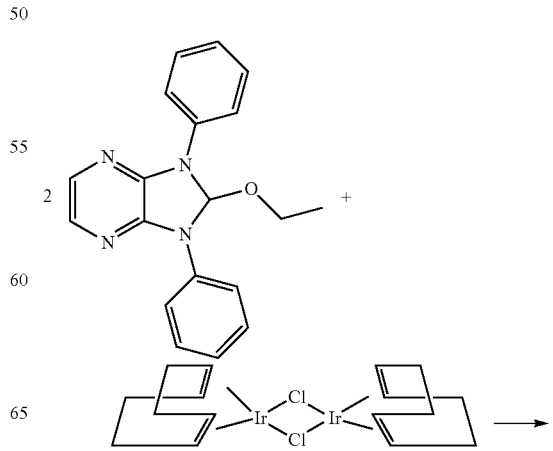

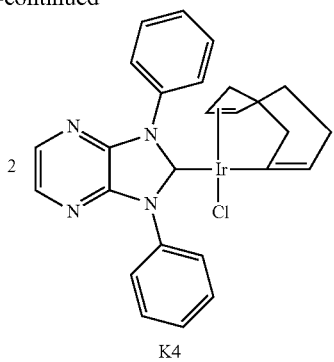

K4

A solution of 0.63 g (0.94 mmol) of bis(1,5-cyclooctadien)diiridium(I) chloride in 50 ml of anhydrous toluene is added dropwise at room temperature to a solution of 0.60 g (1.88 mmol) of 2-ethoxy-1,3-diphenyl-2,3-dihydro-1H-imidazo[4,5-b]pyrazine in 30 ml of anhydrous toluene. The mixture is stirred at 60° C. for 30 min and at 90° C. for 24 h. After cooling, the solvent is removed under reduced pressure and the residue is purified by column chromatography (silica gel, eluent: 100/1 methylene chloride/methanol). This gives 0.85 g (75%) of K4.

$^1$H NMR (CD$_2$Cl$_2$, 500 MHz): δ=1.32-1.38 (m, 2H), 1.44-1.52 (m, 2H), 1.53-1.59 (m, 2H), 1.73-1.81 (m, 2H), 2.55-2.59 (m, 2H), 4.60-4.62 (m, 2H), 7.58-7.65 (m, 6H), 8.13-8.15 (m, 4H), 8.29 (s, 2H).

Complex Em16:

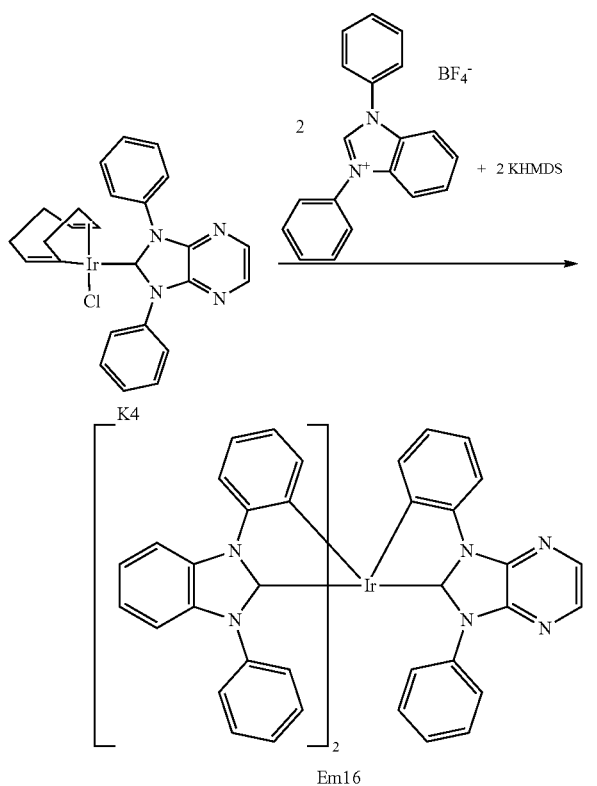

0.75 g (2.09 mmol) of N,N'-diphenylbenzimidazolium tetrafluoroborate (synthesis analogous to WO2005/019373) in 30 ml of anhydrous toluene are admixed at 0° C. with 4.20 ml (2.10 mmol) of a 0.5 molar toluenic potassium hexamethyldisilylamide (KHMDS) solution). The mixture is allowed to thaw to room temperature and is stirred for one hour. Then a solution of 0.61 g (0.99 mmol) of K4 in 150 ml of anhydrous toluene is added dropwise and the mixture is stirred for a further 30 min. Subsequently, the mixture is heated at reflux for one hour. After cooling, the reaction mixture is filtered. The filtrate is freed of the solvent under reduced pressure and purified by column chromatography (silica gel, eluent: cyclohexane/acetone=4/1). This gives 0.30 g of Em16 (30% yield).

$^1$H NMR (CD$_2$Cl$_2$, 500 MHz): δ=6.10-7.20 (very flat, broad signal, 4H), 6.19 (br. d, 1H), 6.22-6.25 (m, 2H), 6.37-6.50 (m, 5H), 6.61 (br. d, 2H), 6.67 (br. d, 1H), 6.72-6.81 (m, 6H), 7.02-7.17 (m, 5H), 7.27-7.34 (m, 4H), 7.95 (d, 1H), 8.00-8.02 (m, 2H), 8.14 (d, 1H), 8.18 (d, 1H), 8.26 (d, 1H), 8.71 (d, 1H).

Photoluminescence (2% in PMMA film):
$\lambda_{max}$=489 nm, CIE: (0.19; 0.38), 98% QY Example 18

Preparation of 2,8-di(dibenzofuran-2-yl)dibenzofuran, Ma14

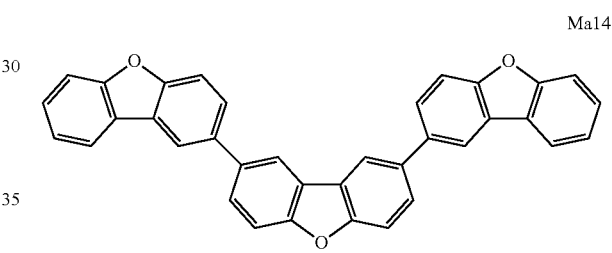

Stage 1:
10.4 g (42.09 mmol) of 2-bromodibenzofuran (prepared according to J. Med. Chem 52(7), 1799-1802, 2009) are weighed into a baked-out 1 l three-neck round-bottom flask provided with magnetic stirrer, thermometer, septum and nitrogen blanketing. 300 ml of THF (made absolute over sodium) are added, and the clear colorless solution is cooled to −78° C. while stirring under an argon atmosphere. Within 30 minutes, 17.1 ml (46.3 mmol) of a 2.7 M solution of butyllithium in hexane are added dropwise, in the course of which the internal temperature is kept at <73° C. This is followed by stirring at this temperature for a further 30 minutes. Thereafter, 8.61 g (46.3 mmol) of 2-isopropoxy-4,4,5,5-tetramethyl-1,3,2-dioxaborolane are added dropwise to the yellow suspension within 40 minutes, in the course of which the internal temperature is kept at <73° C. This is followed by stirring at this temperature for a further 60 minutes. The reaction mixture is warmed to RT and the clear yellow solution is poured onto 200 ml of pH 7 buffer, and 23 ml of 2N HCl are added. The solvent is concentrated on a Rotavap and the aqueous phase is extracted three times with 250 ml of EtOAc. The combined organic phases are washed once with 100 ml of saturated NaCl solution, dried over magnesium sulfate, filtered and concentrated. This gives 12.95 g of a white solid which is admixed with 50 ml of MeOH and heated to reflux. The clear solution which forms is cooled to room temperature while stirring and then to 0° C. The suspension which forms is filtered and the residue is washed twice with 10 ml of ice-cold MeOH, and dried at 50°

C./120T in a vacuum drying cabinet overnight. This gives 8.97 g (71.6% of theory) of 2-dibenzofuran-2-yl-4,4,5,5-tetramethyl-1,3,2-dioxaborolane in a purity of 98.3%. The NMR and MS data agree with the structure proposed.

Stage 2:

4.09 g (9.73 mmol) of 2,8-diiododibenzofuran (prepared according to J. Amer. Chem. Soc. 124(40), 11900-11907, 2002), 6.30 g (21.04 mmol) of 2-dibenzofuran-2-yl-4,4,5,5-tetramethyl-1,3,2-dioxaborolane, 6.86 g (49.67 mmol) of potassium carbonate, 180 ml of toluene, 79 ml of EtOH and 37 ml of $H_2O_2$ are initially charged in a 500 ml three-neck flask provided with magnetic stirrer, thermometer, reflux condenser and nitrogen blanketing, and the apparatus is evacuated and filled with argon four times. Subsequently, 1.58 g (1.36 mmol) of tetrakis(triphenylphospine)palladium are added, and the apparatus is evacuated and filled with argon four times. The reaction mixture is then heated to reflux while stirring vigorously for four hours, then diluted with 200 ml of toluene and cooled to room temperature. The phases are separated and the organic phase is washed twice with 150 ml of water, dried over magnesium sulfate, filtered and concentrated. This gives 5.72 g of a brown solid. Purification by means of flash chromatography with hexane/toluene=5:2 as the eluent gives 1.20 g of 2,8-di(dibenzofuran-2-yl)dibenzofuran as a white solid with a purity of 99.3%. The NMR and MS data agree with the structure proposed.

Example 19

Preparation of Ma7

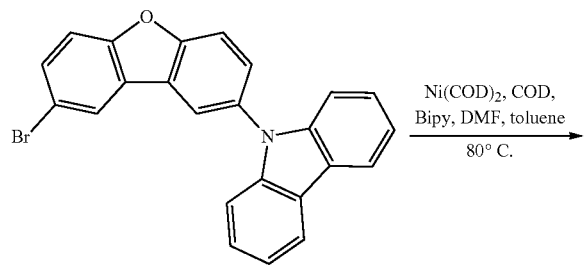

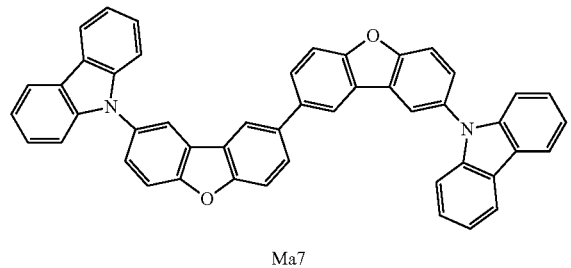

Ma7

$Ni(COD)_2$ (9.03 g, 32.8 mmol), 1,5-cyclooctadiene (3.55 g, 32.8 mmol) and 2,2'-bipyridine (5.12 g, 32.8 mmol) are dissolved in dry DMF (140 ml) in a Schlenk flask (glovebox). The mixture is stirred at 80° C. for 30 min. A solution of 9-(8-bromodibenzofuran-2-yl)-9H-carbazole (11.75 g, 11.8 mmol) in dry toluene (380 ml) is added gradually. After stirring at 80° C. under argon for 24 h, the mixture is cooled to room temperature and added to MeOH/HCl (1:1, 2000 ml) and stirred for 1 h. The organic phase is extracted with toluene, dried over $Na_2SO_4$ and concentrated. LC ($SiO_2$; cyclohexane/$CH_2Cl_2$; 4/1) gives Ma7 (9.14 g, 87%).

$^1$H NMR (400 MHz, $CD_2Cl_2$): 8.25 (2H, d, J=2 Hz), 8.19 (2H, d, J=2 Hz), 8.15 (4H, d, J=8 Hz), 7.88 (1H, d, J=2 Hz), 7.83 (1H, d, J=2 Hz), 7.77 (4H, AB, J=8 Hz), 7.65 (1H, d, J=2 Hz), 7.62 (1H, d, J=2 Hz), 7.43-7.38 (8H, m), 7.31-7.24 (4H, m).

Example 20

Preparation of Ma12

Stage 1:

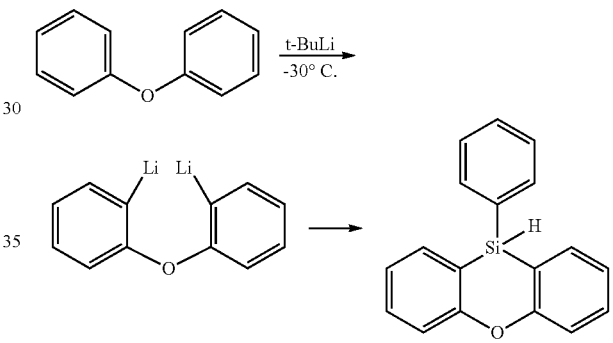

t-BuLi (1.7M in pentane) (46.8 ml, 79.4 mmol) is added dropwise at −30° C. under argon to a solution of diphenyl ether (6 ml, 37.8 mmol) in dry THF (82 ml). The mixture is stirred at −30° C. for 5.5 h and then phenylsilane (4.64 g, 41.6 mmol) is added. The mixture is stirred at −30° C. for a further 1 h and then warmed to room temperature overnight. Acidified ice ($H_2SO_4$) is added and the organic phase is extracted with $CH_2Cl_2$, dried over $Na_2SO_4$, filtered and concentrated. Recrystallization from MeHO gives 10-phenylphenoxasilin (49%).

$^1$H NMR ($CD_2Cl_2$, 400 MHz): 7.57 (2H, dd, J=8.0 Hz, J=1.6 Hz), 7.48-7.35 (7H, m), 7.23 (2H, d, J=8.4 Hz), 7.11 (2H, AB, J=7.2 Hz, J=0.8 Hz), 5.50 (1H, s).

Stage 2:

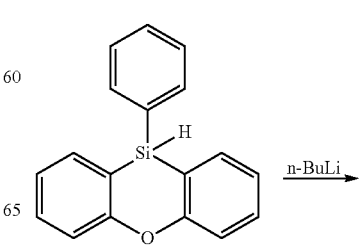

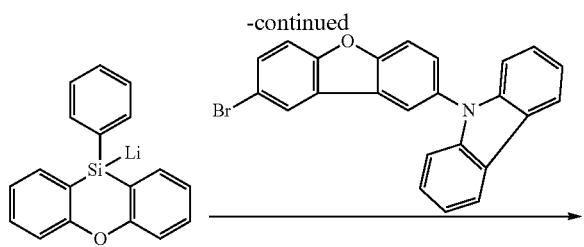

¹H NMR (CD₂Cl₂, 400 MHz): 8.16 (1H, s), 8.14 (2H, d, J=8.0 Hz), 8.03 (1H, d, J=2.0 Hz), 7.78 (1H, d, J=8.4 Hz), 7.72 (1H, d, J=8.0 Hz), 7.65 (1H, d, J=8.4 Hz), 7.62-7.58 (5H, m), 7.46 (2H, t, J=7.4 Hz, J=2.0 Hz), 7.40-7.33 (7H, m), 7.33-7.24 (4H, m), 7.13 (2H, t, J=7.2 Hz). ¹³C NMR (CD₂Cl₂, 125 MHz): 110.0, 112.3, 113.3, 116.4, 118.6, 120.3, 120.5, 120.6, 123.4, 123.6, 124.4, 125.7, 126.4, 127.3, 128.6, 128.8, 129.3, 130.5, 132.2, 133.3, 134.3, 135.7, 136.2, 141.2, 155.6, 158.8, 160.8.

Example 21

Synthesis of Red1

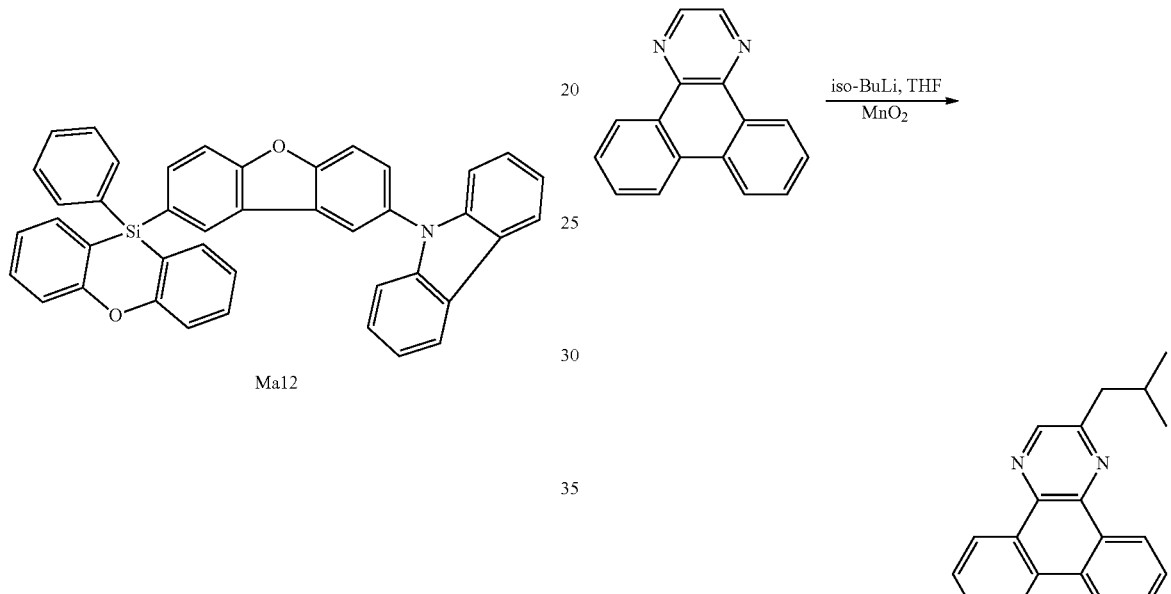

Ma12 n-BuLi (1.6M in hexane) (2.44 ml, 3.9 mmol) is added gradually to a solution of 9-(8-bromodibenzofuran-2yl)-9H-carbazole (1.24 g, 3 mmol) in diethyl ether (60 ml) at 0° C. under Ar. After stirring at 0° C. for 20 min, a solution of 10-phenylphenoxasilin (0.99 g, 3.6 mmol) in diethyl ether (10 ml) is added at 0° C. The mixture is warmed to room temperature while stirring overnight. Saturated NH₄Cl solution is added, and the organic phase is extracted with diethyl ether, dried over Na₂SO₄, filtered and concentrated. Recrystallization from cyclohexane/CH₂Cl₂ gives 9-(8-(10-phenyl-10H-dibenzo[b,e][1,4]oxasilin-10-yl)dibenzo[b,d]furan-2-yl)-9H-carbazole (0.92 g) in 51% yield.

a) 3-Isobutylphenanthro[9,10-b]pyrazine is prepared according to Example 9c in patent application WO2009/100991, proceeding from 32.2 g (0.14 mol) of dibenzo-[f,h]quinoxaline, with 90 ml (0.15 mol) of a 1.7M solution of isobutyllithium in heptane, and 50 g of manganese(IV) oxide. The crude product is filtered hot through silica gel and the filtrate is concentrated under reduced pressure. The resulting solid is stirred overnight in ethanol over a further 18 h. Filtration and washing with ethanol gives the product as a pale beige solid (yield: 8.7 g, 31%).

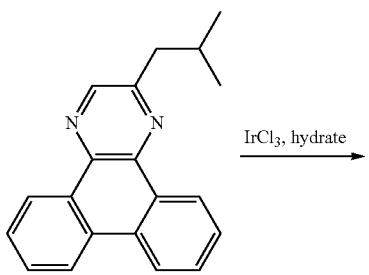

-continued

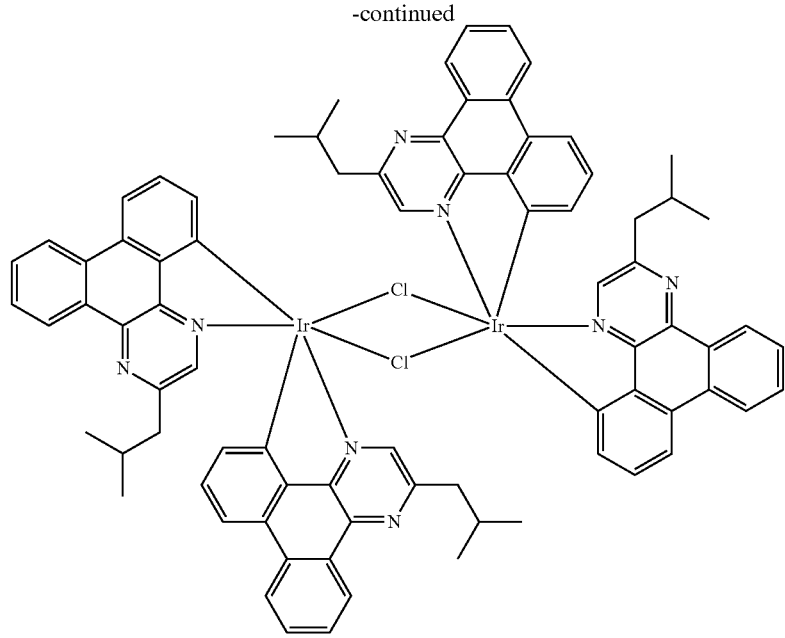

21a b) 8.0 g (28 mmol) of 3-isobutylphenanthro[9,10-b]pyrazine and 4.82 g (13.2 mmol) of iridium(III) chloride hydrate (iridium content 53.01%) are initially charged at room temperature in 100 ml of 2-ethoxyethanol. The gray-black suspension is stirred at 123° C. over 24 h. The resulting red suspension is filtered, and the solids are washed with ethanol and then dried further under reduced pressure. The product 21a is obtained as a red powder (yield: 10.1 g, 95%).

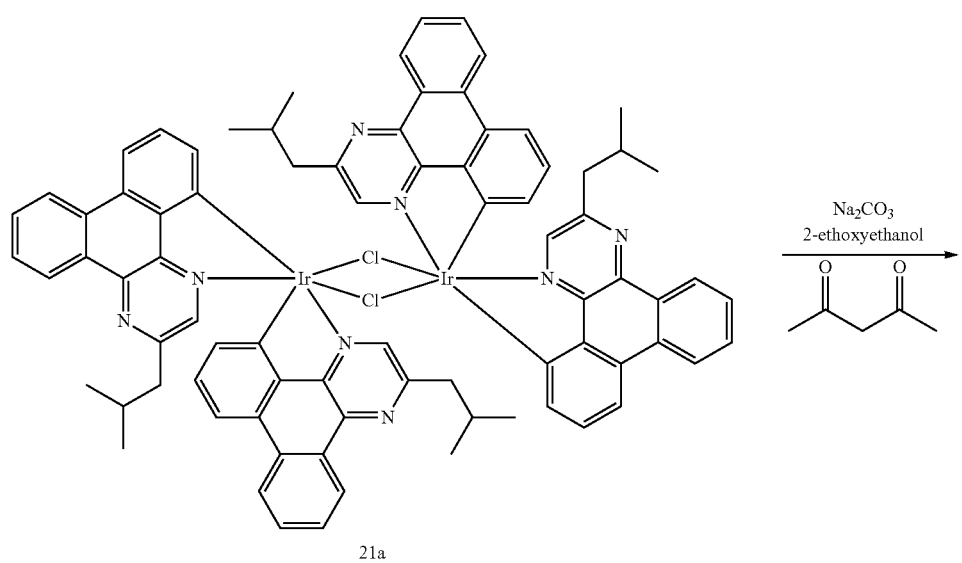

21a

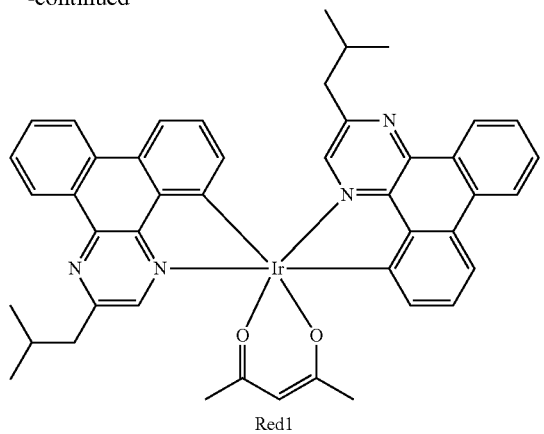

Red1 c) 4.95 g (3.1 mmol) of product 21a and 3.3 g (3.1 mmol) of sodium carbonate are initially charged in 40 ml of 2-ethoxyethanol and 20 ml of N,N-dimethylformamide. The red suspension is admixed with 2.5 g (24.8 mmol) of acetylacetone and then stirred at 121° C. over 70 min. The resulting dark red suspension is filtered and the solids are then stirred once with ethanol and then twice with water, and washed with hexane. The product is obtained as a red powder (yield: 4.3 g, 81%).

$^1$H NMR (CDCl$_3$, 400 MHz): δ=1.15 (t, 12H), 1.86 (s, 6H), 2.40-2.50 (m, 2H), 3.10-3.15 (m, 4H), 5.35 (s, 1H), 6.45 (d, 2H), 7.04 (6, 2H), 7.73-7.82 (m, 4H), 7.93 (d, 2H), 8.56 (d, 2H), 8.67 (s, 2H), 9.33 (d, 2H).

Example 22

Emitter Em17

(2-Chloropyridin-3-yl)isopropylamine

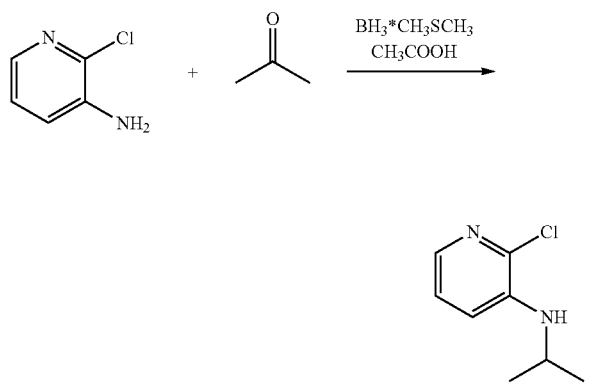

12.5 ml (9.7 g, 167.0 mmol) of acetone and 75 ml of glacial acetic acid are added to a solution of 8.0 g (62.2 mmol) of 3-amino-2-chloropyridine in 150 ml of anhydrous dichloromethane. At 0° C., 6.5 ml (5.2 g, 68.4 mmol) of borane-dimethyl sulfide complex are added. After evolution of gas has ended, the mixture is thawed to room temperature and stirred further overnight. Then the pH is adjusted to 8 by adding 25% ammonia solution. 50 ml of water are added. The aqueous phase is extracted three times with 50 ml each time of dichloromethane. The combined organic phases are dried over sodium sulfate and freed of the solvent. This gives 10.5 g (99%) of yellow oil.

$^1$H NMR (DMSO-D$_6$, 500 MHz): δ=1.18 (d, 6H), 3.64 (sept, 1H), 4.96 (d, 1H), 7.07 (d, 1H), 7.17 (dd, 1H), 7.57 (dd, 1H).

2-N-Phenylamino-3-N-isopropylaminopyridine

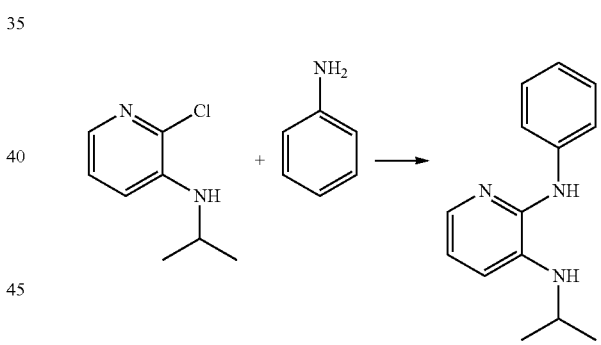

10.5 g (61.5 mmol) of (2-chloropyridin-3-yl)isopropylamine are admixed with 5.84 g (62.5 mmol) of aniline and the mixture is stirred at 184° C. for 16 h. After cooling to room temperature, 50 ml of water are added. The mixture is stirred for 1 h and aqueous NaOH solution to pH=11 adjusted. The mixture is extracted three times with 50 ml each time of dichloromethane. The combined organic phases are dried over sodium sulfate and freed of the solvent under reduced pressure. The residue is purified by column chromatography (silica gel, eluent: cyclohexane/ethyl acetate=5/1). This gives 7.5 g (53%) of light brown solid.

$^1$H NMR (CD$_2$Cl$_2$, 500 MHz): δ=1.21 (d, 6H), 3.23 (s br, 1H), 3.57 (sept, 1H), 6.26 (s br, 1H), 6.83 (dd, 1H), 6.92-6.99 (m, 2H), 7.25-7.29 (m, 4H), 7.70 (dd, 1H).

1-Phenyl-3-isopropylpyridinoimidazolium iodide

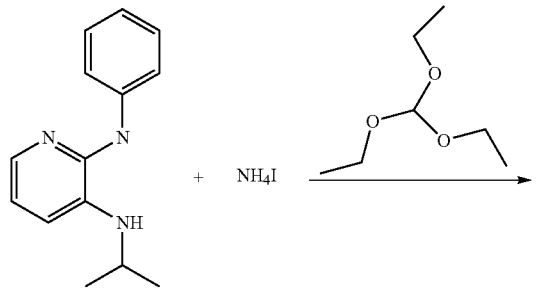

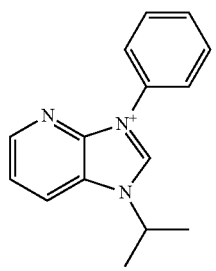

7.3 g (32.1 mmol) of 2-N-phenylamino-3-N-isopropylaminopyridine are dissolved in 30 ml of triethyl orthoformate, and 4.8 g (33.1 mmol) of ammonium iodide are added. The reaction mixture is stirred at 82° C. overnight. After cooling, the pale yellow solid formed is filtered off, washed with 3×15 ml of petroleum ether and 3×30 ml of dichloromethane and dried. This gives 10.2 g (86%) of imidazolium salt.

$^1$H NMR (DMSO-D$_5$, 500 MHz): δ=1.72 (d, 6H), 5.19 (sept, 1H), 7.67-7.70 (m, 1H), 7.73-7.76 (m, 2H), 7.86-7.88 (m, 1H), 7.95-7.97 (m, 2H), 8.81-8.82 (m, 2H), 10.43 (s, 1H).

Complex K5

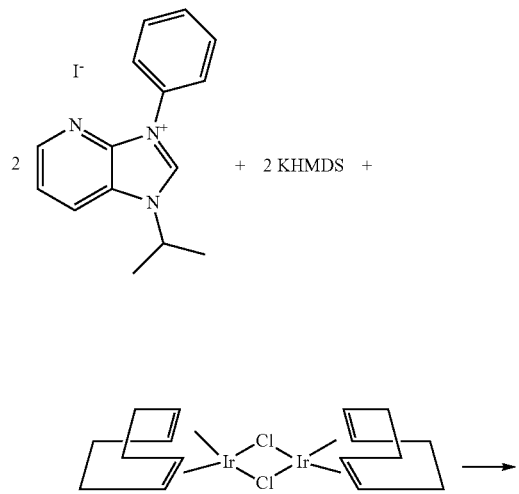

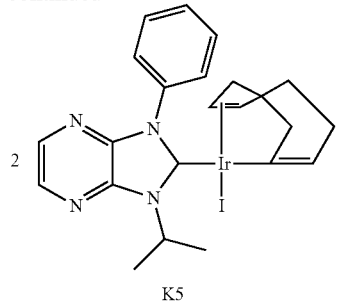

K5

3.00 g (8.21 mmol) of 1-phenyl-3-isopropylpyridinoimidazolium iodide are suspended in 45 ml of anhydrous toluene. At −8° C., 16.42 ml of a 0.5 molar KHMDS solution in toluene (8.21 mmol) are added. The mixture is thawed to room temperature and stirred for one hour. Then the red suspension is added at −78° C. to a solution of 2.76 g (4.11 mmol) of bis(1,5-cyclooctadiene)diiridium(I) chloride in 75 ml of anhydrous toluene. Thereafter, the mixture is heated at room temperature for 1.5 hours and at reflux for one hour. After cooling, the reaction mixture is filtered. The filtrate is freed of the solvent under reduced pressure and purified by column chromatography (silica gel, eluent: methylene chloride). This gives 3.70 g (68%) of complex K5 as a yellow powder.

$^1$H NMR (CD$_2$Cl$_2$, 500 MHz): δ=1.02-1.08 (m, 1H), 1.16-1.21 (m, 1H), 1.37-1.42 (m, 1H), 1.59-1.72 (m, 3H), 1.76 (dd, 6H), 2.07-2.18 (m, 2H), 2.51-2.55 (m, 1H), 3.15-3.18 (m, 1H), 4.65-4.69 (m, 1H), 4.87-4.91 (m, 1H), 6.06 (sept, 1H), 7.23 (dd, 1H), 7.49-7.56 (m, 3H), 7.85 (dd, 1H), 8.04-8.06 (m, 2H), 8.22 (dd, 1H).

Complex Em17:

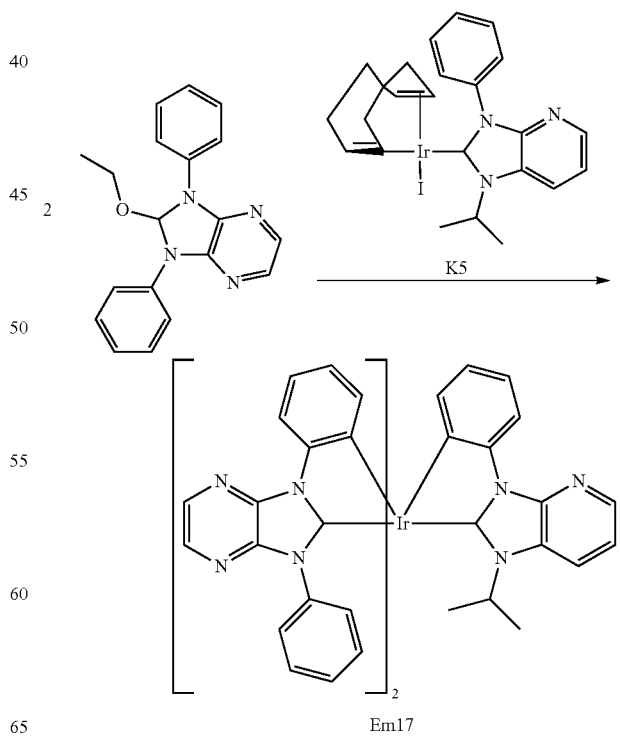

Em17

A solution of 0.90 g (2.83 mmol) of 2-ethoxy-1,3-diphenyl-2,3-dihydro-1H-imidao[4,5-b]pyrazine in 50 ml of anhydrous o-xylene is admixed successively at room temperature with 10 g of molecular sieve and a solution of 0.86 g (1.29 mmol) of K5 in 75 ml of anhydrous o-xylene. The mixture is stirred at 115° C. for 22 hours. It is cooled and then filtered. The filtrate is freed of the solvent under reduced pressure and purified by column chromatography (silica gel, eluent: cyclohexane/acetone=4/1). This gives 0.53 g (42%) of Em117 as a yellow powder.

$^1$H NMR (CD$_2$Cl$_2$, 500 MHz): δ=0.62 (d, 3H), 1.06 (d, 3H), 4.28 (sept, 1H), 6.35-7.53 (very flat, broad signal, 8H, ortho- and meta-H of the two noncyclometallated phenyl rings), 6.52 (dd, 1H), 6.59 (dd, 1H), 6.64 (dd, 1H), 6.72-6.77 (m, 3H), 6.81 (dt, 1H), 6.97-7.01 (m, 1H), 7.05-7.08 (m, 2H), 7.14 (dt, 1H), 7.19 (dt, 1H), 7.41 (dd, 1H), 8.07 (d, 1H), 8.12 (d, 1H), 8.34 (dd, 2H), 8.37 (dd, 1H), 8.69 (dd, 1H), 8.80 (dd, 1H), 8.95 (dd, 1H).

Photoluminescence (2% in a PMMA film): λ$_{max}$=484 nm, CIE: (0.17; 0.34), 95% QY Example 23

Complex Em18:

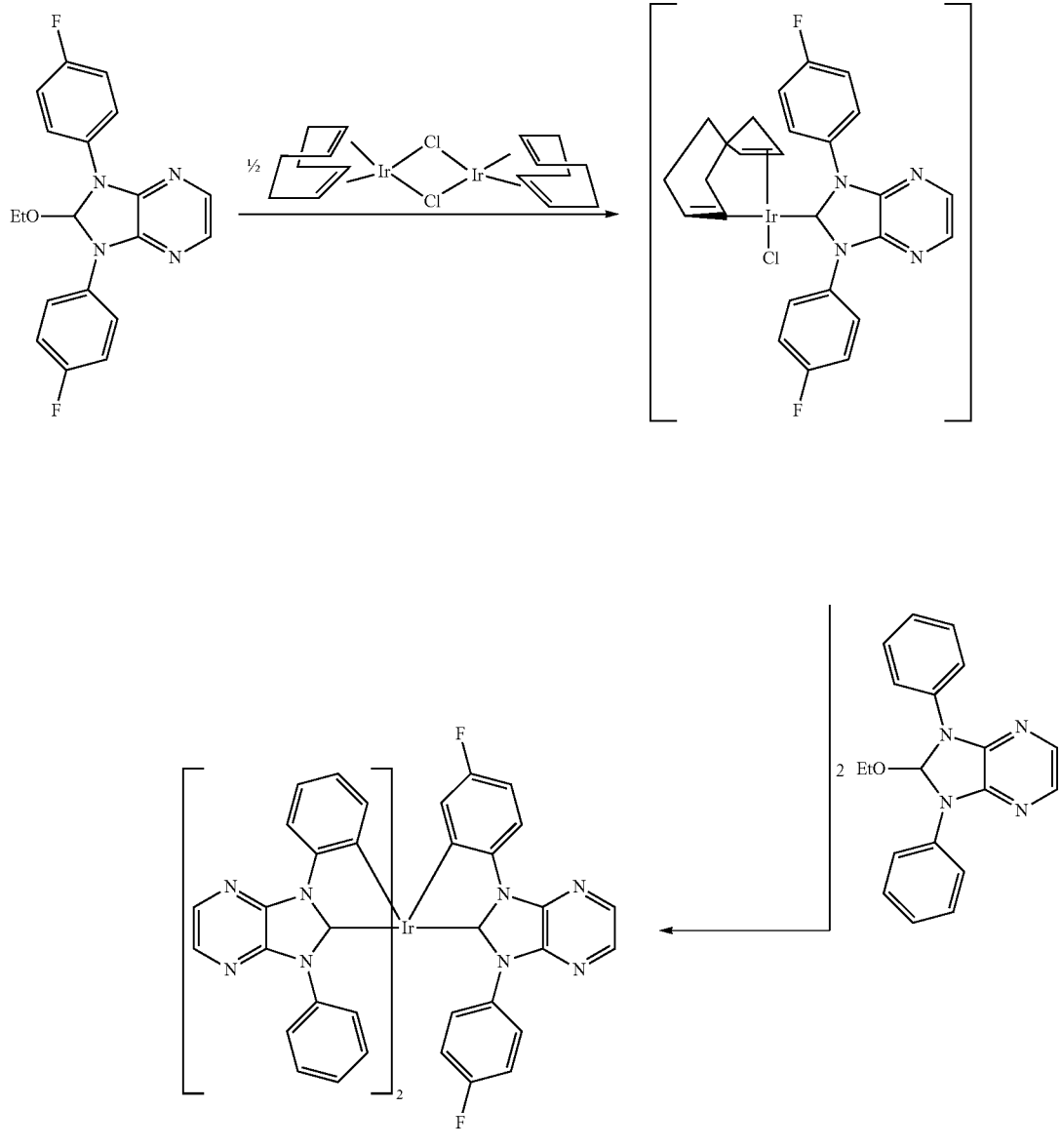

Em18

1.06 g (2.98 mmol) of 2-ethoxy-1,3-bis(4-fluorophenyl)-2,3-dihydro-1H-imidao[4,5-b]pyrazine (2-ethoxy-1,3-bis-(4'-fluorophenyl)pyrazinoimidazoline) was added to a solution of 1.00 g (1.49 mmol) of [(μ-Cl)Ir(η$^4$-1,5-COD)]$_2$ in 100 ml of o-xylene. The resulting solution is subsequently stirred at 65° C. for 20 h. After adding 1.80 g (5.66 mmol) of 2-ethoxy-1,3-diphenyl-2,3-dihydro-1H-imidazo[4,5-b]pyrazine, the reaction mixture is stirred at 95° C. for a further 48 h. After cooling, the precipitate is filtered off and washed with o-xylene and cyclohexane. The combined organic phases are concentrated to dryness and purified by column chromatography (silica gel, eluent ethyl acetate/cyclohexane=1/4). This gives 0.30 g (20%) of Em18 as a yellow powder.

$^1$H NMR (CD$_2$Cl$_2$, 500 MHz):

δ=6.20-6.90 (very flat broad signal, 8H), 6.28 (dd, 1H), 6.65 (ddd, 3H), 6.59 (d, 1H), 6.80-6.86 (m, 6H), 7.14-7.19 (m, 2H), 8.05 (d, 1H), 8.07 (dd, 2H), 8.32 (d, 1H), 8.35 (t, 2H), 8.72 (dd, 1H), 8.76 (dd, 2H).

Photoluminescence (2% in a PMMA film):

λ$_{max}$=466 nm, CIE: (0.15; 0.19); QY=95%

Example 24

Complex Em19:

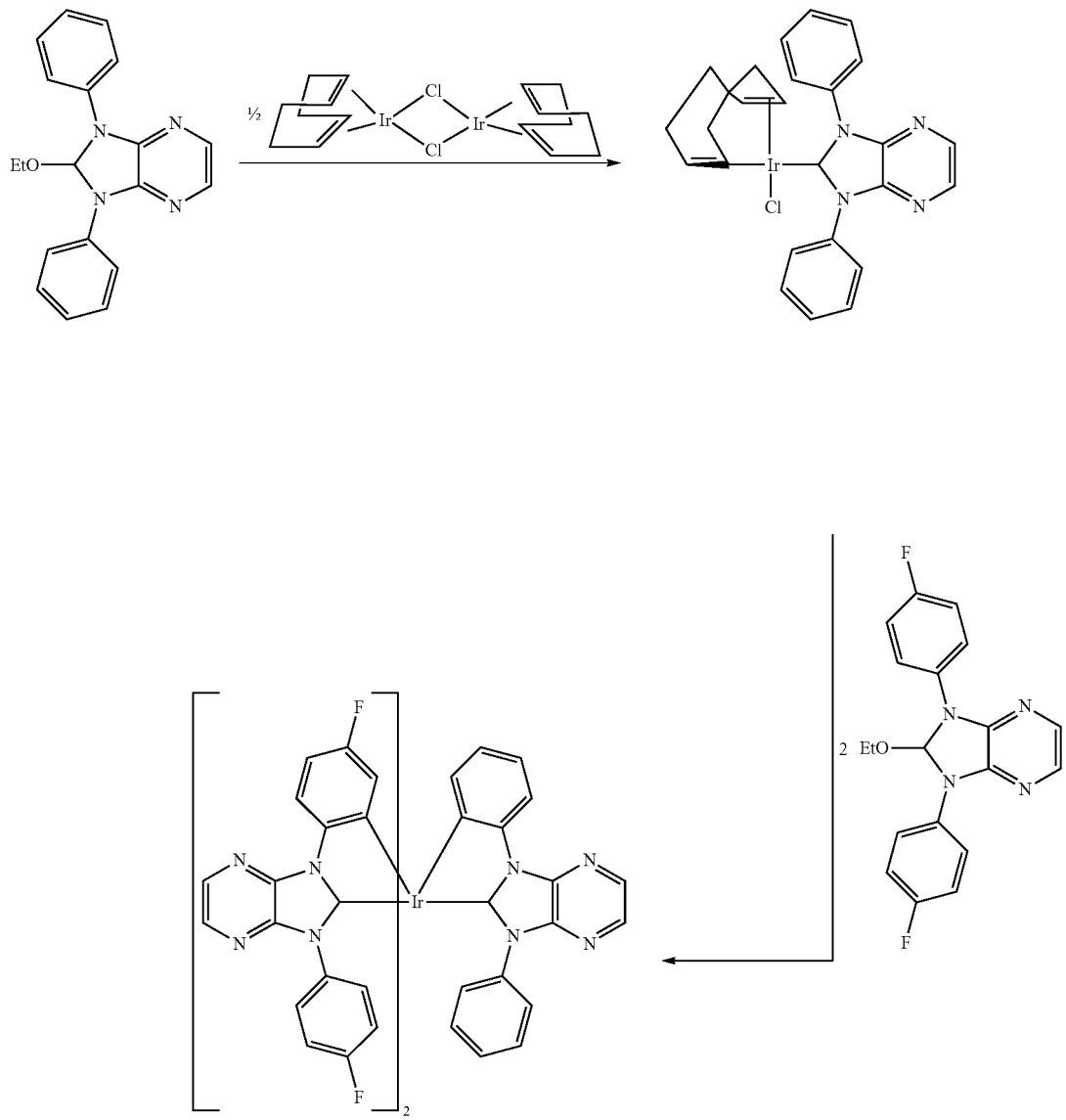

Em19

0.47 g (1.49 mmol) of 2-ethoxy-1,3-diphenyl-2,3-dihydro-1H-imidazo[4,5-b]pyrazine was added to a solution of 0.50 g (0.74 mmol) of [(μ-Cl)Ir(η⁴-1,5-COD)]₂ in 50 ml of o-xylene. The resulting solution is subsequently stirred at 60° C. for 22 h. After adding 1.04 g (2.94 mmol) of 2-ethoxy-1,3-bis(4-fluorophenyl)-2,3-dihydro-1H-imidazo [4,5-b]pyrazine, the reaction mixture is stirred at 95° C. for a further 48 h. After cooling, the reaction mixture is concentrated to dryness. The solid residue is dissolved in dichloromethane/cyclohexane and filtered through Celite. The filtrate is concentrated to dryness and the residue is purified by column chromatography (silica gel, eluent ethyl acetate/cyclohexane=1/4). This gives 0.17 g (11%) of Em19 as a yellow powder.

¹H NMR (CD₂Cl₂, 500 MHz):

δ=6.20-6.90 (very flat broad signal, 8H), 6.31 (ddd, 3H), 6.68 (dd, 2H), 6.83-6.88 (m, 4H), 7.21 (dt, 1H), 8.10 (dd, 2H), 8.12 (d, 1H), 8.37 (t, 2H), 8.40 (d, 1H), 8.71-8.75 (m, 2H), 8.79 (dd, 1H).

Photoluminescence (2% in a PMMA film):
$\lambda_{max}$=461 nm, CIE: (0.15; 0.16); QY=90%

Example 25

Emitter Em20
Pyrazine Compound (f)

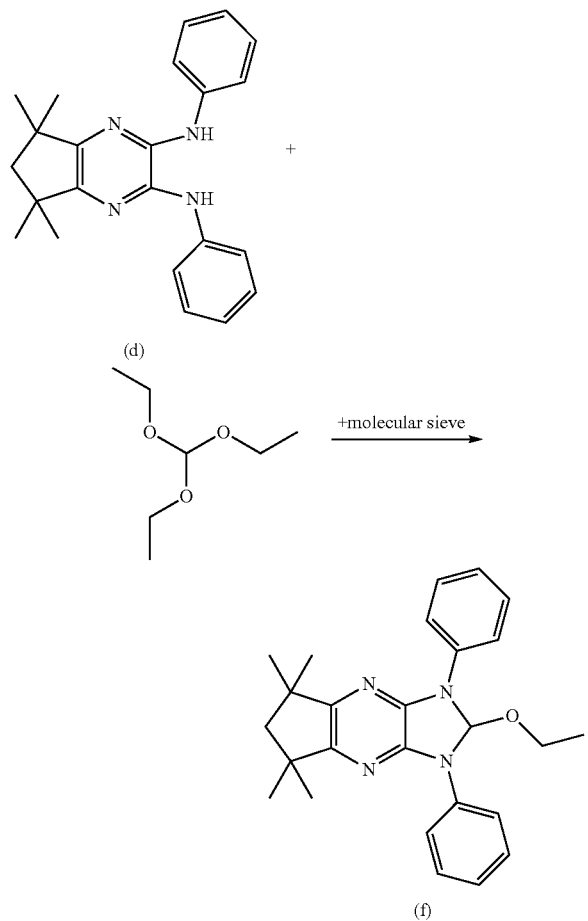

10.5 g (29.3 mmol) of pyrazine compound (d) and 15.0 g of molecular sieve (5A) are heated to 120° C. in 230 ml of triethyl orthoformate for 48 h. After cooling, the solids are filtered off and the filtrate is freed of the solvent under reduced pressure. The brown oil obtained is purified by column chromatography (silica gel, eluent: cyclohexane/ethyl acetate=9/1). The production fractions are combined and recrystallized from methyl tert-butyl ether. This gives 4.63 g (38%) of pyrazine compound (f).

¹H NMR (CD₂Cl₂, 500 MHz): δ=1.06 (t, 3H), 1.33 (s, 6H), 1.34 (s, 6H), 1.98 (s, 2H), 3.32 (q, 2H), 7.12-7.16 (m, 2H), 7.21 (s, 1H), 7.40-7.47 (m, 4H), 8.11-8.16 (m, 4H).

Complex Em20:

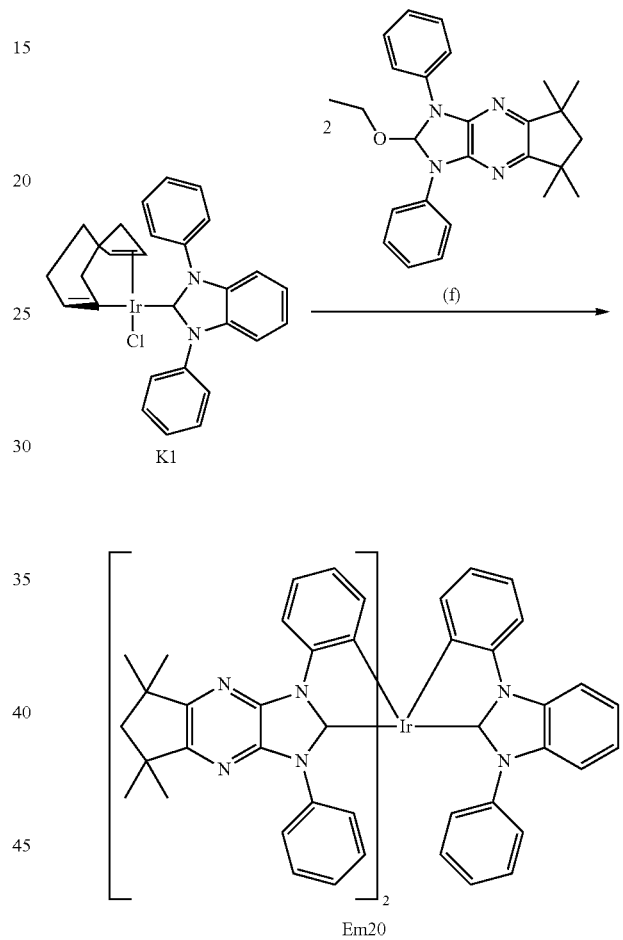

A solution of 1.9 g (1.8 mmol) of pyrazine compound (f) in 200 ml of o-xylene (anhydrous) is initially charged with 20 g of molecular sieve, and a solution of 1.26 g (0.8 mmol) of complex K1 in 150 ml of o-xylene (anhydrous) is added. The reaction mixture is subsequently stirred at 115° C. for 18 h. After cooling, the reaction mixture is filtered. The filtrate is concentrated to dryness, purified by column chromatography (silica gel, eluent cyclohexane/acetone=4/1) and then recrystallized from methylene chloride/methanol. This is followed by another purification by column chromatography (silica gel, eluent cyclohexane/acetone=10/1). This gives 0.75 g (30%) of Em20 as a pale yellow powder.

¹H NMR (CD₂Cl₂, 500 MHz): δ=1.13 (d, 6H), 1.36 (d, 6H), 1.45 (d, 6H), 1.58 (d, 6H), 2.03-2.16 (m, 4H), 6.18-6.43 (m, 5H), 6.44-6.97 (m, broad, 15H), 6.98-7.22 (m, 6H), 7.32 (t, 1H), 7.99 (d, 1H), 8.17 (d, 1H), 8.78 (d, 1H), 8.90 (d, 1H).

Photoluminescence (2% in a PMMA film):
$\lambda_{max}$=479 nm, CIE: (0.14; 0.29), 95% QY

Example 26

Emitter Em21

2,3-Di(N-phenylamino)pyridine

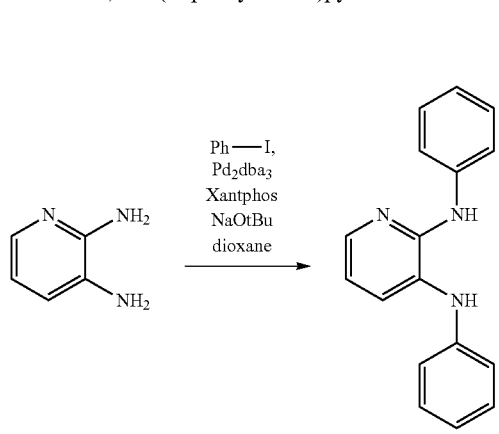

A suspension of 2,3-diaminopyridine (8.9 g, 9 mmol) and iodobenzene (17.8 ml, 18 mmol) in dioxane (270 ml) is admixed with tris(dibenzylideneacetone)dipalladium (838 mg, 0.1 mmol), 9,9-dimethyl-4,5-bis(diphenylphosphine) xanthene (1.4 g, 0.3 mmol), sodium tert-butoxide (15.4 g, 18 mmol) and water (2.3 g). The mixture is stirred under reflux overnight. After cooling to room temperature, the precipitate is filtered off with suction and washed with dichloromethane. The combined filtrates are concentrated to dryness and the residue is dissolved in dichloromethane (125 ml) and cyclohexane (150 ml) and column-filtered. The product fractions are concentrated and precipitated product is filtered off. Yield: 14.2 g (67%).

$^1$H NMR (CD$_2$Cl$_2$, 500 MHz, 0698403439): δ=5.19 (br s, 1H), 6.71-6.76 (m, 3H), 6.84 (dd, 1H), 6.89-6.96 (m, 2H), 7.19 (dd, 2H), 7.23 (dd, 2H), 7.39 (d, 1H), 7.51 (d, 2H), 8.02 (d, 1H).

2,3-Di(N-phenylamino)pyridine hydrochloride

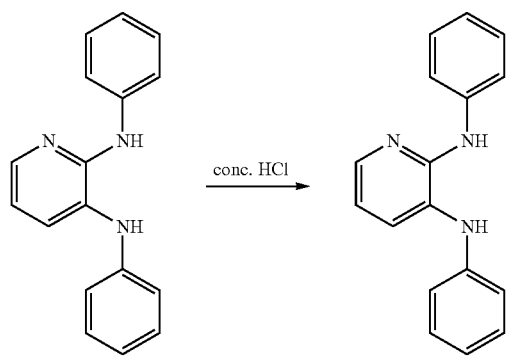

A suspension of 2,3-di(N-phenylamino)pyridine (14.2 g, 54 mmol) in hydrochloric acid (200 ml) is stirred at room temperature overnight. The mixture is concentrated to dryness. Yield: 14.0 g (87%).

$^1$H NMR (d$_6$-DMSO, 500 MHz, 0698403873): δ=6.94-7.00 (m, 2H), 7.17 (d, 2H), 7.30 (m$_c$, 3H), 7.40-7.51 (m, 5H), 7.74 (dd, 1H). The NH protons are undetectable.

1,3-Diphenyl-4-azabenzimidazolium chloride

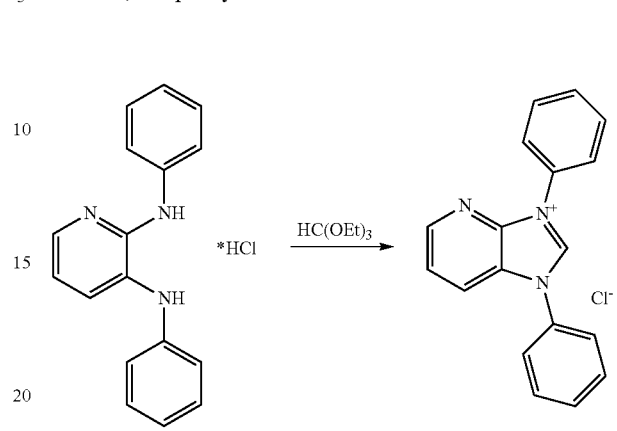

A mixture of 2,3-di(N-phenylamino)pyridine hydrochloride (14.0 g, 47 mmol) in triethyl orthoformate (160 ml) is stirred at 105° C. overnight. After cooling to room temperature, the solids are filtered off with suction and washed with triethyl orthoformate. Yield: 10.3 g (71%).

$^1$H NMR (CD$_2$Cl$_2$, 500 MHz): δ=7.55-7.73 (m, 7H), 8.08 (dd, 2H), 8.19 (dd, 1H), 8.33 (dd, 2H), 8.80 (dd, 1H), 12.24 (s, 1H).

Complex Em21

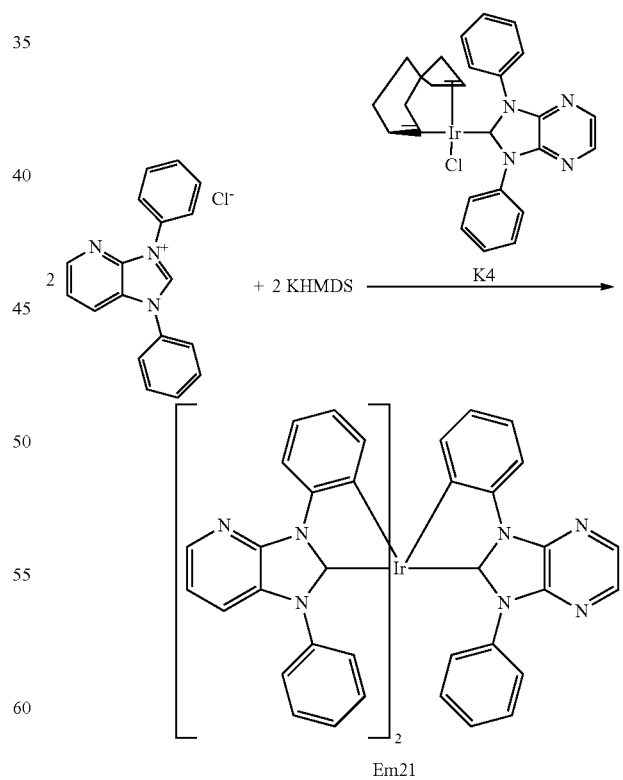

0.65 g of 1,3-diphenyl-4-azabenzimidazolium chloride (2.1 mmol) is suspended in 100 ml of anhydrous toluene and cooled to 0° C. Then 4.2 ml of potassium bis(trimethylsilyl)

amide (KHMDS, 0.5M in toluene, 2.1 mmol) are added gradually. The mixture is stirred at room temperature for 1 h and then a solution of 0.61 g of K4 (1.0 mmol) in 100 ml of anhydrous toluene is added. The mixture is stirred at room temperature for 1 h and then heated at reflux for 18 h. The mixture is cooled and then concentrated to dryness. The residue is purified by column chromatography (silica gel, eluent: cyclohexane/acetone=4/1). This gives 0.13 g (13%) of Em21 as a pale yellow powder.

$^1$H NMR (CD$_2$Cl$_2$, 500 MHz): δ=6.23-6.32 (m, 3H), 6.38 (t, 1H), 6.40-6.85 (m, 17H), 7.00-7.05 (m, 2H), 7.10-7.16 (m, 3H), 7.32 (t, 2H), 8.01 (d, 1H), 8.28 (d, 1H), 8.39 (dt, 2H), 8.72 (d, 1H), 8.94 (d, 1H), 8.98 (d, 1H).

Photoluminescence (2% in a PMMA film):
$\lambda_{max}$=480 nm, CIE: (0.17; 0.30), 95% QY

Example 27

Emitter Em22

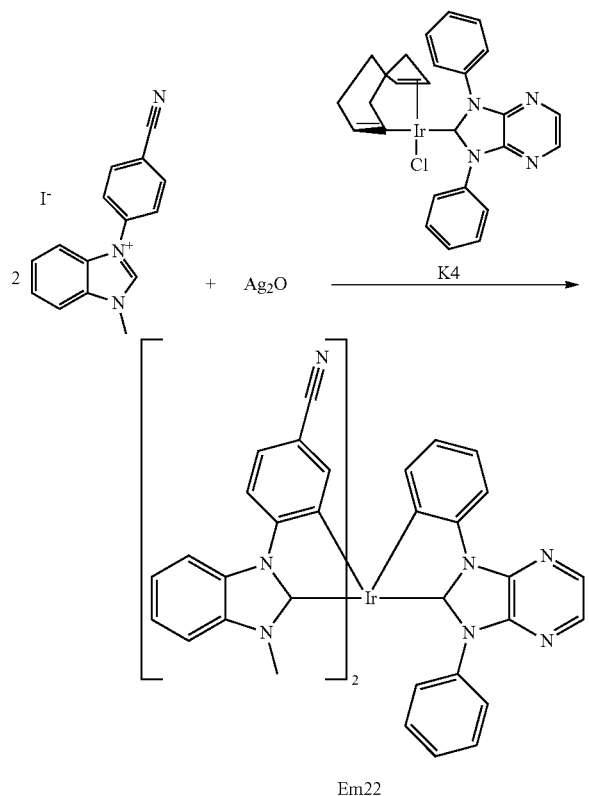

Em22

A solution of 2.30 g (6.4 mmol) of 1-(4-cyanophenyl)-3-methylbenzimidazolium iodide (for preparation see WO2006/056418) in 200 ml of 1,4-dioxane (anhydrous, ultradry) is admixed with 1.11 g (4.8 mmol) of silver(I) oxide and 20 g of molecular sieve, and stirred at room temperature overnight. Then a solution of 1.29 g (2.1 mmol) of complex K4 in 200 ml of anhydrous o-xylene is added and the mixture is stirred at 110° C. for 22 h. After cooling, the reaction mixture is filtered. The filtrate is freed of the solvent under reduced pressure and then separated by column chromatography (silica gel, eluent: cyclohexane/acetone=2/1). This gives 0.61 g (31%) of Em22 isomer 1 ($R_F$=0.31), 0.45 g (23%) of Em22 isomer 2 ($R_F$=0.25) and 0.25 g (13%) of Em22 isomer 3 ($R_F$=0.20), each of which are recrystallized once more from methylene chloride/methanol.

Em22 Isomer 1:
$^1$H NMR (CD$_2$Cl$_2$, 500 MHz): δ=2.78 (s, 3H), 3.15 (s, 3H), 6.31 (d, very broad, 2H), 6.53 (d, 1H), 6.68 (t, 1H), 6.77 (t, 1H), 6.92 (d, 1H), 7.11-7.16 (m, 2H), 7.23-7.52 (m, 10H), 7.88 (d, 1H), 7.91 (d, 1H), 7.99 (d, 1H), 8.11 (d, 1H), 8.18 (d, 1H), 8.41 (d, 1H), 8.76 (d, 1H).

Photoluminescence (2% in a PMMA film):
$\lambda_{max}$=484 nm, CIE: (0.19; 0.33), 87% QY Em22 Isomer 2:
$^1$H NMR (CD$_2$Cl$_2$, 500 MHz): δ=3.20 (s, 3H), 3.37 (s, 3H), 5.67-6.92 (very flat broad signal, 2H), 6.51 (d, 1H), 6.70-6.77 (m, 2H), 6.97-7.00 (m, 1H), 7.06-7.12 (m, 3H), 7.20-7.47 (m, 10H), 7.90 (d, 1H), 8.06 (t, 2H), 8.24 (d, 1H), 8.45 (d, 1H), 8.80 (d, 1H).

Photoluminescence (2% in a PMMA film):
$\lambda_{max}$=494 nm, CIE: (0.22; 0.41), 87% QY Em22 Isomer 3:
$^1$H NMR (CD$_2$Cl$_2$, 500 MHz): δ=2.75 (s, 3H), 3.56 (s, 3H), 6.02-7.26 (very flat broad signal, 4H), 6.48 (dd, 1H), 6.68 (d, 1H), 6.69-6.73 (m, 1H), 6.78 (dt, 1H), 6.86 (d, 1H), 6.90 (d, broad, 1H), 7.14 (dt, 1H), 7.24 (dt, 1H), 7.30-7.39 (m, 5H), 7.49 (dd, 1H), 7.87 (d, 1H), 7.94 (d, 1H), 8.03 (d, 1H), 8.08 (d, 1H), 8.17 (d, 1H), 8.41 (d, 1H), 8.79 (dd, 1H).

Photoluminescence (2% in a PMMA film):
$\lambda_{max}$=468 nm, CIE: (0.16; 0.21), 90% QY

Example 28

Production of Doped OLEDs

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer AJ20-1000 from Plexcore is spun on from solution.

Example 28a

After the hole injection layer, the organic materials specified hereinafter are applied at a rate of approx. 0.5-5 nm/min to the cleaned substrate at about 10$^{-7}$-10$^{-9}$ mbar. The hole conductor applied by vapor deposition is 20 nm of the mixture of Ir(DPBIC)$_3$ with 4% of the p-dopant F6-TNAP. The exciton blocker applied to the substrate is Ir(DPBIC)$_3$ with a thickness of 10 nm.

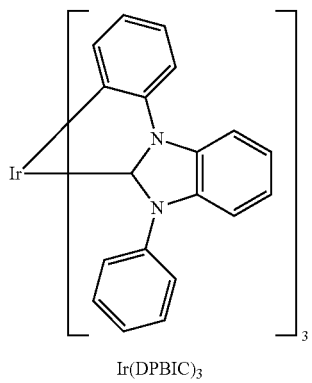

Ir(DPBIC)$_3$

-continued

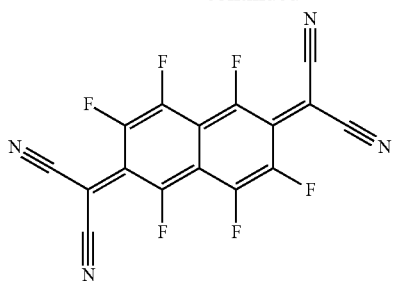

F6-TNAP

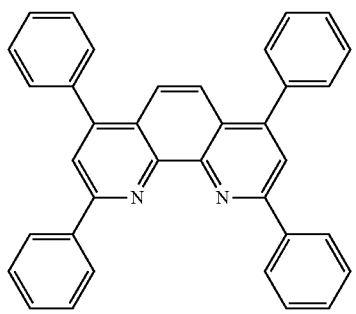

ETM2

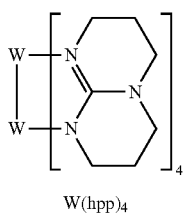

W(hpp)₄

(for preparation of Ir(DPBIC)₃ see Ir complex (7) in the application WO 2005/019373 A2).

Subsequently, a mixture of 30% emitter fac-Em1, 60% of the compound Ma7 and 10% of the compound Ir(DPBIC)₃ with a thickness of 30 nm is applied by vapor deposition as an emissive layer, the latter two compounds functioning as matrix material.

The subsequent electron conductor layer used is an ETM2 layer (see compound No. 28 in EP1097981) doped with 8% W(hpp)₄ (see EP1786050) with a layer thickness of 25 nm.

An aluminum cathode of thickness 100 nm concludes the diode.

All components are encapsulated with a glass lid in an inert nitrogen atmosphere.

Example 28b

The OLED from Example 28b is of the same structure as the OLED from Example 28a, except with the difference that the emissive layer consists of 30% Em8 and 70% matrix material Ma7.

To characterize the OLEDs, electroluminescence spectra are recorded at different currents and voltages. In addition, the current-voltage characteristic is measured in combination with the light output emitted. The light output can be converted to photometric parameters by calibration with a photometer.

For the two working examples of a doped OLED, the following electrooptical data are obtained:

| Ex. | Emitter | Voltage [V] at 300 nits | EQE [%] at 300 nits |
|---|---|---|---|
| 28a | fac-Em1 | 2.75 V | 10.9% |
| 28b | Em8 | 3.38 V | 10.8% |

*EQE—external quantum efficiency. Measured in forward direction assuming a Lambertian light intensity distribution.

Example 29

Diodes with Different Emitters

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the 40 nm-thick hole injection layer, AJ20-1000 from Plexcore, is spun on from solution.

Thereafter, the organic materials specified below are applied by vapor deposition at a rate of approx. 0.5-5 nm/min to the clean substrate at about $10^{-7}$-$10^{-9}$ mbar.

The hole conductor and exciton blocker applied is Ir(DPBIC)₃ in a thickness of 20 nm, of which the first 15 nm have been doped with 5% ReO₃. Thereafter, a 20 nm-thick emission layer consisting of an emitter and two matrix materials is applied by vapor deposition. This is followed by a 5 nm-thick layer of exciton and hole blocker. Next, a mixture of 50% Liq and 50% ETM1 as an electron transport layer is applied in a thickness of 40 nm. Finally, a 4 nm-thick layer of KF and a 100 nm-thick Al electrode are applied by vapor deposition.

Example 29a

The diode is constructed as described above with an emission layer consisting of 10% of the emitter Em16 and 45% each of the matrix materials Ir(DPBIC)₃ and Ma13. The exciton and hole blocker used is Ma13.

The diode exhibits the color coordinates CIE 0.20, 0.43. At 300 cd/m², the voltage is 3.6 V and the external quantum efficiency 17.7%.

Example 29b

The diode is constructed as described above with an emission layer consisting of 10% of the emitter Em16 and 45% each of the matrix materials Ir(DPBIC)₃ and Ma7. The exciton and hole blocker used is Ma7.

The diode exhibits the color coordinates CIE 0.19, 0.43. At 300 cd/m², the voltage is 3.6 V and the external quantum efficiency 14.7%.

Example 29c

The diode is constructed as described above with an emission layer consisting of 10% of the emitter Em17 and 45% each of the matrix materials Ir(DPBIC)$_3$ and Ma13. The exciton and hole blocker used is Ma13.

The diode exhibits the color coordinates CIE 0.20, 0.44. At 300 cd/m$^2$, the luminous efficiency is 45.5 lm/W and the external quantum efficiency 19.6%.

Example 29d

The diode is constructed as described above with an emission layer consisting of 10% of the emitter Em117 and 45% each of the matrix materials Ir(DPBIC)$_3$ and Ma7. The exciton and hole blocker used is Ma7.

The diode exhibits the color coordinates CIE 0.18, 0.39. At 300 cd/m$^2$, the voltage is 3.8 V and the luminous efficiency 40.4 lm/W.

Example 29e

The diode is constructed as described above with an emission layer consisting of 10% of the emitter Em20 and 45% each of the matrix materials Ir(DPBIC)$_3$ and Ma7. The exciton and hole blocker used is Ma7.

The diode exhibits the color coordinates CIE 0.15, 0.29. At 300 cd/m$^2$, the voltage is 3.6 V and the external quantum efficiency 19.9%.

Example 29f

The diode is constructed as described above with an emission layer consisting of 10% of the emitter Em20 and 45% each of the matrix materials Ir(DPBIC)$_3$ and Ma13. The exciton and hole blocker used is Ma13.

The diode exhibits the color coordinates CIE 0.15, 0.29. At 300 cd/m$^2$, the voltage is 3.3 V and the external quantum efficiency 19.0%.

Example 30

Homojunction OLEDs

Example 30a

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the 40 nm-thick hole injection layer, AJ20-1000 from Plexcore, is spun on from solution.

Thereafter, the organic materials specified below are applied by vapor deposition at a rate of approx. 0.5-5 nm/min to the clean substrate at about $10^{-7}$-$10^{-9}$ mbar.

The hole conductor and exciton blocker applied is Ma4 in a thickness of 20 nm, of which the first 15 nm have been doped with 5% ReO$_3$. Thereafter, a 20 nm-thick emission layer consisting of 10% fac-Em1, 35% Ir(DPBIC)$_3$ and 55% Ma4 is applied by vapor deposition. This is followed by a 5 nm-thick layer of Ma4 of exciton and hole blocker. Next, a mixture of 50% Liq and 50% Ma4 as an electron transport layer is applied in a thickness of 40 nm. Finally, a 4 nm-thick layer of KF and a 100 nm-thick Al electrode are applied by vapor deposition.

The diode exhibits the color coordinates CIE 0.15, 0.25. At 300 cd/m$^2$, the external quantum efficiency is 18.7%.

Example 30b

The diode is constructed analogously to Example 30a with the difference that the emission layer consists of 30% fac-Em1, 35% Ir(DPBIC)$_3$ and 35% Ma4.

The diode exhibits the color coordinates CIE 0.16, 0.31. At 300 cd/m$^2$, the external quantum efficiency is 16.2%.

Example 30c

The diode is constructed analogously to Example 30a with the difference that Ma4 is replaced by Ma7 in the particular layers and the emission layer consists of 10% fac-Em1, 45% Ir(DPBIC)$_3$ and 45% Ma7.

The diode exhibits the CIE color coordinates 0.16, 0.28. At 300 cd/m$^2$ the external quantum efficiency is 11.9%.

Example 30d

The diode is constructed analogously to Example 30a with the difference that Ma4 is replaced by Ma7 in the particular layers and the emission layer consists of 30% fac-Em1, 35% Ir(DPBIC)$_3$ and 35% Ma7.

The diode exhibits the CIE color coordinates 0.18, 0.34. At 300 cd/m$^2$ the external quantum efficiency is 16.3%.

Example 31

Synthesis of ETM3

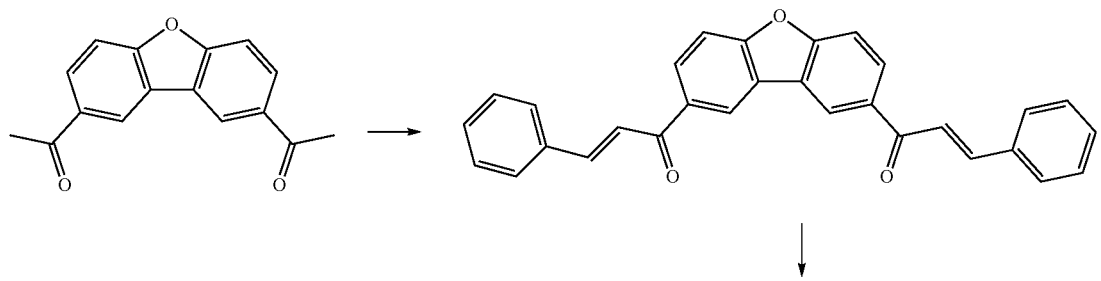

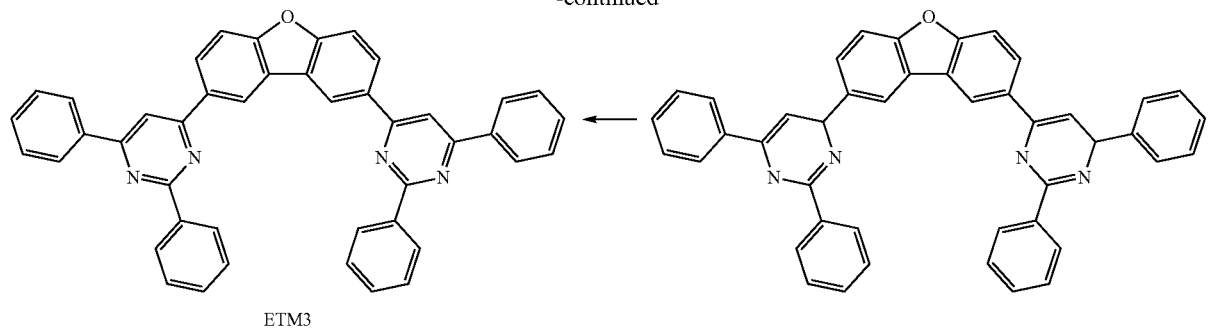

ETM3

Stage 1

A 250 ml three-neck round-bottom flask provided with magnetic stirrer, thermometer, dropping funnel, reflux condenser and nitrogen blanketing is initially charged with 150 ml of methanol, and 3.8 g of potassium hydroxide (≥85%) are added. The mixture is stirred at room temperature until a clear colorless solution forms. Subsequently, an ice bath is used to cool it to 0° C., and 14.3 g (56.7 mmol) of 1-(8-acetyldibenzofuran-2-yl)ethanone (prepared according to M. J. Bruce, Perkin Transactions I, 1789 (1995)) are added. The suspension is stirred at 0° C. for 1 h and then 17.3 ml (170 mmol) of benzaldehyde are added dropwise within 3 min. The reaction mixture is subsequently warmed to room temperature and stirred for 14 h. The fine beige-yellow suspension is filtered and the residue is washed with 50 ml of ethanol. The crude product is suspended in 150 ml of ethanol and stirred under reflux for 30 min. Then it is cooled to room temperature and then to 0° C., filtered and washed twice with 10 ml of ice-cold ethanol, and the residue is dried at 50° C./150 mbar overnight. This gives 21.6 g (88.9% of theory) of 3-phenyl-1-{8-(3-phenylacryloyl)]-dibenzofuran-2-yl}propenone as pale beige crystals.

$^1$H NMR (CDCl$_3$, 300 MHz):

8.67 (s, 2H), 8.25 (d, J=7 Hz, 2H), 7.89 (s, J=12 Hz, 2H), 7.8-7.65 (m, 8H), 7.55-7.4 (m, 6H).

Stage 2

A 100 ml three-neck round-bottom flask provided with magnetic stirrer, thermometer, reflux condenser and nitrogen blanketing is initially charged with 60 ml of methanol and cooled to 0° C. with an ice bath while stirring. Subsequently, 15.7 g (240 mmol) of potassium tert-butoxide are added in portions within 10 min. A 500 ml three-neck round-bottom flask provided with magnetic stirrer, thermometer, dropping funnel, reflux condenser and nitrogen blanketing is initially charged with 90 ml of methanol, and then 8.6 g (20 mmol) of 3-phenyl-1-{8-(3-phenylacryloyl)]dibenzofuran-2-yl}propenone and 41.8 g (80 mmol) of benzamidine hydrochloride (30% in methanol) are added while stirring. The beige suspension is heated to reflux and then the potassium tert-butoxide solution previously prepared is added dropwise within 20 min. The beige-brown suspension is stirred under reflux overnight. Subsequently, it is cooled to room temperature and then 150 ml of water are added dropwise and the mixture is stirred for 4 h. A suspension forms, which is filtered. The residue is suspended in 200 ml of water and heated to reflux for 2 h. Subsequently, the mixture is cooled to room temperature and filtered, and the residue is washed with 50 ml of water and then dried at 60° C./150 mbar overnight. This gives 10.9 g of 2,8-bis(2,4-diphenyl-1,4-dihydro-pyrimidinyl)dibenzofuran (85.8% of theory) as yellow crystals. The crude product is used further without purification.

Stage 3

A 500 ml three-neck round-bottom flask provided with magnetic stirrer, thermometer, reflux condenser and nitrogen blanketing is initially charged with 10.9 g (17 mmol) of crude 2,8-bis(2,4-diphenyl-1,4-dihydropyrimidinyl)dibenzofuran in 100 ml of o-dichlorobenzene and heated to 60° C. while stirring. Thereafter, 19.1 g (78 mmol) of chloranil are added and the dark-colored reaction mixture is heated to reflux for 14 h. Subsequently, 160 ml of MeOH are added and the mixture is stirred under reflux for 15 min. Thereafter, it is cooled to 0° C. with an ice bath, the dark brown suspension is filtered and the residue is washed three times with 50 ml each time of MeOH and twice with 50 ml each time of water. After drying at 60° C./125 mbar overnight, 18.0 g of brown crystals are obtained. The crude product is suspended in 100 ml of MeOH under reflux for 1 h, then cooled to 0° C., washed twice with 20 ml each time of MeOH and dried at 60° C./125 mbar. This gives 16.4 g of brown crystals. 5.7 g of this material are suspended in 50 ml of EtOH under reflux for 30 min, then cooled to 0° C., washed twice with 20 ml each time of EtOH and dried at 60° C./125 mbar. This gives 5.0 g of brown crystals. This crude product is slurried in 190 ml of toluene and stirred under reflux for 30 min. Thereafter, it is cooled to 0° C. with an ice bath, the suspension is filtered and the residue is washed three times with 20 ml each time of toluene. After drying at 60° C./125 mbar overnight, 3.0 g (81% of theory) of the desired product are obtained as white-beige crystals.

HPLC-MS: purity 99.5%, [M+1]=629.5 m/z.

$^1$H NMR (CDCl$_3$, 300 MHz):

8.97 (s, 2H), 8.73 (d, J=9 Hz, 4H), 8.43 (d, J=10 Hz, 2H), 8.42-8.28 (m, 4H), 8.11 (s, 2H), 7.73 (d, J=9 Hz, 2H) 7.60-7.35 (m, 12H)

Example 32

First, the ITO substrate used as the anode is treated as in Example 30a and provided with a 40 nm-thick hole injection layer of AJ20-1000 from Plexcore as described above.

Thereafter, the organic materials specified hereinafter are applied by vapor deposition at a rate of approx. 0.5-5 nm/min to the clean substrate at about $10^{-7}$-$10^{-9}$ mbar:

Example 32a

The hole conductor and exciton blocker applied is Ir(DPBIC)$_3$ in a thickness of 20 nm, of which the first 15 nm have been doped with 5% ReO$_3$. Thereafter, a 20 nm-thick emission layer consisting of 10% fac-Em1, 45% Ir(DPBIC)$_3$ and 45% Ma13 is applied by vapor deposition. This is followed by a 5 nm-thick layer Ma13 of exciton and hole blocker. Next, a mixture of 50% Liq and 50% ETM3 as an electron transport layer is applied in a thickness of 40 nm.

Finally, a 4 nm-thick layer of KF and a 100 nm-thick Al electrode are applied by vapor deposition.

The diode exhibits the CIE color coordinates 0.16, 0.27. At 300 cd/m², the external quantum efficiency is 13.7%.

Example 32b

The diode is constructed as described in Example 32a with the difference that the electron transport layer consists of pure ETM3.

The diode exhibits the CIE color coordinates 0.16, 0.27. At 300 cd/m², the voltage is 3.4 V.

Example 32c

The diode is constructed as described in Example 32a with the difference that the emission layer consists of 30% fac-Em1, 35% Ir(DPBIC)₃ and 35% Ma13.

The diode exhibits the CIE color coordinates 0.17, 0.32. At 300 cd/m², the voltage is 3.4 V.

Example 32d

The diode is constructed as described in Example 32c with the difference that the electron transport layer consists of pure ETM3.

The diode exhibits the CIE color coordinates 0.17, 0.31. At 300 cd/m², the external quantum efficiency is 14.2%.

Example 33

Synthesis of ETM4

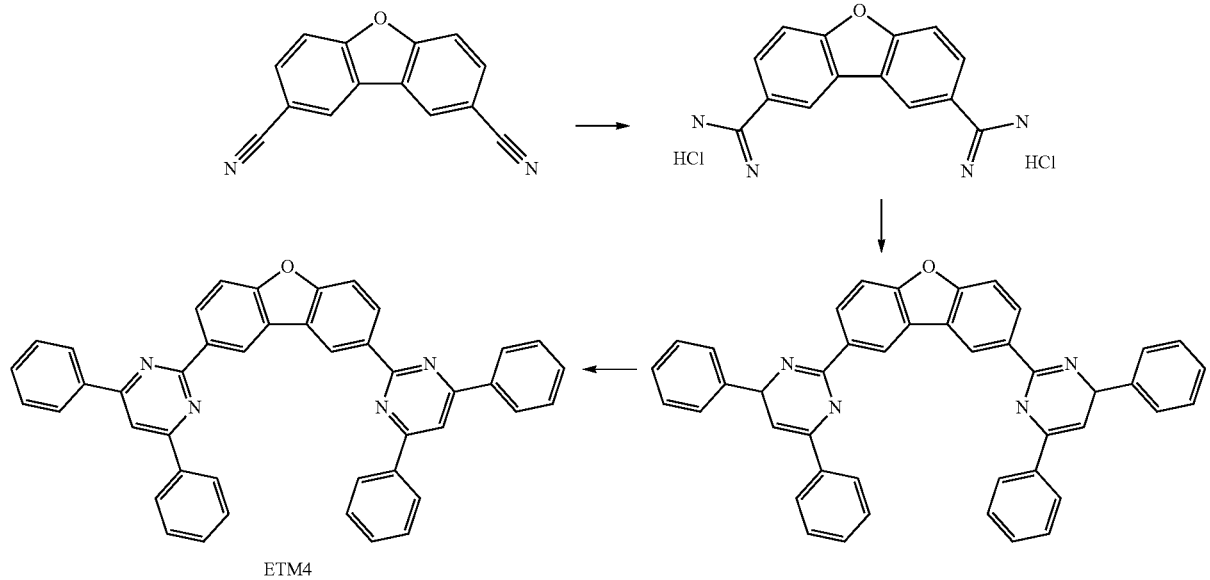

ETM4

Stage 1

A 100 ml three-neck round-bottom flask, magnetic stirrer, thermometer, reflux condenser, gas inlet tube, nitrogen blanketing and gas wash bottle is initially charged with 1.09 g (5.0 mmol) of dibenzofuran-2,8-dicarbonitrile (prepared according to S. Wang, Eur. J. Med. Chem. 34, 215 (1999)) in a mixture of 1.8 ml of ethanol and 50 ml of 1,4-dioxane, and is cooled to 0° C. with an EtOH/CO₂ bath, and then HCl gas is introduced until saturation. Thereafter, the flask is sealed and the white suspension is warmed to RT and stirred for 48 h. Subsequently, dry N₂ is blown into the suspension until no HCl can be detected any longer in the offgas. 25 ml of t-butyl methyl ether are added and the yellowish suspension is filtered. The residue is washed twice with 25 ml each time of t-butyl methyl ether, then suspended in 40 ml of 2M H₃ in ethanol and stirred at 60° C. for 18 h. Subsequently, the suspension is cooled and dry N₂ is blown into the suspension until no NH₃ can be detected any longer in the offgas. Then it is cooled with an ice bath and HCl gas is again introduced until saturation. Thereafter, it is blown out again with dry N₂, and the beige suspension is filtered and washed with portions totaling 25 ml of ice-cold EtOH. The residue is dried at 50° C./125 mbar overnight. This gives 1.71 g (99.2% of theory) of dibenzofuran-2,8-bisamidine hydrochloride as beige crystals.

¹H NMR (DMSO, 300 MHz):
8.90-8.75 (m, 2H), 8.25-8.00 (m, 4H)

Stage 2

A 100 ml three-neck round-bottom flask provided with magnetic stirrer, thermometer, reflux condenser and nitrogen blanketing is initially charged with 40 ml of methanol and cooled to 0° C. with an ice bath while stirring. Subsequently, 2.85 g (25.4 mmol) of potassium tert-butoxide are added in portions within 10 min. A 250 ml three-neck round-bottom flask provided with magnetic stirrer, thermometer, dropping funnel, reflux condenser and nitrogen blanketing is initially charged with 60 ml of methanol and then 1.7 g of dibenzofuran-2,8-bisamidine hydrochloride and 4.08 g (19 mmol) of benzylidenacetophenone are added while stirring. The beige suspension is heated to reflux and then the previously prepared potassium tert-butoxide solution is added dropwise within 5 min. The beige suspension is stirred under reflux overnight. Subsequently, the mixture is cooled to 0° C. and filtered, and the residue is washed with 15 ml of ice-cold MeOH and three times with 60 ml of water, and dried at 60° C./150 mbar overnight. This gives 1.59 g of 2,8-bis(4,6-diphenyl-1,4-dihydro-pyrimidinyl)dibenzofuran (39.6% of theory) as yellow crystals. The crude product is used further without purification.

Stage 3

A 100 ml three-neck round-bottom flask provided with magnetic stirrer, thermometer, reflux condenser and nitrogen blanketing is initially charged with 1.59 g (2.45 mmol) of 2,8-di(4,6-diphenyl-1,4-dihydropyrimidinyl)dibenzofuran in 15 ml of o-dichlorobenzene. The mixture is heated to internal temperature 50° C. while stirring and then 2.41 g (9.80 mmol) of chloranil are added. The beige-brown suspension is heated to reflux for 4 h, then 30 ml of MeOH and subsequently 1 g of NaOH dissolved in 5 ml of water are added dropwise. The dark brown suspension is stirred under reflux for 30 min, then cooled to 0° C. with an ice bath and filtered. The residue is washed three times with 20 ml of MeOH and five times with 20 ml of hot water. The beige solid is suspended in 50 ml of toluene and refluxed while stirring for 30 min. This is followed by cooling to an internal temperature of 60° C. and filtration, and the residue is washed twice with 10 ml of toluene and dried at 60° C./125 mbar overnight. This gives 0.85 g (55.2% of theory) of the desired product as white crystals.

HPLC-MS: purity 99.3%, [M+1]=629.5 m/z.

$^1$H NMR (CDCl$_3$, 300 MHz):

9.41 (s, 2H), 8.89 (d, J=9 Hz, 2H), 8.35-8.20 (m, 8H), 7.98 (s, 2H), 7.68 (d, J=9 Hz, 2H) 7.70-7.45 (m, 12H)

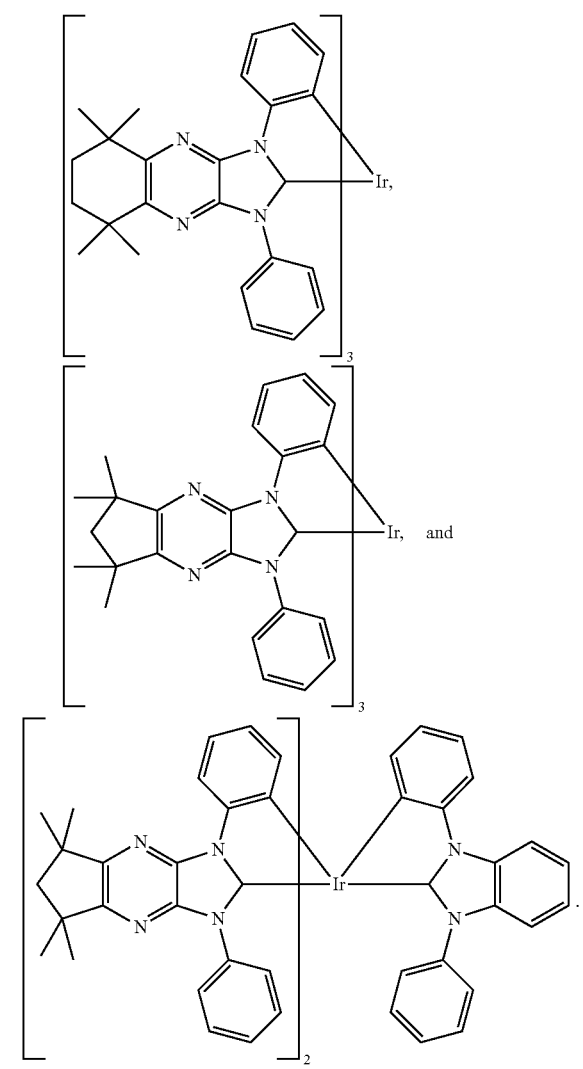

The invention claimed is:

1. A metal-carbene complex of the general formula (I):

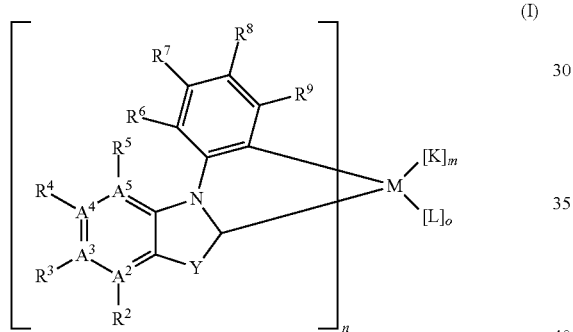

wherein
M is Ir or Pt,
n is an integer selected from 1, 2 or 3,
Y is NR$^1$, O, S or C(R$^{10}$)$_2$,
A$^2$ and A$^5$ are each N,
A$^3$ and A$^4$ are each C,
R$^1$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms,
R$^2$ and R$^5$ are each a free electron pair;
R$^3$ and R$^4$ together with A$^3$ and A$^4$ form an optionally substituted, unsaturated ring optionally interrupted by at least one further heteroatom and having a total of 5 to 18 carbon atoms and/or heteroatoms, wherein R$^3$ and R$^4$ together with A$^3$ and A$^4$ do not form a phenyl ring, R$^6$, R$^7$, R$^8$, R$^9$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, with a base skeleton selected from the group consisting of pyridyl, pyrimidyl, pyrazyl, triazolyl, pyrrole, furan, thiophene, pyrazole, triazole, oxazole and thiazole, group with donor or acceptor action, at least one selected from the group consisting of a halogen radical, a silyl radical, a siloxy radical, an alkoxy radical, an aryloxy radical, a carbonyl radical, an ester radical, CH$_2$F, CHF$_2$, CF$_3$, CN, a thio group, and SCN,
or
R$^6$ and R$^7$, R$^7$ and R$^8$ or R$^8$ and R$^9$, together with the carbon atoms to which they are bonded, form a saturated, unsaturated or aromatic, optionally substituted ring optionally interrupted by at least one heteroatom and having a total of 5 to 18 carbon atoms and/or heteroatoms,
R$^{10}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms,
K is an uncharged mono- or bidentate ligand,
L is a mono- or dianionic ligand,
m is 0, 1 or 2, where, when m is 2, the K ligands may be the same or different, and
o is 0, 1 or 2, where, when o is 2, the L ligands may be the same or different.

2. The metal-carbene complex according to claim 1, wherein:
M is Ir,
n is 1, 2 or 3,
Y is NR$^1$,
A$^2$ and A$^5$ are each N,
A$^3$ and A$^4$ are each C,
R$^1$ is a linear or branched alkyl radical having 1 to 6 carbon atoms, substituted or unsubstituted aryl radical having 6 to 30 carbon atoms, substituted or unsubstituted heteroaryl radical having a total of 5 to 18 carbon atoms and/or heteroatoms,
R$^2$ and R$^5$ are each a free electron pair;
R$^3$ and R$^4$ together with A$^3$ and A$^4$ form an optionally substituted, unsaturated ring optionally interrupted by at least one further heteroatom and having a total of 5 to 18 carbon atoms and/or heteroatoms, wherein $R^3$ and $R^4$ together with $A^3$ and $A^4$ do not form a phenyl ring, $R^6$, $R^7$, $R^8$, $R^9$ are each independently hydrogen, linear or branched alkyl radical optionally interrupted by at least one heteroatom, optionally bearing at least one functional group and having 1 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, with a base skeleton selected from the group consisting of pyridyl, pyrimidyl, pyrazyl, triazolyl, pyrrole, furan, thiophene, pyrazole, triazole, oxazole and thiazole, L is a monoanionic bidentate ligand, m is 0, and o is 0, 1 or 2.

3. The metal-carbene complex according to claim 1, wherein:

M is Ir, n is 2 or 3,

Y is $NR^1$, $A^2$ and $A^5$ are each N and $A^3$ and $A^4$ are each C $R^1$ is a linear or branched alkyl radical having 1 to 6 carbon atoms, substituted or unsubstituted phenyl radical, substituted or unsubstituted heteroaryl radical having a total of 6 to 18 carbon atoms and/or heteroatoms, $R^2$ and $R^5$ are each a free electron pair;

$R^3$ and $R^4$ together with $A^3$ and $A^4$ form an optionally substituted, monounsaturated ring having a total of 5 to 7 carbon atoms, $R^6$, $R^7$, $R^8$, $R^9$ are each independently hydrogen, linear or branched alkyl radical having 1 to 20 carbon atoms, o,o'-dialkylated aryl radical having 6 to 30 carbon atoms, L is a monoanionic bidentate ligand, m is 0, and o is 0 or 1.

4. The metal-carbene complex of claim 1, wherein, in the general formula (I), L is a carbene ligand of the general formula (II):

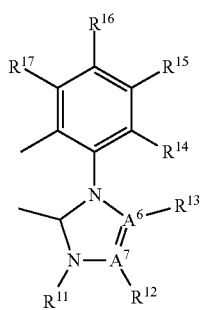

(II)

wherein $A^6$, $A^7$ are each independently C or N, $R^{11}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^{12}$, $R^{13}$ are each independently, when A is N, a free electron pair, or, when A is C, hydrogen, linear or branched alkyl radical optionally interrupted by at least one heteroatom, optionally bearing at least one functional group and having 1 to 20 carton atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, R14, $R^{15}$, R16, $R^{17}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carton atoms and/or heteroatoms, group with donor or acceptor action, or $R^{12}$ and $R^{13}$, $R^{14}$ and $R^{15}$, $R^{15}$ and $R^{16}$ or $R^{16}$ and $R^{17}$ form, together with A or the carbon atoms to which they are bonded, an unsaturated or aromatic, optionally substituted ring optionally interrupted by at least one heteroatom and having a total of 5 to 18 carbon atoms and/or heteroatoms, and/or if $A^6$ is C, $R^{13}$ and $R^{14}$ together form a saturated or unsaturated, linear or branched bridge optionally comprising heteroatoms, aromatic units, heteroaromatic units and/or functional groups and having a total of 1 to 30 carbon atoms and/or heteroatoms, to which is optionally fused a substituted or unsubstituted, five- to eight-membered ring comprising carbon atoms and/or heteroatoms.

5. The metal-carbene complex of claim 1, wherein L in the general formula (I) is a heterocyclic noncarbene ligand of the general formula (III):

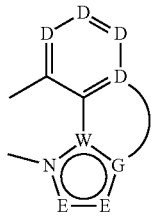

(III)

wherein:
D are each independently $CR^{18}$ or N;
W is C, N;
E are each independently $CR^{19}$, N, or $NR^{20}$;
G is $CR^{21}$, N, $NR^{22}$, S, or O;
$R^{18}$, $R^{19}$, $R^{21}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action,
or in each case 2 $R^{18}$, $R^{19}$ and $R^{21}$ radicals, together with the carbon atoms to which they are bonded, form a saturated, unsaturated or aromatic, optionally substituted ring optionally interrupted by at least one heteroatom and having a total of 5 to 18 carbon atoms and/or heteroatoms;
$R^{20}$, $R^{22}$ are each independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action;
the solid curved line is an optional bridge between one of the D groups and the G group, and the optional bridge is selected from the group consisting of alkylene, arylene, heteroarylene, alkynylene, alkenylene, $NR^{23}$, O, S, $SiR^{24}R^{25}$ and $(CR^{25}R^{27})_d$, where one or more nonadjacent $(CR^{26}R^{27})$ groups may be replaced by $NR^{23}$, O, $SiR^{24}R^{25}$, where
d is 2 to 10;
and
$R^{24}$, $R^{25}$, $R^{26}$, $R^{27}$ independently represent H, alkyl, aryl, heteroaryl, alkenyl, or alkynyl.

6. A process for preparing the metal-carbene of claim 1, the process comprising contacting at least one compound comprising M with at least one ligand or ligand precursor.

7. The process according to claim 6, comprising contacting the at least one compound with at least one ligand precursor, wherein the ligand precursor is a Ag-carbene complex.

8. The process according to claim 6, comprising contacting the at least one compound with at least one ligand precursor, wherein the ligand precursor is a compound of the general formula (IV):

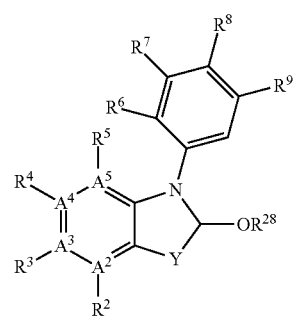

(IV)

wherein
Y is $NR^1$, O, S or $C(R^{10})_2$,
$A^2$ and $A^5$ are each N,
$A^3$ and $A^4$ are each C,
$R^2$ and $R^5$ are each a free electron pair;
$R^3$ and $R^4$ together with $A^3$ and $A^4$ form an optionally substituted, unsaturated ring optionally interrupted by at least one further heteroatom and having a total of 5 to 18 carbon atoms and/or heteroatoms, wherein $R^3$ and $R^4$ together with $A^3$ and $A^4$ do not form a phenyl ring,
$R^6$, $R^7$, $R^8$, $R^9$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, with a base skeleton selected from the group consisting of pyridyl, pyrimidyl, pyrazyl, triazolyl, pyrrole, furan, thiophene, pyrazole, triazole, oxazole and thiazole, group with donor or acceptor action, selected from the group consisting of a halogen radical, a silyl radical, a siloxy radical, an alkoxy radical, an aryloxy radical, a carbonyl radical, an ester radical, $CH_2F$, $CHF_7CF_3$, CN, a thio group and SCN, or $R^6$ and $R^7$, $R^7$ and $R^8$ or $R^8$ and $R^9$, together with the carbon atoms to which they are bonded, form a saturated, unsaturated or aromatic, optionally substituted ring optionally interrupted by at least one heteroatom and having a total of 5 to 18 carbon atoms and/or heteroatoms, R28 is independently $SiR^{29}R^{30}R^{31}$, aryl, heteroaryl, alkyl, cycloalkyl or heterocycloalkyl, and $R^{29}$, $R^{30}$, $R^{31}$ are each independently aryl, heteroaryl, alkyl, cycloalkyl or heterocycloalkyl.

9. An organic electronic component comprising at least one metal-carbene complex of claim 1.

10. The organic electronic component according to claim 9, which is an organic light-emitting diode (OLED), organic photovoltaic cell (OPV), organic field-effect transistor (OFET) or light-emitting electrochemical cell (LEEC).

11. A light-emitting layer comprising at least one metal-carbene complex according to claim 1.

12. An OLED comprising a light-emitting layer according to claim 11.

13. An OLED comprising at least one metal-carbene complex according to claim 1, and at least one compound of the formula (X):

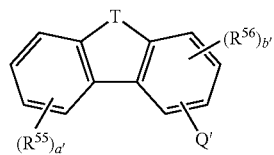

(X)

wherein:
T is $NR^{57}$, S, O or $PR^{57}$;
$R^{57}$ is aryl, heteroaryl, alkyl, cycloalkyl or heterocycloalkyl;
Q' is $-NR^{58}R^{59}$, $-P(O)R^{60}R^{61}$, $-PR^{62}R^{63}$, $-S(O)_2R^{64}$, $-S(O)R^{65}$, $-SR^{66}$ or $-OR^{67}$;
$R^{55}$, $R^{56}$ are each independently alkyl, cycloalkyl, heterocycloalkyl, aryl, heteroaryl, $SiR^{70}R^{71}R^{72}$, a Q' group or a group with donor or acceptor action;
a" is 0, 1, 2, 3 or 4;
b' is 0, 1, 2 or 3;
$R^{58}$, $R^{59}$ form, together with the nitrogen atom, a cyclic radical which has 3 to 10 ring atoms and may be unsubstituted or substituted by one or more substituents selected from the group consisting of alkyl, cycloalkyl, heterocycloalkyl, aryl, heteroaryl and a group with donor or acceptor action, and/or may be fused to one or more further cyclic radicals having 3 to 10 ring atoms, where the fused radicals may be unsubstituted or substituted by one or more substituents selected from the group consisting of alkyl, cycloalkyl, heterocycloalkyl, aryl, heteroaryl and a group with donor or acceptor action;
$R^{70}$, $R^{71}$, $R^{72}$, $R^{60}$, $R^{61}$, $R^{62}$, $R^{63}$, $R^{64}$, $R^{65}$, $R^{66}$, $R^{67}$ are each independently aryl, heteroaryl, alkyl, cycloalkyl or heterocycloalkyl, or two units of the general formula (X) are bridged to one another through a linear or branched, saturated or unsaturated bridge optionally interrupted by at least one heteroatom, through a bond or through O.

14. The OLED according to claim 13, comprising at least one compound of the formula (XI) or (XI*):

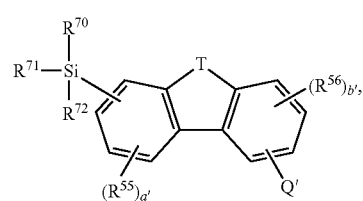

(XI)

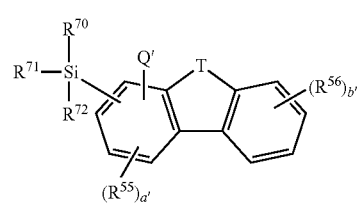

(XI*)

wherein:
T is $NR^{57}$, S, O or $PR^{57}$;
$R^{57}$ is aryl, heteroaryl, alkyl, cycloalkyl or heterocycloalkyl;
Q' is $-NR^{58}R^{59}$, $-P(O)R^{60}R^{61}$, $-PR^{62}R^{63}$, $-S(O)_2R^{64}$, $-S(O)R^{65}$, $-SRS^{66}$ or $-OR^{67}$;
$R^{70}$, $R^{71}$, $R^{72}$ are each independently aryl, heteroaryl, alkyl, cycloalkyl, heterocycloalkyl, where at least one of the $R^{70}$, $R^{71}$, $R^{72}$ radicals comprises at least two carbon atoms, or $OR^{73}$,
$R^{55}$, $R^{56}$ are each independently alkyl, cycloalkyl, heterocycloalkyl, aryl, heteroaryl, a Q' group or a group with donor or acceptor action;
a', b' for the compound of the formula (XI): are each independently 0, 1, 2, 3; for the compound of formula (XI*), a' is 0, 1, 2 and b' is 0, 1, 2, 3, 4;
$R^{58}$, $R^{59}$ form, together with the nitrogen atom, a cyclic radical which has 3 to 10 ring atoms and may be unsubstituted or substituted by one or more substituents selected from the group consisting of alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from the group consisting of alkyl, cycloalkyl, heterocycloalkyl, aryl, heteroaryl and a group with donor or acceptor action;
$R^{73}$ are each independently $SiR^{74}R^{75}R^{76}$, aryl, heteroaryl, alkyl, cycloalkyl or heterocycloalkyl, optionally substituted by an $OR^{77}$ group,
$R^{77}$ are each independently $SiR^{74}R^{75}R^{78}$, aryl, heteroaryl, alkyl, cycloalkyl or heterocycloalkyl,
$R^{60}$, $R^{61}$, $R^{62}$, $R^{63}$, $R^{64}$, $R^{65}$, $R^{66}$, $R^{67}$, $R^{74}$, $R^{75}$, $R^{76}$ are each independently aryl, heteroaryl, alkyl, cycloalkyl or heterocycloalkyl, or two units of the general formulae (XI) and/or (XI*) are bridged to one another through a linear or branched, saturated or unsaturated bridge optionally interrupted by at least one heteroatom or through O, where this bridge in the general formulae (XI) and/or (XI*) is in each case attached to the silicon atoms in place of $R^{71}$.

15. The OLED according to claim 14, wherein $R^{70}$ and/or $R^{71}$ and/or $R^{72}$ in the compounds of the general formula (XI) or (XI*) are aromatic units of the general formulae (XIi) and/or (XIi*):

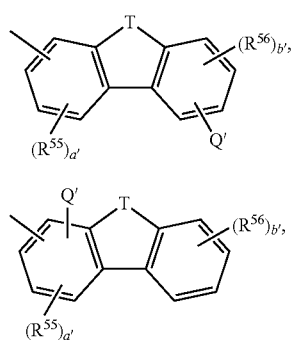

(XIi)

(XIi*)

wherein:
T is $NR^{57}$, S, O or $PR^{57}$;
Q' is $-NR^{58}R^{59}$, $-P(O)R^{60}R^{61}$, $-PR^{62}R^{63}$, $-S(O)_2R^{64}$, $-S(O)R^{65}$, $-SRS^{66}$ or $-OR^{67}$;
$R^{55}R^{56}$ are each independently alkyl, cycloalkyl, heterocycloalkyl, aryl, heteroaryl, a Q' group or a group with donor or acceptor action; and
a', b' for the compound of the formula (XIi): are each independently 0, 1, 2, 3; for the compound of the formula (XIi*), a' is 0, 1, 2 and b' is 0, 1, 2, 3, 4.

16. The OLED according to claim 13, comprising an emission layer comprising the at least one metal-carbene complex, and at least one matrix material.

17. The OLED according to claim 12, comprising an electron-transporting layer comprising at least two different materials, of which at least one material is electron-conducting.

18. The OLED according to claim 17, wherein the electron-transporting layer comprises at least one phenanthroline derivative and/or pyridine derivative.

19. A device comprising at least one OLED according to claim 12, wherein the device is at least one selected from the group consisting of a stationary visual display unit, a mobile visual display unit, and an illumination unit.

20. An OLED comprising the metal-carbene complex according to claim 1.

21. The OLED according to claim 20, wherein the metal-carbene complex is at least one selected from the group consisting of an emitter, a matrix material, a charge transport material and a charge blocker.

22. The metal-carbene complex according to claim 1, wherein:
$R^3$ and $R^4$ together with $A^3$ and $A^4$ form an optionally substituted, monounsaturated ring optionally interrupted by at least one further heteroatom and having a total of 5 to 18 carbon atoms and/or heteroatoms.

23. The metal-carbene complex according to claim 1, wherein the complex is selected from the group consisting of